United States Patent
Ziff et al.

(10) Patent No.: US 11,008,302 B2
(45) Date of Patent: May 18, 2021

(54) SUBSTITUTED PYRIDINE AND PYRIMIDINES AND THEIR USE AS GLUN2B RECEPTOR MODULATORS

(71) Applicant: JANSSEN PHARMACEUTICA NV, Beerse (BE)

(72) Inventors: Jeannie M. Ziff, San Diego, CA (US); Cathy Preville, San Diego, CA (US); Brock T. Shireman, Poway, CA (US)

(73) Assignee: JANSSEN PHARMACEUTICA NV, Beerse (BE)

( * ) Notice: Subject to any disclaimer, the term of this patent is extended or adjusted under 35 U.S.C. 154(b) by 0 days.

(21) Appl. No.: 16/373,906

(22) Filed: Apr. 3, 2019

(65) Prior Publication Data
US 2019/0308950 A1    Oct. 10, 2019

Related U.S. Application Data

(60) Provisional application No. 62/652,458, filed on Apr. 4, 2018.

(51) Int. Cl.
| | |
|---|---|
| *C07D 401/04* | (2006.01) |
| *C07D 401/14* | (2006.01) |
| *A61K 31/4545* | (2006.01) |
| *A61P 25/24* | (2006.01) |
| *C07D 401/12* | (2006.01) |
| *A61P 25/18* | (2006.01) |
| *C07D 213/89* | (2006.01) |
| *C07D 213/68* | (2006.01) |
| *C07D 239/42* | (2006.01) |
| *C07D 403/04* | (2006.01) |
| *C07D 471/10* | (2006.01) |
| *C07D 213/74* | (2006.01) |
| *C07D 487/10* | (2006.01) |

(52) U.S. Cl.
CPC ............ *C07D 401/12* (2013.01); *A61P 25/18* (2018.01); *A61P 25/24* (2018.01); *C07D 213/68* (2013.01); *C07D 213/74* (2013.01); *C07D 213/89* (2013.01); *C07D 239/42* (2013.01); *C07D 401/04* (2013.01); *C07D 401/14* (2013.01); *C07D 403/04* (2013.01); *C07D 471/10* (2013.01); *C07D 487/10* (2013.01)

(58) Field of Classification Search
CPC .................. C07D 401/04; C07D 401/14
See application file for complete search history.

(56) References Cited

U.S. PATENT DOCUMENTS

| | | |
|---|---|---|
| 7,622,486 B2 | 11/2009 | Pal et al. |
| 8,765,784 B2 | 7/2014 | Arrington et al. |
| 8,785,438 B2 | 7/2014 | Ohtsuka et al. |
| 8,877,772 B2 | 11/2014 | Gelbard et al. |
| 9,434,743 B2 | 9/2016 | Cheruvallath et al. |
| 9,963,447 B2 | 5/2018 | Chrovian et al. |
| 9,981,950 B2 | 5/2018 | Schindler et al. |
| 10,071,988 B2 | 9/2018 | Gang et al. |
| 10,155,727 B2 | 12/2018 | Schindler et al. |
| 10,233,173 B2 | 3/2019 | Chen et al. |
| 10,323,021 B2 | 6/2019 | Schindler et al. |
| 10,377,753 B2 | 8/2019 | Chrovian et al. |
| 10,617,676 B2 | 4/2020 | Chrovian et al. |
| 2007/0275965 A1 | 11/2007 | Thomas et al. |
| 2008/0300239 A1 | 12/2008 | Adams et al. |
| 2014/0275011 A1 | 9/2014 | Mastracchio et al. |
| 2015/0210681 A1 | 7/2015 | Bourque et al. |
| 2016/0024087 A1 | 1/2016 | Gelbard et al. |
| 2018/0125826 A1 | 5/2018 | Chrovian et al. |
| 2018/0208595 A1 | 7/2018 | Chrovian et al. |
| 2018/0282305 A1 | 10/2018 | Schindler et al. |
| 2018/0334451 A1 | 11/2018 | Chen et al. |
| 2019/0135791 A1 | 5/2019 | Chen et al. |

FOREIGN PATENT DOCUMENTS

| | | |
|---|---|---|
| EP | 0 928 789 A1 | 7/1999 |
| EP | 2194045 A1 | 6/2010 |
| JP | 2012-188363 A | 4/2012 |
| WO | 95/28400 | 10/1995 |
| WO | 2002/060877 A1 | 8/2002 |
| WO | 2003082868 A1 | 10/2003 |
| WO | 2003/097637 A1 | 11/2003 |

(Continued)

OTHER PUBLICATIONS

Iadarola et al. Therapeutic Advances in Chronic Disease vol. 6(3), p. 97-114. (Year: 2015).*

(Continued)

*Primary Examiner* — Emily A Bernhardt
(74) *Attorney, Agent, or Firm* — Biospark Intellectual Property Law

(57) ABSTRACT

Substituted pyrimidine and pyridines as NR2B receptor ligands, for example

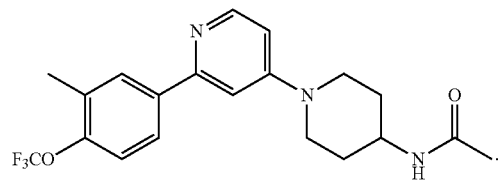

Such compounds may be used in NR2B receptor modulation and in pharmaceutical compositions and methods for the treatment of disease states, disorders, and conditions mediated by NR2B receptor activity.

15 Claims, No Drawings

(56) References Cited

FOREIGN PATENT DOCUMENTS

| WO | 2005080379 A1 | 9/2005 |
|---|---|---|
| WO | 2008145616 A1 | 12/2008 |
| WO | 2009/004430 A1 | 1/2009 |
| WO | 2009058261 A1 | 5/2009 |
| WO | 2009118187 A1 | 10/2009 |
| WO | 2010043396 A1 | 4/2010 |
| WO | 2010/108187 A1 | 9/2010 |
| WO | 2011/140202 A2 | 11/2011 |
| WO | 2013/060029 A1 | 5/2013 |
| WO | 2013130855 A1 | 9/2013 |
| WO | 2014124651 A1 | 8/2014 |
| WO | 2015/002754 A2 | 1/2015 |
| WO | 2016025917 | 2/2016 |
| WO | 2016/081649 A1 | 5/2016 |

OTHER PUBLICATIONS

Addy et al., 2009, "Single-Dose Administration of MK-0657, an NR2B-Selective NMDA Antagonist, Does Not Result in Clinically Meaningful Improvement in Motor Function in Patients With Moderate Parkinson's Disease," Journal of Clinical Pharmacology, 49:856-864.
Arnold et al., 2009, "Glutamate receptor gene (*GRIN2B*) associated with reduced anterior cingulate glutamatergic concentration in pediatric obsessive-compulsive disorder," Psychiatry Research: Neuroimaging, 172(2):136-139.
Bagshawe, Kenneth D., 1995, "Antibody-Directed Enzyme Prodrug Therapy : A Review," Drug Development Research, 34:220-230.
Berberich et al., 2007, "The role of NMDAR subtypes and charge transfer during hippocampal LTP induction," Neuropharmacology, 52:77-86.
Berge et al., 1977, "Pharmaceutical Salts," Journal of Pharmaceutical Sciences, 66(1):1-19.
Bertolini et al., 1997, "A New Rational Hypothesis for the Pharmacophore of the Active Metabolite of Leflunomide, a Potent Immunosuppressive Drug," Journal of Medicinal Chemistry, 40(13):2011-2016.
Bodor, Nicholas, 1984, "Novel Approaches to the Design of Safer Drugs: Soft Drugs and Site-Specific Chemical Delivery Systems," Advances in Drug Research, 13:256-331.
Bullock et al., 1999, "An Open-Label Study of CP-101,606 in Subjects with a Severe Traumatic Head Injury or Spontaneous Intracerebral Hemorrhage," Annals New York Academy of Sciences, 890:51-58.
Buonarati et al., 1990, "Role of sulfation and acetylation in the activation of 2-hydroxyamino-1-methyl-6-phenylimidazo[4,5-b]pyridine to intermediates which bind DNA," Mutation Research, 245:185-190.
Chattopadhyay et al., 2010, "Fused Tetrazoles as Azide Surrogates in Click Reaction: Efficient Synthesis of N-Heterocycle-Substituted 1,2,3-Triazoles," Organic Letters, 12(9):2166-2169.
Considine, Glenn D., Van Nostrand's Encyclopedia of Chemistry, Encyclopedia of Chemistry, 2005, pp. 261, Chapter 5.
Cull-Candy et al., 2001, "NMDA receptor subunits: diversity, development and disease," Current Opinion in Neurobiology, 11(3):327-335.
Dalmau et al., 2008 "Anti-NMDA-receptor encephalitis: case series and analysis of the effects of antibodies," Lancet Neurol, 7:1091-1098.
Dorval et al., 2007, "Association of the glutamate receptor subunit gene *GRIN2B* with attention-deficit/hyperactivity disorder," genes, Brain and Behavior, 6(5):444-452.
Duty, Susan, 2012, "Targeting Glutamate Receptors to Tackle the Pathogenesis, Clinical Symptoms and Levodopa-Induced Dyskinesia Associated with Parkinson's Disease," CNS Drugs, 26:1017-1032.
Farjam et al., 2014, "Inhibition of NR2B-Containing N-methyl-D-Aspartate Receptors (NMDARs) in Experimental Autoimmune Encephalomyelitis, a Model of Multiple Sclerosis," Iranian Journal of Pharmaceutical Research, 13(2):695-705.
Fleisher et al., 1996, "Improved oral drug delivery: solubility limitations overcome by the use of prodrugs," Advanced Drug Delivery Reviews, 19:115-130.
Fuller et al., 2006, "Differential expression of the NMDA NR2B receptor subunit in motoneuron populations susceptible and resistant to amyotrophic lateral sclerosis," Neuroscience Letters, 399:157-161.
Grasselli et al., 2013, "Abnormal NMDA receptor function exacerbates experimental autoimmune encephalomyelitis," British Journal of Pharmacology, 168:502-517.
Grimwood et al., 1999, "NR2B-containing NMDA receptors are upregulated in temporal cortex in schizophrenia," NeuroReport, 10:461-465.
Guitton et al., 2007, "Blockade of Cochlear NMDA Receptors Prevents Long-Term Tinnitus during a Brief Consolidation Window after Acoustic Trauma," Neural Plasticity, 2007(Article ID 80904):1-11.
Haller et al., 2011, "NR2B subunit-specific NMDA antagonist Ro25-6981 inhibits the expression of conditioned fear: a comparison with the NMDA antagonist MK-801 and fluoxetine," Behavioural Pharmacology, 22:113-121.
Hanson et al., 2015, "Altered GluN2B NMDA receptor function and synaptic plasticity during early pathology in the PS2APP mouse model of Alzheimer's disease," Neurobiology of Disease, 74:254-262.
Hu et al., 2016, "Expression of immediate-early genes in the dorsal cochlear nucleus in salicylate-induced tinnitus," Eur Arch Otorhinolaryngol, 273:325-332.
Ito et al., 2003, "A Medium-term rat liver bioassay for rapid in vivo detection of carcinogenic potential of chemicals," Cancer Sci, 94(1):3-8.
Kolb et al., 2004, "Click Chemistry: Diverse Chemical Function from a Few Good Reactions," Angew. Chem. Int. Ed, 40:2004-2021.
Kowal et al., 2006, "Human lupus autoantibodies against NMDA receptors mediate cognitive impairment," PNAS, 103(52):19854-19859.
Layton et al., 2016, "Discovery of 5-aryl-1,3-dihydro-2H-imidazo[4,5-b]pyridin-2-ones as positive allosteric modulators of metabotropic glutamate subtype-2 (mGlu2) receptors with efficacy in a preclinical model of psychosis," Bioorganic & Medicinal Chemistry Letters, 26:1260-1264.
Leaderbrand et al., 2013, "Co-activation of NR2A and NR2B subunits induces resistance to fear extinction," Neurobiol Learn Mem, 113:35-40.
Leaver et al., 2008, "Neuroprotective Effects of a Selective N-Methyl-D-Aspartate NR2B Receptor Antagonist in the 6-Hydroxydopamine Rat Model of Parkinson's Disease," Clinical and Experimental Pharmacology and Physiology, 35:1388-1394.
Leyva et al., 1989, "Photochemistry of Fluorinated Aryl Azides in Toluene Solution and in Frozen Polycrystals," J. Org. Chem, 54:5938-5945.
Li et al., 2004, "Enhanced Striatal NR2B-Containing N-Methyl-D-Aspartate Receptor-Mediated Synaptic Currents in a Mouse Model of Huntington Disease," J Neurophysiol, 92:2738-2746.
Li et al., 2011, "Glutamate N-methyl-D-aspartate Receptor Antagonists Rapidly Reverse Behavioral and Synaptic Deficits Caused by Chronic Stress Exposure," Biol Psychiatry, 69:754-761.
Li et al., 2011, "Soluble Aβ Oligomers Inhibit Long-Term Potentiation through a Mechanism Involving Excessive Activation of Extrasynaptic NR2B-Containing NMDA Receptors," The Journal of Neuroscience, 31(18):6627-6638.
Lima-Ojeda et al., 2013, "Pharmacological blockade of GluN2B-containing NMDA receptors induces antidepressant-like effects lacking psychotomimetic action and neurotoxicity in the perinatal and adult rodent brain," Progress in Neuro-Psychopharmacology & Biological Psychiatry, 45:28-33.
Martucci et al., 2006, "N-methyl-D-aspartate receptor NR2B subunit gene GRIN2B in schizophrenia and bipolar disorder: Polymorphisms and mRNA levels," Schizophrenia Research, 84:214-221.

(56) References Cited

OTHER PUBLICATIONS

Massey et al., 2004, "Differential Roles of NR2A and NR2B-Containing NMDA Receptors in Cortical Long-Term Potentiation and Long-Term Depression," The Journal of Neuroscience, 24(36)7821-7828.
Miller et al., 2014, "GluN2B-containing NMDA receptors regulate depression-like behavior and are critical for the rapid antidepressant actions of ketamine," eLife, 3:1-22.
Morissette et al., 2006, "Prevention of Levodopa-Induced Dyskinesias by a Selective NR1A/2B N-Methyl-D-aspartate Receptor Antagonist in Parkinsonian Monkeys: Implication of Preproenkephalin," Movement Disorders, 21(1):9-17.
Nagy, Jozsef, 2004, "The NR2B Subtype of NMDA Receptor: A Potential Target for the Treatment of Alcohol Dependence," Current Drug Targets—CNS & Neurological Disorders, 3:169-179.
Naskar et al., 1999, "Saving the Nerve from Glaucoma: Memantine to Caspaces," Seminars in Ophthalmology, 14(3):152-158.
Naspolini et al., 2012, "Traxoprodil decreases pentylenetetrazol-induced seizures," Epilepsy Research, 100:12-19.
Nutt et al., 2008, "Effects of a NR2B Selective NMDA Glutamate Antagonist, CP-101,606, on Dyskinesia and Parkinsonism," Movement Disorders, 23(13):1860-1866.
Orgogozo et al., 2002, "Efficacy and Safety of Memantine in Patients With Mild to Moderate Vascular Dementia A Randomized, Placebo-Controlled Trial (MMM 300)," Stroke, 33:1834-1839, doi: 10.1161/01.STR.0000020094.08790.49.
Paoletti et al., 2013, "NMDA receptor subunit diversity: impact on receptor properties, synaptic plasticity and disease," Nature Reviews |Neuroscience, 14:383-400.
Paulekuhn et al., 2007, "Trends in Active Pharmaceutical Ingredient Salt Selection based on Analysis of the Orange Book Database," Journal of Medicinal Chemistry, 50:6665-6672.
Peeters et al., 2007, "Effects of Pan- and Subtype-Selective N-Methyl-D-aspartate Receptor Antagonists on Cortical Spreading Depression in the Rat: Therapeutic Potential for Migraine," The Journal of Pharmacology and Experimental Therapeutics, 321(2):564-572.
Porsolt et al., 1977, "Behavioural Despair in Mice: A Primary Screening Test for Antidepressants," Arch int Pharmacodyn, 229:327-336.
Preskorn et al., 2008, "An Innovative Design to Establish Proof of Concept of the Antidepressant Effects of the NR2B Subunit Selective N-Methyl-D-Aspartate Antagonist, CP-101,606, in Patients With Treatment-Refractory Major Depressive Disorder," Journal of Clinical Psychopharmacology, 28(6):631-637.
Remington, 1985, "Remington Pharmaceutical Sciences.," Pharmaceutical Sciences., 76:1418.
Robinson et al., 1996, "Discovery of the Hemifumarate and (α-L-Alanyloxy)methyl Ether as Prodrugs of an Antirheumatic Oxindole: Prodrugs for the Enolic OH Group," Journal of Medicinal Chemistry, 39:10-18.
Shan et al., 1977, "Prodrug Strategies Based on Intramolecular Cyclization Reactions," Journal of Pharmaceutical Sciences, 86(7):765-767.
Shen et al., 2011, "Heroin relapse requires long-term potentiation-like plasticity mediated by NMDA2b-containing receptors," PNAS, 108(48):19407-19412.
Starck et al., 1997, "Drug therapy for acquired pendular nystagmus in multiple sclerosis," J Neurol, 244:9-16.
Steece-Collier et al., 2000, "Antiparkinsonian Actions of CP-101,606, an Antagonist of NR2B Subunit-Containing N-Methyl-D-Aspartate Receptors," Experimental Neurology, 163:239-243.

STN Registry database entry for CAS RN 1394745-67-5, entered STN Sep. 18, 2012. Accessed Sep. 8, 2017.
Straube, Andreas, 2005, "Pharmacology of vertigo/nystagmus/oscillopsia," Current Opinion in Neurology, 18:11-14.
Tang et al., 2005, "Disturbed $Ca^{2+}$ signaling and apoptosis of medium spiny neurons in Huntington's disease," PNAS, 102(7):2602-2607.
Tang et al., 1999, "Genetic enhancement of learning and memory in mice", Nature, 401:63-69.
Traynelis et al., 2010, "Glutamate Receptor Ion Channels: Structure, Regulation, and Function," Pharmacol Rev, 62:405-496.
Wang et al., 2014, "Targeting the NMDA receptor subunit NR2B for treating or preventing age-related memory decline," Expert Opin. Ther. Targets, 18(10):1121-1130.
Watanabe et al., 1993, "Distinct Distributions of Five N-Methyl-D-Aspartate Receptor Channel Subunit mRNAs in the Forebrain," The Journal of Comparative Neurology, 338:377-390.
Weickert et al., 2013, "Molecular evidence of N-methyl-D-aspartate receptor hypofunction in schizophrenia," Molecular Psychiatry, 18:1185-1192.
Won et al., 2012, "Autistic-like social behaviour in *Shank*2-mutant mice improved by restoring NMDA receptor function," Nature, 486:261-265.
Wu and Zhuo, 2009, "Targeting the NMDA Receptor Subunit NR2B for the Treatment of Neuropathic Pain," Neurotherapeutics:, 6:693-702.
Yang et al., 2003, "Reduced brain infarct volume and improved neurological outcome by inhibition of the NR2B subunit of NMDA receptors by using CP101,606-27 alone and in combination with rt-PA in a thromboembolic stroke model in rats," J. Neurosurg, 98:397-403.
Yuan et al., 2015, "Context-Dependent GluN2B-Selective Inhibitors of NMDA Receptor Function Are Neuroprotective with Minimal Side Effects," Neuron, 85:1305-1318.
Zarate et al., 2006, "A Randomized Trail of an N-methyl-D-aspartate Antagonist in Treatment-Resistant Major Depression," Arch Gen Psychiatry, 63:856-864.
International Search Report for International Application No. PCT/US2015/045412, dated Nov. 10, 2015.
International Search Report for International Application No. PCT/US2015/045413, dated Nov. 27, 2015.
International Search Report for International Application No. PCT/US2016/041339 dated Sep. 27, 2016.
International Search Report for International Application No. PCT/US2017/017093, dated Apr. 7, 2017.
International Search Report for International Application No. PCT/US2017/055278, dated Mar. 9, 2018.
Chemical Abstract Service (CAS), Database Registry [Online], STN Sep. 18, 2012, pp. 1-1, Database Accession No. 1394745_67_5.
Park et al., 2001, "Metabolism of Fluorine-containing drugs" Annu. Rev. Pharmacol. Toxicol, 41: 443-470.
PUBCHEM-CID-90046926, Create Date: Feb. 13, 2015, entire document.
STN Registry database entry for CAS RN 1493474-46-6, 1491341-24-2, 1479235-62-5, and 1477636-42-4, Accessed Apr. 10, 2019.
International Search Report for International Application No. PCT/IB2019/052731, dated Nov. 1, 2019.
Written Opinion of the International Searching Authority for International Application No. PCT/IB2019/052731, dated Nov. 1, 2019.
Kamalesh B. Ruppa, et al., Chapter 7: NMDA Antagonists of GluN2b Subtype and Modulators of GluN2A, GluN2C, and GluN2d Subtypes—Recent Results and Developments, Annual Reports in Medicinal Chemistry, Jan. 1, 2012, pp. 89-103, vol. 47.

* cited by examiner

SUBSTITUTED PYRIDINE AND PYRIMIDINES AND THEIR USE AS GLUN2B RECEPTOR MODULATORS

CROSS-REFERENCE TO RELATED APPLICATIONS

This application claims the priority benefit of U.S. provisional application No. 62/652,458, filed Apr. 4, 2018, the contents of which are incorporated herein in their entireties by reference thereto.

FIELD OF THE INVENTION

The present invention is related to compounds having NR2B modulating properties, pharmaceutical compositions comprising these compounds, chemical processes for preparing these compounds and their use in the treatment of diseases associated with NR2B receptor activity in animals, in particular humans.

BACKGROUND OF THE INVENTION

Glutamate is one of the major excitatory neurotransmitters that is widely spread in the brain. First indication of its role as an excitatory messenger was in the 1950's when it was observed that intravenous administration of glutamate induces convulsions. However, the detection of the whole glutamatergic neurotransmitter system with its various receptors did not take place before the 1970's and 1980's when numerous antagonists were developed or, as in the case of PCP and ketamine, were identified as antagonists. Finally, in the 1990's molecular biology provided the tools for the classification of the glutamatergic receptors.

N-methyl-D-aspartate (NMDA) receptors are a subtype of ionotropic glutamate receptors that mediate excitatory synaptic transmission in the brain. NMDA receptors are ubiquitously distributed throughout the brain and play a key role in synaptic plasticity, synaptogenesis, excitotoxicity, memory acquisition and learning. NMDA receptors are distinct from other major subtypes of ionotropic glutamate receptors (AMPA and kainate receptors) in that they are blocked by $Mg^{2+}$ at resting membrane potentials, are highly $Ca^{2+}$ permeable, and require co-activation by two distinct neurotransmitters: glutamate and glycine (or D-serine) (Traynelis S F et al., *Pharmacol Rev.* 2010; 62(3):405-96). The influx of $Ca^{2+}$ through NMDA receptors triggers signaling cascades and regulates gene expression that is critical for different forms of synaptic plasticity including both long-term potentiation of synapse efficacy (LTP) (Berberich S et al., *Neuropharmacology* 2007; 52(1):77-86) and long-term depression (LTD) (Massey, P V et al., *J Neurosci.* 2004 Sep. 8; 24(36):7821-8).

The vast majority of the mammalian NMDA receptors form a heterotetramer made of two obligatory GluN1 units and two variable GluN2 receptor subunits encoded by the GRIN1 gene and one of four GRIN2 genes, respectively. One or both GluN2 subunits can be potentially replaced by a GluN3A or a GluN3B subunit. The GRIN1 gene product has 8 splice variants while there are 4 different GRIN2 genes (GRIN2A-D) encoding four distinct GluN2 subunits. The glycine binding site is present on the GluN1 subunit and the glutamate binding site is present on the GluN2 subunit.

The GluNR2 subunits play a dominant role in determining the functional and pharmacological properties of the NMDA receptor assembly and exhibit distinct distribution in different areas of the brain. For instance, GluN2B subunits are expressed primarily in the forebrain in the adult mammalian brain (Paoletti P et al., *Nat Rev Neurosci.* 2013; 14(6):383-400; Watanabe M et al., *J Comp Neurol.* 1993; 338(3):377-90) and are implicated in learning, memory processing, mood, attention, emotion and pain perception (Cull-Candy S et al., *Curr Opin Neurobiol.* 2001; 11(3):327-35).

Compounds that modulate GluN2B-containing NMDA receptor function can be useful in treatment of many neurological and psychiatric disorders including but not limited to bipolar disorder (Martucci L et al., *Schizophrenia Res,* 2006; 84(2-3):214-21), major depressive disorder (Miller O H et al., *eLife.* 2014; 3:e03581; Li N et al., *Biol Psychiatry.* 2011; 69(8):754-61), treatment-resistant depression (Preskorn S H et al. *J Clin Psychopharmacol.* 2008; 28(6): 631-7) and other mood disorders (including schizophrenia (Grimwood S et al., *Neuroreport.* 1999; 10(3):461-5; Weickert C S et al. *Molecular Psychiatry* (2013) 18, 1185-1192), ante- and postpartum depression, seasonal affective disorder and the like), Alzheimer's disease (Hanson J E et al., *Neurobiol Dis.* 2015; 74:254-62; Li S et al., *J Neurosci.* 2011; 31(18):6627-38) and other dementias (Orgogozo J M et al. *Stroke* 2002, 33: 1834-1839), Parkinson's disease (Duty S, *CNS Drugs.* 2012; 26(12):1017-32; Steece-Collier K et al., *Exp Neurol.* 2000; 163(1):239-43; Leaver K R et al. *Clin Exp Pharmacol Physiol.* 2008; 35(11): 1388-94), Huntington's chorea (Tang T S et al., *Proc Natl Acad Sci USA.* 2005; 102(7):2602-7; Li L et al., *J Neurophysiol.* 2004; 92(5):2738-46), multiple sclerosis (Grasselli G et al., *Br J Pharmacol.* 2013; 168(2):502-17; Farjam M et al., *Iran J Pharm Res.* 2014; 13(2):695-705), cognitive impairment (Wang D et al. 2014, *Expert Opin Ther Targets Expert Opin Ther Targets.* 2014; 18(10):1121-30), head injury (Bullock M R et al., *Ann NY Acad Sci.* 1999; 890:51-8), spinal cord injury, stroke (Yang Y et al., *J Neurosurg.* 2003; 98(2):397-403), epilepsy (Naspolini A P et al., *Epilepsy Res.* 2012 June; 100(1-2): 12-9), movement disorders (e.g. dyskinesias) (Morissette M et al., *Mov Disord.* 2006; 21(1):9-17), various neurodegenerative diseases (e.g. amyotrophic lateral sclerosis (Fuller P1 et al., *Neurosci Lett.* 2006; 399(1-2):157-61) or neurodegeneration associated with bacterial or chronic infections), glaucoma (Naskar R et al. *Semin Ophthalmol.* 1999 September; 14(3):152-8), pain (e.g. chronic, cancer, post-operative and neuropathic pain (Wu L J and Zhuo M, *Neurotherapeutics.* 2009; 6(4):693-702), diabetic neuropathy, migraine (Peeters M et al., *J Pharmacol Exp Ther.* 2007; 321(2):564-72), cerebral ischemia (Yuan H et al., *Neuron.* 2015; 85(6):1305-18), encephalitis (Dalmau J. et al., *Lancet Neurol.* 2008; 7(12):1091-8.), autism and autism spectrum disorders (Won H. et al., *Nature.* 2012; 486(7402):261-5), memory and learning disorders (Tang, Y. P. et al., *Nature.* 1999; 401(6748):63-9), obsessive compulsive disorder (Arnold P D et al., *Psychiatry Res.* 2009; 172(2):136-9.), attention deficit hyperactivity disorder (ADHD) (Dorval K M et al., *Genes Brain Behav.* 2007; 6(5):444-52), PTSD (Haller J et al. *Behav Pharmacol.* 2011; 22(2):113-21; Leaderbrand K et al. *Neurobiol Learn Mem.* 2014; 113:35-40), tinnitus (Guitton M J, and Dudai Y, Neural Plast. 2007; 80904; Hu S S et al. 2016; 273(2): 325-332), sleep disorders (like narcolepsy or excessive daytime sleepiness, patent WO 2009058261 A1), vertigo and nystagmus (Straube A. et al., *Curr Opin Neurol.* 2005; 18(1):11-4; Starck M et al. *J Neurol.* 1997 January; 244(1):9-16), anxiety autoimmunological disorders like neuropsychiatric systemic lupus erythematosus (Kowal C et al. *Proc. Natl. Acad. Sci. U.S.A.* 2006; 103, 19854-19859) and addictive illnesses (e.g. alcohol addiction, drug addiction) (Nagy J, 2004, *Curr Drug*

*Targets CNS Neurol Disord.* 2004; 3(3):169-79.; Shen H et al., *Proc Natl Acad Sci USA*. 2011; 108(48): 19407-12).

In view of the clinical importance of NR2B, the identification of compounds that modulate NR2B receptor function represents an attractive avenue into the development of new therapeutic agents. Such compounds are provided herein.

SUMMARY OF THE INVENTION

The invention is directed, in some aspects, to the general and preferred embodiments defined, respectively, by the independent and dependent claims appended hereto, which are incorporated by reference herein.

One aspect of this invention (this aspect referred to herein as "aspect 1") concerns compounds of Formula (I):

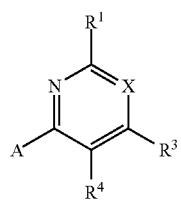

(I)

wherein
R$^1$ is selected from the group consisting of: H, OH, C$_{1-4}$alkyl, CH$_2$OH, CH$_2$F, CHF$_2$, OC$_{1-4}$alkyl, OCHF$_2$, CN, and cyclopropyl;
X is C—R$^2$ or N; wherein R$^2$ is selected from the group consisting of: H, halo, C$_{1-4}$alkyl, OC$_{1-4}$alkyl, and CN;
R$^3$ is:

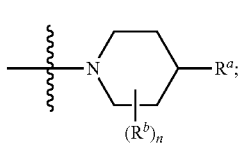

(a)

wherein
R$^a$ is selected from the group consisting of: OH, (C=O)NH$_2$, (C=O)NHCH$_3$, (C=O)NHCH$_2$CH$_2$OH, CH$_2$(C=O)NH$_2$, CH$_2$C(=O)CH$_3$, (C=O)CH$_3$, CH$_2$NH(C=O)CH$_3$, NH(C=O)C$_{1-4}$alkyl, NCH$_3$(C=O)C$_{1-4}$alkyl, NH(C=O)CH$_2$CH$_2$NH$_2$, NH(C=O)CH$_2$CH$_2$OH, NH(C=O)haloC$_{1-4}$alkyl, NH(C=O)cyclopropyl, NHSO$_2$CH$_3$,

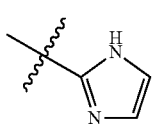 , 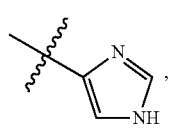 , 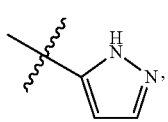 , and

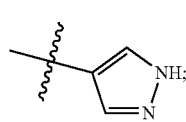 ;

each R$^b$ is independently selected from the group consisting of: H, F, CH$_3$ and OH;
n is 0, 1 or 2;

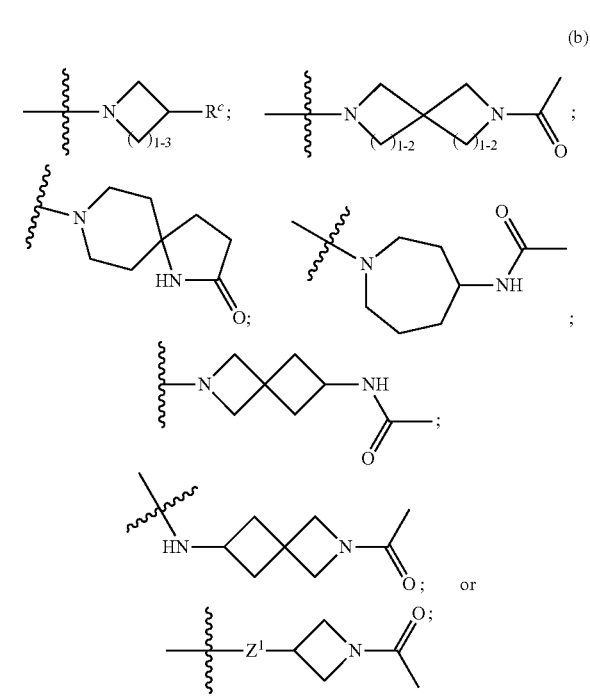

(b)

wherein
R$^c$ is selected from the group consisting of: NH(C=O)CH$_3$, CH$_2$NH(C=O)CH$_3$, (C=O)CH$_3$, and (C=O)NHCH$_3$;
Z$^1$ is NHCH$_2$;

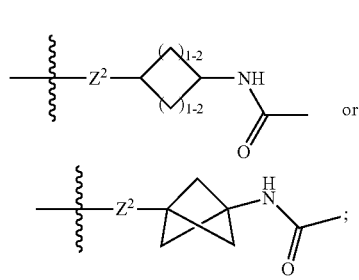

(c)

wherein
Z$^2$ is NH or CH$_2$NH; or
(d) Z$^3$—C$_{1-6}$alkyl-NH(C=O)CH$_3$ or Z$^3$—C$_{4-6}$cycloalkyl-NH(C=O)CH$_3$;
Z$^3$ is NH, NCH$_3$, or O;
R$^4$ is H or CH$_3$; and
A is selected from the group consisting of:

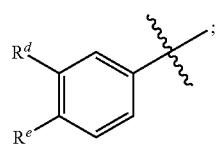

(a)

wherein
$R^d$ is selected from the group consisting of: halo, $C_{1-4}$alkyl, $CH_2OH$, $C_{1-4}$haloalkyl, $OC_{1-4}$alkyl, and $OC_{1-4}$haloalkyl;
$R^e$ is selected from the group consisting of: halo, $C_{1-4}$alkyl, $CH_2OH$, $OC_{1-4}$alkyl, $C_{1-4}$haloalkyl, $OC_{1-4}$haloalkyl, and $(C=O)CH_3$;

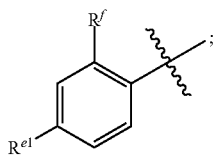
(b)

wherein
$R^f$ is H or F;
$R^{e1}$ is selected from the group consisting of: $C_{1-4}$alkyl, $C_{1-4}$haloalkyl, and $OC_{1-4}$haloalkyl; and

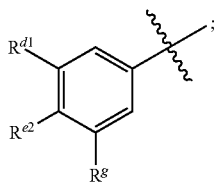
(c)

wherein
$R^{d1}$ and $R^{e2}$ are halo; and
$R^g$ is $OC_{1-4}$haloalkyl;
and pharmaceutically acceptable salts, stereoisomers, isotopic variants, N-oxides, and solvates of compounds of Formula (I).

Further embodiments are provided by pharmaceutically acceptable salts of compounds of Formula (I), pharmaceutically acceptable prodrugs of compounds of Formula (I), and pharmaceutically active metabolites of compounds of Formula (I).

In certain embodiments, the compounds of Formula (I) are compounds selected from those species described or exemplified in the detailed description below.

In a further aspect, the invention relates to enantiomers and diastereomers of the compounds of Formula (I), as well as the pharmaceutically acceptable salts.

In a further aspect, the invention relates to pharmaceutical compositions comprising at least one compound of Formula (I) (e.g., one), or a pharmaceutically acceptable salt, solvate, stereoisomer, isotopic variant, or N-oxide thereof. Such pharmaceutical compositions can be used, for example, for treating a disease, disorder, or medical condition mediated by NR2B receptor activity. In some embodiments, a pharmaceutical composition of the invention comprises at least one compound selected from compounds of Formula (I), pharmaceutically acceptable salts of compounds of Formula (I), pharmaceutically acceptable prodrugs of compounds of Formula (I), and pharmaceutically active metabolites of Formula (I).

Pharmaceutical compositions according to the invention may further comprise one or more pharmaceutically acceptable excipients.

In another aspect, the compounds of the present invention (e.g., compounds of Formula (I) and pharmaceutically acceptable salts, solvates, stereoisomers, isotopic variants, and N-oxides thereof) are useful as NR2B receptor modulators. Thus, in some aspects, the invention is directed to a method for modulating NR2B receptor activity, including when such receptor is in a subject, comprising exposing NR2B receptors to an effective amount of at least one compound selected from compounds of Formula (I), pharmaceutically acceptable salts of compounds of Formula (I), pharmaceutically acceptable prodrugs of compounds of Formula (I), and pharmaceutically active metabolites of compounds of Formula (I).

In another aspect, the invention is directed to a method of treating a subject suffering from, or diagnosed with a disease, disorder, or medical condition mediated by NR2B receptor activity, comprising administering to the subject in need of such treatment an effective amount of at least one compound selected from compounds of Formula (I), pharmaceutically acceptable salts of compounds of Formula (I), pharmaceutically acceptable prodrugs of compounds of Formula (I), and pharmaceutically active metabolites of compounds of Formula (I). Additional embodiments of methods of treatment are set forth in the detailed description.

In another aspect, the invention is directed to compounds (e.g, a compound of Formula (I), or a pharmaceutically acceptable salt thereof) that are isotopically labeled. Isotopically labeled compounds can be used, for example, in metabolic studies (preferably with $^{14}C$), reaction kinetic studies (with, for example $^{2}H$ or $^{3}H$), detection or imaging techniques [such as positron emission tomography (PET) or single-photon emission computed tomography (SPECT)] including drug or substrate tissue distribution assays, or in radioactive treatment of patients. For example, an $^{18}F$ or $^{11}C$ labeled compound may be particularly preferred for PET or SPECT studies.

Additional embodiments of this invention include methods of making compounds of Formula (I), pharmaceutically acceptable salts of compounds of Formula (I), pharmaceutically acceptable prodrugs of compounds of Formula (I), and pharmaceutically active metabolites of Formula (I).

An object of the present invention is to overcome or ameliorate at least one of the disadvantages of the conventional methodologies and/or prior art, or to provide a useful alternative thereto.

Additional embodiments, features, and advantages of the invention will be apparent from the following detailed description and through practice of the invention.

DETAILED DESCRIPTION OF INVENTION

In one aspect, provided herein are compounds of Formula (I), and pharmaceutically acceptable salts, stereoisomers, isotopic variants, N-oxides, and solvates thereof,

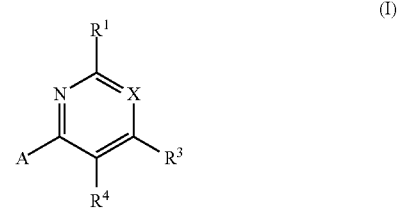
(I)

wherein
$R^1$ is selected from the group consisting of: H, OH, $C_{1-4}$alkyl, $CH_2OH$, $CH_2F$, $CHF_2$, $OC_{1-4}$alkyl, $OCHF_2$, CN, and cyclopropyl;

X is C—R² or N; wherein R² is selected from the group consisting of: H, halo, C₁₋₄alkyl, OC₁₋₄alkyl, and CN;
R³ is:

(a)

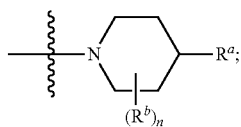

wherein
Rᵃ is selected from the group consisting of: OH, (C=O)NH₂, (C=O)NHCH₃, (C=O)NHCH₂CH₂OH, CH₂(C=O)NH₂, CH₂C(=O)CH₃, (C=O)CH₃, CH₂NH(C=O)CH₃, NH(C=O)C₁₋₄alkyl, NCH₃(C=O)C₁₋₄alkyl, NH(C=O)CH₂CH₂NH₂, NH(C=O)CH₂CH₂OH, NH(C=O)haloC₁₋₄alkyl, NH(C=O)cyclopropyl, NHSO₂CH₃,

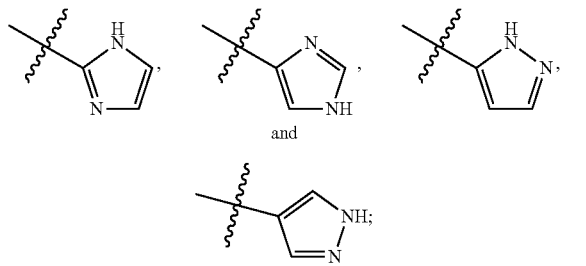

and each Rᵇ is independently selected from the group consisting of: H, F, CH₃ and OH;
n is 0, 1 or 2;

(b)

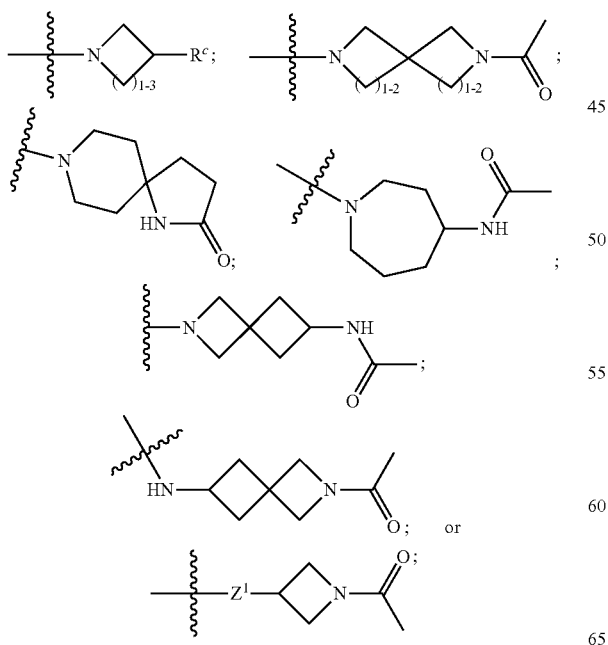

or wherein
Rᶜ is selected from the group consisting of: NH(C=O)CH₃, CH₂NH(C=O)CH₃, (C=O)CH₃, and (C=O)NHCH₃;
Z¹ is NHCH₂;

(c)

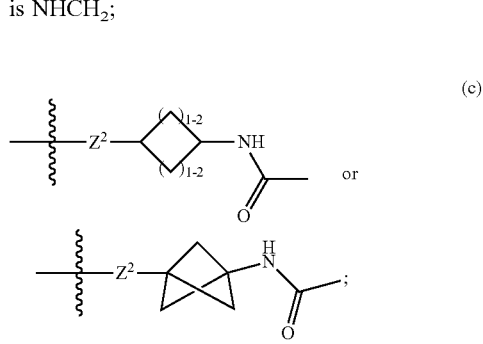

wherein
Z² is NH or CH₂NH; or
(d) Z³—C₁₋₆alkyl-NH(C=O)CH₃ or Z³—C₄₋₆cycloalkyl-NH(C=O)CH₃;
  Z³ is NH, NCH₃, or O;
R⁴ is H or CH₃; and
A is selected from the group consisting of:

(a)

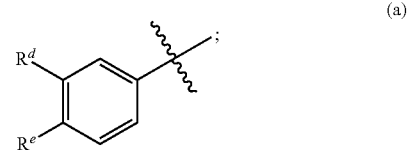

wherein
Rᵈ is selected from the group consisting of: halo, C₁₋₄alkyl, CH₂OH, C₁₋₄haloalkyl, OC₁₋₄alkyl, and OC₁₋₄haloalkyl;
Rᵉ is selected from the group consisting of: halo, C₁₋₄alkyl, CH₂OH, OC₁₋₄alkyl, C₁₋₄haloalkyl, OC₁₋₄haloalkyl, and (C=O)CH₃;

(b)

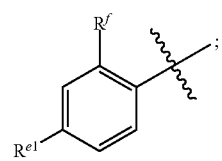

wherein
Rᶠ is H or F;
Rᵉ¹ is selected from the group consisting of: C₁₋₄alkyl, C₁₋₄haloalkyl, and OC₁₋₄haloalkyl; and (c)

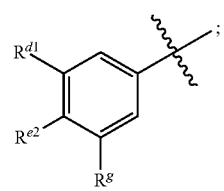

wherein $R^{d1}$ and $R^{e2}$ are halo; and
$R^g$ is $OC_{1-4}$haloalkyl.

An additional embodiment of the invention is a compound of Formula (I) wherein $R^1$ is H, OH, $CH_3$, $CH_2CH_3$, $CH_2OH$, $OCH_3$, $CH_2F$, $CHF_2$, $OCHF_2$, CN, or cyclopropyl.

An additional embodiment of the invention is a compound of Formula (I) wherein $R^1$ is H.

An additional embodiment of the invention is a compound of Formula (I) wherein X is C—$R^2$, and wherein $R^2$ is H, F, $CH_3$, $OCH_3$, or CN.

An additional embodiment of the invention is a compound of Formula (I) wherein X is C—$R^2$, and wherein $R^2$ is H.

An additional embodiment of the invention is a compound of Formula (I) wherein X is N.

An additional embodiment of the invention is a compound of Formula (I) wherein $R^3$ is

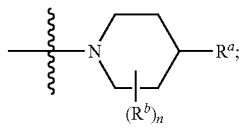

wherein $R^a$ is OH, (C=O)$NH_2$, (C=O)$NHCH_3$, (C=O)$NHCH_2CH_2OH$, $CH_2$(C=O)$NH_2$, $CH_2$C(=O)$CH_3$, (C=O)$CH_3$, $CH_2NH$(C=O)$CH_3$, NH(C=O)$C_{1-4}$alkyl, $NCH_3$(C=O)$C_{1-4}$alkyl, NH(C=O)$CH_2CH_2NH_2$, NH(C=O)$CH_2CH_2OH$, NH(C=O)halo$C_{1-4}$alkyl, NH(C=O)cyclopropyl, $NHSO_2CH_3$,

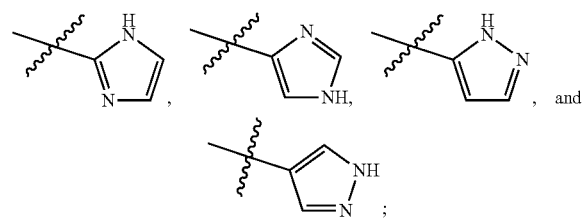

and n is 0.

An additional embodiment of the invention is a compound of Formula (I) wherein
$R^3$ is

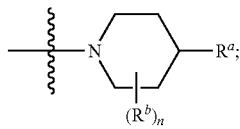

wherein $R^a$ is NH(C=O)$C_{1-4}$alkyl, or NH(C=O)$CH_2CH_2NH_2$;
$R^b$ is F, OH, or $CH_3$;
and n is 1 or 2.

An additional embodiment of the invention is a compound of Formula (I) wherein $R^3$ is

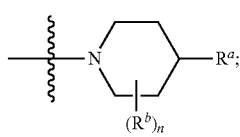

$R^a$ is NH(C=O)$C_{1-4}$alkyl; $R^b$ is F; and n is 1.

An additional embodiment of the invention is a compound of Formula (I) wherein $R^3$ is

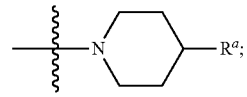

wherein $R^a$ is NH(C=O)$C_{1-4}$alkyl, $CH_2$C(=O)$NH_2$, or C(=O)$NH_2$.

An additional embodiment of the invention is a compound of Formula (I) wherein $R^3$ is

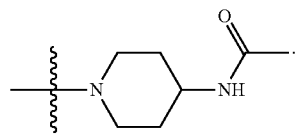 [SMILES: *N1CCC(NC(C)=O)CC1]

An additional embodiment of the invention is a compound of Formula (I) wherein $R^3$ is

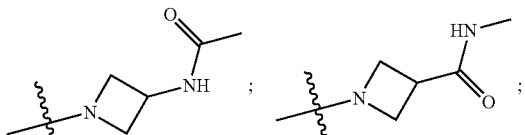

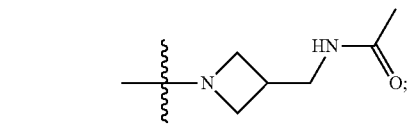

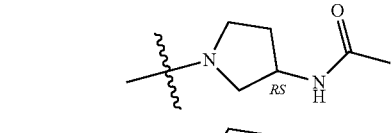

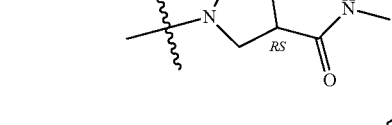

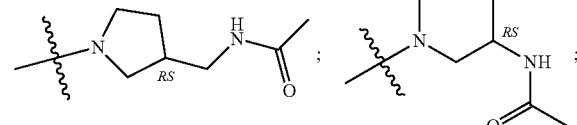

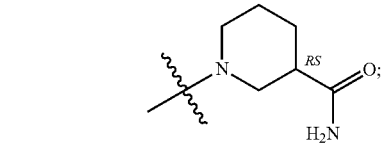

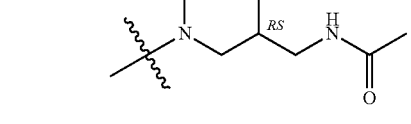

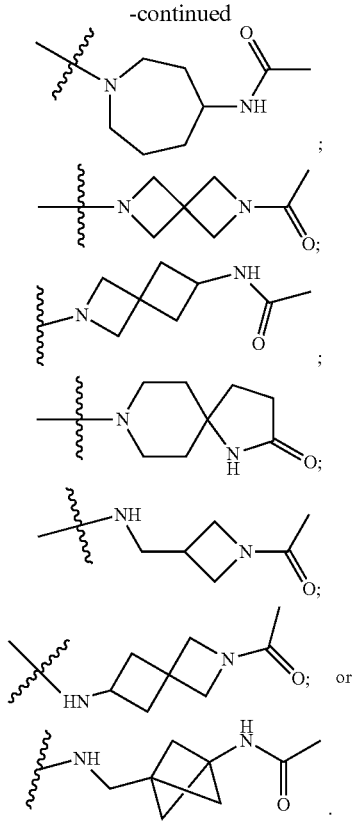
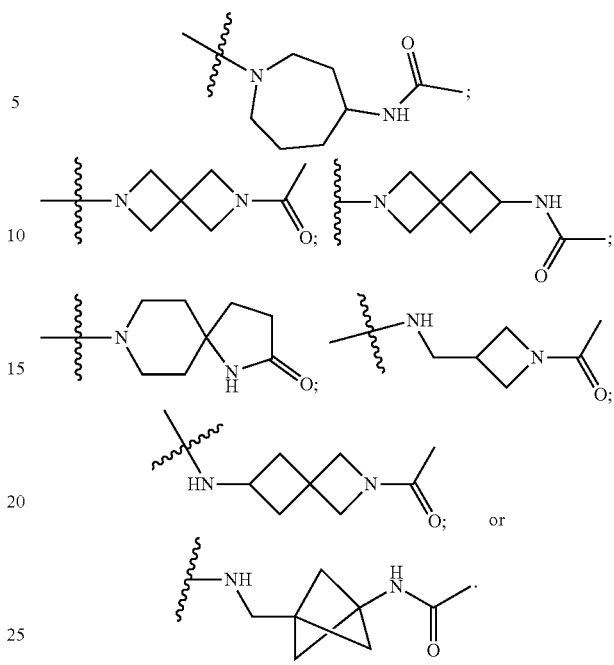
An additional embodiment of the invention is a compound of Formula (I) wherein R³ is
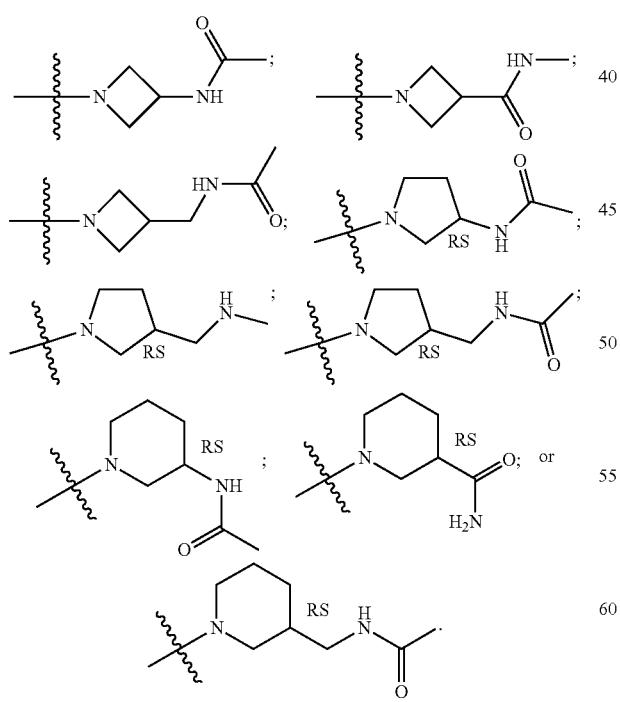
An additional embodiment of the invention is a compound of Formula (I) wherein R³ is
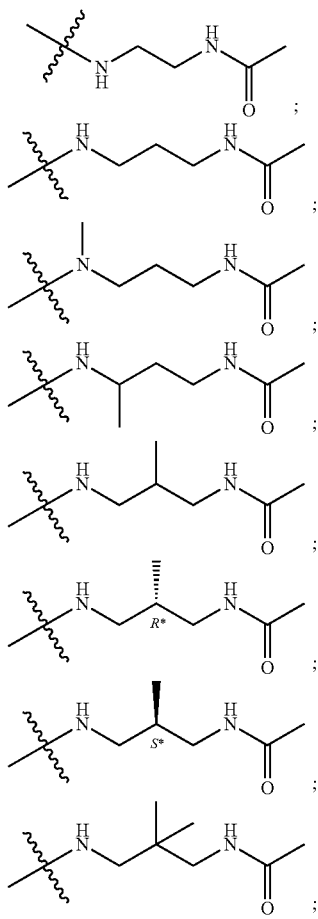

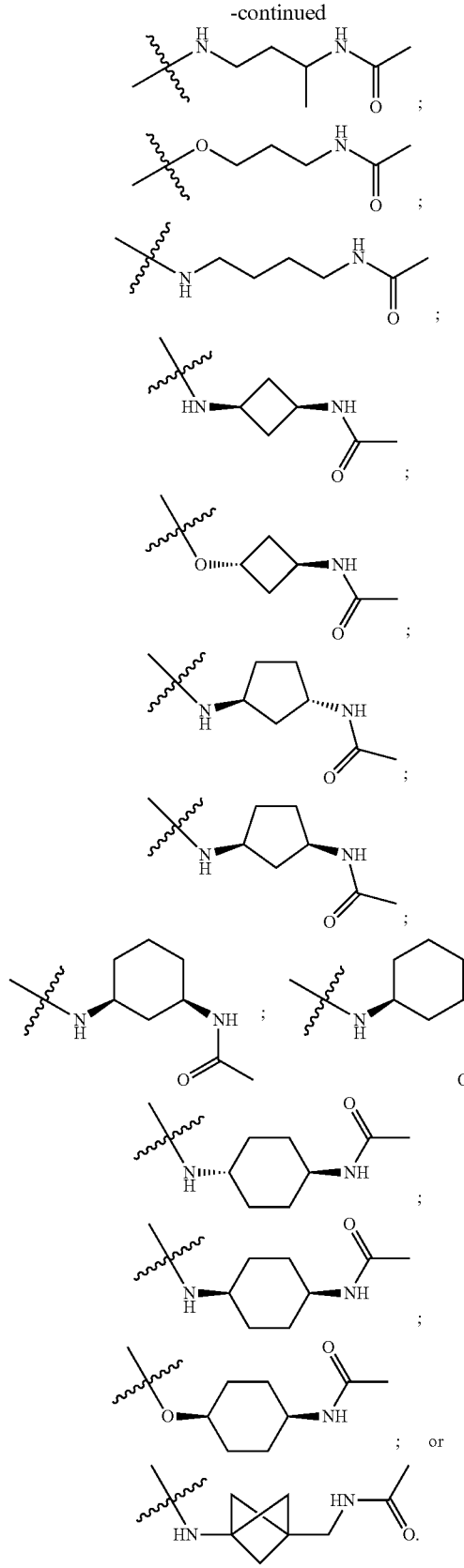
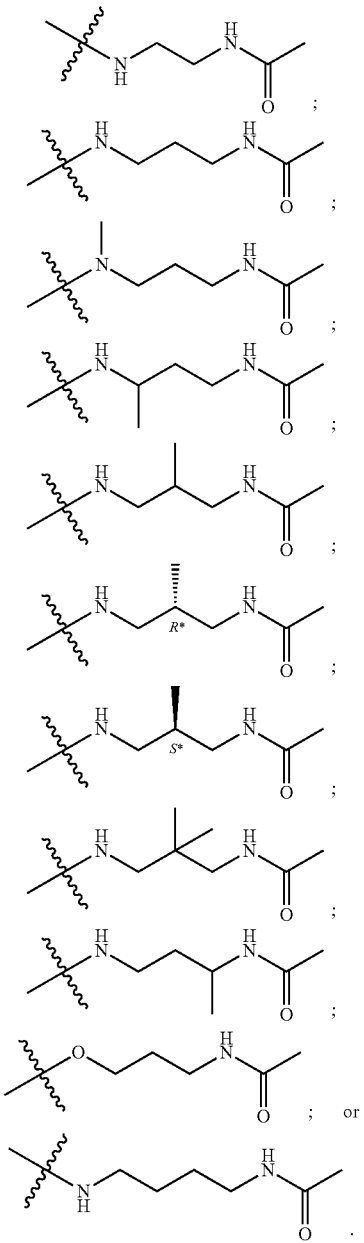
An additional embodiment of the invention is a compound of Formula (I) wherein $R^3$ is
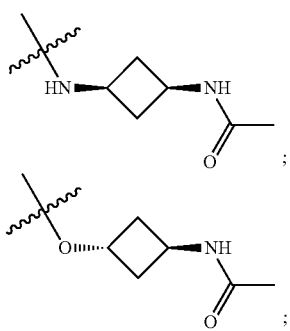
An additional embodiment of the invention is a compound of Formula (I) wherein $R^3$ is -continued

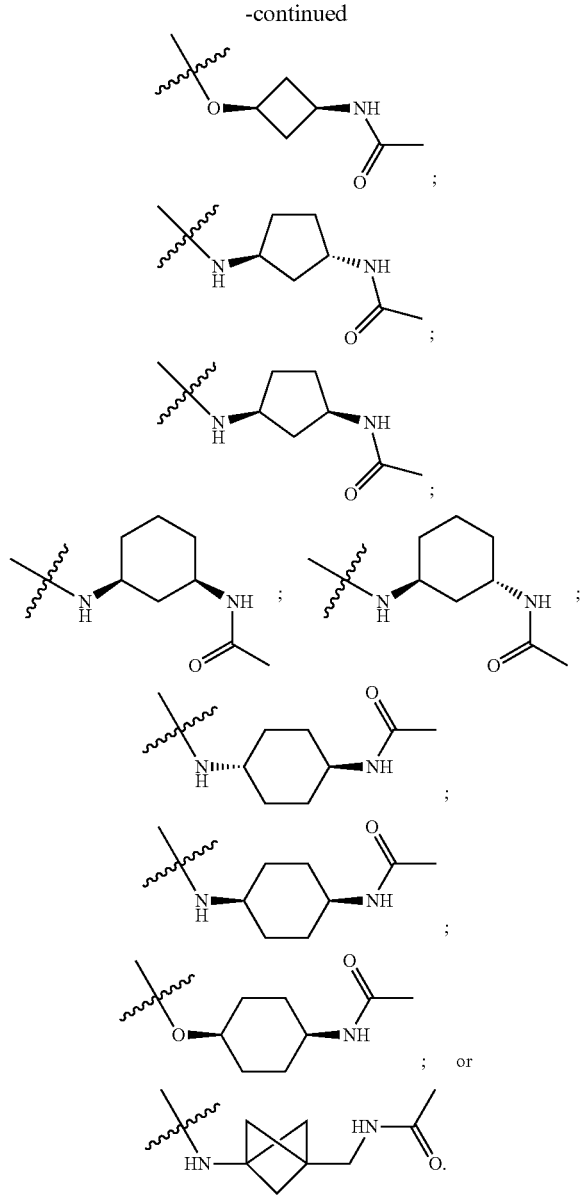

An additional embodiment of the invention is a compound of Formula (I) wherein $R^4$ is H.

An additional embodiment of the invention is a compound of Formula (I) wherein A is

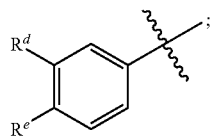

$R^e$ wherein $R^d$ is Cl, F, $C_{1-4}$alkyl, $CH_2OH$, $C_{1-4}$haloalkyl, $OC_{1-4}$alkyl, or $OC_{1-4}$haloalkyl; and $R^e$ is halo, $C_{1-4}$alkyl, $CH_2OH$, $OC_{1-4}$alkyl, $C_{1-4}$haloalkyl, $OC_{1-4}$haloalkyl, or $(C=O)CH_3$.

An additional embodiment of the invention is a compound of Formula (I) wherein A is

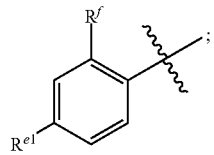

$R^e$ wherein $R^d$ is Cl, $CH_3$ or F; and $R^e$ is $C_{1-4}$haloalkyl, or $OC_{1-4}$haloalkyl.

An additional embodiment of the invention is a compound of Formula (I) wherein A is 3-fluoro-4-(trifluoromethoxy)phenyl, 3-chloro-4-(trifluoromethoxy)phenyl, 3-methyl-4-(trifluoromethoxy)phenyl, 3-methoxy-4-(trifluoromethoxy)phenyl, 4-(trifluoromethoxy)-3-(trifluoromethyl)phenyl, 3-(hydroxymethyl)-4-(trifluoromethoxy)phenyl, 3-fluoro-4-(2,2,2-trifluoroethoxy)phenyl, 4-(difluoromethoxy)-3-fluoro-phenyl, 3-(difluoromethoxy)-4-fluoro-phenyl, 3-chloro-4-(trifluoromethyl)phenyl, 3-fluoro-4-(trifluoromethyl)phenyl, 3-methyl-4-(trifluoromethyl)phenyl, 4-chloro-3-fluoro-phenyl, 4-chloro-3-methyl-phenyl, 3,4-dichloro-phenyl, 3-fluoro-4-methoxy-phenyl, 3-chloro-4-methoxy-phenyl, 3-chloro-4-(hydroxymethyl)phenyl, 3-chloro-4-methyl-phenyl, 3-fluoro-4-methyl-phenyl, 4-(difluoromethoxy)-3-methyl-phenyl, 3-(difluoromethyl)-4-fluoro-phenyl, 3-fluoro-4-(trifluoromethyl)phenyl, 4-acetyl-3-fluoro-phenyl, 3-fluoro-4-isopropoxy-phenyl, or 4-ethoxy-3-fluoro-phenyl.

An additional embodiment of the invention is a compound of Formula (I) wherein A is 3-fluoro-4-(trifluoromethoxy)phenyl.

An additional embodiment of the invention is a compound of Formula (I) wherein A is

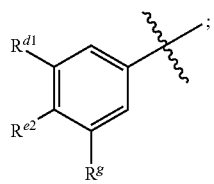

$R^f$ is H or F; and $R^{e1}$ is $CH_3$, $C_{1-4}$haloalkyl, or $OC_{1-4}$haloalkyl.

An additional embodiment of the invention is a compound of Formula (I) wherein A is 4-(trifluoromethoxy)phenyl.

An additional embodiment of the invention is a compound of Formula (I) wherein A is $R^{d1}$ and $R^{e2}$ are F; and $R^g$ is $OC_{1-4}$haloalkyl.

An additional embodiment of the invention is a compound of Formula (I) wherein A is 3,5-difluoro-4-(trifluoromethoxy)phenyl.

An additional embodiment of the invention is a compound of Formula (I) having the Formula (IA):

(IA)

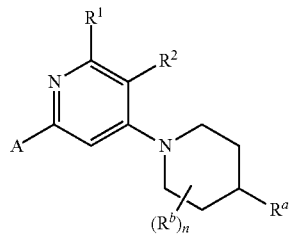

or a pharmaceutically acceptable salt, solvate, stereoisomer, isotopic variant, or N-oxide thereof,
wherein
$R^1$ is selected from the group consisting of: H, $CH_3$, $CH_2OH$, $CH_2F$, $CHF_2$, $OCHF_2$, OH, $OCH_3$, and CN;
$R^2$ is selected from the group consisting of: H, F, $CH_3$, CN, and $OCH_3$;
$R^a$ is selected from the group consisting of: OH, (C=O)$NH_2$, $CH_2$(C=O)$NH_2$, $CH_2$C(=O)$CH_3$, NH(C=O)$C_{1-4}$alkyl, $NHSO_2CH_3$,

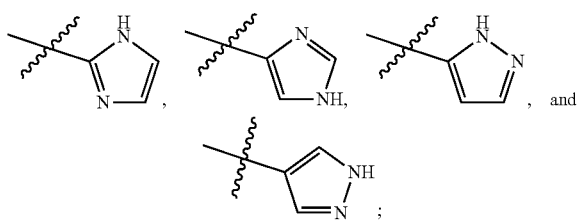

, and

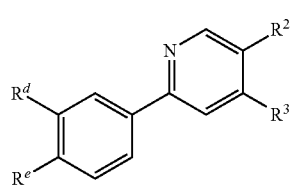

;

$R^b$ is independently selected from the group consisting of: H, F, $CH_3$ and OH;
n is 0, 1 or 2; and
A is selected from the group consisting of: 4-(methyl)phenyl, 4-(1,1-difluoroethyl)phenyl, 4-(difluoromethyl)phenyl, 4-(trifluoromethyl)phenyl, 4-(difluoromethoxy)phenyl, 4-(trifluoromethoxy)phenyl, 3-fluoro-4-(trifluoromethoxy)phenyl, 4-chloro-3-fluoro-phenyl, 3-fluoro-4-(trifluoromethyl)phenyl, 3-(difluoromethyl)-4-fluoro-phenyl, 3-fluoro-4-methoxy-phenyl, 4-acetyl-3-fluoro-phenyl, 4-(difluoromethoxy)-3-methyl-phenyl, 4-(difluoromethoxy)-3-fluoro-phenyl, 3-(difluoromethoxy)-4-fluoro-phenyl, 4-(difluoromethoxy)-3-fluoro-phenyl, 4-ethoxy-3-fluoro-phenyl, 3-methyl-4-(trifluoromethoxy)phenyl, 3-fluoro-4-isopropoxy-phenyl, 3-fluoro-4-(2,2,2-trifluoroethoxy)phenyl, 3-chloro-4-(trifluoromethoxy)phenyl, and 3,5-difluoro-4-(trifluoromethoxy)phenyl.

An additional embodiment of the invention is a compound of Formula (I) having the Formula (IB):

(IB)

![structure IB]

or a pharmaceutically acceptable salt, solvate, stereoisomer, isotopic variant, or N-oxide thereof, wherein
$R^2$ is H or F;
$R^3$ is:

(a)

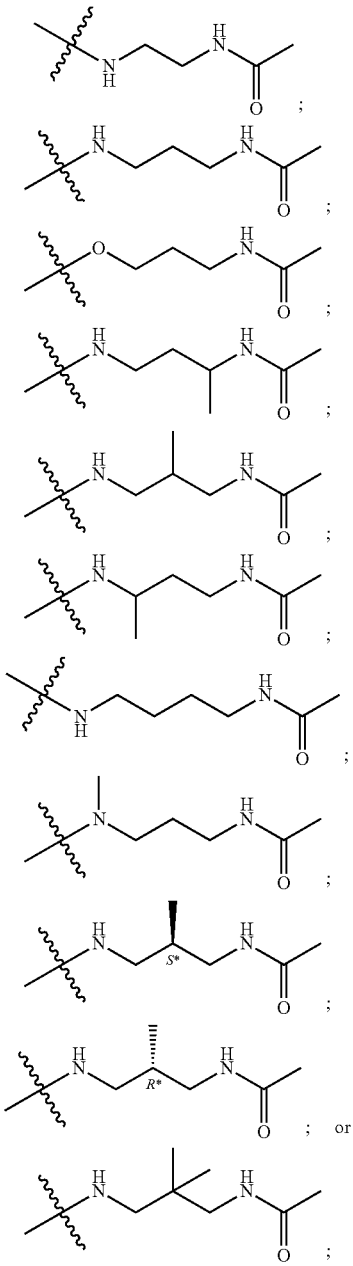

(b)

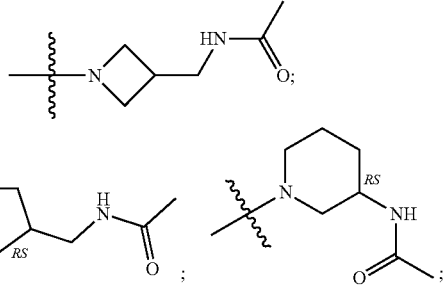

$R^d$ is halo, or $C_{1-4}$haloalkyl; and
$R^e$ is halo, or $OC_{1-4}$haloalky.

An additional embodiment of the invention is a compound of Formula (I) having the Formula (IB), wherein $R^2$ is H.

An additional embodiment of the invention is a compound of Formula (I) having the Formula (IB):

wherein
$R^3$ is

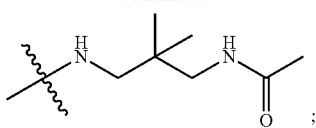

$R^d$ is F, or $C_{1-4}$haloalkyl; and
$R^e$ is F, or $OC_{1-4}$haloalkyl.

An additional embodiment of the invention is a compound of Formula (I) having the Formula (IB):

wherein
$R^3$ is

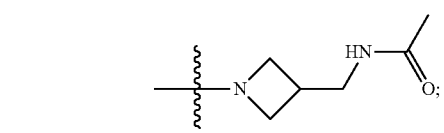

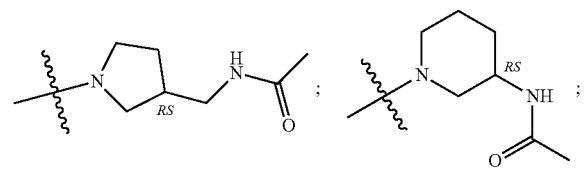

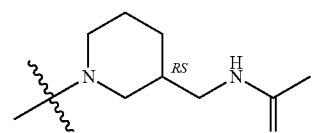

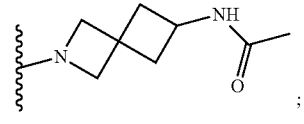

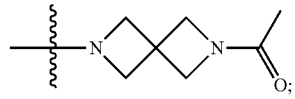

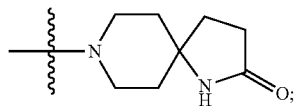

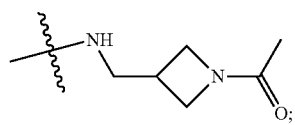

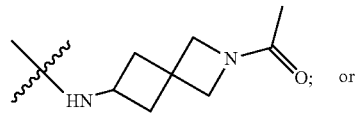

$R^d$ is F, or $C_{1-4}$haloalkyl; and
$R^e$ is F, or $OC_{1-4}$haloalkyl.

An additional embodiment of the invention is a compound of Formula (I) having the Formula (IB):

wherein
$R^3$ is

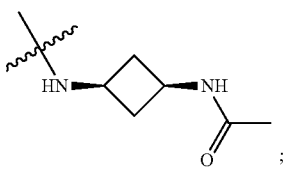

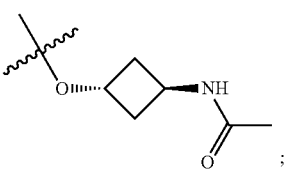

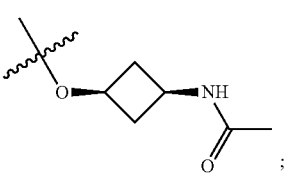

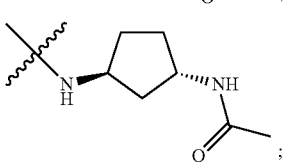

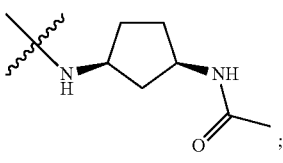

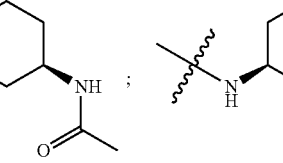

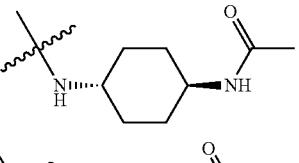

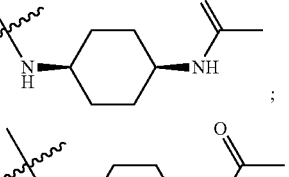

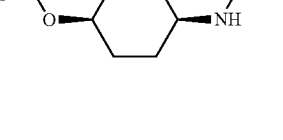

$R^d$ is F, or $C_{1-4}$haloalkyl; and
$R^e$ is F, or $OC_{1-4}$haloalkyl.

An additional embodiment of the invention is a compound of Formula (I) having the Formula (IC):

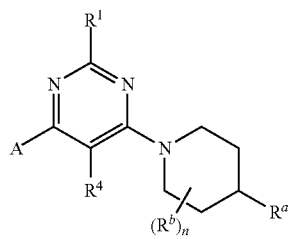

(IC)

or a pharmaceutically acceptable salt, solvate, stereoisomer, isotopic variant, or N-oxide thereof,
wherein
$R^1$ is selected from the group consisting of: H, $CH_3$, $CH_2CH_3$, $CH_2OH$, $OCH_3$, and cyclopropyl;
$R^a$ is selected from the group consisting of: OH, (C=O)$NH_2$, (C=O)$NHCH_3$, (C=O)$NHCH_2CH_2OH$, $CH_2$(C=O)$NH_2$, $CH_2C$(=O)$CH_3$, (C=O)$CH_3$, $CH_2NH$(C=O)$CH_3$, NH(C=O)$C_{1-4}$alkyl, $NCH_3$(C=O)$C_{1-4}$alkyl, NH(C=O)$CH_2CH_2NH_2$, NH(C=O)$CH_2CH_2OH$, NH(C=O)$CHF_2$, NH(C=O)cyclopropyl, $NHSO_2CH_3$,

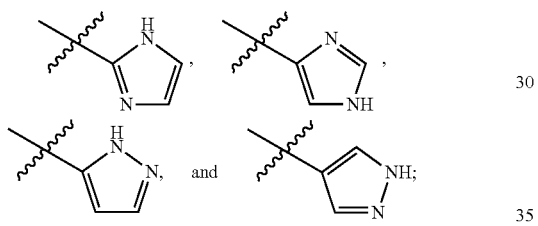

each $R^b$ is independently selected from the group consisting of: H, F, and $CH_3$;
n is 0, 1 or 2;
$R^4$ is H or $CH_3$; and
A is 4-(trifluoromethoxy)phenyl, 4-(trifluoromethyl)phenyl, 4-(1,1-difluoroethyl)phenyl, 4-(difluoromethoxy)phenyl, 4-(difluoromethyl)phenyl, 3-fluoro-4-(trifluoromethoxy)phenyl, 3-methyl-4-(trifluoromethoxy)phenyl, 3-methoxy-4-(trifluoromethoxy)phenyl, 3-chloro-4-(trifluoromethoxy)phenyl, 3-(hydroxymethyl)-4-(trifluoromethoxy)phenyl, 4-(trifluoromethoxy)-3-(trifluoromethyl)phenyl, 3-fluoro-4-(trifluoromethyl)phenyl, 3-fluoro-4-(2,2,2-trifluoroethoxy)phenyl, 3-chloro-4-(trifluoromethyl)phenyl, 3-fluoro-4-methyl-phenyl, 3-fluoro-4-methoxy-phenyl, 3-chloro-4-methyl-phenyl, 4-chloro-3-methyl-phenyl, 4-chloro-3-fluoro-phenyl, 3-chloro-4-(hydroxymethyl)phenyl, 3-chloro-4-methoxy-phenyl, 3,4-dichlorophenyl, 3-(difluoromethoxy)-4-fluoro-phenyl, 3-methyl-4-(trifluoromethyl)phenyl, 4-(difluoromethoxy)-3-fluoro-phenyl, or 3,5-difluoro-4-(trifluoromethoxy)phenyl;
and pharmaceutically acceptable salts, N-oxides or solvates of compounds of Formula (IC).

An additional embodiment of the invention is a compound of Formula (I) having the Formula (IC):
wherein
$R^1$ is H;
$R^a$ is (C=O)$NH_2$, (C=O)$NHCH_3$, or NH(C=O)$C_{1-4}$alkyl;

each $R^b$ is independently selected from the group consisting of: H, F, and $CH_3$;
n is 0 or 1;
$R^4$ is H; and
A is 3-fluoro-4-(trifluoromethoxy)phenyl, 3-methyl-4-(trifluoromethoxy)phenyl, 3-methoxy-4-(trifluoromethoxy)phenyl, or 3-chloro-4-(trifluoromethoxy)phenyl.

An additional embodiment of the invention is a compound of Formula (I) having the Formula (ID):

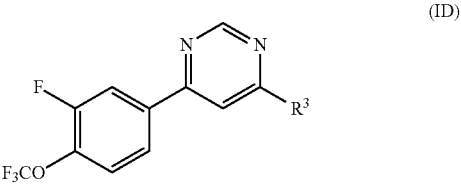

(ID)

or a pharmaceutically acceptable salt, solvate, stereoisomer, isotopic variant, or N-oxide thereof,
wherein $R^3$ is

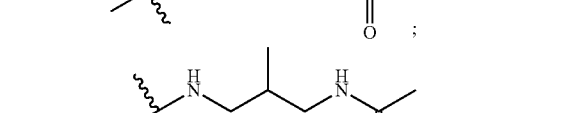

(a)

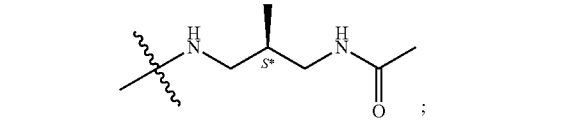

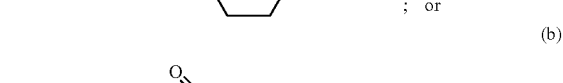

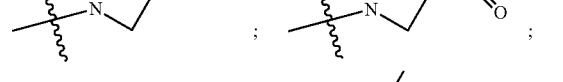

; or

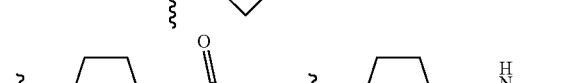

; or (b)

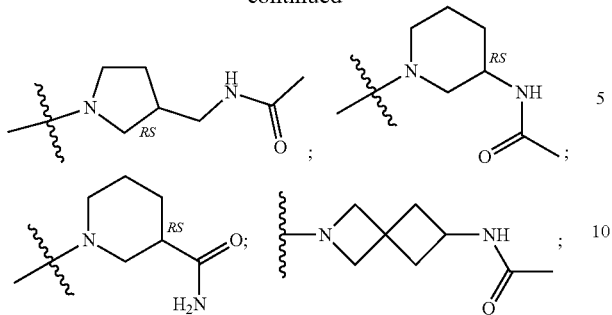
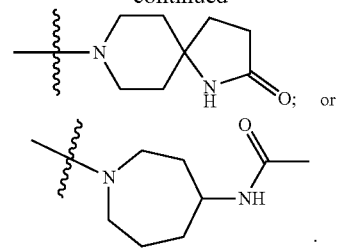

A further embodiment of the current invention is a compound as shown below in Table 1 or a pharmaceutically acceptable salt, N-oxide, or solvate thereof.

| Ex # | Compound Name |
|---|---|
| 11 | N-[1-[2-[3-Fluoro-4-(trifluoromethoxy)phenyl]-4-pyridyl]-4-piperidyl]acetamide; |
| 12 | N-[1-[2-[3-(Difluoromethoxy)-4-fluoro-phenyl]-4-pyridyl]-4-piperidyl]acetamide; |
| 13 | N-[1-[2-[4-(Difluoromethyl)phenyl]-4-pyridyl]-4-piperidyl]acetamide; |
| 14 | N-[1-[2-[3,5-Difluoro-4-(trifluoromethoxy)phenyl]-4-pyridyl]-4-piperidyl]acetamide; |
| 15 | N-[1-[5-Fluoro-2-[3-fluoro-4-(trifluoromethoxy)phenyl]-4-pyridyl]-4-piperidyl]acetamide; |
| 16 | (trans)-N-[3-Fluoro-1-[2-3-fluoro-4-(trifluoromethoxy)phenyl]-4-pyridyl]-4-piperidyl]acetamide; |
| 17 | (*R/*R)-N-[3-Fluoro-1-[5-fluoro-2-[3-fluoro-4-(trifluoromethoxy)phenyl]-4-pyridyl]-4-piperidyl]acetamide; |
| 18 | (racemic)-N-[1-[2-3-Fluoro-4-(trifluoromethoxy)phenyl]-4-pyridyl]-2-methyl-4-piperidyl]acetamide; |
| 19 | N-[1-[5-Cyano-2-[4-(trifluoromethoxy)phenyl]-4-pyridyl]-4-piperidyl]acetamide; |
| 20 | N-[1-[2-Cyano-6-[3-fluoro-4-(trifluoromethoxy)phenyl]-4-pyridyl]-4-piperidyl]acetamide; |
| 21 | N-[1-[2-[3-Fluoro-4-(trifluoromethoxy)phenyl]-6-methyl-4-pyridyl]-4-piperidyl]acetamide; |
| 22 | 1-[2-[2-[3-Fluoro-4-(trifluoromethoxy)phenyl]-4-pyridyl]-2,6-diazaspiro[3;3]heptan-6-yl]ethanone; |
| 23 | 1-[2-[2-[4-(Difluoromethoxy)-3-fluoro-phenyl]-4-pyridyl]-2,6-diazaspiro[3;3]heptan-6-yl]ethanone; |
| 24 | N-[4-[[2-[3-Fluoro-4-(trifluoromethoxy)phenyl]-4-pyridyl]oxy]cyclohexyl]acetamide; |
| 25 | (racemic)-N-[3-[[2-[3-Fluoro-4-(trifluoromethoxy)phenyl]-6-(hydroxymethyl)-4-pyridyl]amino]-2-methyl-propyl]acetamide; |
| 122 | 1-[2-[3-Fluoro-4-(trifluoromethoxy)phenyl]-4-pyridyl]piperidin-4-ol; |
| 123 | N-[1-[2-[4-(Trifluoromethoxy)phenyl]-4-pyridyl]-4-piperidyl]acetamide; |
| 124 | N-[1-[2-[3-Methyl-4-(trifluoromethoxy)phenyl]-4-pyridyl]-4-piperidyl]acetamide; |
| 125 | N-[1-[2-[4-(Difluoromethoxy)-3-methyl-phenyl]-4-pyridyl]-4-piperidyl]acetamide; |
| 126 | 1-[2-[3-Fluoro-4-(trifluoromethoxy)phenyl]-4-pyridyl]piperidine-4-carboxamide; |
| 127 | 1-[1-[2-[3-Fluoro-4-(trifluoromethoxy)phenyl]-4-pyridyl]-4-piperidyl]propan-2-one; |
| 128 | 2-[1-[2-[3-Fluoro-4-(trifluoromethoxy)phenyl]-4-pyridyl]-4-piperidyl]acetamide; |
| 129 | 2-[3-Fluoro-4-(trifluoromethoxy)phenyl]-4-[4-(1H-pyrazol-5-yl)-1-piperidyl]pyridine; |
| 130 | 2-[3-Fluoro-4-(trifluoromethoxy)phenyl]-4-[4-(1H-imidazol-4-yl)-1-piperidyl]pyridine; |
| 131 | 2-[3-Fluoro-4-(trifluoromethoxy)phenyl]-4-[4-(1H-imidazol-2-yl)-1-piperidyl]pyridine; |
| 132 | 2-[3-Fluoro-4-(trifluoromethoxy)phenyl]-4-[4-(1H-pyrazol-4-yl)-1-piperidyl]pyridine; |
| 133 | 8-[2-[3-Fluoro-4-(trifluoromethoxy)phenyl]-4-pyridyl]-4,8-diazaspiro[4;5]decan-3-one; |
| 134 | N-[1-[2-[3-Fluoro-4-(trifluoromethoxy)phenyl]-4-pyridyl]-4-piperidyl]methanesulfonamide; |
| 135 | N-[1-[2-[4-(Difluoromethoxy)phenyl]-4-pyridyl]-4-piperidyl]acetamide; |
| 136 | N-[1-[2-[4-(Difluoromethoxy)-3-fluoro-phenyl]-4-pyridyl]-4-piperidyl]acetamide; |
| 137 | N-[1-[2-[3-(Difluoromethyl)-4-fluoro-phenyl]-4-pyridyl]-4-piperidyl]acetamide; |
| 138 | N-[1-[2-(p-Tolyl)-4-pyridyl]-4-piperidyl]acetamide; |
| 139 | N-[1-[2-[4-(1,1-Difluoroethyl)phenyl]-4-pyridyl]-4-piperidyl]acetamide; |
| 140 | N-[1-[2-[4-(Trifluoromethyl)phenyl]-4-pyridyl]-4-piperidyl]acetamide; |
| 141 | N-[1-[2-[3-Chloro-4-(trifluoromethoxy)phenyl]-4-pyridyl]-4-piperidyl]acetamide; |
| 142 | N-[1-[2-[2-Fluoro-4-(trifluoromethoxy)phenyl]-4-pyridyl]-4-piperidyl]acetamide; |
| 143 | N-[1-[2-[3-Fluoro-4-(2,2,2-trifluoroethoxy)phenyl]-4-pyridyl]-4-piperidyl]acetamide; |

| Ex # | Compound Name |
| --- | --- |
| 144 | N-[1-[2-(4-Chloro-3-fluoro-phenyl)-4-pyridyl]-4-piperidyl]acetamide; |
| 145 | N-[1-[2-(3-Fluoro-4-methoxy-phenyl)-4-pyridyl]-4-piperidyl]acetamide; |
| 146 | N-[1-[2-[3-Fluoro-4-(trifluoromethyl)phenyl]-4-pyridyl]-4-piperidyl]acetamide; |
| 147 | N-[1-[2-(4-Acetyl-3-fluoro-phenyl)-4-pyridyl]-4-piperidyl]acetamide; |
| 148 | N-[1-[2-[3-Fluoro-4-(trifluoromethoxy)phenyl]-5-methyl-4-pyridyl]-4-piperidyl]acetamide; |
| 149 | N-[1-[2-[3-Fluoro-4-(trifluoromethoxy)phenyl]-5-methoxy-4-pyridyl]-4-piperidyl]acetamide; |
| 150 | N-[1-[2-[4-(Difluoromethoxy)phenyl]-6-methyl-4-pyridyl]-4-piperidyl]acetamide; |
| 151 | N-[1-[2-[4-(1,1-Difluoroethyl)phenyl]-6-methyl-4-pyridyl]-4-piperidyl]acetamide; |
| 152 | N-[1-[2-[4-(Difluoromethoxy)-3-fluoro-phenyl]-6-methyl-4-pyridyl]-4-piperidyl]acetamide; |
| 153 | N-[1-[2-(Fluoromethyl)-6-[3-fluoro-4-(trifluoromethoxy)phenyl]-4-pyridyl]-4-piperidyl]acetamide; |
| 154 | N-[1-[2-(Difluoromethyl)-6-[3-fluoro-4-(trifluoromethoxy)phenyl]-4-pyridyl]-4-piperidyl]acetamide; |
| 155 | N-[1-[2-[3-Fluoro-4-(trifluoromethoxy)phenyl]-6-(hydroxymethyl)-4-pyridyl]-4-piperidyl]acetamide; |
| 156 | N-[1-[2-(3-Fluoro-4-isopropoxy-phenyl)-6-(hydroxymethyl)-4-pyridyl]-4-piperidyl]acetamide; |
| 157 | N-[1-[2-(4-Ethoxy-3-fluoro-phenyl)-6-(hydroxymethyl)-4-pyridyl]-4-piperidyl]acetamide; |
| 158 | N-[1-[2-[3-Fluoro-4-(trifluoromethoxy)phenyl]-6-methoxy-4-pyridyl]-4-piperidyl]acetamide; |
| 159 | N-[1-[2-[3-Fluoro-4-(trifluoromethoxy)phenyl]-6-hydroxy-4-pyridyl]-4-piperidyl]acetamide; |
| 160 | N-[1-[2-(Difluoromethoxy)-6-[3-fluoro-4-(trifluoromethoxy)phenyl]-4-pyridyl]-4-piperidyl]acetamide; |
| 161 | (cis)-N-[3-Fluoro-1-[2-[3-fluoro-4-(trifluoromethoxy)phenyl]-4-pyridyl]-4-piperidyl]acetamide; |
| 162 | (*R/*R)-N-[3-Fluoro-1-[2-[3-fluoro-4-(trifluoromethoxy)phenyl]-4-pyridyl]-4-piperidyl]acetamide; |
| 163 | (*S/*S)-N-[3-Fluoro-1-[2-[3-fluoro-4-(trifluoromethoxy)phenyl]-4-pyridyl]-4-piperidyl]acetamide; |
| 164 | (*S/*S)-N-[3-Fluoro-1-[5-fluoro-2-[3-fluoro-4-(trifluoromethoxy)phenyl]-4-pyridyl]-4-piperidyl]acetamide; |
| 165 | (trans)-N-[1-[2-[3-Fluoro-4-(trifluoromethoxy)phenyl]-4-pyridyl]-3-hydroxy-4-piperidyl]acetamide; |
| 166 | (racemic)-N-[1-[2-[3-Fluoro-4-(trifluoromethoxy)phenyl]-4-pyridyl]-3-methyl-4-piperidyl]acetamide; |
| 167 | (trans)-N-[1-[2-[3-Fluoro-4-(trifluoromethoxy)phenyl]-4-pyridyl]-3-methyl-4-piperidyl]acetamide; |
| 168 | (cis)-N-[1-[2-[3-Fluoro-4-(trifluoromethoxy)phenyl]-4-pyridyl]-3-methyl-4-piperidyl]acetamide; |
| 169 | N-[[1-[2-[3-Fluoro-4-(trifluoromethoxy)phenyl]-4-pyridyl]azetidin-3-yl]methyl]acetamide; |
| 170 | (racemic)-N-[[1-[2-[3-Fluoro-4-(trifluoromethoxy)phenyl]-4-pyridyl]pyrrolidin-3-yl]methyl]acetamide; |
| 171 | (racemic)-N-[1-[2-[3-Fluoro-4-(trifluoromethoxy)phenyl]-4-pyridyl]-3-piperidyl]acetamide; |
| 172 | (racemic)-N-[1-[2-[3-Fluoro-4-(trifluoromethoxy)phenyl]-4-pyridyl]-3,3-dimethyl-4-piperidyl]acetamide; |
| 173 | N-[[1-[2-[3-Fluoro-4-(trifluoromethoxy)phenyl]-4-pyridyl]-4-piperidyl]methyl]acetamide; |
| 174 | (racemic)-N-[[1-[2-[3-Fluoro-4-(trifluoromethoxy)phenyl]-4-pyridyl]-3-piperidyl]methyl]acetamide; |
| 175 | 1-[2-[2-[3-(Difluoromethyl)-4-fluoro-phenyl]-4-pyridyl]-2,6-diazaspiro[3.3]heptan-6-yl]ethanone; |
| 176 | 1-[2-[2-[4-(Trifluoromethoxy)phenyl]-4-pyridyl]-2,6-diazaspiro[3.3]heptan-6-yl]ethanone; |
| 177 | 1-[2-[[2-[3-Fluoro-4-(trifluoromethoxy)phenyl]-4-pyridyl]amino]-6-azaspiro[3.3]heptan-6-yl]ethanone; |
| 178 | N-[6-[2-[3-Fluoro-4-(trifluoromethoxy)phenyl]-4-pyridyl]-6-azaspiro[3.3]heptan-2-yl]acetamide; |
| 179 | N-[3-[[2-[3-Fluoro-4-(trifluoromethoxy)phenyl]-4-pyridyl]amino]cyclobutyl]acetamide; |
| 180 | (trans)-N-[3-[[2-[3-Fluoro-4-(trifluoromethoxy)phenyl]-4-pyridyl]amino]cyclopentyl]acetamide; |
| 181 | (cis)-N-[3-[[2-[3-Fluoro-4-(trifluoromethoxy)phenyl]-4-pyridyl]amino]cyclopentyl]acetamide; |
| 182 | (trans)-N-[3-[[2-[3-Fluoro-4-(trifluoromethoxy)phenyl]-4-pyridyl]amino]cyclohexyl]acetamide; |
| 183 | (cis)-N-[3-[[2-[3-Fluoro-4-(trifluoromethoxy)phenyl]-4-pyridyl]amino]cyclohexyl]acetamide; |
| 184 | N-[4-[[2-[3-Fluoro-4-(trifluoromethoxy)phenyl]-4-pyridyl]amino]cyclohexyl]acetamide; |

| Ex # | Compound Name |
| --- | --- |
| 185 | N-[4-[[2-[3-Fluoro-4-(trifluoromethoxy)phenyl]-4-pyridyl]amino]cyclohexyl]acetamide; |
| 186 | 1-[3-[[[2-[3-Fluoro-4-(trifluoromethoxy)phenyl]-4-pyridyl]amino]methyl]azetidin-1-yl]ethanone; |
| 187 | N-[1-[[[2-[3-Fluoro-4-(trifluoromethoxy)phenyl]-4-pyridyl]amino]methyl]-3-bicyclo[1;1;1]pentanyl]acetamide; |
| 188 | N-[2-[[2-[3-Fluoro-4-(trifluoromethoxy)phenyl]-4-pyridyl]amino]ethyl]acetamide; |
| 189 | N-[3-[[2-[3-Fluoro-4-(trifluoromethoxy)phenyl]-4-pyridyl]amino]propyl]acetamide; |
| 190 | N-[3-[[2-[3-Fluoro-4-(trifluoromethoxy)phenyl]-4-pyridyl]-methyl-amino]propyl]acetamide; |
| 191 | (racemic)-N-[3-[[2-[3-Fluoro-4-(trifluoromethoxy)phenyl]-4-pyridyl]amino]butyl]acetamide; |
| 192 | (racemic)-N-[3-[[2-[3-Fluoro-4-(trifluoromethoxy)phenyl]-4-pyridyl]amino]-2-methyl-propyl]acetamide; |
| 193 | (*R)-N-[3-[[2-[3-Fluoro-4-(trifluoromethoxy)phenyl]-4-pyridyl]arnino]-2-methyl-propyl]acetamide; |
| 194 | (*S)-N-[3-[[2-[3-Fluoro-4-(trifluoromethoxy)phenyl]-4-pyridyl]amino]-2-methyl-propyl]acetamide; |
| 195 | (racemic)-N-[3-[[2-[3-Fluoro-4-(trifluoromethoxy)phenyl]-4-pyridyl]amino]-1-methyl-propyl]acetamide; |
| 196 | N-[3-[[2-[3-Fluoro-4-(trifluoromethoxy)phenyl]-4-pyridyl]amino]-2,2-dimethyl-propyl]acetamide; |
| 197 | N-[4-[[2-[3-Fluoro-4-(trifluoromethoxy)phenyl]-4-pyridyl]amino]butyl]acetamide; |
| 198 | N-[3-[[2-[3-Fluoro-4-(trifluoromethoxy)phenyl]-4-pyridyl]oxy]propyl]acetamide; |
| 199 | N-[3-[[2-[3-Fluoro-4-(trifluoromethoxy)phenyl]-4-pyridyl]oxy]cyclobutyl]acetamide; |
| 200 | N-[3-[[2-[3-Fluoro-4-(trifluoromethoxy)phenyl]-4-pyridyl]oxy]cyclobutyl]acetamide; |
| 201 | N-(4-(2-(3-Fluoro-4-(trifluoromethoxy)phenyl)pyridin-4-yl)cyclohexyl)acetamide; |
| 202 | (R/S)-N-(3-((5-Fluoro-2-(3-fluoro-4-(trifluoromethoxy)phenyl)pyridin-4-yl)amino)-2-methylpropyl)acetamide; and |
| 203 | N-(3-((5-Fluoro-2-(3-fluoro-4-(trifluoromethoxy)phenyl)pyridin-4-yl)amino)propyl)acetamide; |

A further embodiment of the current invention is a compound as shown below in Table 2 or a pharmaceutically acceptable salt, N-oxide, or solvate thereof.

| Ex # | Compound Name |
| --- | --- |
| 1 | 1-[6-[4-(Trifluoromethoxy)phenyl]pyrimidin-4-yl]piperidine-4-carboxamide; |
| 2 | N-[1-[6-[3-Fluoro-4-(trifluoromethoxy)phenyl]pyrimidin-4-yl]-4-piperidyl]acetamide; |
| 3 | N-[1-[6-[3-Chloro-4-(trifluoromethoxy)phenyl]-2-methyl-pyrimidin-4-yl]-4-piperidyl]acetamide; |
| 4 | (trans)-N-[3-Fluoro-1-[2-methyl-6-[4-(trifluoromethoxy)phenyl]pyrimidin-4-yl]-4-piperidyl]acetamide; |
| 5 | N-[1-[6-[3-Fluoro-4-(trifluoromethoxy)phenyl]-2-(hydroxymethyl)pyrimidin-4-yl]-4-piperidyl]acetamide; |
| 6 | (racemic)-N-Methyl-1-[6-[4-(trifluoromethoxy)phenyl]pyrimidin-4-yl]pyrrolidine-3-carboxamide; |
| 7 | (Trans)-N-[3-Fluoro-1-[6-[3-fluoro-4-(trifluoromethoxy)phenyl]-2-methyl-pyrimidin-4-yl]-4-piperidyl]acetamide; |
| 8 | N-[1-[6-[3-Fluoro-4-(trifluoromethoxy)phenyl]pyrimidin-4-yl]-4-piperidyl]cyclopropanecarboxamide; |
| 9 | 3-Amino-N-[1-[6-[3-fluoro-4-(trifluoromethoxy)phenyl]pyrimidin-4-yl]-4-piperidyl]propanamide; |
| 10 | N-[1-[6-[3-Fluoro-4-(trifluoromethoxy)phenyl]pyrimidin-4-yl]azetidin-3-yl]acetamide; |
| 26 | 1-[6-[4-(Trifluoromethoxy)phenyl]pyrimidin-4-yl]piperidine-3-carboxamide; |
| 27 | 1-[6-[4-(Difluoromethoxy)phenyl]pyrimidin-4-yl]piperidine-4-carboxamide; |
| 28 | 1-[2-Methyl-6-[4-(trifluoromethoxy)phenyl]pyrimidin-4-yl]piperidine-4-carboxamide; |
| 29 | 1-[6-[3-(Difluoromethoxy)-4-fluoro-phenyl]pyrimidin-4-yl]piperidine-4-carboxamide; |
| 30 | 1-[6-[4-(Trifluoromethyl)phenyl]pyrimidin-4-yl]piperidine-4-carboxamide; |
| 31 | 1-[6-[3-Fluoro-4-(trifluoromethoxy)phenyl]pyrimidin-4-yl]piperidine-4-carboxamide; |
| 32 | 1-[5-Methyl-6-[4-(trifluoromethoxy)phenyl]pyrimidin-4-yl]piperidine-4-carboxamide; |
| 33 | 1-[6-[3-Fluoro-4-(trifluoromethoxy)phenyl]-2-methyl-pyrimidin-4-yl]piperidine-4-carboxamide; |

| Ex # | Compound Name |
|---|---|
| 34 | 1-[6-[3-Fluoro-4-(2,2,2-trifluoroethoxy)phenyl]pyrimidin-4-yl]piperidine-4-carboxamide; |
| 35 | 1-[2-Cyclopropyl-6-[4-(trifluoromethoxy)phenyl]pyrimidin-4-yl]piperidine-4-carboxamide; |
| 36 | 1-[2,5-Dimethyl-6-[4-(trifluoromethoxy)phenyl]pyrimidin-4-yl]piperidine-4-carboxamide; |
| 37 | 1-[6-[3-Chloro-4-(trifluoromethoxy)phenyl]pyrimidin-4-yl]piperidine-4-carboxamide; |
| 38 | 1-[6-[3-Methyl-4-(trifluoromethoxy)phenyl]pyrimidin-4-yl]piperidine-4-carboxamide; |
| 39 | 1-[6-[3-Methoxy-4-(trifluoromethoxy)phenyl]pyrimidin-4-yl]piperidine-4-carboxamide; |
| 40 | 1-[2-Ethyl-6-[4-(trifluoromethoxy)phenyl]pyrimidin-4-yl]piperidine-4-carboxamide; |
| 41 | 1-[2-Methoxy-6-[4-(trifluoromethoxy)phenyl]pyrimidin-4-yl]piperidine-4-carboxamide; |
| 42 | N-[1-[6-[4-(Difluoromethyl)phenyl]pyrimidin-4-yl]-4-piperidyl]acetamide; |
| 43 | N-[1-[6-[3-Methyl-4-(trifluoromethyl)phenyl]pyrimidin-4-yl]-4-piperidyl]acetamide; |
| 44 | N-[1-[6-[3-Fluoro-4-(trifluoromethoxy)phenyl]-2-methyl-pyrimidin-4-yl]-4-piperidyl]acetamide; |
| 45 | N-[1-[6-[3-Chloro-4-(trifluoromethoxy)phenyl]pyrimidin-4-yl]-4-piperidyl]acetamide; |
| 46 | 1-[6-[3-Fluoro-4-(trifluoromethoxy)phenyl]-2-methyl-pyrimidin-4-yl]-N-(2-hydroxyethyl)piperidine-4-carboxamide; |
| 47 | 1-[6-[3-Chloro-4-(trifluoromethoxy)phenyl]pyrimidin-4-yl]-N-(2-hydroxyethyl)piperidine-4-carboxamide; |
| 48 | 1-[6-[3-Chloro-4-(trifluoromethoxy)phenyl]-2-methyl-pyrimidin-4-yl]-N-(2-hydroxyethyl)piperidine-4-carboxamide; |
| 49 | N-[1-[2-Methyl-6-[3-methyl-4-(trifluoromethoxy)phenyl]pyrimidin-4-yl]-4-piperidyl]acetamide; |
| 50 | N-[1-[6-[3-Methyl-4-(trifluoromethoxy)phenyl]pyrimidin-4-yl]-4-piperidyl]acetamide; |
| 51 | N-methyl-N-[1-[6-[3-methyl-4-(trifluoromethoxy)phenyl]pyrimidin-4-yl]-4-piperidyl]acetamide; |
| 52 | N-(2-Hydroxyethyl)-1-[2-methyl-6-[3-methyl-4-(trifluoromethoxy)phenyl]pyrimidin-4-yl]piperidine-4-carboxamide; |
| 53 | N-(2-Hydroxyethyl)-1-[6-[3-methyl-4-(trifluoromethoxy)phenyl]pyrimidin-4-yl]piperidine-4-carboxamide; |
| 54 | N-[1-[6-[4-(1,1-Difluoroethyl)phenyl]pyrimidin-4-yl]-4-piperidyl]acetamide; |
| 55 | N-[1-[6-[3-Fluoro-4-(trifluoromethyl)phenyl]pyrimidin-4-yl]-4-piperidyl]acetamide; |
| 56 | N-[1-[6-(3-Fluoro-4-methoxy-phenyl)pyrimidin-4-yl]-4-piperidyl]acetamide; |
| 57 | N-[1-[6-(3-Chloro-4-methoxy-phenyl)pyrimidin-4-yl]-4-piperidyl]acetamide; |
| 58 | N-[1-[6-[3-Chloro-4-(trifluoromethyl)phenyl]pyrimidin-4-yl]-4-piperidyl]acetamide; |
| 59 | N-[1-[6-(4-Chloro-3-fluoro-phenyl)pyrimidin-4-yl]-4-piperidyl]acetamide; |
| 60 | N-[1-[6-(3-Chloro-4-methyl-phenyl)pyrimidin-4-yl]-4-piperidyl]acetamide; |
| 61 | N-[1-[6-(4-Chloro-3-methyl-phenyl)pyrimidin-4-yl]-4-piperidyl]acetamide; |
| 62 | N-[1-[6-[3-Chloro-4-(hydroxymethyl)phenyl]pyrimidin-4-yl]-4-piperidyl]acetamide; |
| 63 | N-[1-[6-(3,4-Dichlorophenyl)pyrimidin-4-yl]-4-piperidyl]acetamide; |
| 64 | N-[1-[6-(3-Fluoro-4-methyl-phenyl)pyrimidin-4-yl]-4-piperidyl]acetamide; |
| 65 | N-[1-[6-[4-(Difluoromethoxy)-3-fluoro-phenyl]pyrimidin-4-yl]-4-piperidyl]acetamide; |
| 66 | N-[1-[6-[3-(Hydroxymethyl)-4-(trifluoromethoxy)phenyl]pyrimidin-4-yl]-4-piperidyl]acetamide; |
| 67 | N-[1-[6-[3,5-Difluoro-4-(trifluoromethoxy)phenyl]pyrimidin-4-yl]-4-piperidyl]acetamide; |
| 68 | N-[1-[2-Methyl-6-[4-(trifluoromethoxy)phenyl]pyrimidin-4-yl]-4-piperidyl]acetamide; |
| 69 | (trans)-N-[3-Fluoro-1-[2-methyl-6-[3-methyl-4-(trifluoromethoxy)phenyl]pyrimidin-4-yl]-4-piperidyl]acetamide; |
| 70 | N-[1-[6-[4-(Trifluoromethoxy)-3-(trifluoromethyl)phenyl]pyrimidin-4-yl]-4-piperidyl]acetamide; |
| 71 | N-Methyl-1-[6-[4-(trifluoromethoxy)phenyl]pyrimidin-4-yl]piperidine-4-carboxamide; |
| 72 | N-(2-Hydroxyethyl)-1-[6-[4-(trifluoromethoxy)phenyl]pyrimidin-4-yl]piperidine-4-carboxamide; |
| 73 | 4-[4-(1H-Imidazol-4-yl)-1-piperidyl]-6-[4-(trifluoromethoxy)phenyl]pyrimidine; |
| 74 | N-(2-Hydroxyethyl)-1-[2-methyl-6-[4-(trifluoromethoxy)phenyl]pyrimidin-4-yl]piperidine-4-carboxamide; |
| 75 | 4-[4-(1H-Imidazol-4-yl)-1-piperidyl]-2-methyl-6-[4-(trifluoromethoxy)phenyl]pyrimidine; |
| 76 | 1-[6-[3-Fluoro-4-(trifluoromethoxy)phenyl]pyrimidin-4-yl]-N-(2-hydroxyethyl)piperidine-4-carboxamide; |

-continued

| Ex # | Compound Name |
|---|---|
| 77 | 4-[3-Fluoro-4-(trifluoromethoxy)phenyl]-6-[4-(1H-imidazol-4-yl)-1-piperidyl]pyrimidine; |
| 78 | 2-[1-[6-[4-(Trifluoromethoxy)phenyl]pyrimidin-4-yl]-4-piperidyl]acetamide; |
| 79 | N-[1-[6-[4-(Trifluoromethoxy)phenyl]pyrimidin-4-yl]-4-piperidyl]acetamide; |
| 80 | 4-[4-(1H-Imidazol-2-yl)-1-piperidyl]-6-[4-(trifluoromethoxy)phenyl]pyrimidine; |
| 81 | N-[[1-[6-[4-(Trifluoromethoxy)phenyl]pyrimidin-4-yl]-4-piperidyl]methyl]acetamide; |
| 82 | 8-[6-[3-Fluoro-4-(trifluoromethoxy)phenyl]pyrimidin-4-yl]-4,8-diazaspiro[4;5]decan-3-one; |
| 83 | 1-[6-[3-Fluoro-4-(trifluoromethoxy)phenyl]-2-methyl-pyrimidin-4-yl]piperidin-4-ol; |
| 84 | N-Methyl-1-[6-[4-(trifluoromethoxy)phenyl]pyrimidin-4-yl]azetidine-3-carboxamide; |
| 85 | (*R/*R)-N-[3-Fluoro-1-[6-[3-fluoro-4-(trifluoromethoxy)phenyl]-2-methyl-pyrimidin-4-yl]-4-piperidyl]acetamide; |
| 86 | (*S/*S)-N-[3-Fluoro-1-[6-[3-fluoro-4-(trifluoromethoxy)phenyl]-2-methyl-pyrimidin-4-yl]-4-piperidyl]acetamide; |
| 87 | (trans)-N-[3-Fluoro-1-[6-[3-fluoro-4-(trifluoromethoxy)phenyl]pyrimidin-4-yl]-4-piperidyl]acetamide; |
| 88 | (*S/*S)-N-[3-Fluoro-1-[6-[3-fluoro-4-(trifluoromethoxy)phenyl]pyrimidin-4-yl]-4-piperidyl]acetamide; |
| 89 | (*R/*R)-N-[3-Fluoro-1-[6-[3-fluoro-4-(trifluoromethoxy)phenyl]pyrimidin-4-yl]-4-piperidyl]acetamide; |
| 90 | (trans)-N-[3-Fluoro-1-[6-[3-methyl-4-(trifluoromethoxy)phenyl]pyrimidin-4-yl]-4-piperidyl]acetamide; |
| 91 | (*S/*S)-N-[3-Fluoro-1-[6-[3-methyl-4-(trifluoromethoxy)phenyl]pyrimidin-4-yl]-4-piperidyl]acetamide; |
| 92 | (*R/*R)-N-[3-Fluoro-1-[6-[3-methyl-4-(trifluoromethoxy)phenyl]pyrimidin-4-yl]-4-piperidyl]acetamide; |
| 93 | (trans)-N-[1-[6-[3-Chloro-4-(trifluoromethoxy)phenyl]pyrimidin-4-yl]-3-fluoro-4-piperidyl]acetamide; |
| 94 | (*S/*S)-N-[1-[6-[3-Chloro-4-(trifluoromethoxy)phenyl]pyrimidin-4-yl]-3-fluoro-4-piperidyl]acetamide; |
| 95 | (*R/*R)-N-[1-[6-[3-Chloro-4-(trifluoromethoxy)phenyl]pyrimidin-4-yl]-3-fluoro-4-piperidyl]acetamide; |
| 96 | (cis)-N-[3-Fluoro-1-[6-[3-fluoro-4-(trifluoromethoxy)phenyl]pyrimidin-4-yl]-4-piperidyl]acetamide; |
| 97 | (*R/*S)-N-[3-Fluoro-1-[6-[3-fluoro-4-(trifluoromethoxy)phenyl]pyrimidin-4-yl]-4-piperidyl]acetamide; |
| 98 | (*S/*R)-N-[3-Fluoro-1-[6-[3-fluoro-4-(trifluoromethoxy)phenyl]pyrimidin-4-yl]-4-piperidyl]acetamide; |
| 99 | N-[1-[6-[3-fluoro-4-(trifluoromethoxy)phenyl]-2-methyl-pyrimidin-4-yl]-4-methyl-4-piperidyl]acetamide; |
| 100 | N-[1-[6-[3-Fluoro-4-(trifluoromethoxy)phenyl]-2-methyl-pyrimidin-4-yl]-4-piperidyl]methanesulfonamide; |
| 101 | 4-[3-Fluoro-4-(trifluoromethoxy)phenyl]-2-methyl-6-[4-(1H-pyrazol-5-yl)-1-piperidyl]pyrimidine; |
| 102 | 1-[1-[6-[3-Fluoro-4-(trifluoromethoxy)phenyl]pyrimidin-4-yl]-4-piperidyl]ethanone; |
| 103 | 1-[1-[6-[3-Fluoro-4-(trifluoromethoxy)phenyl]pyrimidin-4-yl]-4-piperidyl]propan-2-one; |
| 104 | N-[[1-[6-[3-Fluoro-4-(trifluoromethoxy)phenyl]pyrimidin-4-yl]azetidin-3-yl]methyl]acetamide; |
| 105 | (racemic)-N-[[1-[6-[3-Fluoro-4-(trifluoromethoxy)phenyl]pyrimidin-4-yl]pyrrolidin-3-yl]methyl]acetamide; |
| 106 | (racemic)-N-[1-[6-[3-Fluoro-4-(trifluoromethoxy)phenyl]pyrimidin-4-yl]pyrrolidin-3-yl]acetamide; |
| 107 | (racemic)-N-[1-[6-[3-Fluoro-4-(trifluoromethoxy)phenyl]pyrimidin-4-yl]-3-piperidyl]acetamide; |
| 108 | (racemic)-N-[1-[6-[3-Fluoro-4-(trifluoromethoxy)phenyl]pyrimidin-4-yl]azepan-4-yl]acetamide; |
| 109 | (trans)-N-[3-Fluoro-1-[6-[4-(trifluoromethoxy)phenyl]pyrimidin-4-yl]-4-piperidyl]acetamide; |
| 110 | (racemic)-N-[1-[6-[3-Fluoro-4-(trifluoromethoxy)phenyl]pyrimidin-4-yl]-3-methyl-4-piperidyl]acetamide; |
| 111 | (racemic)-N-[1-[6-[3-Fluoro-4-(trifluoromethoxy)phenyl]pyrimidin-4-yl]-2-methyl-4-piperidyl]acetamide; |
| 112 | 2,2-Difluoro-N-[1-[6-[3-fluoro-4-(trifluoromethoxy)phenyl]pyrimidin-4-yl]-4-piperidyl]acetamide; |
| 113 | 1-[2-[6-[3-Fluoro-4-(trifluoromethoxy)phenyl]pyrimidin-4-yl]-2,6-diazaspiro[3;3]heptan-6-yl]ethanone; |
| 114 | N-[4-[[6-[4-(Trifluoromethoxy)phenyl]pyrimidin-4-yl]amino]cyclohexyl]acetamide; |
| 115 | N-[1-[6-[3-Fluoro-4-(trifluoromethoxy)phenyl]pyrimidin-4-yl]-4-piperidyl]propanamide; |
| 116 | N-[1-[6-[3-Fluoro-4-(trifluoromethoxy)phenyl]pyrimidin-4-yl]-4-piperidyl]-3-hydroxy-propanamide; |

| Ex # | Compound Name |
|---|---|
| 117 | (trans)-3-Amino-N-[3-fluoro-1-[6-[3-fluoro-4-(trifluoromethoxy)phenyl]pyrimidin-4-yl]-4-piperidyl]propanamide; |
| 118 | N-[3-[[6-[3-Fluoro-4-(trifluoromethoxy)phenyl]pyrimidin-4-yl]amino]propyl]acetamide; |
| 119 | (racemic)-N-[3-[[6-[3-Fluoro-4-(trifluoromethoxy)phenyl]pyrimidin-4-yl]amino]-2-methyl-propyl]acetamide; |
| 120 | (*R)-N-[3-[[6-[3-Fluoro-4-(trifluoromethoxy)phenyl]pyrimidin-4-yl]amino]-2-methyl-propyl]acetamide; and |
| 121 | (*S)-N-[3-[[6-[3-Fluoro-4-(trifluoromethoxy)phenyl]pyrimidin-4-yl]amino]-2-methyl-propyl]acetamide; |

A further embodiment of the current invention is a compound selected from the group consisting of:

N-[1-[6-[3-Fluoro-4-(trifluoromethoxy)phenyl]pyrimidin-4-yl]-4-piperidyl]acetamide;
N-[1-[2-[3-Fluoro-4-(trifluoromethoxy)phenyl]-4-pyridyl]-4-piperidyl]acetamide;
N-[1-[6-[3-Methyl-4-(trifluoromethoxy)phenyl]pyrimidin-4-yl]-4-piperidyl]acetamide;
N-[1-[2-[4-(Trifluoromethoxy)phenyl]-4-pyridyl]-4-piperidyl]acetamide;
N-[1-[2-[3-Methyl-4-(trifluoromethoxy)phenyl]-4-pyridyl]-4-piperidyl]acetamide;
N-[1-[2-[4-(Difluoromethoxy)-3-methyl-phenyl]-4-pyridyl]-4-piperidyl]acetamide;
2-[1-[2-[3-Fluoro-4-(trifluoromethoxy)phenyl]-4-pyridyl]-4-piperidyl]acetamide;
N-[1-[2-[3-Chloro-4-(trifluoromethoxy)phenyl]-4-pyridyl]-4-piperidyl]acetamide;
N-[1-[2-(Fluoromethyl)-6-[3-fluoro-4-(trifluoromethoxy)phenyl]-4-pyridyl]-4-piperidyl]acetamide;
N-[1-[2-[3-Fluoro-4-(trifluoromethoxy)phenyl]-6-(hydroxymethyl)-4-pyridyl]-4-piperidyl]acetamide;
(*R/*R)—N-[3-Fluoro-1-[2-[3-fluoro-4-(trifluoromethoxy)phenyl]-4-pyridyl]-4-piperidyl]acetamide; and
(*S)—N-[3-[[2-[3-Fluoro-4-(trifluoromethoxy)phenyl]-4-pyridyl]amino]-2-methyl-propyl]acetamide;

and pharmaceutically acceptable salts, N-oxides, and solvates thereof.

An additional embodiment of the invention is a pharmaceutical composition comprising:

(A) at least one compound selected from compounds of Formula (I):

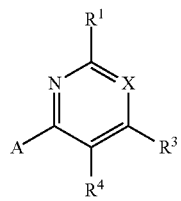

(I)

wherein
$R^1$ is selected from the group consisting of: H, OH, $C_{1-4}$alkyl, $CH_2OH$, $CH_2F$, $CHF_2$, $OC_{1-4}$alkyl, $OCHF_2$, CN, and cyclopropyl;
X is C—$R^2$ or N; wherein $R^2$ is selected from the group consisting of: H, halo, $C_{1-4}$alkyl, $OC_{1-4}$alkyl, and CN;
$R^3$ is:

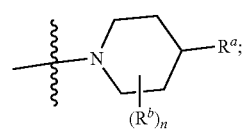

(a)

wherein
$R^a$ is selected from the group consisting of: OH, (C=O)$NH_2$, (C=O)$NHCH_3$, (C=O)$NHCH_2CH_2OH$, $CH_2$(C=O)$NH_2$, $CH_2C$(=O)$CH_3$, (C=O)$CH_3$, $CH_2NH$(C=O)$CH_3$, NH(C=O)$C_{1-4}$alkyl, $NCH_3$(C=O)$C_{1-4}$alkyl, NH(C=O)$CH_2CH_2NH_2$, NH(C=O)$CH_2CH_2OH$, NH(C=O)halo$C_{1-4}$alkyl, NH(C=O)cyclopropyl, $NHSO_2CH_3$,

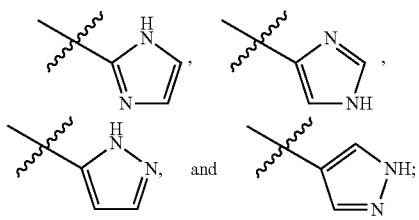

each $R^b$ is independently selected from the group consisting of: H, F, $CH_3$ and OH;
n is 0, 1 or 2;

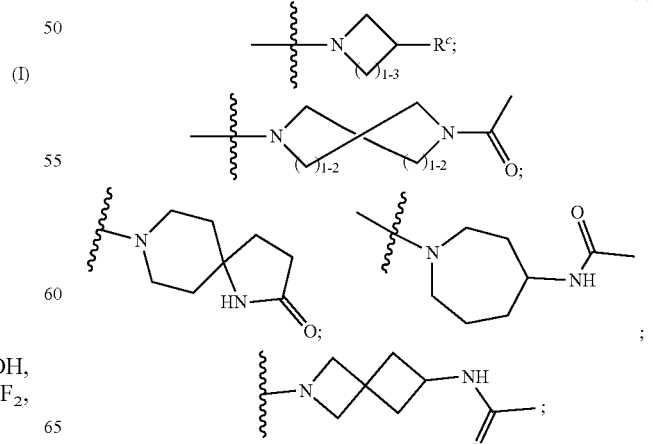

(b)

-continued

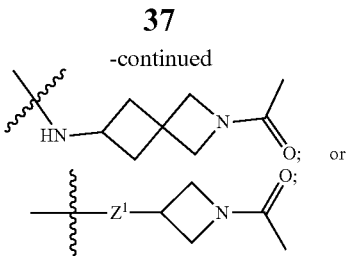

wherein
R$^c$ is selected from the group consisting of: NH(C═O)CH$_3$, CH$_2$NH(C═O)CH$_3$, (C═O)CH$_3$, and (C═O)NHCH$_3$;
Z$^1$ is NHCH$_2$;

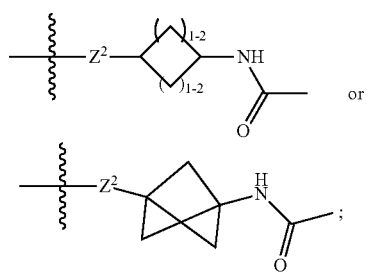

wherein
Z$^2$ is NH or CH$_2$NH; or
(d) Z$^3$—C$_{1-6}$alkyl-NH(C═O)CH$_3$ or Z$^3$—C$_{4-6}$cycloalkyl-NH(C═O)CH$_3$;
wherein Z$^3$ is NH, NCH$_3$, or O;
R$^4$ is H or CH$_3$; and A is selected from the group consisting of:

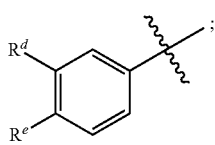

wherein
R$^d$ is selected from the group consisting of: halo, C$_{1-4}$alkyl, CH$_2$OH, C$_{1-4}$haloalkyl, OC$_{1-4}$alkyl, and OC$_{1-4}$haloalkyl;
R$^e$ is selected from the group consisting of: halo, C$_{1-4}$alkyl, CH$_2$OH, OC$_{1-4}$alkyl, C$_{1-4}$haloalkyl, OC$_{1-4}$haloalkyl, and (C═O)CH$_3$;

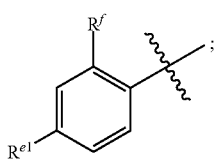

wherein
R$^f$ is H or F;
R$^{e1}$ is selected from the group consisting of: C$_{1-4}$alkyl, C$_{1-4}$haloalkyl, and OC$_{1-4}$haloalkyl; and

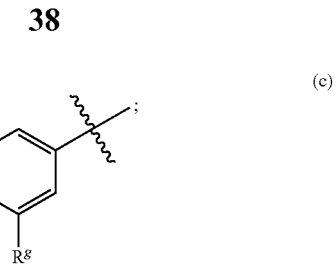

wherein
R$^{d1}$ and R$^{e2}$ are halo; and
R$^g$ is OC$_{1-4}$haloalkyl;
and pharmaceutically acceptable salts, stereoisomers, isotopic variants, N-oxides and solvates of compounds of Formula (I);
and (B) at least one pharmaceutically acceptable excipient.

An additional embodiment of the invention is a pharmaceutical composition comprising at least one compound selected from compounds of Formula (IA), pharmaceutically acceptable salts, N-oxides and solvates of compounds of Formula (IA), pharmaceutically acceptable prodrugs of compounds of Formula (IA), and pharmaceutically active metabolites of compounds of Formula (IA); and at least one pharmaceutically acceptable excipient.

An additional embodiment of the invention is a pharmaceutical composition comprising at least one compound selected from compounds of Formula (IB), pharmaceutically acceptable salts, N-oxides and solvates of compounds of Formula (IB), pharmaceutically acceptable prodrugs of compounds of Formula (IB), and pharmaceutically active metabolites of compounds of Formula (IB); and at least one pharmaceutically acceptable excipient.

An additional embodiment of the invention is a pharmaceutical composition comprising at least one compound selected from compounds of Formula (IC), pharmaceutically acceptable salts, N-oxides and solvates of compounds of Formula (IC), pharmaceutically acceptable prodrugs of compounds of Formula (IC), and pharmaceutically active metabolites of compounds of Formula (IC); and at least one pharmaceutically acceptable excipient.

An additional embodiment of the invention is a pharmaceutical composition comprising at least one compound selected from compounds of Formula (ID), pharmaceutically acceptable salts, N-oxides and solvates of compounds of Formula (ID), pharmaceutically acceptable prodrugs of compounds of Formula (ID), and pharmaceutically active metabolites of compounds of Formula (ID); and at least one pharmaceutically acceptable excipient.

An additional embodiment of the invention is a pharmaceutical composition comprising at least one compound selected from compounds in Table 1, pharmaceutically acceptable salts, N-oxides and solvates of compounds of Table 1, pharmaceutically acceptable prodrugs of compounds of Table 1, and pharmaceutically active metabolites of Table 1; and at least one pharmaceutically acceptable excipient.

An additional embodiment of the invention is a pharmaceutical composition comprising at least one compound selected from compounds in Table 2, pharmaceutically acceptable salts, N-oxides and solvates of compounds of Table 2, pharmaceutically acceptable prodrugs of compounds of Table 2, and pharmaceutically active metabolites of Table 2; and at least one pharmaceutically acceptable excipient.

An additional embodiment of the invention is a pharmaceutical composition comprising at least one compound selected from compounds in Table 3, pharmaceutically acceptable salts, N-oxides and solvates of compounds of Table 3, pharmaceutically acceptable prodrugs of compounds of Table 3, and pharmaceutically active metabolites of Table 3; and at least one pharmaceutically acceptable excipient.

Also within the scope of the invention are enantiomers and diastereomers of the compounds of Formula (I) (as well as Formulas (IA), (IB), (IC), and (ID)). Also within the scope of the invention are the pharmaceutically acceptable salts, N-oxides and solvates of the compounds of Formula (I) (as well as Formulas (IA), (IB), (IC), and (ID)). Also within the scope of the invention are the pharmaceutically acceptable prodrugs of compounds of Formula (I) (as well as Formulas (IA), (IB), (IC), and (ID)), and pharmaceutically active metabolites of the compounds of Formula (I) (as well as Formulas (IA), (IB), (IC), and (ID)).

Also within the scope of the invention are isotopic variations of compounds of Formula (I) (as well as Formulas (IA), (IB), (IC), and (ID)), such as, e.g., deuterated compounds of Formula (I). Also within the scope of the invention are the pharmaceutically acceptable salts, N-oxides and solvates of the isotopic variations of the compounds of Formula (I) (as well as Formulas (IA), (IB), (IC), and (ID)). Also within the scope of the invention are the pharmaceutically acceptable prodrugs of the isotopic variations of the compounds of Formula (I) (as well as Formulas (IA), (IB), (IC), and (ID)), and pharmaceutically active metabolites of the isotopic variations of the compounds of Formula (I) (as well as Formulas (IA), (IB), (IC), and (ID)).

An additional embodiment of the invention is a method of treating a subject suffering from or diagnosed with a disease, disorder, or medical condition mediated by NR2B receptor activity, comprising administering to the subject an effective amount of at least one compound selected from compounds of Formula (I):

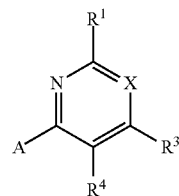

(I)

wherein
$R^1$ is selected from the group consisting of: H, OH, $C_{1-4}$alkyl, $CH_2OH$, $CH_2F$, $CHF_2$, $OC_{1-4}$alkyl, $OCHF_2$, CN, and cyclopropyl;
X is $C-R^2$ or N; wherein $R^2$ is selected from the group consisting of: H, halo, $C_{1-4}$alkyl, $OC_{1-4}$alkyl, and CN; $R^3$:

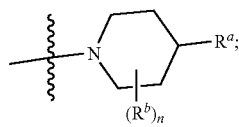

(a)

wherein
$R^a$ is selected from the group consisting of: OH, $(C=O)NH_2$, $(C=O)NHCH_3$, $(C=O)NHCH_2CH_2OH$, $CH_2(C=O)NH_2$, $CH_2C(=O)CH_3$, $(C=O)CH_3$, $CH_2NH(C=O)CH_3$, $NH(C=O)C_{1-4}$alkyl, $NCH_3(C=O)C_{1-4}$alkyl, $NH(C=O)CH_2CH_2NH_2$, $NH(C=O)CH_2CH_2OH$, $NH(C=O)haloC_{1-4}$alkyl, $NH(C=O)$cyclopropyl, $NHSO_2CH_3$,

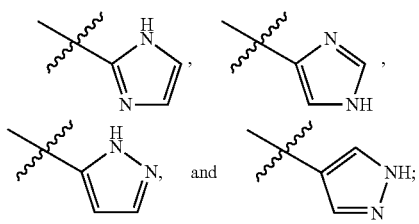

, and each $R^b$ is independently selected from the group consisting of: H, F, $CH_3$ and OH;
n is 0, 1 or 2;

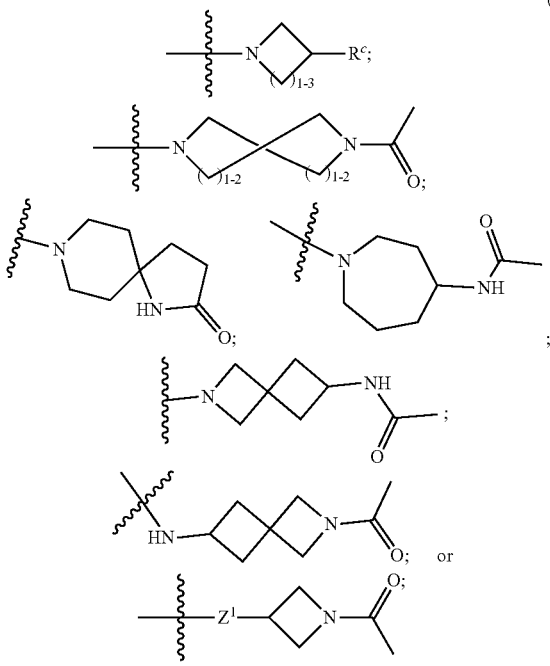

(b)

wherein
$R^c$ is selected from the group consisting of: $NH(C=O)CH_3$, $CH_2NH(C=O)CH_3$, $(C=O)CH_3$, and $(C=O)NHCH_3$;
$Z^1$ is $NHCH_2$

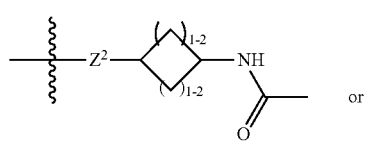

(c)

or

-continued

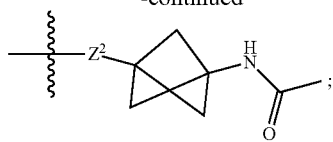

wherein
Z² is NH or CH₂NH; or
(d) $Z^3$—$C_{1-6}$alkyl-NH(C=O)CH₃ or $Z^3$—$C_{4-6}$cycloalkyl-NH(C=O)CH₃;
wherein
Z³ is NH, NCH₃, or O;
R⁴ is H or CH₃; and
A is selected from the group consisting of:

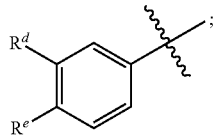
(a)

wherein
$R^d$ is selected from the group consisting of: halo, $C_{1-4}$alkyl, CH₂OH, $C_{1-4}$haloalkyl, $OC_{1-4}$alkyl, and $OC_{1-4}$haloalkyl;
$R^e$ is selected from the group consisting of: halo, $C_{1-4}$alkyl, CH₂OH, $OC_{1-4}$alkyl, $C_{1-4}$haloalkyl, $OC_{1-4}$haloalkyl, and (C=O)CH₃;

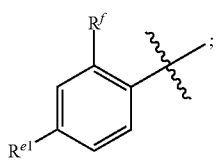
(b)

wherein
$R^f$ is H or F;
$R^{e1}$ is selected from the group consisting of: $C_{1-4}$alkyl, $C_{1-4}$haloalkyl, and $OC_{1-4}$haloalkyl; and

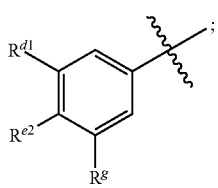
(c)

wherein
$R^{d1}$ and $R^{e2}$ are halo; and
$R^g$ is $OC_{1-4}$haloalkyl;
and pharmaceutically acceptable salts, stereoisomers, isotopic variants, N-oxides, and solvates thereof.

An additional embodiment of the invention is a method of treating a subject suffering from or diagnosed with a disease, disorder, or medical condition mediated by NR2B receptor activity, comprising administering to a subject in need of such treatment an effective amount of at least one compound selected from compounds of Formula (I) (as well as Formulas (IA), (IB), (IC), and (ID)), enantiomers and diastereromers of the compounds of Formula (I), isotopic variations of the compounds of Formula (I), and pharmaceutically acceptable salts of all of the foregoing.

In preferred embodiments of the inventive method, the disease, disorder, or medical condition is selected from: neurologic and psychiatric disorders including, but not limited to: (1) mood disorders and mood affective disorders; (2) neurotic, stress-related and somatoform disorders including anxiety disorders; (3) disorders of psychological development; (4) behavioral syndromes associated with physiological disturbances and physical factors; (5) extrapyramidal and movement disorders; (6) episodic and paroxysmal disorders, epilepsy; (7) pain; (8) forms of neurodegeneration; (9) cerebrovascular diseases, acute and chronic; and any sequelae of cerebrovascular diseases.

Examples of mood disorders and mood affective disorders that can be treated according to the present invention include, but are not limited to, bipolar disorder I depressed, hypomanic, manic and mixed form; bipolar disorder II; depressive disorders, such as single depressive episode or recurrent major depressive disorder, minor depressive disorder, treatment-resistant depression, depressive disorder with postpartum onset, depressive disorders with psychotic symptoms; persistent mood disorders, such as cyclothymia, dysthymia, euthymia; and premenstrual dysphoric disorder. In specific embodiments, the mood disorders and mood affective disorders that can be treated according to the present invention are major depressive disorder, treatment-resistant depression and bipolar disorder.

Examples of disorders belonging to the neurotic, stress-related and somatoform disorders that can be treated according to the present invention include, but are not limited to, anxiety disorders, general anxiety disorder, panic disorder with or without agoraphobia, specific phobia, social anxiety disorder, chronic anxiety disorders; obsessive compulsive disorder; reaction to sever stress and adjustment disorders, such as post-traumatic stress disorder (PTSD); other neurotic disorders such as depersonalisation-derealisation syndrome.

Examples of disorders of psychological development that can be treated according to the present invention include, but are not limited to pervasive developmental disorders, including but not limited to Asperger's syndrome and Rett's syndrome, autistic disorders, childhood autism and overactive disorder associated with mental retardation and stereotyped movements, specific developmental disorder of motor function, specific developmental disorders of scholastic skills.

Examples of behavioral syndromes associated with physiological disturbances and physical factors according to the present invention include, but are not limited to mental and behavioral disorders associated with childbirth, including but not limited to postnatal (postpartum) and prenatal depression; eating disorders, including but not limited to anorexia nervosa, bulimia nervosa, pica and binge eating disorder.

Examples of extrapyramidal and movement disorders that can be treated according to the present invention include, but are not limited to Parkinson's disease; second Parkinsonism, such as postencephalitic Parkinsonism; Parkinsonism comprised in other disorders; Lewis body disease; degenerative diseases of the basal ganglia; other extrapyramidal and movement disorders including but not limited to tremor, essential tremor and drug-induced tremor, myoclonus, chorea and drug-induced chorea, drug-induced tics and tics of organic origin, drug-induced acute dystonia, drug-induced tardive dyskinesia, L-dopa-induced dyskinesia; neuroleptic-induced movement disorders including but not limited to neuroleptic malignant syndrome (NMS), neuroleptic induced parkinsonism, neuroleptic-induced early onset or acute dyskinesia, neuroleptic-induced acute dystonia, neuroleptic-induced acute akathisia, neuroleptic-induced tardive dyskinesia, neuroleptic-induced tremor; restless leg syndrome, Stiff-man syndrome.

Further examples of movement disorders with malfunction and/or degeneration of basal ganglia that can be treated according to the present invention include, but are not limited to dystonia including but not limited to focal dystonia, multiple-focal or segmental dystonia, torsion dystonia, hemispheric, generalised and tardive dystonia (induced by psychopharmacological drugs). Focal dystonia include cervical dystonia (torticolli), blepharospasm (cramp of the eyelid), appendicular dystonia (cramp in the extremities, like the writer's cramp), oromandibular dystonia and spasmodic dysphonia (cramp of the vocal cord);

Examples for episodic and paroxysmal disorders that can be treated according to the present invention include, but are not limited to epilepsy, including localization-related (focal) (partial) idiopathic epilepsy and epileptic syndromes with seizures of localized onset, localization-related (focal)(partial) symptomatic epilepsy and epileptic syndromes with simple partial seizures, localization-related (focal)(partial) symptomatic epilepsy and epileptic syndromes with complex partial seizures, generalized idiopathic epilepsy and epileptic syndromes including but not limited to myoclonic epilepsy in infancy, neonatal convulsions (familial), childhood absence epilepsy (pyknolepsy), epilepsy with grand mal seizures on awakening, absence epilepsy, myoclonic epilepsy (impulsive petit mal) and nonspecific atonic, clonic, myoclonic, tonic, tonic-clonic epileptic seizures.

Further examples of epilepsy that can be treated according to the present invention include, but are not limited to epilepsy with myoclonic absences, myoclonic-astatic seizures, infantile spasms, Lennox-Gastaut syndrome, Salaam attacks, symptomatic early myoclonic encephalopathy, West's syndrome, petit and grand mal seizures; status epilepticus.

Examples of pain include, but are not limited to pain disorders related to psychological factors, such as persistent somatoform disorders; acute, chronic and chronic intractable pain, headache; acute and chronic pain related to physiological processes and physical disorders including but not limited to back pain, tooth pain, abdominal pain, low back pain, pain in joints; acute and chronic pain that is related to diseases of the musculoskeletal system and connective tissue including, but not limited to rheumatism, myalgia, neuralgia and fibromyalgia; acute and chronic pain that is related to nerve, nerve root and plexus disorders, such as trigeminal pain, postzoster neuralgia, phantom limb syndrome with pain, carpal tunnel syndrome, lesion of sciatic nerve, diabetic mononeuropathy; acute and chronic pain that is related to polyneuropathies and other disorders of the peripheral nervous system, such as hereditary and idiopathic neuropathy, inflammatory polyneuropathy, polyneuropathy induced by drugs, alcohol or toxic agents, polyneuropathy in neoplastic disease, diabetic polyneuropathy.

Examples of diseases that include forms of neurodegeneration include, but are not limited to, acute neurodegeneration, such as intracranial brain injuries, such as stroke, diffuse and local brain injuries, epidural, subdural and subarachnoid haemorrhage, and chronic neurodegeneration, such as Alzheimer's disease, Huntington's disease, multiple sclerosis and ALS.

Examples of cerebrovascular diseases include, but are not limited to, subarachnoid haemorrhage, intracerebral haemorrhage and other nontraumatic intracranial haemorrhage, cerebral infarction, stroke, occlusion and stenosis or precerebral and cerebral arteries, not resulting in cerebral infarction, dissection of cerebral arteries, cerebral aneurysm, cerebral atherosclerosis, progressive vascular leukoencephalopathy, hypertensive encephalopathy, non-pyogenic thrombosis of intracranial venous system, cerebral arteritis, cerebral amyloid angiopathy and sequelae of cerebrovascular diseases.

In some embodiments, administration of a compound of the invention, or pharmaceutically acceptable salt thereof, is effective in preventing the disease; for example, preventing a disease, condition or disorder in an individual who may be predisposed to the disease, condition or disorder but does not yet experience or display the pathology or symptomatology of the disease.

Additional embodiments, features, and advantages of the invention will be apparent from the following detailed description and through practice of the invention.

The invention may be more fully appreciated by reference to the following description, including the following glossary of terms and the concluding examples. For the sake of brevity, the disclosures of the publications, including patents, cited in this specification are herein incorporated by reference.

As used herein, the terms "including", "containing" and "comprising" are used herein in their open, non-limiting sense.

The term "alkyl" refers to a straight- or branched-chain alkyl group having from 1 to 12 carbon atoms in the chain. Examples of alkyl groups include methyl (Me, which also may be structurally depicted by the symbol, "/"), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples. The term $C_{1-4}$alkyl as used here refers to a straight- or branched-chain alkyl group having from 1 to 4 carbon atoms in the chain. The term $C_{1-6}$alkyl as used here refers to a straight- or branched-chain alkyl group having from 1 to 6 carbon atoms in the chain.

The term "alkoxy" includes a straight chain or branched alkyl group with a terminal oxygen linking the alkyl group to the rest of the molecule. Alkoxy includes methoxy, ethoxy, propoxy, isopropoxy, butoxy, t-butoxy, pentoxy and so on.

The term "aryl" refers to a monocyclic, aromatic carbocycle (ring structure having ring atoms that are all carbon) having 6 atoms per ring. (Carbon atoms in the aryl groups are $sp^2$ hybridized.)

The term "phenyl" represents the following moiety:

The term "heteroaryl" refers to a monocyclic or fused bicyclic heterocycle (ring structure having ring atoms selected from carbon atoms and up to four heteroatoms selected from nitrogen, oxygen, and sulfur) having from 3 to 9 ring atoms per heterocycle. Illustrative examples of heteroaryl groups include the following entities, in the form of properly bonded moieties:

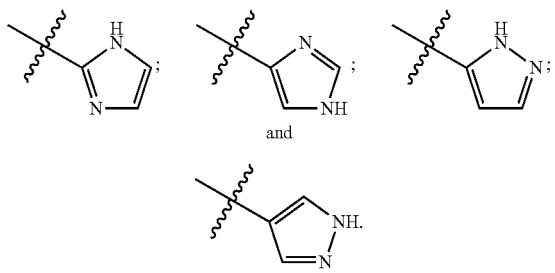

Those skilled in the art will recognize that the species of heteroaryl, cycloalkyl, aryl and heterocycloalkyl groups listed or illustrated above are not exhaustive, and that additional species within the scope of these defined terms may also be selected.

A "heterocycloalkyl" refers to a monocyclic ring structure that is saturated or partially saturated and has from 4 to 7 ring atoms per ring structure selected from carbon atoms and up to two heteroatoms selected from nitrogen, oxygen, and sulfur. The ring structure may optionally contain up to two oxo groups on sulfur ring members. Illustrative entities, in the form of properly bonded moieties, include:

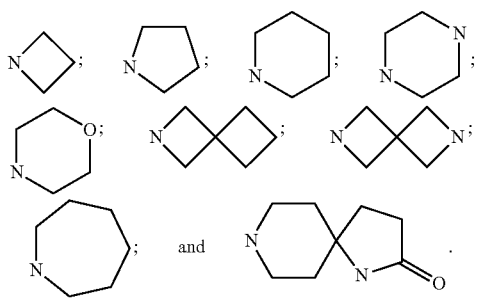

The term "cyano" refers to the group —CN.

The term "cycloalkyl" refers to a saturated or partially saturated, monocyclic, fused polycyclic, or spiro polycyclic carbocycle having from 3 to 12 ring atoms per carbocycle. Illustrative examples of cycloalkyl groups include the following entities, in the form of properly bonded moieties:

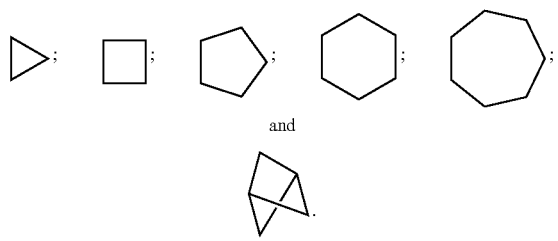

The term "halo" represents chloro, fluoro, bromo or iodo.

The term "perhaloalkyl" or "haloalkyl" refers to a straight- or branched-chain alkyl group having from 1 to 6 carbon atoms in the chain optionally substituting hydrogens with halogens. The term "$C_{1-4}$haloalkyl" as used here refers to a straight- or branched-chain alkyl group having from 1 to 4 carbon atoms in the chain, optionally substituting hydrogens with halogens. The term "$C_{1-6}$haloalkyl" as used here refers to a straight- or branched-chain alkyl group having from 1 to 6 carbon atoms in the chain, optionally substituting hydrogens with halogens. Examples of "perhaloalkyl", "haloalkyl" groups include trifluoromethyl ($CF_3$), difluoromethyl ($CF_2H$), monofluoromethyl ($CH_2F$), pentafluoroethyl ($CF_2CF_3$), tetrafluoroethyl ($CHFCF_3$), monofluoroethyl ($CH_2CH_2F$), trifluoroethyl ($CH_2CF_3$), tetrafluorotrifluoromethylethyl (—$CF(CF_3)_2$), and groups that in light of the ordinary skill in the art and the teachings provided herein would be considered equivalent to any one of the foregoing examples.

The term "perhaloalkoxy" or "haloalkoxy" refers to a straight- or branched-chain alkoxy group having from 1 to 6 carbon atoms in the chain optionally substituting hydrogens with halogens. Examples of perhaloalkoxy groups include trifluoromethoxy ($OCF_3$), difluoromethoxy ($OCF_2H$), monofluoromethoxy ($OCH_2F$), monofluoroethoxy ($OCH_2CH_2F$), pentafluoroethoxy ($OCF_2CF_3$), tetrafluoroethoxy ($OCHFCF_3$), trifluoroethoxy ($OCH_2CF_3$), tetrafluorotrifluoromethylethoxy (—$OCF(CF_3)_2$), and groups that in light of the ordinary skill in the art and the teachings provided herein would be considered equivalent to any one of the foregoing examples.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

The terms "para", "meta", and "ortho" have the meanings as understood in the art. Thus, for example, a fully substituted phenyl group has substituents at both "ortho" (o) positions adjacent to the point of attachment of the phenyl ring, both "meta" (m) positions, and the one "para" (p) position across from the point of attachment. To further clarify the position of substituents on the phenyl ring, the 2 different ortho positions will be designated as ortho and ortho' and the 2 different meta positions as meta and meta' as illustrated below.

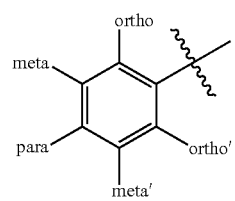

When referring to substituents on a pyridyl group, the terms "para", "meta", and "ortho" refer to the placement of a substituent relative to the point of attachment of the pyridyl ring. For example the structure below is described as 3-pyridyl with the $X^1$ substituent in the ortho position, the $X^2$ substituent in the meta position, and $X^3$ substituent in the para position:

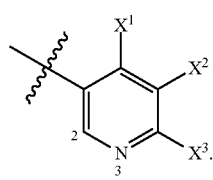

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

The terms "buffered" solution or "buffer" solution are used herein interchangeably according to their standard meaning. Buffered solutions are used to control the pH of a medium, and their choice, use, and function is known to those of ordinary skill in the art. See, for example, G. D. Considine, ed., Van Nostrand's Encyclopedia of Chemistry, p. 261, 5$^{th}$ ed. (2005), describing, inter alia, buffer solutions and how the concentrations of the buffer constituents relate to the pH of the buffer. For example, a buffered solution is obtained by adding $MgSO_4$ and $NaHCO_3$ to a solution in a 10:1 w/w ratio to maintain the pH of the solution at about 7.5.

Any formula given herein is intended to represent compounds having structures depicted by the structural formula as well as certain variations or forms. In particular, compounds of any formula given herein may have asymmetric centers and therefore exist in different enantiomeric forms. All optical isomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers.

It is also to be understood that compounds that have the same molecular formula but differ in the nature or sequence of bonding of their atoms or the arrangement of their atoms in space are termed "isomers."

Stereoisomers that are not mirror images of one another are termed "diastereomers" and those that are non-superimposable mirror images of each other are termed "enantiomers." When a compound has an asymmetric center, for example, it is bonded to four different groups, and a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+)- or (−)-isomers respectively). A chiral compound can exist as either an individual enantiomer or as a mixture thereof. A mixture containing equal proportions of the enantiomers is called a "racemic mixture."

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenyl nitromethane, that are likewise formed by treatment with acid or base.

Tautomeric forms may be relevant to the attainment of the optimal chemical reactivity and biological activity of a compound of interest.

The compounds of this invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

Certain examples contain chemical structures that are depicted as an absolute enantiomer but are intended to indicate enantiopure material that is of unknown configuration. In these cases (R*) or (S*) is used in the name to indicate that the absolute stereochemistry of the corresponding stereocenter is unknown. Thus, a compound designated as (R*) refers to an enantiopure compound with an absolute configuration of either (R) or (S). In cases where the absolute stereochemistry has been confirmed the structures are named using (R) and (S).

The symbols ▬▬ and ◀▬ are used as meaning the same spatial arrangement in chemical structures shown herein. Analogously, the symbols ⦀⦀⦀⦀ and ·····⦀⦀⦀ are used as meaning the same spatial arrangement in chemical structures shown herein.

Additionally, any formula given herein is intended to refer also to hydrates, solvates, and polymorphs of such compounds, and mixtures thereof, even if such forms are not listed explicitly. Certain compounds of Formula (I) (as well as Formulas (IA), (IB), (IC), and (ID)), or pharmaceutically acceptable salts of compounds of Formula (I) (as well as Formulas (IA), (IB), (IC), and (ID)) may be obtained as solvates. Solvates include those formed from the interaction or complexation of compounds of the invention with one or more solvents, either in solution or as a solid or crystalline form. In some embodiments, the solvent is water and the solvates are hydrates. In addition, certain crystalline forms of compounds of Formula (I) (as well as Formulas (IA), (IB), (IC), and (ID)) or pharmaceutically acceptable salts of compounds of Formula (I) (as well as Formulas (IA), (IB), (IC), and (ID)) may be obtained as co-crystals. In certain embodiments of the invention, compounds of Formula (I) can be obtained in a crystalline form. In other embodiments, crystalline forms of compounds of Formula (I) can be cubic in nature. In other embodiments, pharmaceutically acceptable salts of compounds of Formula (I) can be obtained in a crystalline form. In still other embodiments, compounds of Formula (I) can be obtained in one of several polymorphic forms, as a mixture of crystalline forms, as a polymorphic form, or as an amorphous form. In other embodiments, compounds of Formula (I) can convert in solution between one or more crystalline forms and/or polymorphic forms.

Reference to a compound herein stands for a reference to any one of: (a) the actually recited form of such compound, and (b) any of the forms of such compound in the medium in which the compound is being considered when named. For example, reference herein to a compound such as R—COOH, encompasses reference to any one of, for example, R—COOH$_{(s)}$, R—COOH$_{(sol)}$, and R—COO$^-_{(sol)}$. In this example, R—COOH$_{(s)}$ refers to the solid compound, as it could be for example in a tablet or some other solid pharmaceutical composition or preparation; R—COOH$_{(sol)}$ refers to the undissociated form of the compound in a solvent; and R—COO$^-_{(sol)}$ refers to the dissociated form of the compound in a solvent, such as the dissociated form of the compound in an aqueous environment, whether such dissociated form derives from R—COOH, from a salt thereof, or from any other entity that yields R—COO$^-$ upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—COOH$_{(aq)}$ and/or R—COO$^-_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. No further examples in this regard are provided herein because these interactions and transformations in a given medium are known by any one of ordinary skill in the art.

In another example, a zwitterionic compound is encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI:27369 by the Chemical Entities of Biological Interest (ChEBI) dictionary of molecular entities. As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula H$_2$NCH$_2$COOH, and it exists in some media (in this case in neutral media) in the form of the zwitterion+H$_3$NCH$_2$COO$^-$. Zwitterions, zwitterionic compounds, inner salts and dipolar ions in the known and well-established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorus, sulfur, fluorine, chlorine, and iodine such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl, $^{125}$I, respectively. Such isotopically labeled compounds are useful in metabolic studies (preferably with $^{14}$C), reaction kinetic studies (with, for example deuterium (i.e., D or $^2$H); or tritium (i.e., T or $^3$H)), detection or imaging techniques [such as positron emission tomography (PET) or single-photon emission computed tomography (SPECT)] including drug or substrate tissue distribution assays, or in radioactive treatment of patients. In particular, an $^{18}$F or $^{11}$C labeled compound may be particularly preferred for PET or SPECT studies. Further, substitution with heavier isotopes such as deuterium (i.e., $^2$H) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$, and $S^2_{example}$ is one of $S_3$ and $S_4$" is accordingly used herein for the sake of brevity, but not by way of limitation. The foregoing first example on substituent terminology, which is stated in generic terms, is meant to illustrate the various substituent assignments described herein. The foregoing convention given herein for substituents extends, when applicable, to members such as $R^1$, $R^2$, $R^3$, $R^{3a}$, $R^4$, $R^a$, $R^b$, $R^c$, $R^d$, $R^{d1}$, $R^e$, $R^{e1}$, $R^{e2}$, $R^f$, $R^g$, $Z^1$, $Z^2$, $Z^3$, $HAL^1$, n, X, and ring A, and any other generic substituent symbol used herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$" is accordingly used herein for the sake of brevity, but not by way of limitation. The foregoing second example on substituent terminology, which is stated in generic terms, is meant to illustrate the various substituent assignments described herein. The foregoing convention given herein for substituents extends, when applicable, to members such as $R^1$, $R^2$, $R^3$, $R^{3a}$, $R^4$, $R^a$, $R^b$, $R^c$, $R^d$, $R^{d1}$, $R^e$, $R^{e1}$, $R^{e2}$, $R^f$, $R^g$, $Z^1$, $Z^2$, $Z^3$, $HAL^1$, n, X, and ring A, and any other generic substituent symbol used herein.

The nomenclature "$C_{i-j}$" with j>i, when applied herein to a class of substituents, is meant to refer to embodiments of this invention for which each and every one of the number of carbon members, from i to j including i and j, is independently realized. By way of example, the term $C_{1-4}$ refers independently to embodiments that have one carbon member ($C_1$), embodiments that have two carbon members ($C_2$), embodiments that have three carbon members ($C_3$), and embodiments that have four carbon members ($C_4$).

The term $C_{n-m}$alkyl refers to an aliphatic chain, whether straight or branched, with a total number N of carbon members in the chain that satisfies n≤N≤m, with m>n. Any disubstituent referred to herein is meant to encompass the various attachment possibilities when more than one of such possibilities are allowed. For example, reference to disubstituent -A-B—, where A≠B, refers herein to such disubstituent with A attached to a first substituted member and B attached to a second substituted member, and it also refers to such disubstituent with A attached to the second substituted member and B attached to the first substituted member.

The invention includes also pharmaceutically acceptable salts of the compounds of Formula (I) (as well as Formulas (IA), (IB), (IC), and (ID)), preferably of those described above and of the specific compounds exemplified herein, and methods of treatment using such salts.

The term "pharmaceutically acceptable" means approved or approvable by a regulatory agency of Federal or a state government or the corresponding agency in countries other than the United States, or that is listed in the U. S. Pharmacopoeia or other generally recognized pharmacopoeia for use in animals, and more particularly, in humans.

A "pharmaceutically acceptable salt" is intended to mean a salt of a free acid or base of compounds represented by Formula (I) (as well as Formulas (IA), (IB), (IC), and (ID)) that are non-toxic, biologically tolerable, or otherwise biologically suitable for administration to the subject. It should possess the desired pharmacological activity of the parent compound. See, generally, G. S. Paulekuhn, et al., "Trends in Active Pharmaceutical Ingredient Salt Selection based on Analysis of the Orange Book Database", *J. Med. Chem.*, 2007, 50:6665-72, S. M. Berge, et al., "Pharmaceutical Salts", *J Pharm Sci.*, 1977, 66:1-19, and *Handbook of Pharmaceutical Salts, Properties, Selection, and Use*, Stahl and Wermuth, Eds., Wiley-VCH and VHCA, Zurich, 2002. Examples of pharmaceutically acceptable salts are those that are pharmacologically effective and suitable for contact with the tissues of patients without undue toxicity, irritation, or allergic response. A compound of Formula (I) (as well as Formulas (IA), (IB), (IC), and (ID)) may possess a sufficiently acidic group, a sufficiently basic group, or both types of functional groups, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

When the compounds of Formula (I) (as well as Formulas (IA), (IB), (IC), and (ID)) contain a basic nitrogen, the desired pharmaceutically acceptable salt may be prepared by any suitable method available in the art. For example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutaric acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

When the compound of Formula (I) (as well as Formulas (IA), (IB), (IC), and (ID)) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as N-methyl-D-glucamine, lysine, choline, glycine and arginine, ammonia, carbonates, bicarbonates, primary, secondary, and tertiary amines, and cyclic amines, such as tromethamine, benzylamines, pyrrolidines, piperidine, morpholine, and piperazine, and inorganic salts derived from sodium, calcium, potassium, magnesium, manganese, iron, copper, zinc, aluminum, and lithium.

The invention also relates to pharmaceutically acceptable prodrugs of the compounds of Formula (I) (as well as Formulas (IA), (IB), (IC), and (ID)), and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "*Design of Prodrugs*", ed. H. Bundgaard, Elsevier, 1985.

Exemplary prodrugs include compounds having an amino acid residue, or a polypeptide chain of two or more (e.g., two, three or four) amino acid residues, covalently joined through an amide or ester bond to a free amino, hydroxyl, or carboxylic acid group of a compound of Formula (I) (as well as Formulas (IA), (IB), (IC), and (ID)). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) (as well as Formulas (IA), (IB), (IC), and (ID)) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl) amines. Examples of esters of the invention include $C_{1-7}$alkyl, $C_{5-7}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in Fleisher et al., *Adv. Drug Delivery Rev.* 1996, 19, 115-130. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in Robinson et al., *J Med Chem.* 1996, 39 (1), 10-18. Free amines can also be derivatized as amides, sulfonamides or phosphonamides. All of these prodrug moieties may incorporate groups including ether, amine, and carboxylic acid functionalities.

The present invention also relates to pharmaceutically active metabolites of the compounds of Formula (I) (as well as Formulas (IA), (IB), (IC), and (ID)), which may also be used in the methods of the invention. A "pharmaceutically active metabolite" means a pharmacologically active product of metabolism in the body of a compound of Formula (I) (as well as Formulas (IA), (IB), (IC), and (ID) as applicable) or salt thereof. Prodrugs and active metabolites of a compound may be determined using routine techniques known or available in the art. See, e.g., Bertolini, et al., *J Med Chem.* 1997, 40, 2011-2016; Shan, et al., *J Pharm Sci.* 1997, 86 (7), 765-767; Bagshawe, *Drug Dev Res.* 1995, 34, 220-230; Bodor, *Adv Drug Res.* 1984, 13, 224-331; Bundgaard, *Design of Prodrugs* (Elsevier Press, 1985); and Larsen, *Design and Application of Prodrugs, Drug Design and Development* (Krogsgaard-Larsen, et al., eds., Harwood Academic Publishers, 1991).

The compounds of Formula (I) (as well as Formulas (IA), (IB), (IC), and (ID)) and their pharmaceutically acceptable salts, pharmaceutically acceptable prodrugs, and pharmaceutically active metabolites of the present invention are useful as modulators of the NR2B receptor in the methods of the invention. As such modulators, the compounds may act as antagonists, agonists, or inverse agonists. The term "modulators" include both inhibitors and activators, where "inhibitors" refer to compounds that decrease, prevent, inactivate, desensitize, or down-regulate the NR2B receptor expression or activity, and "activators" are compounds that increase, activate, facilitate, sensitize, or up-regulate NR2B receptor expression or activity.

The term "treat", "treatment" or "treating", as used herein, is intended to refer to administration of an active agent or composition of the invention to a subject for the purpose of affecting a therapeutic or prophylactic benefit through modulation of NR2B receptor activity. Treating includes reversing, ameliorating, alleviating, inhibiting the progress of, lessening the severity of, or preventing a disease, disorder, or condition, or one or more symptoms of such disease, disorder or condition mediated through modulation of NR2B receptor activity. The term "subject" refers to a mammalian patient in need of such treatment, such as a human.

Accordingly, the invention relates to methods of using the compounds described herein to treat subjects diagnosed with or suffering from a disease, disorder, or condition mediated by NR2B receptor activity, such as: bipolar disorder I depressed, hypomanic, manic and mixed form; bipolar disorder II; depressive disorders, such as single depressive episode or recurrent major depressive disorder, minor depressive disorder, treatment-resistant depression, depressive disorder with postpartum onset, disruptive mood dysregulation disorder, depressive disorders with psychotic symptoms; persistent mood disorders, such as cyclothymia, dysthymia, euthymia; and premenstrual dysphoric disorder; anxiety disorders, general anxiety disorder, panic disorder with or without agoraphobia, specific phobia, social anxiety disorder, chronic anxiety disorders; obsessive compulsive disorder; reaction to sever stress and adjustment disorders, such as post-traumatic stress disorder (PTSD); other neurotic disorders such as depersonalisation-derealisation syndrome; pervasive developmental disorders, including but not limited to Asperger's syndrome and Rett's syndrome, autistic disorders, childhood autism and overactive disorder associated with mental retardation and stereotyped movements, specific developmental disorder of motor function, specific developmental disorders of scholastic skills; postnatal (postpartum) and prenatal depression; eating disorders, including but not limited to anorexia nervosa, bulimia nervosa, pica and binge eating disorder; Parkinson's disease; second Parkinsonism, such as postencephalitic Parkinsonism; Parkinsonism comprised in other disorders; Lewis body disease; degenerative diseases of the basal ganglia; other extrapyramidal and movement disorders including but not limited to tremor, essential tremor and drug-induced tremor, myoclonus, chorea and drug-induced chorea, drug-induced tics and tics of organic origin, drug-induced acute dystonia, drug-induced tardive dyskinesia, L-dopa-induced dyskinesia; neuroleptic-induced movement disorders including but not limited to neuroleptic malignant syndrome (NMS), neuroleptic induced parkinsonism, neuroleptic-induced early onset or acute dyskinesia, neuroleptic-induced acute dystonia, neuroleptic-induced acute akathisia, neuroleptic-induced tardive dyskinesia, neuroleptic-induced tremor; restless leg syndrome, Stiff-man syndrome; dystonia including but not limited to focal dystonia, multiple-focal or segmental dystonia, torsion dystonia, hemispheric, generalized and tardive dystonia (induced by psychopharmacological drugs). Focal dystonia include cervical dystonia (torticolli), blepharospasm (cramp of the eyelid), appendicular dystonia (cramp in the extremities, like the writer's cramp), oromandibular dystonia and spasmodic dysphonia (cramp of the vocal cord); epilepsy, including localization-related (focal)(partial) idiopathic epilepsy and epileptic syndromes with seizures of localized onset, localization-related (focal)(partial) symptomatic epilepsy and epileptic syndromes with simple partial seizures, localization-related (focal)(partial) symptomatic epilepsy and epileptic syndromes with complex partial seizures, generalized idiopathic epilepsy and epileptic syndromes including but not limited to myoclonic epilepsy in infancy, neonatal convulsions (familial), childhood absence epilepsy (pyknolepsy), epilepsy with grand mal seizures on awakening, absence epilepsy, myoclonic epilepsy (impulsive petit mal) and nonspecific atonic, clonic, myoclonic, tonic, tonic-clonic epileptic seizures; epilepsy with myoclonic absences, myoclonic-astatic seizures, infantile spasms, Lennox-Gastaut syndrome, Salaam attacks, symptomatic early myoclonic encephalopathy, West's syndrome, petit and grand mal seizures; status epilepticus; persistent somatoform disorders; acute, chronic and chronic intractable pain, headache; acute and chronic pain related to physiological processes and physical disorders including but not limited to back pain, tooth pain, abdominal pain, low back pain, pain in joints; acute and chronic pain that is related to diseases of the musculoskeletal system and connective tissue including, but not limited to rheumatism, myalgia, neuralgia and fibromyalgia; acute and chronic pain that is related to nerve, nerve root and plexus disorders, such as trigeminal pain, postzoster neuralgia, phantom limb syndrome with pain, carpal tunnel syndrome, lesion of sciatic nerve, diabetic mononeuropathy; acute and chronic pain that is related to polyneuropathies and other disorders of the peripheral nervous system, such as hereditary and idiopathic neuropathy, inflammatory polyneuropathy, polyneuropathy induced by drugs, alcohol or toxic agents, polyneuropathy in neoplastic disease, diabetic polyneuropathy; and acute neurodegeneration, such as intracranial brain injuries, such as stroke, diffuse and local brain injuries, epidural, subdural and subarachnoid haemorrhage, and chronic neurodegeneration, such as Alzheimer's disease, Huntington's disease, multiple sclerosis, and ALS; subarachnoid haemorrhage, intracerebral haemorrhage and other nontraumatic intracranial haemorrhage, cerebral infarction, stroke, occlusion and stenosis or precerebral and cerebral arteries, not resulting in cerebral infarction, dissection of cerebral arteries, cerebral aneurysm, cerebral atherosclerosis, progressive vascular leukoencephalopathy, hypertensive encephalopathy, non-pyogenic thrombosis of intracranial venous system, cerebral arteritis, cerebral amyloid angiopathy and sequelae of cerebrovascular diseases; glaucoma and other neuropathies; dementias, vascular dementia, Lewy body dementia, frontotemporal dementia, and HIV-dementia; vertigo and nystagmus; tinnitus; neuropsychiatric systemic lupus erythematosus; disruptive mood dysregulation disorder; schizophrenia spectrum disorder; and sleep/wake disorders. In specific embodiments, subjects that can be treated according to the present invention are diagnosed with or suffering from major depressive disorder, treatment-resistant depression and bipolar disorder.

In treatment methods according to the invention, an effective amount of a pharmaceutical agent according to the invention is administered to a subject suffering from or diagnosed as having such a disease, disorder, or condition. An "effective amount" means an amount or dose sufficient to generally bring about the desired therapeutic or prophylactic benefit in patients in need of such treatment for the designated disease, disorder, or condition. Effective amounts or doses of the compounds of the present invention may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the active agents of the invention may be used in combination with additional active ingredients in the treatment of the above conditions. For example, the additional active ingredients may be co-administered separately with an active agent of compounds of Table 1 (as well as Table 2, and Table 3) or included with such an agent in a pharmaceutical composition according to the invention. In an exemplary embodiment, additional active ingredients are those that are known or discovered to be effective in the treatment of conditions, disorders, or diseases mediated by NR2B activity, such as another NR2B modulator or a compound active against another target associated with the particular condition, disorder, or disease. The combination may serve to increase efficacy (e.g., by including in the combination a compound potentiating the potency or effectiveness of an active agent according to the invention), decrease one or more side effects, or decrease the required dose of the active agent according to the invention.

The active agents of the invention can be used, alone or in combination with one or more additional active ingredients, to formulate pharmaceutical compositions of the invention. A pharmaceutical composition of the invention can comprise: (a) at least one active agent in accordance with the invention (e.g., an effective amount for treating a specific disease, disorder, or medical condition); and (b) a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the invention can be provided in the form of tablets or capsules, or as a solution, emulsion, or suspension. To prepare the oral compositions, the compounds may be formulated to yield a dosage of, e.g., from about 0.05 to about 100 mg/kg daily, or from about 0.05 to about 35 mg/kg daily, or from about 0.1 to about 10 mg/kg daily. For example, a total daily dosage of about 5 mg to 5 g daily may be accomplished by dosing once, twice, three, or four times per day.

Oral tablets may include a compound according to the invention mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, compounds of the invention may be mixed with a solid, semisolid, or liquid diluent. Soft gelatin capsules may be prepared by mixing the compound of the invention with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, the compositions may be formulated for rectal administration as a suppository. For parenteral use, including intravenous, intramuscular, intraperitoneal, or subcutaneous routes, the compounds of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 µg/kg/minute of compound, admixed with a pharmaceutical carrier over a period ranging from several minutes to several days.

For topical administration, the compounds may be mixed with a pharmaceutical carrier at a concentration of about 0.1% to about 10% of drug to vehicle. Another mode of administering the compounds of the invention may utilize a patch formulation to affect transdermal delivery.

Compounds of the invention may alternatively be administered in methods of this invention by inhalation, via the nasal or oral routes, e.g., in a spray formulation also containing a suitable carrier.

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between the melting point and the reflux temperature of the solvent, and preferably between 0° C. and the reflux temperature of the solvent. Reactions may be heated employing conventional heating or microwave heating. Reactions may also be conducted in sealed pressure vessels above the normal reflux temperature of the solvent.

Abbreviations and acronyms used herein include the following:

TABLE 3

| Term | Acronym |
|---|---|
| Acetonitrile | ACN |
| Aqueous | aq |
| Atmosphere | atm |
| n-Butanol | n-BuOH |
| tert-Butylcarbamoyl | Boc |
| Broad | br |
| Diatomaceous Earth | Celite ® |
| (1-Cyano-2-ethoxy-2-oxoethylidenaminooxy)dimethylamino-morpholino-carbenium hexafluorophosphate | COMU |
| Dichloromethane | DCM |
| Diisopropylethylamine | DIPEA, DIEA, or Hunig's base |
| 4-Dimethylaminopyridine | DMAP |
| N,N-Dimethylformamide | DMF |
| Dimethylsulfoxide | DMSO |
| 1,1'-Bis(diphenylphosphino)ferrocene | dppf |
| 1-Ethyl-3-(3-dimethylaminopropyl)carbodiimide | EDCI, EDAC, or EDC |
| Diethyl ether | Ether, $Et_2O$ |
| Ethyl Acetate | EtOAc, or EA |
| Ethanol | EtOH |
| Electrospray ionization | ESI |
| Normal-phase silica gel chromatography | FCC |
| Grams | g |
| Hours | h |
| 1-[Bis(dimethylamino)methylene]-1H-1,2,3-triazolo[4,5-b]pyridinium 3-oxid hexafluorophosphate | HATU |
| N,N,N',N'-Tetramethyl-O-(1H-benzotriazol-1-yl)uronium hexafluorophosphate | HBTU |
| Hydroxybenzotriazole | HOBt |
| High-pressure liquid chromatography | HPLC |
| Hertz | Hz |
| Isopropyl alcohol | iPrOH, IPA |
| Liquid chromatography and mass spectrometry | LCMS |
| Lithium bis(trimethylsilyl)amide | LHMDS |
| Molar | M |
| Mass to charge ratio | m/z |
| Methanol | MeOH |
| Milligrams | mg |
| Minute | min |
| Milliliter | mL |
| Microliter | µL |
| Millimoles | mmol |
| Mass spectrometry | MS |
| Normal | N |
| Nuclear magnetic resonance | NMR |
| Palladium(II)bis(triphenylphosphine) dichloride | $Pd(PPh_3)_2Cl_2$ |
| Tetrakis(triphenylphosphine)palladium(0) | $Pd(PPh_3)_4$ |
| Tris(dibenzylideneacetone)dipalladium(0) | $Pd_2(dba)_3$ |
| [1,1'-Bis(di-tert-butylphosphino)ferrocene]dichloropalladium(II) | $PdCl_2(dtbpf)$ or $Pd(dtbpf)_2Cl_2$ |
| [1,1'-Bis(diphenylphosphino)ferrocene]-dichloropalladium(II) | $PdCl_2(dppf)$ or $Pd(dppf)_2Cl_2$ |
| Palladium(II) acetate | $Pd(OAc)_2$ |
| Parts per million | ppm |
| Precipitate | ppt |
| Polytetrafluoroethylene | PTFE |
| Retention time | $R_t$ |
| Room temperature | rt |
| Saturated | sat |
| Supercritical Fluid Chromatography | SFC |
| Temperature | T |
| Triethylamine | TEA |
| Trifluoroacetic acid | TFA |
| Tetrahydrofuran | THF |
| Thin layer chromatography | TLC |
| Volume in milliliters of solvent per gram of substrate | V, or volumes |
| 4,5-bis(diphenylphosphino)-9,9-dimethylxanthene | XantPhos |

PREPARATIVE EXAMPLES

Exemplary compounds useful in methods of the invention will now be described by reference to the illustrative synthetic schemes for their general preparation below and the specific examples to follow.

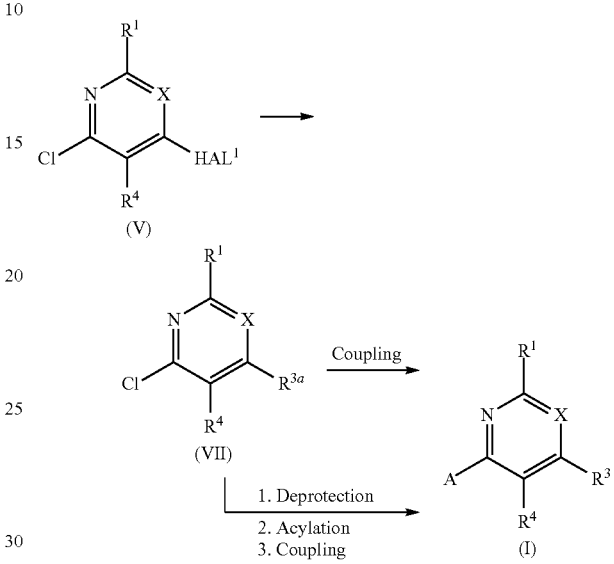

SCHEME 1

According to SCHEME 1, a compound of formula (VII) is prepared from a compound of formula (V), where $HAL^1$ is Cl, F, or I; $R^1$ is H, $C_{1-4}$alkyl, or $CH_2OH$; X is N or $C-R^2$, where $R^2$ is H, or F; and $R^4$ is H or $CH_3$; by reaction with an optionally substituted alkyl-amine or a substituted 4-8 membered cyclic, bridged, or spirocyclic amine such as azetidine, pyrrolidine, piperidine, and the like; a base such as DIPEA, TEA, and the like, in a solvent such as n-BuOH, EtOH, THF, and the like, at a temperature ranging from 80 to 160° C., employing microwave or conventional heating, for a period of about 30 min to 48 h, to provide a compound of formula (VII), where $R^{3a}$ is an optionally substituted alkyl-amine or a substituted 4-8 membered cyclic, bridged, or spirocyclic amine.

In the instance where a compound of formula (VII), where $R^{3a}$ is a substituted alkyl-amine or a substituted 4-8 membered cyclic, bridged, or spirocyclic amine, such as tert-butyl ((3S,4S)-3-fluoropiperidin-4-yl)carbamate, tert-butyl 2,6-diazaspiro[3.3]heptane-2-carboxylate, and the like (where the protecting group is a suitable nitrogen protecting group such as tert-butyl carbamate, and the like); is deprotected under conditions known to one skilled in the art. For example, deprotection of the nitrogen protecting group is achieved by reaction with an acid such as TFA, HCl, and the like, in a suitable solvent such as DCM, and the like, at rt. The deprotected amine moiety is acetylated, employing conditions known to one skilled in the art, for example employing acetic anhydride; a catalyst such as DMAP, and the like; in a suitable solvent such as pyridine, at room temperature, for a period of 10-24 h. Acetylation conditions such as, employing acetyl chloride, a base such as sodium carbonate, in a suitable solvent such as THF/water may also be used. The $R^{3a}$ amine moiety can be deprotected and acetylated either prior to the metal-mediated cross coupling or after the coupling.

A compound of formula (VII) is reacted in a metal-mediated cross coupling reaction to provide a compound of Formula (I), where A is phenyl substituted with 1-3 substituents independently selected from halo, $C_{1-4}$alkyl, $CH_2OH$, $OC_{1-4}$alkyl, $C_{1-4}$haloalkyl, $OC_{1-4}$haloalkyl, and (C=O)$CH_3$. For example, a compound of formula (VII), is reacted with a suitably substituted commercially available or synthetically accessible aryl boronic acid, boronate ester, and the like, in the presence of a palladium catalyst such as $PdCl_2$(dtbpf), Pd(PPh$_3$)$_4$, $PdCl_2$(dppf), Pd(PPh$_3$)$_2$Cl$_2$, Pd(OAc)$_2$, and the like; with or without the addition of a ligand such as DPPF; a base such as $K_3PO_4$, $K_2CO_3$, aq. $Na_2CO_3$, $Na_2CO_3$, $Cs_2CO_3$, and the like; in a suitable solvent such as 1,2-dimethoxyethane, 1,4-dioxane, DMF, water, or a mixture thereof; at a temperature ranging from 60 to 180° C., employing microwave or conventional heating; for a period of about 30 min to 16 h, to provide a compound of Formula (I).

The $R^{3a}$ amine moiety can be deprotected and acetylated either prior to the metal-mediated cross coupling or after the coupling.

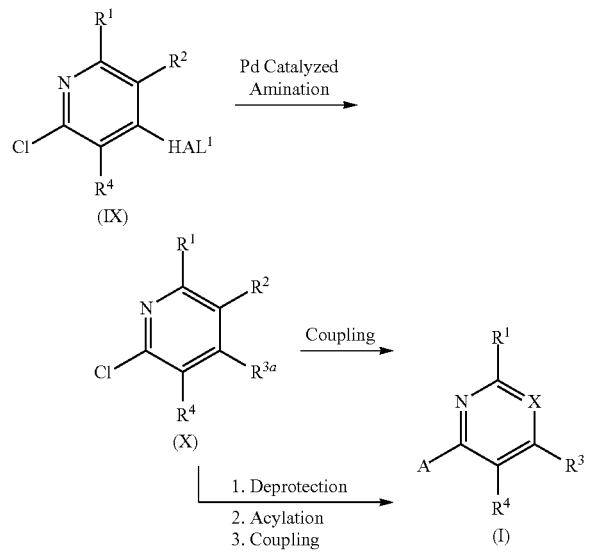

SCHEME 2

According to SCHEME 2, a compound of formula (IX), where $R^1$ is H; $HAL^1$ is I, $R^2$ is H or F; and $R^4$ is H; is reacted with an optionally substituted alkyl-amine or a substituted 4-8 membered cyclic, bridged, or spirocyclic amine such as azetidine, pyrrolidine, piperidine, and the like; under Pd-catalyzed amination of heteroaryl halide conditions. For example, 2-chloro-5-fluoro-4-iodopyridine is reacted with a substituted 4-8 membered cyclic, bridged, or spirocyclic amine such as N-(piperidin-4-yl)acetamide, and the like; a palladium catalyst such as Pd$_2$(dba)$_3$, Pd(OAc)$_2$, and the like; a ligand such as 4,5-bis(diphenylphosphino)-9,9-dimethylxanthene (XantPhos), or (±)-2,2'-bis(diphenylphosphino)-1,1'-binaphthalene (rac-BINAP); a base such as Cs$_2$CO$_3$, LHMDS, NaOtBu, K$_3$PO$_4$, and the like; in a suitable solvent such as toluene, THF, DMF, dioxane, or a mixture thereof; at temperatures ranging from 80-150° C., employing microwave or conventional heating; for a period of 0.5 h to 18 h; to provide a compound of formula (X).

Subsequent coupling with a suitably substituted commercially available or synthetically accessible aryl boronic acid, boronate ester, under conditions previously described provides a compound of Formula (I). For example, N-(1-(2-chloropyridin-4-yl)piperidin-4-yl)acetamide, is reacted with (4-(difluoromethyl)phenyl)boronic acid, in the presence of a palladium catalyst (2-dicyclohexylphosphino-2',6'-diisopropoxy-1,1'-biphenyl)[2-(2'-amino-1,1'-biphenyl)]palladium(II) methanesulfonate (RuPhos Pd G3), a base such as Cs$_2$CO$_3$, in dioxane, at 100° C. for 16 hours, to provide a compound of Formula (I).

The $R^{3a}$ amine moiety can be deprotected and acetylated either prior to the metal mediated cross coupling or after the coupling.

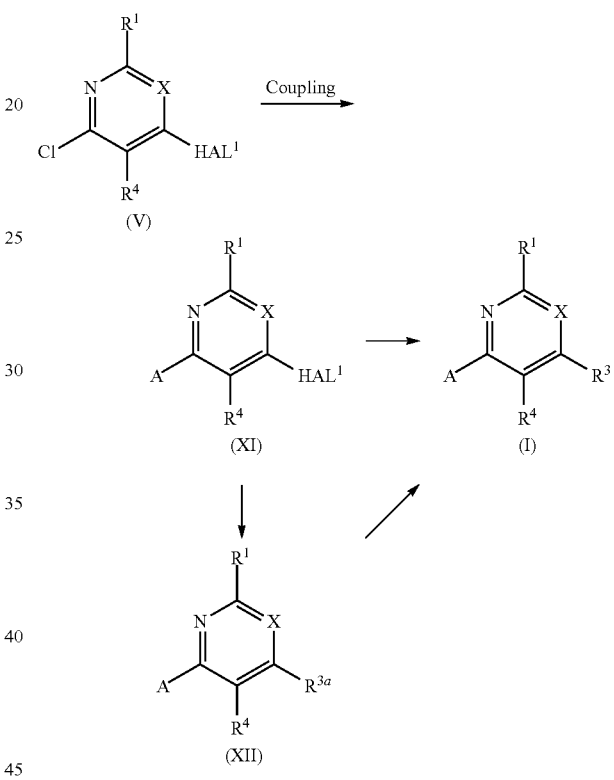

SCHEME 3

According to SCHEME 3, a compound of formula (XI) is prepared from a compound of formula (V), where $HAL^1$ is Cl or F, and $R^1$, $R^4$, and X are as defined in aspect 1; and a suitably substituted commercially available or synthetically accessible aryl boronic acid, boronate ester; employing a metal-mediated cross coupling reaction as previously described. A compound of Formula (I) (as well as a compound of formula (XII) is prepared from a compound of formula (XI), a base such as DIPEA, NaH, and the like, and tert-butyl ((1,4-cis)-4-hydroxycyclohexyl)carbamate, an optionally substituted alkyl-amine or a substituted 4-8 membered cyclic, bridged, or spirocyclic amine, employing conditions previously described.

A compound of Formula (I), is prepared from a compound of formula (XII), where $R^{3a}$ is an alkyl-amine or a 4-8 membered cyclic, bridged, or spirocyclic amine with a functional group that can be further elaborated (such as $R^{3a}$ is a pyrrolidine substituted with $CO_2H$, and piperidine substituted with $NH_2$), under conventional amide bond forming techniques such as coupling reactions which are well known to those skilled in the art.

For example, reaction of a compound of formula (XII), where $R^{3a}$ is piperidine substituted with $NH_2$, is reacted with a suitable acid such as 3-((tert-butoxycarbonyl)amino)propanoic acid, cyclopropane carboxylic acid, and the like; a suitable coupling agent such as COMU, HBTU, HATU, and the like; in a suitable solvent such as DCM, THF, DMF and the like, optionally in the presence of a tertiary amine such as N-methylmorpholine, N-ethyldiisopropylamine (DIEA, DIPEA), or triethylamine (TEA); at a temperature ranging from about 0° C. to rt; to provide a compound of Formula (I), where $R^3$ is piperidine substituted with cyclopropanecarboxamide, or propanamide. In a similar fashion, a compound of formula (XII), where $R^{3a}$ is pyrrolidine substituted with $CO_2H$, is reacted with a suitable amine such as methylamine; a suitable coupling agent such as COMU, HBTU, HATU, and the like; in a suitable solvent such as DCM, THF, DMF and the like, optionally in the presence of a tertiary amine such as N-methylmorpholine, N-ethyldiisopropylamine (DIEA, DIPEA), or triethylamine (TEA), at a temperature ranging from about 0° C. to rt, to provide a compound of Formula (I), where $R^3$ is N-methyl-pyrrolidine-3-carboxamide.

The $R^{3a}$ amine moiety can be deprotected and acetylated either prior to the metal-mediated cross coupling or after the coupling.

According to SCHEME 4, a compound of formula (VII) undergoes a Curtius rearrangement employing conditions known to one skilled in the art, to provide a compound of formula (XIII). For example, a compound of formula (VII), where $R^1$ and $R^4$ are H; and $R^{3a}$ is an azetidine substituted with $CO_2H$, is reacted with diphenyl phosphorazidate (DPPA), in a suitable solvent such as toluene, at a temperature of about 70° C., to form the isocyanate intermediate. The isocyanate intermediate is further reacted with benzyl alcohol, at a temperature of about 90° C., for a period of 16-20 h, to provide a Cbz-protected compound of formula (XIII). Coupling of a compound of formula (XIII) with a suitably substituted commercially available or synthetically accessible aryl boronic acid, boronate ester; employing a metal-mediated cross coupling reaction as previously described, provides a compound of formula (XIV). A compound of Formula (I) is prepared in two steps from a compound of formula (XIV). In a first step, Cbz deprotection of a compound of formula (XIV) is achieved employing hydrogenation conditions. In a second step, acetylation of the deprotected amine, employing acetylation conditions previously described, provides a compound of Formula (I).

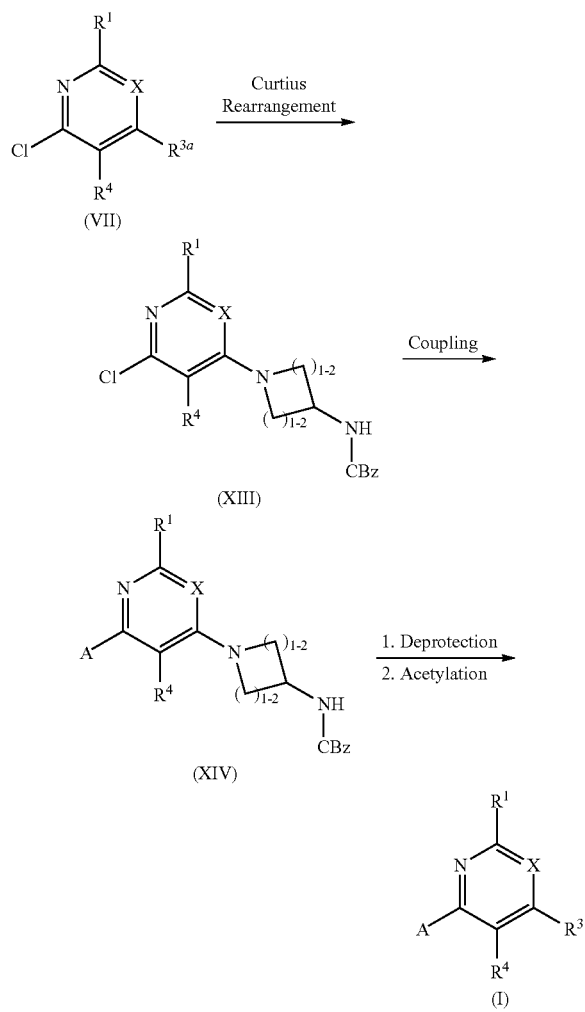

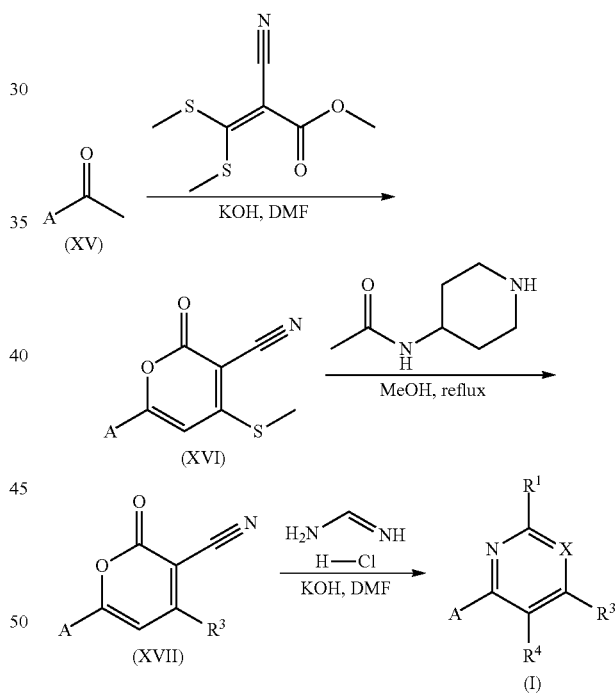

According to SCHEME 5, methyl 2-cyano-3,3-bis(methylthio)acrylate is treated with an aromatic ketone of formula (XV), where A is a phenyl ring substituted with 1-3 substituents as defined in aspect 1; a base such as KOH; in a suitable solvent such as DMF, and the like; to provide an aryl-2-pyranone compound of formula (XVI). The methylthio group on the pyranone ring of a compound of formula (XVI) is readily displaced with a suitable secondary amine nucleophile such as N-(piperidin-4-yl)acetamide, and the like; in a suitable solvent such as MeOH, and the like; to provide a compound of formula (XVII). A compound of formula (XVII), is reacted with formimidamide hydrochloride; a base such as KOH, TEA, and the like; in a suitable solvent such as DMF; at elevated temperature; provided a pyridine compound of Formula (I).

Compounds of Formula (I) may be converted to their corresponding salts using methods known to one of ordinary skill in the art. For example, an amine of Formula (I) is treated with trifluoroacetic acid, HCl, or citric acid in a solvent such as $Et_2O$, $CH_2Cl_2$, THF, MeOH, chloroform, or isopropanol to provide the corresponding salt form. Alternately, trifluoroacetic acid or formic acid salts are obtained as a result of reverse phase HPLC purification conditions. Cyrstalline forms of pharmaceutically acceptable salts of compounds of Formula (I) may be obtained in crystalline form by recrystallization from polar solvents (including mixtures of polar solvents and aqueous mixtures of polar solvents) or from non-polar solvents (including mixtures of non-polar solvents).

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Compounds prepared according to the schemes described above may be obtained as single forms, such as single enantiomers, by form-specific synthesis, or by resolution. Compounds prepared according to the schemes above may alternately be obtained as mixtures of various forms, such as racemic (1:1) or non-racemic (not 1:1) mixtures. Where racemic and non-racemic mixtures of enantiomers are obtained, single enantiomers may be isolated using conventional separation methods known to one of ordinary skill in the art, such as chiral chromatography, recrystallization, diastereomeric salt formation, derivatization into diastereomeric adducts, biotransformation, or enzymatic transformation. Where regioisomeric or diastereomeric mixtures are obtained, as applicable, single isomers may be separated using conventional methods such as chromatography or crystallization.

The following specific examples are provided to further illustrate the invention and various preferred embodiments.

EXAMPLES

In obtaining the compounds described in the examples below and the corresponding analytical data, the following experimental and analytical protocols were followed unless otherwise indicated.

Unless otherwise stated, reaction mixtures were magnetically stirred at room temperature (rt) under a nitrogen atmosphere. Where solutions were "dried," they were generally dried over a drying agent such as $Na_2SO_4$ or $MgSO_4$. Where mixtures, solutions, and extracts were "concentrated", they were typically concentrated on a rotary evaporator under reduced pressure. Reactions under microwave irradiation conditions were carried out in a Biotage Initiator or CEM (Microwave Reactor) Discover instrument.

For the reactions conducted under continuous flow conditions, "flowed through a LTF-VS mixer" refers to the use of a Chemyx Fusion 100 Touch Syringe Pump that is in line via ¹⁄₁₆" PTFE tubing to a LTF-VS mixer (Little Things Factory GmbH (http://www.ltf-gmbh.com), unless otherwise indicated.

Normal-phase silica gel chromatography (FCC) was performed on silica gel ($SiO_2$) using prepacked cartridges.

Preparative reverse-phase high performance liquid chromatography (RP HPLC) was performed on either:

METHOD A. An Agilent HPLC with an Xterra Prep RP18 column (5 μM, 30×100 or 50×150 mm) or an XBridge C18 OBD column (5 μM, 30×100 or 50×150 mm), and a mobile phase of 5% ACN in 20 mM $NH_4OH$ was held for 2 min, then a gradient of 5-99% ACN over 15 min, then held at 99% ACN for 5 min, with a flow rate of 40 or 80 mL/min.

or

METHOD B. A Shimadzu LC-8A Series HPLC with an Inertsil ODS-3 column (3 μm, 30×100 mm, T=45° C.), mobile phase of 5% ACN in $H_2O$ (both with 0.05% TFA) was held for 1 min, then a gradient of 5-99% ACN over 6 min, then held at 99% ACN for 3 min, with a flow rate of 80 mL/min.

or

METHOD C. A Shimadzu LC-8A Series HPLC with an XBridge C18 OBD column (5 μm, 50×100 mm), mobile phase of 5% ACN in $H_2O$ (both with 0.05% TFA) was held for 1 min, then a gradient of 5-99% ACN over 14 min, then held at 99% ACN for 10 min, with a flow rate of 80 mL/min.

or

METHOD D. A Gilson HPLC with an XBridge C18 column (5 μm, 100×50 mm), mobile phase of 5-99% ACN in 20 mM $NH_4OH$ over 10 min and then hold at 99 ACN for 2 min, at a flow rate of 80 mL/min.

Preparative supercritical fluid high performance liquid chromatography (SFC) was performed either on a Jasco preparative SFC system, an APS 1010 system from Berger instruments, or a SFC-PICLAB-PREP 200 (PIC SOLUTION, Avignon, France). The separations were conducted at 100 to 150 bar with a flow rate ranging from 40 to 60 mL/min. The column was heated to 35 to 40° C.

Mass spectra (MS) were obtained on an Agilent series 1100 MSD using electrospray ionization (ESI) in positive mode unless otherwise indicated. Calculated (calcd.) mass corresponds to the exact mass.

Nuclear magnetic resonance (NMR) spectra were obtained on Bruker model DRX spectrometers. Definitions for multiplicity are as follows: s=singlet, d=doublet, t=triplet, q=quartet, m=multiplet, br=broad. It will be understood that for compounds comprising an exchangeable proton, said proton may or may not be visible on an NMR spectrum depending on the choice of solvent used for running the NMR spectrum and the concentration of the compound in the solution.

Chemical names were generated using ChemDraw Ultra 12.0, ChemDraw Ultra 14.0 (CambridgeSoft Corp., Cambridge, Mass.) or ACD/Name Version 10.01 (Advanced Chemistry).

Compounds designated as R* or S* are enantiopure compounds where the absolute configuration was not determined.

Intermediate 1: 4,4,5,5-Tetramethyl-2-(4-(trifluoromethoxy)-3-(trifluoromethyl)phenyl)-1,3,2-dioxaborolane

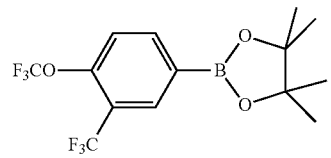 [SMILES: CC1(C)OB(c2ccc(OC(F)(F)F)c(C(F)(F)F)c2)OC1(C)C]

A solution of 4-bromo-1-(trifluoromethoxy)-2-(trifluoromethyl)benzene (340 mg, 1.1 mmol), 4,4,4',4',5,5,5',5'-octamethyl-2,2'-bi(1,3,2-dioxaborolane) (307 mg, 1.21 mmol), potassium acetate (324 mg, 3.3 mmol) and PdCl$_2$(PPh$_3$)$_2$ (39 mg, 0.55 mmol) in dioxane (11 mL) was degassed for 5 minutes with nitrogen then stirred at 90° C. for 3 hours. The crude mixture was cooled to room temperature, diluted with EtOAc, and filtered through Celite®. The organic phase was washed with water, then brine, dried over MgSO$_4$, filtered, and concentrated under reduced pressure. Purification via silica gel chromatography (0-30% EtOAc in hexanes) gave the title compound (209 mg, 53%). $^1$H NMR (400 MHz, Chloroform-d) δ ppm 1.28 (s, 12H), 7.34-7.29 (m, 1H), 8.06 (d, J=1.6 Hz, 1H), 7.96-7.92 (m, 1H).

Intermediate 2: 2-(3-(Difluoromethyl)-4-fluorophenyl)-4,4,5,5-tetramethyl-1,3,2-dioxaborolane

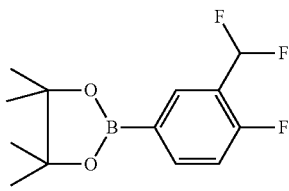 [SMILES: CC1(C)OB(c2ccc(F)c(C(F)F)c2)OC1(C)C]

The title compound was prepared in a manner analogous to Intermediate 1, using 4-bromo-2-(difluoromethyl)-1-fluorobenzen instead of 4-bromo-1-(trifluoromethoxy)-2-(trifluoromethyl)benzene. MS (ESI): mass calcd. for C$_{13}$H$_{16}$BF$_3$O$_2$, 272.1; m/z found, 273.0 [M+H]$^+$. $^1$H NMR (500 MHz, Chloroform-d) δ ppm 8.07-8.02 (m, 1H), 7.94-7.87 (t, J=7.0 Hz, 1H), 7.16-7.08 (m, 1H), 7.01-6.75 (t, J=55.0 Hz, 1H), 1.38-1.33 (s, 12H).

Intermediate 3: N-(3-(Aminomethyl)bicyclo[1.1.1]pentan-1-yl)acetamide trifluoroacetic Salt

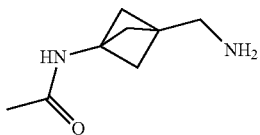

Step A: tert-Butyl ((3-acetamidobicyclo[1.1.1]pentan-1-yl)methyl)carbamate

To a solution of tert-butyl ((3-aminobicyclo[1.1.1]pentan-1-yl)methyl)carbamate (100 mg, 0.47 mmol) in pyridine (4.7 mL) was added acetic anhydride (89 μL, 0.94 mmol) and 4-dimethylaminopyridine (DMAP) (3 mg, 0.024 mmol). The reaction mixture was stirred at room temperature for 16 hours. The solvent was concentrated under reduced pressure and the residue was dissolved in EtOAc. The EtOAc phase was washed with a sat. (aq.) NaHCO$_3$ and the aqueous phase was then extracted with EtOAc (2x). The combined organic layers were dried over MgSO$_4$, filtered, and concentrated under reduced pressure to afford the title compound (119 mg, quant.) which was used in the next step without any further purification. MS (ESI): mass calcd. for C$_{13}$H$_{22}$N$_2$O$_3$, 254.2; m/z found, 255.2 [M+H]$^+$.

Step B: N-(3-(Aminomethyl)bicyclo[1.1.1]pentan-1-yl)acetamide trifluoroacetic salt To a solution of tert-butyl ((3-acetamidobicyclo[1.1.1]pentan-1-yl)methyl)carbamate (119 mg, 0.47 mmol) in DCM (9.3 mL) was added trifluoroacetic acid (0.72 mL, 9.4 mmol). The reaction mixture was stirred at room temperature for 4 hours then the reaction mixture was concentrated under reduced pressure to afford the title compound (125 mg, quant.), which was used without purification. MS (ESI): mass calcd. for C$_8$H$_{14}$N$_2$O, 154.1; m/z found, 155.1 [M+H]$^+$.

Intermediate 4: 1-(Piperidin-4-yl)propan-2-one

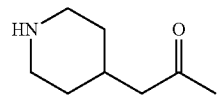

The title compound was prepared according to Tetrahedron, Vol. 38, No. 19, pp. 2883, 1982. MS (ESI): mass calcd. for C$_8$H$_{15}$NO, 141.1; m/z found, 142.1 [M+H]$^+$. $^1$H NMR (500 MHz, Chloroform-d) δ ppm 3.05-2.99 (m, 2H), 2.61 (td, J=12.2, 2.6 Hz, 2H), 2.33 (d, J=6.8 Hz, 2H), 2.12 (s, 3H), 1.99-1.87 (m, 1H), 1.67-1.62 (m, 3H), 1.18-1.05 (m, 2H).

Example 1: 1-[6-[4-(Trifluoromethoxy)phenyl]pyrimidin-4-yl]piperidine-4-carboxamide

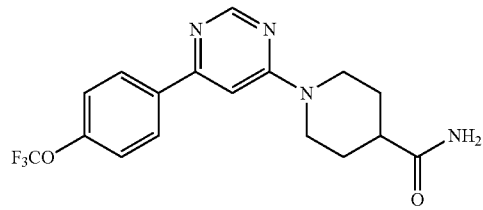 [SMILES: NC(=O)C1CCN(c2cc(-c3ccc(OC(F)(F)F)cc3)ncn2)CC1]

Step A: 1-(6-Chloropyrimidin-4-yl)piperidine-4-carboxamide

To a solution of 4,6-dichloropyrimidine (300 mg, 1.95 mmol) and piperidine-4-carboxamide (300 mg, 2.34 mmol) in 1,4-dioxane (1.5 mL) was added triethylamine (0.75 mL, 5.4 mmol). The reaction mixture was heated in the microwave for 1 h at 100° C. Water and ethyl acetate were added and the aqueous layer was extracted four times with a mixture of 10% MeOH in DCM. The combined organic layers were dried over MgSO$_4$, filtered, and concentrated under reduced pressure. The resulting pale orange solid (469 mg, 100%) was used in the next step without further purification. MS (ESI): mass calcd. for C$_{10}$H$_{13}$ClN$_4$O, 240.1; m/z found, 241.1 [M+H]$^+$.

Step B: 1-[6-[4-(Trifluoromethoxy)phenyl]pyrimidin-4-yl]piperidine-4-carboxamide A solution of 1-(6-chloropyrimidin-4-yl)piperidine-4-carboxamide (75 mg, 0.31 mmol), (4-(trifluoromethoxy)phenyl)boronic acid (77 mg, 0.37 mmol), and Pd(PPh$_3$)$_4$ (18 mg, 0.016 mmol) in 1M aqueous sodium carbonate (0.94 mL, 0.94 mmol) and DMF (1.6 mL) was heated in the microwave for 30 minutes at 100° C. Water and ethyl acetate were added and the aqueous layer was extracted with ethyl acetate (3×). The combined organic layers were dried over MgSO$_4$, filtered, and concentrated under reduced pressure. Purification by basic prep HPLC (Agilent, Waters XBridge C18 5 um 50×100 mm column, 5-90% MeCN/20 mM NH$_4$OH over 15 min, 80 mL/min) gave the title compound (58 mg, 51%). MS (ESI): mass calcd. for C$_{17}$H$_{17}$F$_3$N$_4$O$_2$, 366.1; m/z found, 367.2 [M+H]$^+$. $^1$H NMR (400 MHz, Methanol-d$_4$) δ ppm 8.55 (d, J=1.1 Hz, 1H), 8.13-8.06 (m, 2H), 7.41 (dd, J=9.3, 1.2 Hz, 2H), 7.20 (d, J=1.2 Hz, 1H), 4.65 (d, J=13.2 Hz, 2H), 3.16-3.02 (m, 2H), 2.61 (tt, J=11.6, 3.9 Hz, 1H), 1.95 (d, J=13.1 Hz, 2H), 1.72 (qd, J=12.3, 4.1 Hz, 2H).

Example 2: N-[1-[6-[3-Fluoro-4-(trifluoromethoxy)phenyl]pyrimidin-4-yl]-4-piperidyl]acetamide

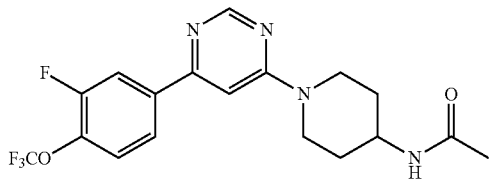

Step A: N-(1-(6-Chloropyrimidin-4-yl)piperidin-4-yl)acetamide

To a solution of 4,6-dichloropyrimidine (3.0 g, 19.5 mmol) and 4-acetamidopiperidine (2.7 g, 19.5 mmol) in n-BuOH (40 mL) was added DIPEA (10.1 mL, 58.6 mmol). The reaction was heated to 100° C. and stirred for 90 minutes. The reaction was cooled to room temperature and concentrated under reduced pressure to 10 mL. The resulting solution was partitioned between DCM and H$_2$O. The layers were separated and the organic layer was washed with H$_2$O (50 mL), then brine (50 mL). The organic layer was separated, dried over MgSO$_4$, filtered, and concentrated under reduced pressure. Purification (FCC, SiO$_2$, 0-10% MeOH in DCM over 10 minutes) afforded the title compound as a pale yellow solid (3.65 g, 73%). MS (ESI): mass calcd. for C$_{11}$H$_{15}$ClN$_4$O, 254.1; m/z found, 255.1 [M+H]$^+$. $^1$H NMR (500 MHz, DMSO-d$_6$) δ ppm 8.32 (d, J=0.9 Hz, 1H), 7.84 (d, J=7.6 Hz, 1H), 6.99 (d, J=0.9 Hz, 1H), 4.53-4.01 (m, 2H), 3.89-3.79 (m, 1H), 3.11 (ddd, J=13.9, 11.4, 2.9 Hz, 2H), 1.83-1.73 (m, 5H), 1.33-1.21 (m, 2H).

Step B: N-[1-[6-[3-Fluoro-4-(trifluoromethoxy)phenyl]pyrimidin-4-yl]-4-piperidyl]acetamide N-(1-(6-chloropyrimidin-4-yl)piperidin-4-yl)acetamide (3.6 g, 14.3 mmol), 3-fluoro-4-(trifluoromethoxy)phenylboronic acid (3.7 g, 15.8 mmol), and Pd(PPh$_3$)$_4$ (414 mg, 0.358 mmol) was combined in 1,4-dioxane (60 mL) DMF (15 mL) and 2M Na$_2$CO$_3$ (aq) (18 mL). The resulting mixture was degassed with N$_2$ and heated overnight at 100° C. The reaction was cooled to room temperature and partitioned between DCM and H$_2$O. The layers were separated and the aqueous was extracted with DCM (3×). The organic layers were combined and washed with brine (2×50 mL), dried over MgSO$_4$, filtered and concentrated. The crude residue was dissolved in ~50 mL of DMF and SiliaMetS Thiol Pd scavenger (1.1 g, 1.28 mmol/g) was added as a powder. The resulting suspension was capped and stirred at room temperature overnight. The suspension was filtered through a pad of Celite® and 100 mL of H$_2$O was added to the solution. The resulting precipitate was collected and via filtration to obtain a yellow solid. These solids were suspended in a mixture of 4:1 Hexanes:EtOAc (100 mL) and stirred vigorously for 30 minutes. The mixture was filtered and the solids were dried under vacuum to obtain a pale yellow solid. These solids were dissolved in 1:1 DCM:MeOH (100 mL) and activated charcoal was added. The suspension was stirred overnight at room temperature. The activated charcoal was removed via filtration and the filtrate was concentrated and dried under vacuum to obtain the title compound as a white solid (3.6 g, 63%). MS (ESI): mass calcd. for C$_{18}$H$_{18}$F$_4$N$_4$O$_2$, 398.1; m/z found, 399.2 [M+H]$^+$. $^1$H NMR (500 MHz, DMSO-d$_6$) δ ppm 8.58 (d, J=1.1 Hz, 1H), 8.30 (dd, J=12.0, 2.1 Hz, 1H), 8.15 (ddd, J=8.6, 2.1, 1.1 Hz, 1H), 7.81 (d, J=7.6 Hz, 1H), 7.72-7.66 (m, 1H), 7.44 (d, J=1.2 Hz, 1H), 4.44 (d, J=12.9 Hz, 2H), 3.94-3.83 (m, 1H), 3.15 (ddd, J=13.8, 11.2, 2.6 Hz, 2H), 1.87-1.77 (m, 5H), 1.40-1.27 (m, 2H).

Example 3: N-[1-[6-[3-Chloro-4-(trifluoromethoxy)phenyl]-2-methyl-pyrimidin-4-yl]-4-piperidyl]acetamide

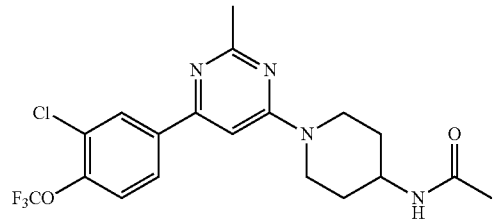 [SMILES: CC(=O)NC1CCN(c2cc(-c3ccc(OC(F)(F)F)c(Cl)c3)nc(C)n2)CC1]

Step A: N-(1-(6-Chloro-2-methylpyrimidin-4-yl)piperidin-4-yl)acetamide

To a solution of 4,6-dichloro-2-methylpyrimidine (250 mg, 1.5 mmol) and N-(piperidin-4-yl)acetamide (278 mg, 1.95 mmol) in n-butanol (3 mL) was added DIPEA (0.78 mL, 4.5 mmol). The reaction mixture was heated in the microwave for 1 h at 100° C. Water was added and the aqueous layer was extracted four times with a mixture of 10% MeOH in DCM. The combined organic layers were dried over MgSO$_4$, filtered, and concentrated under reduced pressure. The resulting pale yellow solid (380 mg, 94%) was used in the next step without any further purification. MS (ESI): mass calcd. for C$_{12}$H$_{17}$ClN$_4$O, 268.1; m/z found, 269.2 [M+H]$^+$.

Step B: N-[1-[6-[3-Chloro-4-(trifluoromethoxy)phenyl]-2-methyl-pyrimidin-4-yl]-4-piperidyl]acetamide A solution of 1-(6-chloropyrimidin-4-yl)piperidine-4-carboxamide (50 mg, 0.19 mmol), (3-chloro-4-(trifluoromethoxy)phenyl)boronic acid (54 mg, 0.22 mmol), and Pd(PPh$_3$)$_4$ (11 mg, 0.009 mmol) in 1M aqueous sodium carbonate (0.56 mL, 0.56 mmol) and DMF (0.93 mL) was heated in the microwave for 30 minutes at 100° C. The reaction was diluted with MeOH, filtered through a Celite® cartridge and concentrated under reduced pressure. The crude product was resuspended in MeOH and filtered a second time through a Silicycle thiol cartridge and concentrated under reduced pressure. Purification by basic prep HPLC (Agilent, Waters XBridge C18 5 um 50×100 mm column, 5-90% MeCN/20 mM NH$_4$OH over 15 min, 80 mL/min) gave the title compound (39 mg, 44%). MS (ESI): mass calcd. for C$_{19}$H$_{20}$ClF$_3$N$_4$O$_2$, 428.1; m/z found, 429.2 [M+H]$^+$. $^1$H NMR (500 MHz, DMSO-d$_6$) δ ppm 8.46 (d, J=2.1 Hz, 1H), 8.26 (dd, J=8.7, 2.1 Hz, 1H), 7.81 (d, J=7.7 Hz, 1H), 7.67 (dq, J=8.7, 1.5 Hz, 1H), 7.29 (s, 1H), 4.45 (d, J=12.3 Hz, 2H), 3.92-3.80 (m, 1H), 3.11 (ddd, J=14.0, 11.6, 2.8 Hz, 2H), 2.45 (s, 3H), 1.87-1.77 (m, 5H), 1.37-1.24 (m, 2H).

Example 4: (trans)-N-[3-Fluoro-1-[2-methyl-6-[4-(trifluoromethoxy)phenyl]pyrimidin-4-yl]-4-piperidyl]acetamide

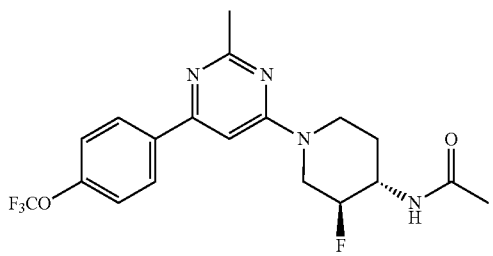 [SMILES: CC(=O)N[C@H]1CCN(c2cc(-c3ccc(OC(F)(F)F)cc3)nc(C)n2)C[C@@H]1F]

Step A: tert-Butyl ((3,4-trans)-1-(6-chloro-2-methylpyrimidin-4-yl)-3-fluoropiperidin-4-yl)carbamate The title compound was prepared in a manner analogous to Example 3, Step A, using tert-butyl ((3,4-trans)-3-fluoropiperidin-4-yl)carbamate instead of N-(piperidin-4-yl)acetamide. MS (ESI): mass calcd. for C$_{15}$H$_{22}$ClFN$_4$O$_2$, 344.1; m/z found, 345.2 [M+H]$^+$.

Step B: N-((3,4-trans)-1-(6-Chloro-2-methylpyrimidin-4-yl)-3-fluoropiperidin-4-yl)acetamide To a solution of tert-butyl ((3,4-trans)-1-(6-chloro-2-methylpyrimidin-4-yl)-3-fluoropiperidin-4-yl)carbamate (315 mg, 0.91 mmol) in DCM (18 mL) was added TFA (1.4 mL, 18.3 mmol). The reaction mixture was stirred at room temperature for 2.5 hours then the solvent was evaporated. The residue was taken up in pyridine (9 mL) and acetic anhydride (0.17 mL, 1.8 mmol) was added followed by 4-dimethylaminopyridine (DMAP) (5.5 mg, 0.05 mmol). The reaction mixture was stirred at room temperature overnight then the solvent was evaporated. To the residue was added EtOAc and a saturated solution of NaHCO$_3$. The aqueous solution was extracted twice with EtOAc and the combined organic layers were dried over MgSO$_4$, filtered and evaporated to afford the title compound (261 mg, quant.) which was used in the next step without any further purification. MS (ESI): mass calcd. for C$_{12}$H$_{16}$ClFN$_4$O, 286.1; m/z found, 287.1 [M+H]$^+$.

Step C: (trans)-N-[3-Fluoro-1-[2-methyl-6-[4-(trifluoromethoxy)phenyl]pyrimidin-4-yl]-4-piperidyl]acetamide A solution of N-((3,4-trans)-1-(6-chloro-2-methylpyrimidin-4-yl)-3-fluoropiperidin-4-yl)acetamide (35 mg, 0.12 mmol), (4-(trifluoromethoxy)phenyl)boronic acid (30 mg, 0.15 mmol), and Pd(PPh$_3$)$_4$ (7 mg, 0.0061 mmol) in 1M aqueous sodium carbonate (0.37 mL, 0.37 mmol) and DMF (0.61 mL) was heated in the microwave for 30 minutes at 100° C. The crude product was diluted with MeOH, filtered through a Celite® cartridge and concentrated under reduced pressure. The crude product was resuspended in MeOH and filtered a second time through a Silicycle thiol cartridge and concentrated. Purification by basic prep HPLC (Agilent, Waters XBridge C18 5 um 50×100 mm column, 5-90% MeCN/20 mM NH$_4$OH over 15 min, 80 mL/min) gave the title compound (38 mg, 75%). MS (ESI): mass calcd. for C$_{19}$H$_{20}$F$_4$N$_4$O$_2$, 412.2; m/z found, 413.2 [M+H]$^+$. $^1$H NMR (400 MHz, DMSO-d$_6$) δ ppm 8.32-8.27 (m, 2H), 8.03 (d, J=8.1 Hz, 1H), 7.50-7.45 (m, 2H), 7.30 (s, 1H), 4.59-4.43 (m, 2H), 4.39-4.30 (m, 1H), 4.22 (d, J=13.6 Hz, 1H), 4.15-4.00 (m, 1H), 3.45 (ddd, J=13.2, 8.7, 6.1 Hz, 1H), 2.47 (s, 3H), 1.96-1.87 (m, 1H), 1.85 (s, 3H), 1.42 (dtd, J=13.6, 9.9, 3.9 Hz, 1H).

Example 5: N-[1-[6-[3-Fluoro-4-(trifluoromethoxy)phenyl]-2-(hydroxymethyl)pyrimidin-4-yl]-4-piperidyl]acetamide

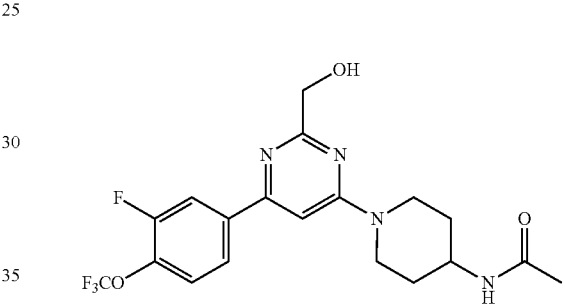

Step A: (4-Chloro-6-(3-fluoro-4-(trifluoromethoxy)phenyl)pyrimidin-2-yl)methanol A solution of (4,6-dichloropyrimidin-2-yl)methanol (78 mg, 0.44 mmol), (3-fluoro-4-(trifluoromethoxy)phenyl)boronic acid (100 mg, 0.44 mmol), K$_2$CO$_3$ (302 mg, 2.2 mmol), and Pd(dppf)Cl$_2$.CH$_2$Cl$_2$ (18 mg, 0.02 mmol), in dioxane (3 mL) and water (0.36 mL, 20 mmol) was degassed with a stream of nitrogen for 5 minutes then heated to 100° C. overnight. The reaction mixture was cooled to room temperature, diluted with EtOAc and filtered through Celite®. Purification via silica gel chromatography (0-40% EtOAc in heptane) gave the title compound (60 mg, 42%). MS (ESI): mass calcd. for C$_{12}$H$_7$ClF$_4$N$_2$O$_2$, 322.0; m/z found, 323.0 [M+H]$^+$.

Step B: N-[1-[6-[3-Fluoro-4-(trifluoromethoxy)phenyl]-2-(hydroxymethyl)pyrimidin-4-yl]-4-piperidyl]acetamide To a solution of (4-chloro-6-(3-fluoro-4-(trifluoromethoxy)phenyl)pyrimidin-2-yl)methanol (60 mg, 0.19 mmol) and 4-acetamidopiperidine (35 mg, 0.24 mmol) in n-butanol (0.93 mL) was added DIPEA (0.096 mL, 0.56 mmol) and the reaction mixture was heated at 100° C. overnight. The reaction mix was concentrated under reduced pressure and purified (FCC, SiO$_2$, 0-20% MeOH in DCM) to afford the title compound (26 mg, 33%). MS (ESI): mass calcd. for C$_{19}$H$_{20}$F$_4$N$_4$O$_3$, 428.1; m/z found, 429.1 [M+H]$^+$.

$^1$H NMR (500 MHz, DMSO-d$_6$) δ ppm 8.38 (dd, J=12.1, 2.2 Hz, 1H), 8.20 (d, J=8.8 Hz, 1H), 7.83 (d, J=7.7 Hz, 1H), 7.69 (t, J=8.3 Hz, 1H), 7.33 (s, 1H), 4.94-4.87 (m, 1H), 4.56-4.45 (m, 2H), 4.43 (d, J=6.1 Hz, 2H), 3.92-3.81 (m, 1H), 3.13 (t, J=12.4 Hz, 2H), 1.87-1.77 (m, 5H), 1.32 (d, J=12.0 Hz, 2H).

Example 6: (racemic)-N-Methyl-1-[6-[4-(trifluoromethoxy)phenyl]pyrimidin-4-yl]pyrrolidine-3-carboxamide

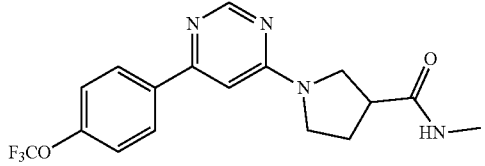 [SMILES: CNC(=O)C1CCN(c2cc(-c3ccc(OC(F)(F)F)cc3)ncn2)C1]

Step A:
4-Chloro-6-(4-(trifluoromethoxy)phenyl)pyrimidine

The title compound was prepared in a manner analogous to Example 5, Step A, using 4,6-dichloropyrimidine instead of (4,6-dichloropyrimidin-2-yl)methanol and (4-(trifluoromethoxy)phenyl)boronic acid instead of (3-fluoro-4-(trifluoromethoxy)phenyl)boronic acid. MS (ESI): mass calcd. for C$_{11}$H$_6$ClF$_3$N$_2$O, 274.0; m/z found, 275.0 [M+H]$^+$.

Step B: 1-(6-(4-(Trifluoromethoxy)phenyl)pyrimidin-4-yl)pyrrolidine-3-carboxylic acid The title compound was prepared in a manner analogous to Example 5, Step B using pyrrolidine-3-carboxylic acid instead of N-(piperidin-4-yl)acetamide. MS (ESI): mass calcd. for C$_{16}$H$_{14}$F$_3$N$_3$O$_3$, 353.1; m/z found, 354.1 [M+H]$^+$.

Step C: (racemic)-N-Methyl-1-[6-[4-(trifluoromethoxy)phenyl]pyrimidin-4-yl]pyrrolidine-3-carboxamide To a solution of 1-(6-(4-(trifluoromethoxy)phenyl)pyrimidin-4-yl)pyrrolidine-3-carboxylic acid (32 mg, 0.09 mmol) in DMF (1 mL) was added methylamine (2M in THF) (0.18 mL, 0.36 mmol), DIPEA (31 μL, 0.18 mmol) followed by COMU (100 mg, 0.22 mmol). The reaction mixture was stirred at room temperature for 20 hours then a saturated aqueous solution of NaCl was added. The aqueous phase was extracted twice with EtOAc and the combined organic layers were dried over MgSO$_4$, filtered and evaporated. Purification by basic prep HPLC (Agilent, Waters XBridge C18 5 um 50×100 mm column, 5-90% MeCN/20 mM NH$_4$OH over 15 min, 80 mL/min) gave the title compound (23 mg, 69%). MS (ESI): mass calcd. for C$_{17}$H$_{17}$F$_3$N$_4$O$_2$, 366.1; m/z found, 367.1 [M+H]$^+$. $^1$H NMR (400 MHz, Chloroform-d) δ ppm 8.66 (d, J=1.2 Hz, 1H), 8.09-7.95 (m, 2H), 7.35-7.28 (m, 2H), 6.63 (d, J=1.3 Hz, 1H), 5.63 (s, 1H), 3.86-3.71 (m, 3H), 3.63-3.47 (m, 1H), 3.11-2.97 (m, 1H), 2.87 (d, J=4.8 Hz, 3H), 2.38-2.23 (m, 2H).

Example 7: (Trans)-N-[3-Fluoro-1-[6-[3-fluoro-4-(trifluoromethoxy)phenyl]-2-methyl-pyrimidin-4-yl]-4-piperidyl]acetamide

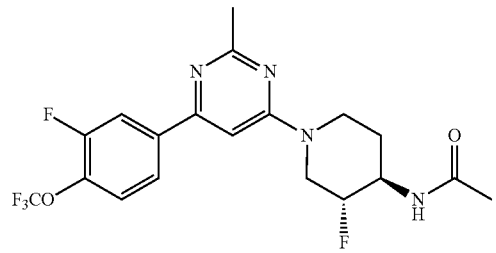 [SMILES: CC(=O)N[C@@H]1CCN(c2cc(-c3ccc(OC(F)(F)F)c(F)c3)nc(C)n2)C[C@H]1F]

Step A: 4-Chloro-6-(3-fluoro-4-(trifluoromethoxy)phenyl)-2-methylpyrimidine

A solution of 4,6-dichloro-2-methylpyrimidine (573 mg, 3.45 mmol), (3-fluoro-4-(trifluoromethoxy)phenyl)boronic acid (309 mg, 1.38 mmol), K$_2$CO$_3$ (1.4 g, 10.2 mmol), and Pd(dppf)Cl$_2$.CH$_2$Cl$_2$ (225 mg, 0.28 mmol), in dioxane (11.5 mL) and water (1.14 mL, 63 mmol) was degassed with a stream of nitrogen for 5 minutes then heated to 100° C. overnight. The reaction mixture was cooled to room temperature, diluted with EtOAc and filtered through Celite®. Purification via silica gel chromatography (0-10% EtOAc in hexanes) gave the title compound (208 mg, 49%). MS (ESI): mass calcd. for C$_{12}$H$_7$ClF$_4$N$_2$O, 306.0; m/z found, 307.0 [M+H]$^+$.

Step B: tert-butyl ((3,4-trans)-3-fluoro-1-(6-(3-fluoro-4-(trifluoromethoxy)phenyl)-2-methylpyrimidin-4-yl)piperidin-4-yl)carbamate To a solution of 4-chloro-6-(3-fluoro-4-(trifluoromethoxy)phenyl)-2-methylpyrimidine (38 mg, 0.12 mmol) and tert-butyl ((3,4-trans)-3-fluoropiperidin-4-yl)carbamate (35 mg, 0.16 mmol) in n-butanol (1.2 mL) was added DIPEA (64 μL, 0.37 mmol). The reaction mixture was heated in the microwave for 1 h at 100° C. Solvent was then evaporated under reduced pressure. Purification via silica gel chromatography (0-35% EtOAc in hexanes) gave the title compound (45 mg, 74%). MS (ESI): mass calcd. for C$_{22}$H$_{25}$F$_5$N$_4$O$_3$, 488.2; m/z found, 489.2 [M+H]$^+$.

Step C: (trans)-N-[3-fluoro-1-[6-[3-fluoro-4-(trifluoromethoxy)phenyl]-2-methyl-pyrimidin-4-yl]-4-piperidyl]acetamide To a solution of tert-butyl ((3,4-trans)-3-fluoro-1-(6-(3-fluoro-4-(trifluoromethoxy)phenyl)-2-methylpyrimidin-4-yl)piperidin-4-yl)carbamate (45 mg, 0.092 mmol) in DCM (1 mL) was added TFA (0.14 mL, 1.84 mmol). The reaction mixture was stirred at room temperature for 18 hours then the solvent was evaporated. The residue was taken up in pyridine (1 mL) and acetic anhydride was added (17 μL, 0.18 mmol) followed by 4-dimethylaminopyridine (DMAP) (0.6 mg, 0.005 mmol). The reaction mixture was stirred for 18 hours then the solvent was evaporated. Purification by basic prep HPLC (Agilent, Waters XBridge C18 5 um 50×100 mm column, 5-90% MeCN/20 mM NH$_4$OH over 15 min, 80 mL/min) gave the title compound (30 mg, 76%). MS (ESI): mass calcd. for C$_{19}$H$_{19}$F$_5$N$_4$O$_2$, 430.1; m/z found, 431.1 [M+H]⁺. ¹H NMR (500 MHz, Chloroform-d) δ ppm 7.85 (dd, J=11.1, 2.1 Hz, 1H), 7.76-7.72 (m, 1H), 7.41-7.35 (m, 1H), 6.69 (s, 1H), 5.52 (d, J=7.5 Hz, 1H), 4.84-4.75 (m, 1H), 4.47-4.30 (m, 1H), 4.28-4.15 (m, 2H), 3.23-3.13 (m, 2H), 2.58 (s, 3H), 2.34-2.25 (m, 1H), 2.04 (s, 3H), 1.55-1.44 (m, 1H).

Example 8: N-[1-[6-[3-Fluoro-4-(trifluoromethoxy)phenyl]pyrimidin-4-yl]-4-piperidyl]cyclopropanecarboxamide

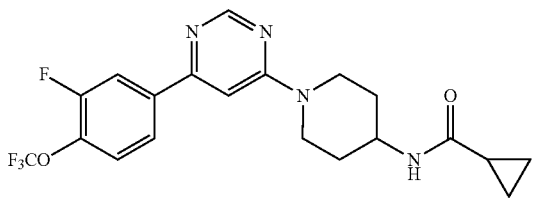 [SMILES: O=C(NC1CCN(c2cc(-c3ccc(OC(F)(F)F)c(F)c3)ncn2)CC1)C1CC1]

Step A: tert-Butyl (1-(6-(3-fluoro-4-(trifluoromethoxy)phenyl)pyrimidin-4-yl)piperidin-4-yl)carbamate The title compound was prepared in a manner analogous to Example 5, using 4,6-dichloropyrimidine instead of (4,6-dichloropyrimidin-2-yl)methanol in Step A; and using tert-butyl piperidin-4-ylcarbamate instead of N-(piperidin-4-yl)acetamide in Step B. MS (ESI): mass calcd. for $C_{21}H_{24}F_4N_4O_3$, 456.2; m/z found, 457.2 [M+H]⁺.

Step B: 1-(6-(3-Fluoro-4-(trifluoromethoxy)phenyl)pyrimidin-4-yl)piperidin-4-amine TFA Salt To a solution of tert-butyl (1-(6-(3-fluoro-4-(trifluoromethoxy)phenyl)pyrimidin-4-yl)piperidin-4-yl)carbamate (245 mg, 0.54 mmol) in DCM (11 mL) was added TFA (0.82 mL, 10.7 mmol). The reaction mixture was stirred at room temperature for 3 hours. Solvent was evaporated and the residue was used as is in the next step without any further purification (252 mg, quant.). MS (ESI): mass calcd. for $C_{16}H_{16}F_4N_4O$, 356.1; m/z found, 357.1 [M+H]⁺.

Step C: N-[1-[6-[3-Fluoro-4-(trifluoromethoxy)phenyl]pyrimidin-4-yl]-4-piperidyl]cyclopropanecarboxamide To a solution of 1-(6-(3-fluoro-4-(trifluoromethoxy)phenyl)pyrimidin-4-yl)piperidin-4-amine TFA salt (31 mg, 0.07 mmol) in DMF (1 mL) was added cyclopropanecarboxylic acid (17 μL, 0.26 mmol), DIPEA (34 μL, 0.2 mmol) followed by COMU (73 mg, 0.17 mmol). The reaction mixture was stirred at room temperature for 3 hours. Solvent was evaporated. Purification by basic prep HPLC (Agilent, Waters XBridge C18 5 um 50×100 mm column, 5-90% MeCN/20 mM NH₄OH over 15 min, 80 mL/min) gave the title compound (23 mg, 82%). MS (ESI): mass calcd. for $C_{20}H_{20}F_4N_4O_2$, 424.2; m/z found, 425.2 [M+H]⁺. ¹H NMR (400 MHz, Chloroform-d) δ ppm 8.66 (d, J=1.1 Hz, 1H), 7.85 (dd, J=11.1, 2.1 Hz, 1H), 7.79-7.74 (m, 1H), 7.42-7.35 (m, 1H), 6.85 (d, J=1.3 Hz, 1H), 5.55 (d, J=7.9 Hz, 1H), 4.46 (d, J=13.6 Hz, 2H), 4.18-4.04 (m, 1H), 3.16-3.05 (m, 2H), 2.15-2.06 (m, 2H), 1.50-1.36 (m, 1H), 1.34-1.26 (m, 1H), 1.01-0.94 (m, 2H), 0.79-0.71 (m, 2H).

Example 9: 3-Amino-N-[1-[6-[3-fluoro-4-(trifluoromethoxy)phenyl]pyrimidin-4-yl]-4-piperidyl]propanamide

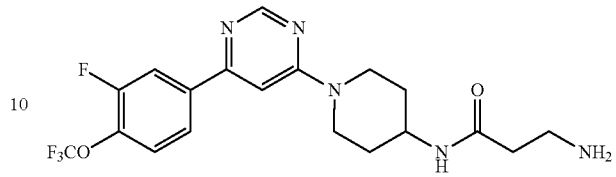

Step A: tert-Butyl (3-((1-(6-(3-fluoro-4-(trifluoromethoxy)phenyl)pyrimidin-4-yl)piperidin-4-yl)amino)-3-oxopropyl)carbamate The title compound was prepared in a manner analogous to Example 8, Step C, using 1-(6-(3-fluoro-4-(trifluoromethoxy)phenyl)pyrimidin-4-yl)piperidin-4-amine TFA salt (Example 8, product from Step B) and using 3-((tert-butoxycarbonyl)amino)propanoic acid instead of cyclopropanecarboxylic acid. MS (ESI): mass calcd. for $C_{24}H_{29}F_4N_5O_4$, 527.2; m/z found, 528.2 [M+H]⁺.

Step B: 3-Amino-N-[1-[6-[3-fluoro-4-(trifluoromethoxy)phenyl]pyrimidin-4-yl]-4-piperidyl]propanamide To a solution of tert-butyl (3-((1-(6-(3-fluoro-4-(trifluoromethoxy)phenyl)pyrimidin-4-yl)piperidin-4-yl)amino)-3-oxopropyl)carbamate (35 mg, 0.07 mmol) in DCM (1 mL) was added TFA (0.1 mL, 1.3 mmol) and the reaction mixture was stirred at room temperature for 16 hours. Purification by basic prep HPLC (Agilent, Waters XBridge C18 5 um 50×100 mm column, 5-90% MeCN/20 mM NH₄OH over 15 min, 80 mL/min) gave the title compound (9 mg, 32% over 2 steps). MS (ESI): mass calcd. for $C_{19}H_{21}F_4N_5O_2$, 427.2; m/z found, 428.1 [M+H]⁺. ¹H NMR (400 MHz, Chloroform-d) δ ppm 8.66 (d, J=1.1 Hz, 1H), 7.85 (dd, J=11.1, 2.1 Hz, 1H), 7.79-7.74 (m, 1H), 7.47-7.34 (m, 2H), 6.85 (d, J=1.2 Hz, 1H), 4.37 (d, J=13.7 Hz, 2H), 4.18-4.07 (m, 1H), 3.25-3.15 (m, 2H), 3.06-2.97 (m, 2H), 2.33-2.29 (m, 2H), 2.12-2.03 (m, 2H), 1.52-1.40 (m, 2H).

Example 10: N-[1-[6-[3-Fluoro-4-(trifluoromethoxy)phenyl]pyrimidin-4-yl]azetidin-3-yl]acetamide

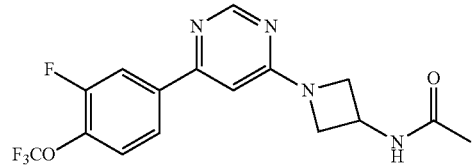 [SMILES: CC(=O)NC1CN(c2cc(-c3ccc(OC(F)(F)F)c(F)c3)ncn2)C1]

Step A: 1-(6-Chloropyrimidin-4-yl)azetidine-3-carboxylic acid

The title compound was prepared in a manner analogous to Example 3, Step A using 4,6-dichloropyrimidine instead of 4,6-dichloro-2-methylpyrimidine and azetidine-3-carboxylic acid instead of N-(piperidin-4-yl)acetamide. MS (ESI): mass calcd. for $C_8H_8ClN_3O_2$, 213.0; m/z found, 214.0 $[M+H]^+$.

Step B: Benzyl (1-(6-chloropyrimidin-4-yl)azetidin-3-yl)carbamate

To a solution of 1-(6-chloropyrimidin-4-yl)azetidine-3-carboxylic acid (146 mg, 0.68 mmol) in toluene was added triethylamine (0.1 mL, 0.75 mmol). The reaction mixture was heated to 70° C. and DPPA (0.16 mL, 0.75 mmol) dissolved in toluene (0.5 mL) was added. After 2.5 hours, benzyl alcohol (68 μL, 0.65 mmol) was added and the reaction mixture was stirred at 90° C. for 16 hours. The mixture was cooled to room temperature, diluted with EtOAc and washed a saturated aqueous solution of NaHCO₃. The aqueous layer was extracted twice with EtOAc. The combined organic layers were washed with a saturated aqueous solution of NaCl, dried over MgSO₄, filtered and evaporated. Purification via silica gel chromatography (0-50% [10% (NH₃ in MeOH, 2M)/DCM] in DCM) gave a mixture of the title compound and unknown compound. Used as is in the next step without any further purification (considered quant., 218 mg). MS (ESI): mass calcd. for $C_{15}H_{15}ClN_4O_2$, 318.1; m/z found, 319.1 $[M+H]^+$.

Step C: Benzyl (1-(6-(3-fluoro-4-(trifluoromethoxy)phenyl)pyrimidin-4-yl)azetidin-3-yl)carbamate A solution of benzyl (1-(6-chloropyrimidin-4-yl)azetidin-3-yl)carbamate (86 mg, 0.27 mmol), (3-fluoro-4-(trifluoromethoxy)phenyl)boronic acid (63 mg, 0.27 mmol), K₂CO₃ (276 mg, 1.9 mmol), and Pd(dppf)Cl₂.CH₂Cl₂ (11 mg, 0.013 mmol), in dioxane (1.8 mL) and water (0.22 mL) was degassed with a stream of nitrogen for 5 minutes then heated to 100° C. overnight. The reaction mixture was cooled to room temperature, diluted with EtOAc and filtered through Celite®. Purification via silica gel chromatography (0% to 100% [10% (NH₃ in MeOH, 2M)/DCM] in DCM) gave the title compound (82 mg, 66%). MS (ESI): mass calcd. for $C_{22}H_{18}F_4N_4O_3$, 462.1; m/z found, 463.1 $[M+H]^+$.

Step D: 1-(6-(3-Fluoro-4-(trifluoromethoxy)phenyl)pyrimidin-4-yl)azetidin-3-amine Benzyl (1-(6-(3-fluoro-4-(trifluoromethoxy)phenyl)pyrimidin-4-yl)azetidin-3-yl)carbamate (82 mg, 0.18 mmol) was dissolved in ethanol (1.8 mL) and the round bottom flask was flushed with nitrogen. To the solution was added 10 wt % Pd/C Degussa wet (10 mg). The reaction mixture was then flushed with H₂ and the stirred under an atmosphere of H₂ for 16 hours. The mixture was filtered and solvent evaporated. Purification by basic prep HPLC (Agilent, Waters XBridge C18 5 um 50×100 mm column, 5-90% MeCN/20 mM NH₄OH over 15 min, 80 mL/min) gave the title compound (12 mg, 21%). MS (ESI): mass calcd. for $C_{14}H_{12}F_4N_4O$, 328.1; m/z found, 329.1 $[M+H]^+$.

Step E: N-[1-[6-[3-Fluoro-4-(trifluoromethoxy)phenyl]pyrimidin-4-yl]azetidin-3-yl]acetamide To a solution of 1-(6-(3-fluoro-4-(trifluoromethoxy)phenyl)pyrimidin-4-yl)azetidin-3-amine (12 mg, 0.04 mmol) in pyridine (0.75 mL) was added acetic anhydride (7 μL, 0.07 mmol) and 4-dimethylaminopyridine (DMAP) (1 mg, 0.01 mmol). The reaction mixture was stirred at room temperature for 16 hours then the solvent was evaporated. Purification by basic prep HPLC (Agilent, Waters XBridge C18 5 um 50×100 mm column, 5-90% MeCN/20 mM NH₄OH over 15 min, 80 mL/min) gave the title compound (12 mg, 87%). MS (ESI): mass calcd. for $C_{16}H_{14}F_4N_4O_2$, 370.1; m/z found, 371.1 $[M+H]^+$. ¹H NMR (400 MHz, Methanol-d₄) δ ppm 8.51 (d, J=1.2 Hz, 1H), 8.02 (dd, J=11.5, 2.1 Hz, 1H), 7.95-7.91 (m, 1H), 7.57-7.50 (m, 1H), 6.86 (d, J=1.3 Hz, 1H), 4.79-4.71 (m, 1H), 4.52-4.44 (m, 2H), 4.07-4.00 (m, 2H), 1.99 (s, 3H).

Example 11: N-[1-[2-[3-Fluoro-4-(trifluoromethoxy)phenyl]-4-pyridyl]-4-piperidyl]acetamide

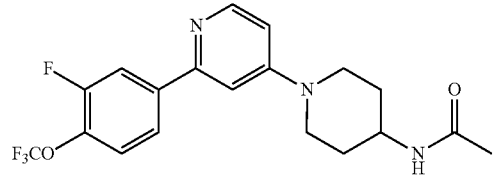

Step A: 4-Fluoro-2-(3-fluoro-4-(trifluoromethoxy)phenyl)pyridine

A solution of 2-chloro-4-fluoropyridine (209 mg, 1.5 mmol), (3-fluoro-4-(trifluoromethoxy)phenyl)boronic acid (359 mg, 1.5 mmol), K₂CO₃ (1.6 g, 11.4 mmol), and Pd(dppf)Cl₂.CH₂Cl₂ (63 mg, 0.08 mmol), in dioxane (10 mL) and water (1.3 mL, 70 mmol) was degassed with a stream of nitrogen for 5 minutes then heated to 100° C. overnight. The reaction mixture was cooled to room temperature, diluted with EtOAc and filtered through Celite®. Purification via silica gel chromatography (0-10% EtOAc in heptane) gave the title compound (295 mg, 70%). MS (ESI): mass calcd. for $C_{12}H_6F_5NO$, 275.0; m/z found, 276.0 $[M+H]^+$.

Step B: N-[1-[2-[3-fluoro-4-(trifluoromethoxy)phenyl]-4-pyridyl]-4-piperidyl]acetamide To a solution of 4-fluoro-2-(3-fluoro-4-(trifluoromethoxy)phenyl)pyridine (63 mg, 0.23 mmol) and N-(piperidin-4-yl)acetamide (33 mg, 0.23 mmol) in 1-butanol (2.3 mL) was added DIPEA (0.12 mL, 0.69 mmol). The reaction mixture was then heated to 130° C. for 2 days. Solvent was evaporated and purification by basic prep HPLC (Agilent, Waters XBridge C18 5 um 50×100 mm column, 5-90% MeCN/20 mM NH₄OH over 15 min, 80 mL/min) gave the title compound (66 mg, 72%). MS (ESI): mass calcd. for $C_{19}H_{19}F_4N_3O_2$, 397.1; m/z found, 398.1 $[M+H]^+$. ¹H NMR (500 MHz, Chloroform-d) δ ppm 8.34 (d, J=5.9 Hz, 1H), 7.79 (dd, J=11.3, 2.2 Hz, 1H), 7.70 (d, J=8.6 Hz, 1H), 7.39-7.33 (m, 1H), 7.02 (d, J=2.5 Hz, 1H), 6.69-6.64 (m, 1H), 5.41 (d, J=7.8 Hz, 1H), 4.12-4.01 (m, 1H), 3.93 (d, J=13.3 Hz, 2H), 3.10-3.00 (m, 2H), 2.07 (d, J=12.9 Hz, 2H), 1.99 (s, 3H), 1.53-1.40 (m, 2H).

Example 12: N-[1-[2-[3-(Difluoromethoxy)-4-fluoro-phenyl]-4-pyridyl]-4-piperidyl]acetamide

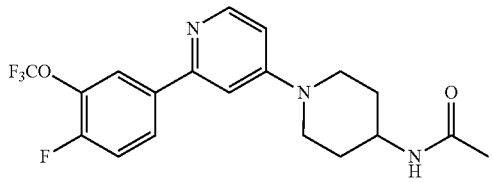 [SMILES: CC(=O)NC1CCN(c2ccnc(-c3ccc(F)c(OC(F)(F)F)c3)c2)CC1]

Step A: N-(1-(2-Chloropyridin-4-yl)piperidin-4-yl)acetamide

To a solution of 2-chloro-4-fluoropyridine (110 mg, 0.81 mmol) and N-(piperidin-4-yl)acetamide (118 mg, 0.81 mmol) in 1-butanol (4 mL) was added DIPEA (0.42 mL, 2.4 mmol). The reaction mixture was heated in the microwave for 2 hours at 110° C. then more of N-(piperidin-4-yl)acetamide (24 mg, 0.16 mmol). Solvent was evaporated and purification via silica gel chromatography (0-100% [10% (NH$_3$ in MeOH, 2M)/DCM] in DCM) gave the title compound (155 mg, 75%). MS (ESI): mass calcd. for $C_{12}H_{16}ClN_3O$, 253.1; m/z found, 254.1 [M+H]$^+$.

Step B: N-[1-[2-[3-(Difluoromethoxy)-4-fluoro-phenyl]-4-pyridyl]-4-piperidyl]acetamide A solution of N-(1-(2-chloropyridin-4-yl)piperidin-4-yl)acetamide (42 mg, 0.17 mmol), (3-(difluoromethoxy)-4-fluorophenyl)boronic acid (34 mg, 0.17 mmol), K$_2$CO$_3$ (169 mg, 1.23 mmol), and Pd(dppf)Cl$_2$.CH$_2$Cl$_2$ (7 mg, 0.008 mmol), in dioxane (1.1 mL) and water (0.14 mL, 1.6 mmol) was degassed with a stream of nitrogen for 5 minutes then heated to 100° C. overnight. The reaction mixture was cooled to room temperature, diluted with EtOAc and filtered through Celite®. Purification by basic prep HPLC (Agilent, Waters XBridge C18 5 um 50×100 mm column, 5-90% MeCN/20 mM NH$_4$OH over 15 min, 80 mL/min) gave the title compound (58 mg, 71%). MS (ESI): mass calcd. for $C_{19}H_{20}F_3N_3O_2$, 379.2; m/z found, 380.1 [M+H]$^+$. $^1$H NMR (400 MHz, Methanol-d$_4$) δ ppm 8.12 (d, J=7.5 Hz, 1H), 7.81 (dd, J=7.2, 2.4 Hz, 1H), 7.77-7.71 (m, 1H), 7.52 (dd, J=10.1, 8.6 Hz, 1H), 7.35 (d, J=2.8 Hz, 1H), 7.19 (dd, J=7.5, 2.9 Hz, 1H), 6.99 (t, J=73.0 Hz, 1H), 4.31 (d, J=13.9 Hz, 2H), 4.11-4.00 (m, 1H), 3.46-3.36 (m, 2H), 2.13-2.04 (m, 2H), 1.95 (s, 3H), 1.64-1.52 (m, 2H).

Example 13: N-[1-[2-[4-(Difluoromethyl)phenyl]-4-pyridyl]-4-piperidyl]acetamide

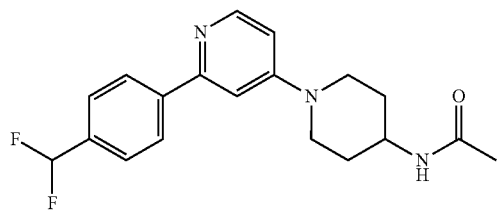 [SMILES: CC(=O)NC1CCN(c2ccnc(-c3ccc(C(F)F)cc3)c2)CC1]

A solution of N-(1-(2-chloropyridin-4-yl)piperidin-4-yl)acetamide (Example 12, product from Step A, 35 mg, 0.14 mmol), (4-(difluoromethyl)phenyl)boronic acid (28 mg, 0.17 mmol), cesium carbonate (135 mg, 0.41 mmol), and RuPhos Pd G3 (6 mg, 0.0069 mmol) in dioxane, was degassed with nitrogen and heated to 100° C. for 16 hours. EtOAc and water were added and the aqueous layer was extracted twice with EtOAc. The combined organic layers were dried over MgSO$_4$, filtered and evaporated. Purification by basic prep HPLC (Agilent, Waters XBridge C18 5 um 50×100 mm column, 5-90% MeCN/20 mM NH$_4$OH over 15 min, 80 mL/min) gave the title compound (7 mg, 16%). MS (ESI): mass calcd. for $C_{19}H_{21}F_2N_3O$, 345.2; m/z found, 346.2 [M+H]$^+$. $^1$H NMR (400 MHz, DMSO-d$_6$) δ ppm 8.26 (d, J=5.9 Hz, 1H), 8.21 (dt, J=8.5, 1.0 Hz, 2H), 7.82 (d, J=7.7 Hz, 1H), 7.67-7.62 (m, 2H), 7.39 (d, J=2.5 Hz, 1H), 7.09 (t, J=55.9 Hz, 1H), 6.85 (dd, J=6.0, 2.5 Hz, 1H), 4.01 (dt, J=13.5, 3.9 Hz, 2H), 3.90-3.77 (m, 1H), 3.04 (ddd, J=13.3, 11.5, 2.7 Hz, 2H), 1.85-1.76 (m, 5H), 1.39 (qd, J=11.5, 3.9 Hz, 2H).

Example 14: N-[1-[2-[3,5-Difluoro-4-(trifluoromethoxy)phenyl]-4-pyridyl]-4-piperidyl]acetamide

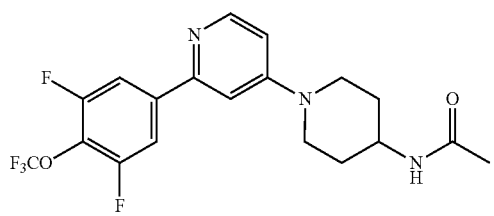 [SMILES: CC(=O)NC1CCN(c2ccnc(-c3cc(F)c(OC(F)(F)F)c(F)c3)c2)CC1]

A solution of N-(1-(2-chloropyridin-4-yl)piperidin-4-yl)acetamide (Example 12, product from Step A, 35 mg, 0.14 mmol), (3,5-difluoro-4-(trifluoromethoxy)phenyl)boronic acid (35 mg, 0.14 mmol), K$_2$CO$_3$ (57 mg, 0.41 mmol), and Pd(dppf)Cl$_2$.CH$_2$Cl$_2$ (6 mg, 0.0069 mmol), in dioxane (1 mL) and water (124 μL, 7 mmol) was degassed with a stream of nitrogen for 5 minutes then heated to 100° C. overnight. The reaction mixture was cooled to room temperature, diluted with EtOAc and filtered through Celite®. Purification by basic prep HPLC (Agilent, Waters XBridge C18 5 um 50×100 mm column, 5-90% MeCN/20 mM NH$_4$OH over 15 min, 80 mL/min) gave the title compound (44 mg, 77%). MS (ESI): mass calcd. for $C_{19}H_{18}F_5N_3O_2$, 415.1; m/z found, 416.2 [M+H]$^+$. $^1$H NMR (500 MHz, DMSO-d$_6$) δ ppm 8.25 (d, J=5.9 Hz, 1H), 8.14 (dd, J=11.9, 2.0 Hz, 2H), 7.82 (d, J=7.7 Hz, 1H), 7.48 (d, J=2.5 Hz, 1H), 6.88 (dd, J=6.0, 2.4 Hz, 1H), 4.04 (dt, J=12.8, 3.9 Hz, 2H), 3.89-3.78 (m, 1H), 3.09-2.98 (m, 2H), 1.85-1.74 (m, 5H), 1.43-1.30 (m, 2H).

Example 15: N-[1-[5-Fluoro-2-[3-fluoro-4-(trifluoromethoxy)phenyl]-4-pyridyl]-4-piperidyl]acetamide

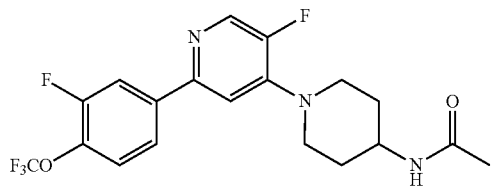 [SMILES: CC(=O)NC1CCN(c2cc(-c3ccc(OC(F)(F)F)c(F)c3)ncc2F)CC1]

Step A: N-(1-(2-Chloro-5-fluoropyridin-4-yl)piperidin-4-yl)acetamide

A solution of N-(piperidin-4-yl)acetamide (60 mg, 0.42 mmol), 2-chloro-5-fluoro-4-iodopyridine (200 mg, 0.76 mmol), and cesium carbonate (412 mg, 1.27 mmol) in toluene (2.8 mL) was degassed and placed under atmosphere of nitrogen. $Pd_2(dba)_3$ (77 mg, 0.08 mmol) was then added followed by 4,5-bis(diphenylphosphino)-9,9-dimethylxanthene (XantPhos) (100 mg, 0.17 mmol). The reaction mixture was heated at 110° C. for 18 hours then filtered through Celite® and the solvent was evaporated. Purification via silica gel chromatography (0-100% [10% [$NH_3$ in MeOH, 2M]/DCM] in DCM) gave the title compound (74 mg, 65%). MS (ESI): mass calcd. for $C_{12}H_{15}ClFN_3O$, 271.1; m/z found, 272.1 $[M+H]^+$.

Step B: N-[1-[5-Fluoro-2-[3-fluoro-4-(trifluoromethoxy)phenyl]-4-pyridyl]-4-piperidyl]acetamide A solution of N-(1-(2-chloro-5-fluoropyridin-4-yl)piperidin-4-yl)acetamide (74 mg, 0.27 mmol), (3-fluoro-4-(trifluoromethoxy)phenyl)boronic acid (83 mg, 0.35 mmol), $K_2CO_3$ (188 mg, 1.36 mmol), and $Pd(dppf)Cl_2 \cdot CH_2Cl_2$ (11 mg, 0.014 mmol), in dioxane (2.7 mL) and water (0.22 mL) was degassed with a stream of nitrogen for 5 minutes then heated to 100° C. overnight. The reaction mixture was filtered through a pad a Celite® and rinsed with EtOAc. The solvent was removed under reduced pressure. The crude product was taken up in MeOH and filtered through a cartridge Silicycle Silia Prep Thiol to remove Pd. Solvent was concentrated under reduced pressure, crude purified by basic prep HPLC (Agilent, Waters XBridge C18 5 um 50×100 mm column, 5-90% MeCN/20 mM $NH_4OH$ over 15 min, 80 mL/min). MS (ESI): mass calcd. for $C_{19}H_{18}F_5N_3O_2$, 415.1; m/z found, 416.1 $[M+H]^+$. $^1H$ NMR (500 MHz, Chloroform-d) δ ppm 8.26 (d, J=5.1 Hz, 1H), 7.75 (dd, J=11.2, 2.2 Hz, 1H), 7.65 (d, J=8.6 Hz, 1H), 7.36 (t, J=8.1 Hz, 1H), 7.09 (d, J=7.2 Hz, 1H), 5.44 (d, J=7.6 Hz, 1H), 4.07-3.96 (m, 1H), 3.77 (d, J=12.6 Hz, 2H), 3.07-2.95 (m, 2H), 2.14-2.06 (m, 2H), 2.00 (s, 3H), 1.64-1.52 (m, 2H).

Example 16: (trans)-N-[3-Fluoro-1-[2-[3-fluoro-4-(trifluoromethoxy)phenyl]-4-pyridyl]-4-piperidyl]acetamide

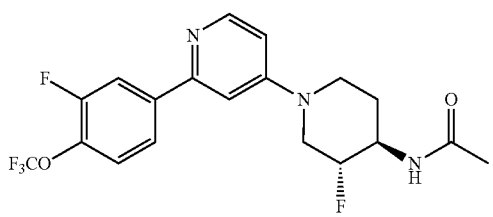

Step A: tert-Butyl ((3,4-trans)-1-(2-chloropyridin-4-yl)-3-fluoropiperidin-4-yl)carbamate To a solution of 2-chloro-4-fluoropyridine (60 mg, 0.44 mmol) and tert-butyl ((3,4-trans)-3-fluoropiperidin-4-yl)carbamate (97 mg, 0.44 mmol) in 1-butanol (2.2 mL) was added DIPEA (0.23 mL, 1.3 mmol). The reaction mixture was heated at 150° C. for 18 hours. Solvent was evaporated and purification via silica gel chromatography (0-100% [10% ($NH_3$ in MeOH, 2M)/DCM] in DCM) gave the title compound (68 mg, 47%). MS (ESI): mass calcd. for $C_{15}H_{21}ClFN_3O_2$, 329.1; m/z found, 330.1 $[M+H]^+$.

Step B: N-((3,4-trans)-1-(2-Chloropyridin-4-yl)-3-fluoropiperidin-4-yl)acetamide To a solution of tert-butyl ((3,4-trans)-1-(2-chloropyridin-4-yl)-3-fluoropiperidin-4-yl)carbamate (68 mg, 0.21 mmol) in DCM (4 mL) was added TFA (0.32 mL, 4.1 mmol). The reaction mixture was stirred at room temperature for 16 hours then the solvent was evaporated. The residue was taken up in pyridine (4 mL) and acetic anhydride (39 μL, 0.41 mmol) was added followed by 4-dimethylaminopyridine (DMAP) (1 mg, 0.01 mmol). The reaction mixture was stirred at room temperature for 5 days then the solvent was evaporated. Purification via silica gel chromatography (0-100% [10% ($NH_3$ in MeOH, 2M)/DCM] in DCM) gave the title compound (42 mg, 75%). MS (ESI): mass calcd. for $C_{12}H_{15}ClFN_3O$, 271.1; m/z found, 272.1 $[M+H]^+$.

Step C: (trans)-N-[3-Fluoro-1-[2-[3-fluoro-4-(trifluoromethoxy)phenyl]-4-pyridyl]-4-piperidyl]acetamide A solution of N-((3,4-trans)-1-(2-chloropyridin-4-yl)-3-fluoropiperidin-4-yl)acetamide (42 mg, 0.16 mmol), (3-fluoro-4-(trifluoromethoxy)phenyl)boronic acid (47 mg, 0.20 mmol), $K_2CO_3$ (107 mg, 0.77 mmol), and $Pd(dppf)Cl_2 \cdot CH_2Cl_2$ (6 mg, 0.008 mmol), in dioxane (1 mL) and water (0.13 mL, 7 mmol) was degassed with a stream of nitrogen for 5 minutes then heated to 100° C. overnight. The reaction mixture was cooled to room temperature, diluted with EtOAc and filtered through Celite®. Purification by basic prep HPLC (Agilent, Waters XBridge C18 5 um 50×100 mm column, 5-90% MeCN/20 mM $NH_4OH$ over 15 min, 80 mL/min) gave the title compound (38 mg, 59%). MS (ESI): mass calcd. for $C_{19}H_{18}F_5N_3O_2$, 415.1; m/z found, 416.1 $[M+H]^+$. $^1H$ NMR (500 MHz, Chloroform-d) δ ppm 8.35 (d, J=5.9 Hz, 1H), 7.78 (dd, J=11.3, 2.1 Hz, 1H), 7.72-7.64 (m, 1H), 7.39-7.32 (m, 1H), 7.02 (d, J=2.5 Hz, 1H), 6.67 (dd, J=6.0, 2.5 Hz, 1H), 5.90 (d, J=7.7 Hz, 1H), 4.52-4.34 (m, 1H), 4.23-4.08 (m, 2H), 3.80 (d, J=12.9 Hz, 1H), 3.16-3.02 (m, 2H), 2.30-2.21 (m, 1H), 2.01 (s, 3H), 1.62-1.48 (m, 1H).

Example 17: (*R/*R)—N-[3-Fluoro-1-[5-fluoro-2-[3-fluoro-4-(trifluoromethoxy)phenyl]-4-pyridyl]-4-piperidyl]acetamide

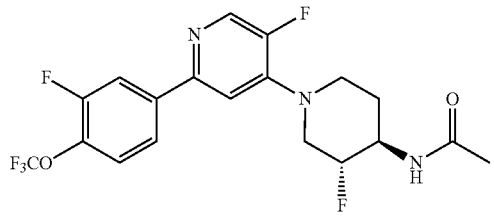 [SMILES: CC(=O)N[C@@H]1CCN(c2cc(-c3ccc(OC(F)(F)F)c(F)c3)ncc2F)C[C@H]1F]

Step A: tert-butyl ((3,4-trans)-1-(2-chloro-5-fluoropyridin-4-yl)-3-fluoropiperidin-4-yl)carbamate To a solution of tert-butyl ((3,4-trans)-3-fluoropiperidin-4-yl)carbamate (61 mg, 0.27 mmol), 2-chloro-5-fluoro-4- iodopyridine (128 mg, 0.49 mmol), and cesium carbonate (265 mg, 0.81 mmol) in toluene (1.8 mL) under nitrogen, was added Pd$_2$(dba)$_3$ (50 mg, 0.05 mmol) then followed by XantPhos (64 mg, 0.11 mmol). The reaction mixture was heated at 110° C. for 18 hours then filtered through Celite® and the solvent was evaporated. Purification via silica gel chromatography (0-100% [10% (NH$_3$ in MeOH, 2M)/DCM] in DCM) gave the title compound with impurities but was taken on to the next step without any further purification (130 mg). MS (ESI): mass calcd. for C$_{15}$H$_{20}$ClF$_2$N$_3$O$_2$, 347.1; m/z found, 348.1 [M+H]$^+$.

Step B: N-((3,4-trans)-1-(2-chloro-5-fluoropyridin-4-yl)-3-fluoropiperidin-4-yl)acetamide To a solution of tert-butyl ((3,4-trans)-1-(2-chloro-5-fluoropyridin-4-yl)-3-fluoropiperidin-4-yl)carbamate (130 mg, 0.37 mmol) in DCM (18 mL) was added TFA (0.58 mL, 7.5 mmol). The reaction mixture was stirred at room temperature for 16 hours then the solvent was evaporated.

The residue was taken up in pyridine (7.5 mL) and acetic anhydride (71 µL, 0.75 mmol) was added followed by 4-dimethylaminopyridine (DMAP) (3 mg, 0.02 mmol). The reaction mixture was stirred at room temperature for 16 hours then the solvent was evaporated. Purification by basic prep HPLC (Agilent, Waters XBridge C18 5 um 50×100 mm column, 5-90% MeCN/20 mM NH$_4$OH over 15 min, 80 mL/min) gave the title compound (32 mg, 30%). MS (ESI): mass calcd. for C$_{12}$H$_{14}$ClF$_2$N$_3$O, 289.1; m/z found, 290.1 [M+H]$^+$.

Step C: (*R/*R)—N-[3-fluoro-1-[5-fluoro-2-[3-fluoro-4-(trifluoromethoxy)phenyl]-4-pyridyl]-4-piperidyl]acetamide A solution of N-((3,4-trans)-1-(2-chloro-5-fluoropyridin-4-yl)-3-fluoropiperidin-4-yl)acetamide (32 mg, 0.11 mmol), (3-fluoro-4-(trifluoromethoxy)phenyl)boronic acid (34 mg, 0.14 mmol), K$_2$CO$_3$ (76 mg, 0.55 mmol), and Pd(dppf)Cl$_2$.CH$_2$Cl$_2$ (5 mg, 0.006 mmol), in dioxane (1.1 mL) and water (0.1, 5 mmol), was degassed with a stream of nitrogen for 5 minutes, then heated to 100° C. for 16 hours. The reaction mixture was cooled to room temperature, diluted with EtOAc and filtered through Celite®. Purification by basic prep HPLC (Agilent, Waters XBridge C18 5 um 50×100 mm column, 5-90% MeCN/20 mM NH$_4$OH over 15 min, 80 mL/min) gave the racemic title compound (26 mg, 54%). The racemic compound was then separated via SFC chiral separation (Stationary phase: Chiralpak IF 5 µm 250×21 mm, Mobile phase: 18% methanol, 82% CO$_2$, 2 mL/min, 150 Bar, retention time: 3.30 min at 254 nM) to afford the tile compound (11 mg, 22%). MS (ESI): mass calcd. for C$_{19}$H$_{17}$F$_6$N$_3$O$_2$, 433.1; m/z found, 434.1 [M+H]$^+$. $^1$H NMR (500 MHz, Chloroform-d) δ ppm 8.31 (d, J=4.7 Hz, 1H), 7.77 (dd, J=11.2, 2.1 Hz, 1H), 7.68-7.63 (m, 1H), 7.40-7.34 (m, 1H), 7.11 (d, J=7.1 Hz, 1H), 5.61 (d, J=7.7 Hz, 1H), 4.53 (dtd, J=49.4, 9.4, 4.8 Hz, 1H), 4.22-4.10 (m, 1H), 4.08-4.00 (m, 1H), 3.72-3.65 (m, 1H), 3.12-3.00 (m, 2H), 2.36-2.26 (m, 1H), 2.05 (s, 3H), 1.72-1.61 (m, 1H).

Example 18: (racemic)-N-[1-[2-[3-Fluoro-4-(trifluoromethoxy)phenyl]-4-pyridyl]-2-methyl-4-piperidyl]acetamide

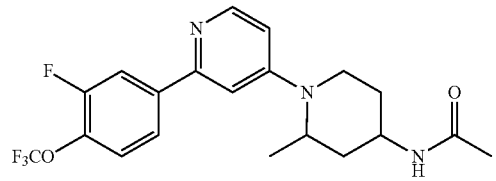 [SMILES: CC(=O)NC1CCN(c2ccnc(-c3ccc(OC(F)(F)F)c(F)c3)c2)C(C)C1]

Step A: tert-butyl (1-(2-Chloropyridin-4-yl)-2-methylpiperidin-4-yl)carbamate

To a solution of 2-chloro-4-fluoropyridine (61 mg, 0.45 mmol) and tert-butyl (2-methylpiperidin-4-yl)carbamate (99 mg, 0.45 mmol) in 1-butanol (2.2 mL) was added DIPEA (0.23 mL, 1.35 mmol). The reaction mixture was heated to 150° C. for 16 hours. Solvent was evaporated and purification via silica gel chromatography (0-100% [10% (NH$_3$ in MeOH, 2M)/DCM] in DCM) gave the title compound (28 mg, 19%). MS (ESI): mass calcd. for C$_{16}$H$_{24}$ClN$_3$O$_2$, 325.2; m/z found, 326.2 [M+H]$^+$.

Step B: tert-butyl (1-(2-(3-Fluoro-4-(trifluoromethoxy)phenyl)pyridin-4-yl)-2-methylpiperidin-4-yl)carbamate tert-Butyl (1-(2-chloropyridin-4-yl)-2-methylpiperidin-4-yl)carbamate (25 mg, 0.086 mmol), (3-fluoro-4-(trifluoromethoxy)phenyl)boronic acid (20 mg, 0.086 mmol), K$_2$CO$_3$ (59 mg, 0.43 mmol), and Pd(dppf)Cl$_2$.CH$_2$Cl$_2$ (3.5 mg, 0.004 mmol), dioxane (1.2 mL) and water (71 µL, 3.9 mmol) was combined, degassed with a stream of nitrogen for 5 minutes, and heated to 100° C. for 16 hours. The reaction mixture was cooled to room temperature, diluted with EtOAc and filtered through Celite®. Purification via silica gel chromatography (0-100% [10% (NH$_3$ in MeOH, 2M)/DCM] in DCM) gave the title compound (12 mg, 30%). MS (ESI): mass calcd. for C$_{23}$H$_{27}$F$_4$N$_3$O$_3$, 469.2; m/z found, 470.9 [M+H]$^+$.

Step C: (racemic)-N-[1-[2-[3-Fluoro-4-(trifluoromethoxy)phenyl]-4-pyridyl]-2-methyl-4-piperidyl]acetamide To a solution of tert-butyl (1-(2-(3-fluoro-4-(trifluoromethoxy)phenyl)pyridin-4-yl)-2-methylpiperidin-4-yl)carbamate (12 mg, 0.026 mmol) in DCM (1.3 mL) was added TFA (39 µL, 0.51 mmol).

The reaction mixture was stirred at room temperature for 16 hours then the solvent was evaporated. The residue was taken up in pyridine (0.5 mL) and acetic anhydride (5 µL, 0.051 mmol) was added followed by 4-dimethylaminopyridine (DMAP) (0.2 mg, 0.0013 mmol). The reaction mixture was stirred at room temperature overnight then the solvent was evaporated. Purification by basic prep HPLC (Agilent, Waters XBridge C18 5 um 50×100 mm column, 5-90% MeCN/20 mM NH$_4$OH over 15 min, 80 mL/min) gave the title compound (6 mg, 57%). MS (ESI): mass calcd. for C$_{20}$H$_{21}$F$_4$N$_3$O$_2$, 411.2; m/z found, 412.1 [M+H]$^+$. $^1$H NMR (500 MHz, Chloroform-d) δ ppm 8.34 (dd, J=11.0, 5.9 Hz, 1H), 7.79 (ddd, J=11.3, 3.4, 2.1 Hz, 1H), 7.73-7.64 (m, 1H), 7.41-7.31 (m, 1H), 7.00 (t, J=3.0 Hz, 1H), 6.65 (ddd, J=6.5, 4.1, 2.5 Hz, 1H), 5.49 (d, J=7.3 Hz, 0.5H), 5.32 (d, J=7.9 Hz, 0.5H), 4.45-4.37 (m, 0.5H), 4.32-4.22 (m, 0.5H), 4.10-4.02 (m, 0.5H), 3.99-3.90 (m, 0.5H), 3.81-3.74 (m, 0.5H), 3.54-3.47 (m, 0.5H), 3.37-3.29 (m, 0.5H), 3.19-3.10 (m, 0.5H), 2.24-2.13 (m, 1.5H), 2.02-1.97 (m, 3H), 1.72-1.58 (m, 2H), 1.45-1.33 (m, 0.5H), 1.29-1.21 (m, 3H).

Example 19: N-[1-[5-Cyano-2-[4-(trifluoromethoxy)phenyl]-4-pyridyl]-4-piperidyl]acetamide

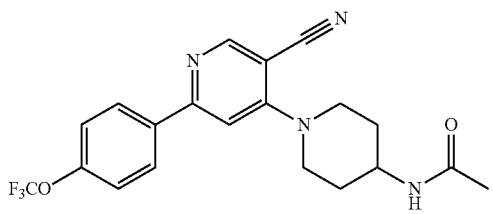 [SMILES: CC(=O)NC1CCN(c2cc(-c3ccc(OC(F)(F)F)cc3)ncc2C#N)CC1]

Step A: 4-(Methylthio)-2-oxo-6-(4-(trifluoromethoxy)phenyl)-2H-pyran-3-carbonitrile To a solution of 1-(4-(trifluoromethoxy)phenyl)ethan-1-one (207 mg, 0.99 mmol) and methyl 2-cyano-3,3-bis(methylthio)acrylate (213 mg, 0.99 mmol) in DMF (5 mL) was added KOH powder (112 mg, 1.99 mmol). The reaction mixture was stirred at room temperature for 16 hours and then poured into 100 mL of ice-water and stirred for 5 hours. The resulting precipitate was filtered, washed with water then dried under high vacuum to afford the title compound (226 mg, 69%). MS (ESI): mass calcd. for $C_{14}H_8F_3NO_3S$, 327.0; m/z found, 328.0 [M+H]$^+$.

Step B: N-(1-(3-Cyano-2-oxo-6-(4-(trifluoromethoxy)phenyl)-2H-pyran-4-yl)piperidin-4-yl)acetamide 4-(Methylthio)-2-oxo-6-(4-(trifluoromethoxy)phenyl)-2H-pyran-3-carbonitrile (226 mg, 0.69 mmol) was suspended in methanol (14 mL) and N-(piperidin-4-yl)acetamide was added. The reaction mixture was heated to reflux for 3 hours. Solvent was evaporated and purification via silica gel chromatography (0-100% [10% (NH$_3$ in MeOH, 2M)/DCM] in DCM) gave the title compound (210 mg, 72%). MS (ESI): mass calcd. for $C_{20}H_{18}F_3N_3O_4$, 421.1; m/z found, 422.1 [M+H]$^+$.

Step C: N-[1-[5-Cyano-2-[4-(trifluoromethoxy)phenyl]-4-pyridyl]-4-piperidyl]acetamide To a solution of N-(1-(3-cyano-2-oxo-6-(4-(trifluoromethoxy)phenyl)-2H-pyran-4-yl)piperidin-4-yl)acetamide (120 mg, 0.29 mmol) in DMF (1.9 mL) was added formimidamide hydrochloride (35 mg, 0.43 mmol) and KOH (32 mg, 0.57 mmol). The reaction mixture was stirred at room temperature for 24 hours then more formimidamide hydrochloride (18 mg, 0.22 mmol) was added. After 5 days at room temperature was added water and the resulting precipitate was filtered and washed with water. Purification by basic prep HPLC (Agilent, Waters XBridge C18 5 um 50×100 mm column, 5-90% MeCN/20 mM NH$_4$OH over 15 min, 80 mL/min) gave the title compound (42 mg, 38%). MS (ESI): mass calcd. for $C_{20}H_{19}F_3N_4O_2$, 404.1; m/z found, 405.1 [M+H]$^+$. $^1$H NMR (500 MHz, Chloroform-d) δ ppm 8.61 (s, 1H), 8.00-7.94 (m, 2H), 7.33-7.27 (m, 2H), 7.09 (s, 1H), 5.71 (d, J=7.9 Hz, 1H), 4.10-3.98 (m, 3H), 3.20-3.11 (m, 2H), 2.17-2.09 (m, 2H), 1.99 (s, 3H), 1.68-1.55 (m, 2H).

Example 20: N-[1-[2-Cyano-6-[3-fluoro-4-(trifluoromethoxy)phenyl]-4-pyridyl]-4-piperidyl]acetamide

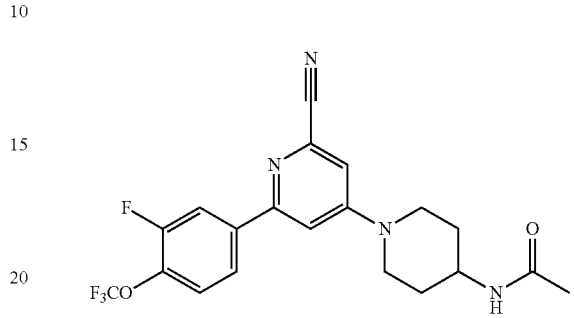

Step A: 4-Chloro-6-(3-fluoro-4-(trifluoromethoxy)phenyl)picolinonitrile

A solution of (4,6-dichloropyridine-2-carbonitrile) (150 mg, 0.87 mmol), (3-fluoro-4-(trifluoromethoxy)phenyl)boronic acid (198 mg, 0.87 mmol), palladium(II) acetate (9.7 mg, 0.043 mmol), cesium carbonate (706 mg, 2.17 mmol), and DPPF (24 mg, 0.043 mmol), in dioxane (4.3 mL) and water (0.94 mL), was degassed with nitrogen for 5 minutes, then heated to 70° C. for 16 hours. The reaction mixture was partitioned between EtOAc and a saturated aqueous solution of NaCl. The aqueous phase was extracted twice with EtOAc. The combined organic layers were dried over MgSO$_4$, filtered and evaporated. Purification via silica gel chromatography (0-20% EtOAc in hexanes) gave the title compound (86 mg, 31%). $^1$H NMR (400 MHz, DMSO-d$_6$) δ 8.64 (d, J=1.8 Hz, 1H), 8.38 (d, J=1.7 Hz, 1H), 8.32-8.27 (m, 1H), 8.16-8.11 (m, 1H), 7.79-7.70 (m, 1H).

Step B: N-[1-[2-Cyano-6-[3-fluoro-4-(trifluoromethoxy)phenyl]-4-pyridyl]-4-piperidyl]acetamide A solution of (4-chloro-6-(3-fluoro-4-(trifluoromethoxy)phenyl)picolinonitrile (60 mg, 0.19 mmol), N-(piperidin-4-yl)acetamide (135 mg, 0.95 mmol), potassium phosphate (121 mg, 0.57 mmol), Pd$_2$(dba)$_3$ (14 mg, 0.015 mmol), and (±)-2,2'-bis(diphenylphosphino)-1,1'-binaphthalene (rac-BINAP) (19 mg, 0.030 mmol), in DMF (0.15 mL) and dioxane (0.95 mL) was heated in the microwave at 150° C. for 30 min then filtered through Celite®. Purification by basic prep HPLC (Agilent, Waters XBridge C18 5 μm 50×100 mm column, 5-90% MeCN/20 mM NH$_4$OH over 15 min, 80 mL/min) gave the title compound (43 mg, 54%). MS (ESI): mass calcd. for $C_{20}H_{18}F_4N_4O_2$, 422.1; m/z found, 423.2 [M+H]$^+$. $^1$H NMR (400 MHz, DMSO-d$_6$) δ ppm 8.23 (dd, J=12.0, 2.1 Hz, 1H), 8.07 (ddd, J=8.7, 2.1, 1.1 Hz, 1H), 7.84 (d, J=7.6 Hz, 1H), 7.72-7.65 (m, 1H), 7.60 (d, J=2.4 Hz, 1H), 7.54 (d, J=2.3 Hz, 1H), 4.12 (d, J=13.6 Hz, 2H), 3.93-3.80 (m, 1H), 3.19-3.09 (m, 2H), 1.87-1.77 (m, 5H), 1.44-1.30 (m, 2H).

Example 21: N-[1-[2-[3-Fluoro-4-(trifluoromethoxy)phenyl]-6-methyl-4-pyridyl]-4-piperidyl]acetamide

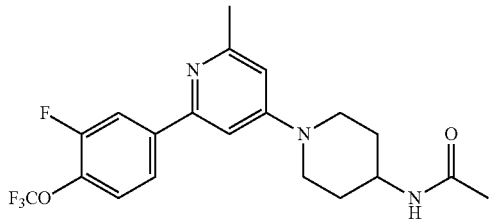 [SMILES: CC(=O)NC1CCN(c2cc(C)nc(-c3ccc(OC(F)(F)F)c(F)c3)c2)CC1]

Step A: 4-Chloro-2-(3-fluoro-4-(trifluoromethoxy)phenyl)-6-methylpyridine

A solution of 2,4-dichloro-6-methylpyridine (150 mg, 0.93 mmol), (3-fluoro-4-(trifluoromethoxy)phenyl)boronic acid (212 mg, 0.93 mmol), palladium(II) acetate (10 mg, 0.046 mmol), cesium carbonate (754 mg, 2.3 mmol), and DPPF (26 mg, 0.046 mmol), in dioxane (4.6 mL) and water (1 mL), was degassed with nitrogen for 5 minutes, then heated to 70° C. for 16 hours. The reaction mixture was partitioned between EtOAc and a saturated aqueous solution of NaCl. The aqueous phase was extracted twice with EtOAc. The combined organic layers were dried over $MgSO_4$, filtered and evaporated. Purification via silica gel chromatography (0-20% EtOAc in hexanes) gave the title compound (170 mg, 60%). MS (ESI): mass calcd. for $C_{13}H_8ClF_4NO$, 305.0; m/z found, 306.0 $[M+H]^+$.

Step B: N-[1-[2-[3-Fluoro-4-(trifluoromethoxy)phenyl]-6-methyl-4-pyridyl]-4-piperidyl]acetamide A solution of 4-chloro-2-(3-fluoro-4-(trifluoromethoxy)phenyl)-6-methylpyridine (60 mg, 0.20 mmol), N-(piperidin-4-yl)acetamide (140 mg, 0.98 mmol), potassium phosphate (125 mg, 0.59 mmol), $Pd_2(dba)_3$ (14 mg, 0.016 mmol), and (±)-2,2'-bis(diphenylphosphino)-1,1'-binaphthalene (rac-BINAP) (20 mg, 0.021 mmol) in dioxane (1 mL) was heated in the microwave at 150° C. for 30 minutes then filtered through Celite®. Purification by basic prep HPLC (Agilent, Waters XBridge C18 5 um 50×100 mm column, 5-90% MeCN/20 mM $NH_4OH$ over 15 min, 80 mL/min) gave the title compound (47 mg, 58%). MS (ESI): mass calcd. for $C_{20}H_{21}F_4N_3O_2$, 411.2; m/z found, 412.2 $[M+H]^+$. $^1H$ NMR (400 MHz, Methanol-$d_4$) δ ppm 7.84-7.78 (m, 1H), 7.75-7.70 (m, 1H), 7.51-7.44 (m, 1H), 7.04 (d, J=2.4 Hz, 1H), 6.74 (d, J=2.4 Hz, 1H), 4.04 (d, J=13.3 Hz, 2H), 3.97-3.87 (m, 1H), 3.06 (ddd, J=13.5, 11.6, 2.7 Hz, 2H), 2.46 (s, 3H), 1.99-1.91 (m, 5H), 1.56-1.43 (m, 2H).

Example 22: 1-[2-[2-[3-Fluoro-4-(trifluoromethoxy)phenyl]-4-pyridyl]-2,6-diazaspiro[3.3]heptan-6-yl]ethanone

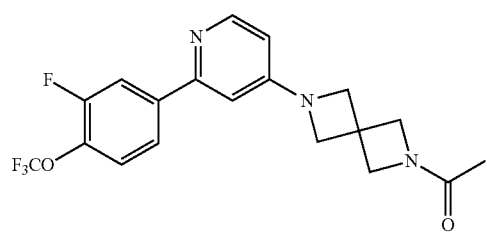 [SMILES: CC(=O)N1CC2(C1)CN(c1ccnc(-c3ccc(OC(F)(F)F)c(F)c3)c1)C2]

Step A: tert-Butyl 6-(2-(3-fluoro-4-(trifluoromethoxy)phenyl)pyridin-4-yl)-2,6-diazaspiro[3.3]heptane-2-carboxylate To a solution of 4-fluoro-2-(3-fluoro-4-(trifluoromethoxy)phenyl)pyridine (Example 11, product of Step A, 34 mg, 0.12 mmol) and tert-butyl 2,6-diazaspiro[3.3]heptane-2-carboxylate oxalate (49 mg, 0.16 mmol) in 1-butanol (1.2 mL) was added DIPEA (64 µL, 0.37 mmol). The reaction mixture was then heated to 150° C. for 16 hours. Solvent was evaporated and purification via silica gel chromatography (0-100% [10% ($NH_3$ in MeOH, 2M)/DCM] in DCM) gave the title compound (43 mg, 77%). MS (ESI): mass calcd. for $C_{22}H_{23}F_4N_3O_3$, 453.2; m/z found, 454.2 $[M+H]^+$.

Step B: 1-[2-[2-[3-Fluoro-4-(trifluoromethoxy)phenyl]-4-pyridyl]-2,6-diazaspiro[3.3]heptan-6-yl]ethanone To a solution of tert-butyl 6-(2-(3-fluoro-4-(trifluoromethoxy)phenyl)pyridin-4-yl)-2,6-diazaspiro[3.3]heptane-2-carboxylate (43 mg, 0.095 mmol) in DCM (4.7 mL) was added TFA (0.15 mL, 1.9 mmol).

The reaction mixture was stirred at room temperature for 16 hours then the solvent was evaporated. The residue was taken up in pyridine (1.9 mL) and acetic anhydride (18 µL, 0.19 mmol) was added followed by 4-dimethylaminopyridine (DMAP) (0.5 mg, 0.005 mmol). The reaction mixture was stirred at room temperature for 16 hours then solvent was evaporated. Purification by basic prep HPLC (Agilent, Waters XBridge C18 5 um 50×100 mm column, 5-90% MeCN/20 mM $NH_4OH$ over 15 min, 80 mL/min) gave the title compound (22 mg, 59%). MS (ESI): mass calcd. for $C_{19}H_{17}F_4N_3O_2$, 395.1; m/z found, 396.1 $[M+H]^+$. $^1H$ NMR (500 MHz, Chloroform-d) δ ppm 8.31 (d, J=5.6 Hz, 1H), 7.79 (dd, J=11.4, 2.1 Hz, 1H), 7.69 (ddd, J=8.6, 2.2, 1.2 Hz, 1H), 7.38-7.32 (m, 1H), 6.60 (d, J=2.1 Hz, 1H), 6.27 (dd, J=5.6, 2.2 Hz, 1H), 4.34 (s, 2H), 4.20 (s, 2H), 4.18-4.12 (m, 4H), 1.89 (s, 3H).

Example 23: 1-[2-[2-[4-(Difluoromethoxy)-3-fluoro-phenyl]-4-pyridyl]-2,6-diazaspiro[3.3]heptan-6-yl]ethanone

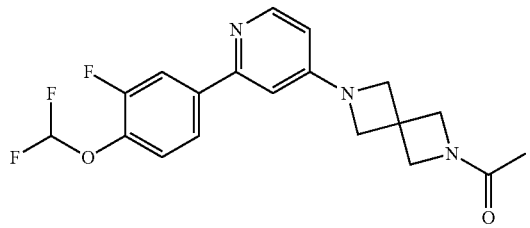 [SMILES: CC(=O)N1CC2(C1)CN(c1ccnc(-c3ccc(OC(F)F)c(F)c3)c1)C2]

Step A: tert-Butyl 6-(2-chloropyridin-4-yl)-2,6-diazaspiro[3.3]heptane-2-carboxylate To a solution of 2-chloro-4-fluoropyridine (110 mg, 0.81 mmol) and tert-butyl 2,6-diazaspiro[3.3]heptane-2-carboxylate oxalate (395 mg, 0.81 mmol) in 1-butanol (4 mL) was added DIPEA (0.42 mL, 2.4 mmol). The reaction mixture was heated in the microwave for 1 hours at 100° C. Solvent was evaporated and purification via silica gel chromatography (FCC, 0-20% EtOAc in hexanes) gave the title compound (115 mg, 46%). MS (ESI): mass calcd. for $C_{15}H_{20}ClN_3O_2$, 309.1; m/z found, 310.2 $[M+H]^+$.

Step B: 2-(2-Chloropyridin-4-yl)-2,6-diazaspiro[3.3]heptane

To a solution of tert-butyl 6-(2-chloropyridin-4-yl)-2,6-diazaspiro[3.3]heptane-2-carboxylate (120 mg, 0.39 mmol) in DCM (7.7 mL) was added TFA (0.59 mL, 7.7 mmol). The reaction mixture was stirred at room temperature for 16 hours then the solvent was concentrated under reduced pressure. The crude product was used in the next step without further purification.

Step C: 1-(6-(2-Chloropyridin-4-yl)-2,6-diazaspiro[3.3]heptan-2-yl)ethan-1-one 2-(2-Chloropyridin-4-yl)-2,6-diazaspiro[3.3]heptane was taken up in pyridine (4 mL) and acetic anhydride (74 µL, 0.78 mmol) was added followed by 4-dimethylaminopyridine (DMAP) (2 mg, 0.02 mmol). The reaction mixture was stirred at room temperature overnight then the solvent was evaporated. To the residue was added EtOAc and a saturated solution of NaHCO₃. The aqueous solution was extracted twice with EtOAc and the combined organic layers were dried over MgSO₄, filtered and evaporated. Purification via silica gel chromatography (0-10% MeOH in DCM) gave the title compound (98 mg, 100%). MS (ESI): mass calcd. for $C_{12}H_{14}ClN_3O$, 251.1; m/z found, 252.1 $[M+H]^+$.

Step D: 1-[2-[2-[4-(Difluoromethoxy)-3-fluoro-phenyl]-4-pyridyl]-2,6-diazaspiro[3.3]heptan-6-yl]ethenone A solution of 1-(6-(2-chloropyridin-4-yl)-2,6-diazaspiro[3.3]heptan-2-yl)ethan-1-one (33 mg, 0.13 mmol), 2-(4-(difluoromethoxy)-3-fluorophenyl)-4,4,5,5-tetramethyl-1,3,2-dioxaborolane (40 mg, 0.14 mmol), and Pd(PPh₃)₄ (8 mg, 0.007 mmol) in 1M aqueous sodium carbonate (0.4 mL, 0.4 mmol) in DMF (0.7 mL) was heated in the microwave for 30 minutes at 100° C. Water and ethyl acetate were added and the aqueous layer was extracted with ethyl acetate (3×). The combined organic layers were dried over MgSO₄, filtered, and concentrated under reduced pressure. Purification by basic prep HPLC (Agilent, Waters XBridge C18 5 um 50×100 mm column, 5-90% MeCN/20 mM NH₄OH over 15 min, 80 mL/min) gave the title compound (10 mg, 20%). MS (ESI): mass calcd. for $C_{19}H_{18}F_3N_3O_2$, 377.1; m/z found, 378.1 $[M+H]^+$. ¹H NMR (400 MHz, DMSO-d₆) δ ppm 8.22 (d, J=5.6 Hz, 1H), 8.05 (dd, J=12.4, 2.1 Hz, 1H), 7.95 (ddd, J=8.6, 2.1, 1.1 Hz, 1H), 7.44 (t, J=8.4 Hz, 1H), 7.31 (t, J=73.2 Hz, 1H), 6.94 (d, J=2.1 Hz, 1H), 6.37 (dd, J=5.6, 2.1 Hz, 1H), 4.32 (s, 2H), 4.14 (s, 4H), 4.04 (s, 2H), 1.76 (s, 3H).

Example 24: N-[4-[[2-[3-Fluoro-4-(trifluoromethoxy)phenyl]-4-pyridyl]oxy]cyclohexyl]acetamide

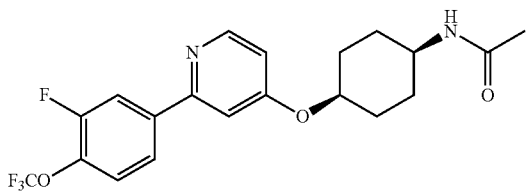 [SMILES: CC(=O)N[C@H]1CC[C@@H](Oc2ccnc(-c3ccc(OC(F)(F)F)c(F)c3)c2)CC1]

Step A: tert-Butyl ((1,4-cis)-4-((2-(3-fluoro-4-(trifluoromethoxy)phenyl)pyridin-4-yl)oxy)cyclohexyl)carbamate To a solution 4-fluoro-2-(3-fluoro-4-(trifluoromethoxy)phenyl)pyridine (Example 11, product from Step A, 0 mg, 0.18 mmol) in DMF (1.8 mL) cooled at 0° C. was added NaH (60% dispersion in oil) (9 mg, 0.24 mmol) and stirred at this temperature for 15 minutes. Then tert-butyl ((1,4-cis)-4-hydroxycyclohexyl)carbamate (47 mg, 0.22 mmol) dissolved in 0.3 mL DMF was added. The reaction mixture was warmed up to room temperature and stirred for 16 hours. Water was then added and the reaction mixture was diluted with EtOAc. The aqueous phase was extracted twice with EtOAc and the combined organic layers were dried over MgSO4, filtered and evaporated. Purification via silica gel chromatography (0-100% EtOAc in hexanes) gave the title compound (35 mg, 41%). MS (ESI): mass calcd. for $C_{23}H_{26}F_4N_2O_4$, 470.2; m/z found, 471.2 $[M+H]^+$.

Step B: N-[4-[[2-[3-Fluoro-4-(trifluoromethoxy)phenyl]-4-pyridyl]oxy]cyclohexyl]acetamide The title compound was prepared in a manner analogous to Example 4, Step B. MS (ESI): mass calcd. for $C_{20}H_{20}F_4N_2O_3$, 412.1; m/z found, 413.1 $[M+H]^+$. ¹H NMR (500 MHz, Chloroform-d) δ ppm 8.48 (d, J=5.7 Hz, 1H), 7.83 (dd, J=11.3, 2.1 Hz, 1H), 7.75-7.70 (m, 1H), 7.40-7.34 (m, 1H), 7.16 (d, J=2.3 Hz, 1H), 6.77 (dd, J=5.7, 2.3 Hz, 1H), 5.49 (d, J=8.1 Hz, 1H), 4.68-4.62 (m, 1H), 3.95-3.85 (m, 1H), 2.10-2.02 (m, 2H), 1.98 (s, 3H), 1.87-1.79 (m, 2H), 1.79-1.71 (m, 2H), 1.67-1.55 (m, 2H).

Example 25: (racemic)-N-[3-[[2-[3-Fluoro-4-(trifluoromethoxy)phenyl]-6-(hydroxymethyl)-4-pyridyl]amino]-2-methyl-propyl]acetamide

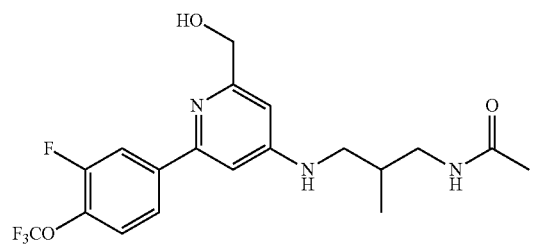 [SMILES: CC(=O)NCC(C)CNc1cc(CO)nc(-c2ccc(OC(F)(F)F)c(F)c2)c1]

Step A: (4-Chloro-6-(3-fluoro-4-(trifluoromethoxy)phenyl)pyridin-2-yl)methanol

A solution of (4,6-dichloropyridin-2-yl)methanol (80 mg, 0.45 mmol), (3-fluoro-4-(trifluoromethoxy)phenyl)boronic acid (103 mg, 0.45 mmol), palladium(II) acetate (5 mg, 0.022 mmol), cesium carbonate (366 mg, 1.12 mmol), and DPPF (12 mg, 0.022 mmol), in dioxane (2.2 mL) and water (0.5 mL), was degassed with nitrogen for 5 minutes then heated to 70° C. for 16 hours. The reaction mixture was partitioned between EtOAc and a saturated aqueous solution of NaCl. The aqueous phase was extracted twice with EtOAc. The combined organic layers were dried over MgSO₄, filtered and evaporated. Purification via silica gel chromatography (0-20% EtOAc in hexanes) gave the title compound (104 mg, 72%). MS (ESI): mass calcd. for $C_{13}H_8ClF_4NO_2$, 321.0; m/z found, 322.9 [M+H]$^+$.

Step B: tert-Butyl (3-((2-(3-fluoro-4-(trifluoromethoxy)phenyl)-6-(hydroxymethyl)pyridin-4-yl)amino)-2-methylpropyl)carbamate A solution of (4-chloro-6-(3-fluoro-4-(trifluoromethoxy)phenyl)pyridin-2-yl)methanol (25 mg, 0.077 mmol), tert-butyl (3-amino-2-methylpropyl)carbamate (77 mg, 0.39 mmol), potassium phosphate (49 mg, 0.23 mmol), Pd$_2$(dba)$_3$ (6 mg, 0.006 mmol), and rac-BINAP (8 mg, 0.012 mmol) in dioxane (1.1 mL) was heated in the microwave at 150° C. for 1.5 hours then filtered through Celite®. Purification by basic prep HPLC (Agilent, Waters XBridge C18 5 um 50×100 mm column, 5-90% MeCN/20 mM NH$_4$OH over 15 min, 80 mL/min) gave the title compound (25 mg, 68%). MS (ESI): mass calcd. for $C_{22}H_{27}F_4N_3O_4$, 473.2; m/z found, 474.2 [M+H]$^+$.

Step C: (racemic)-N-[3-[[2-[3-Fluoro-4-(trifluoromethoxy)phenyl]-6-(hydroxymethyl)-4-pyridyl]amino]-2-methyl-propyl]acetamide To a solution of tert-butyl (3-((2-(3-fluoro-4-(trifluoromethoxy)phenyl)-6-(hydroxymethyl)pyridin-2-yl)amino)-2-methylpropyl)carbamate (25 mg, 0.053 mmol) in DCM (1.8 mL) was added TFA (81 µL, 1.06 mmol). The reaction mixture was stirred at room temperature for 16 hours then the solvent was evaporated.

The residue was taken up in THF (1.1 mL) and acetyl chloride (15 µL, 0.21 mmol) followed by sodium carbonate (34 mg, 0.32 mmol) and water (0.4 mL) were added. The reaction mixture was stirred at room temperature for 24 hours then was filtered through Celite® and solvent was evaporated. Purification by basic prep HPLC (Agilent, Waters XBridge C18 5 um 50×100 mm column, 5-90% MeCN/20 mM NH$_4$OH over 15 min, 80 mL/min) gave the title compound (17 mg, 75%). MS (ESI): mass calcd. for $C_{19}H_{21}F_4N_3O_3$, 415.2; m/z found, 416.1 [M+H]$^+$. $^1$H NMR (400 MHz, Chloroform-d) δ ppm 7.81 (dd, J=11.4, 2.1 Hz, 1H), 7.77-7.68 (m, 1H), 7.38-7.32 (m, 1H), 6.75 (d, J=2.0 Hz, 1H), 6.35 (s, 1H), 5.75-5.68 (m, 1H), 5.54 (t, J=6.3 Hz, 1H), 4.64 (s, 2H), 3.44-3.35 (m, 1H), 3.22-3.12 (m, 2H), 3.04-2.95 (m, 1H), 2.04 (s, 3H), 2.01-1.93 (m, 1H), 0.99 (d, J=6.9 Hz, 3H).

Example 26: 1-[6-[4-(Trifluoromethoxy)phenyl]pyrimidin-4-yl]piperidine-3-carboxamide

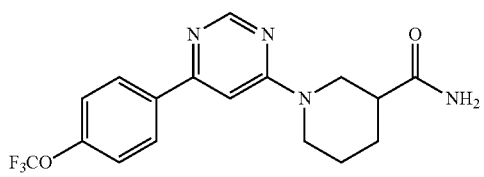 [SMILES: NC(=O)C1CCCN(c2cc(-c3ccc(OC(F)(F)F)cc3)ncn2)C1]

The title compound was prepared in a manner analogous to Example 1, using piperidine-3-carboxamide instead of piperidine-4-carboxamide in Step A. MS (ESI): mass calcd. for $C_{17}H_{17}F_3N_4O_2$, 366.1; m/z found, 367.2 [M+H]$^+$. $^1$H NMR (400 MHz, DMSO-d$_6$) δ ppm 8.58 (d, J=1.0 Hz, 1H), 8.33-8.26 (m, 2H), 7.48 (ddd, J=8.8, 2.0, 1.0 Hz, 2H), 7.40 (t, J=2.4 Hz, 2H), 6.92 (s, 1H), 4.68-4.40 (m, 2H), 3.09-2.88 (m, 2H), 2.36-2.25 (m, 1H), 1.92 (d, J=12.4 Hz, 1H), 1.80-1.61 (m, 2H), 1.41 (dd, J=12.3, 4.4 Hz, 1H).

Example 27: 1-[6-[4-(Difluoromethoxy)phenyl]pyrimidin-4-yl]piperidine-4-carboxamide

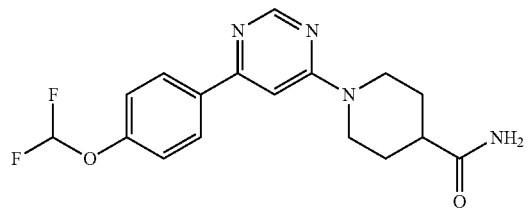 [SMILES: NC(=O)C1CCN(c2cc(-c3ccc(OC(F)F)cc3)ncn2)CC1]

The title compound was prepared in a manner analogous to Example 1, using (4-(difluoromethoxy)phenyl)boronic acid instead of (4-(trifluoromethoxy)phenyl)boronic acid in Step A. MS (ESI): mass calcd. for $C_{17}H_{18}F_2N_4O_2$, 348.1; m/z found, 349.2 [M+H]$^+$. $^1$H NMR (400 MHz, DMSO-d$_6$) δ ppm 8.55 (d, J=1.0 Hz, 1H), 8.27-8.21 (m, 2H), 7.55-7.15 (m, 5H), 6.82 (s, 1H), 4.55 (d, J=12.7 Hz, 2H), 3.02-2.90 (m, 2H), 2.43 (ddt, J=11.5, 7.7, 3.9 Hz, 1H), 1.79 (dd, J=13.0, 3.6 Hz, 2H), 1.50 (qd, J=12.4, 4.0 Hz, 2H).

Example 28: 1-[2-Methyl-6-[4-(trifluoromethoxy)phenyl]pyrimidin-4-yl]piperidine-4-carboxamide

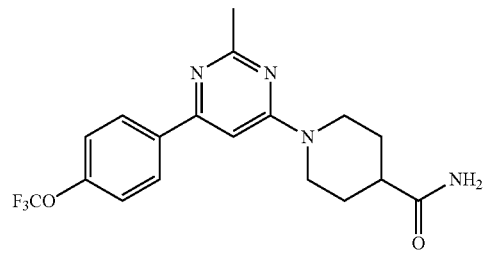 [SMILES: Cc1nc(-c2ccc(OC(F)(F)F)cc2)cc(N2CCC(C(N)=O)CC2)n1]

The title compound was prepared in a manner analogous to Example 1, using 4,6-dichloro-2-methylpyrimidine instead of 4,6-dichloropyrimidine in Step A. MS (ESI): mass calcd. for $C_{18}H_{19}F_3N_4O_2$, 380.1; m/z found, 381.2 [M+H]$^+$. $^1$H NMR (400 MHz, DMSO-d$_6$) δ ppm 8.29-8.23 (m, 2H), 7.50-7.43 (m, 2H), 7.32 (s, 1H), 7.19 (s, 1H), 6.82 (s, 1H), 4.55 (d, J=12.4 Hz, 2H), 3.01-2.88 (m, 2H), 2.44 (s, 3H), 2.44-2.35 (m, 1H), 1.84-1.73 (m, 2H), 1.49 (qd, J=12.4, 4.0 Hz, 2H).

Example 29: 1-[6-[3-(Difluoromethoxy)-4-fluorophenyl]pyrimidin-4-yl]piperidine-4-carboxamide

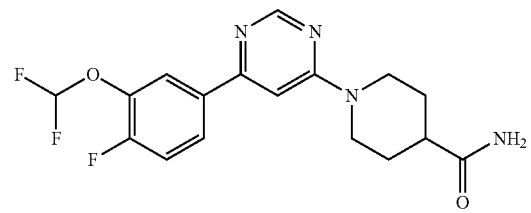 [SMILES: NC(=O)C1CCN(c2cc(-c3ccc(F)c(OC(F)F)c3)ncn2)CC1]

The title compound was prepared in a manner analogous to Example 1, using (3-(difluoromethoxy)-4-fluorophenyl) boronic acid instead of (4-(trifluoromethoxy)phenyl)boronic acid in Step B. MS (ESI): mass calcd. for $C_{17}H_{17}F_3N_4O_2$, 366.1; m/z found, 367.2 [M+H]+. 1H NMR (400 MHz, DMSO-$d_6$) δ ppm 8.56 (d, J=1.0 Hz, 1H), 8.20-8.12 (m, 2H), 7.57-7.53 (m, 1H), 7.52-7.17 (m, 3H), 6.83 (s, 1H), 4.56 (d, J=12.8 Hz, 2H), 2.99 (t, J=12.0 Hz, 2H), 2.43 (ddt, J=11.4, 7.7, 3.8 Hz, 1H), 1.84-1.74 (m, 2H), 1.50 (qd, J=12.5, 4.1 Hz, 2H).

Example 30: 1-[6-[4-(Trifluoromethyl)phenyl]pyrimidin-4-yl]piperidine-4-carboxamide

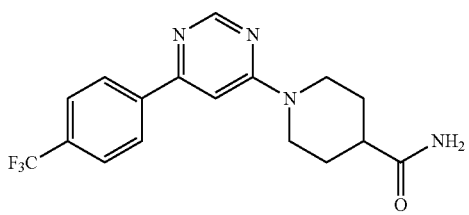 [SMILES: NC(=O)C1CCN(c2cc(-c3ccc(C(F)(F)F)cc3)ncn2)CC1]

The title compound was prepared in a manner analogous to Example 1, using 4-(trifluoromethyl)phenylboronic acid instead of (4-(trifluoromethoxy)phenyl)boronic acid in Step B. MS (ESI): mass calcd. for $C_{17}H_{17}F_3N_4O$, 350.1; m/z found, 351.2 [M+H]+. 1H NMR (400 MHz, DMSO-$d_6$) δ ppm 8.60 (d, J=1.0 Hz, 1H), 8.41-8.35 (m, 2H), 7.86 (d, J=8.1 Hz, 2H), 7.45 (d, J=1.3 Hz, 1H), 7.33 (s, 1H), 6.83 (s, 1H), 4.57 (d, J=12.2 Hz, 2H), 3.06-2.93 (m, 2H), 2.44 (ddt, J=11.4, 7.7, 3.8 Hz, 1H), 1.81 (dd, J=13.5, 3.2 Hz, 2H), 1.51 (qd, J=12.5, 4.0 Hz, 2H).

Example 31: 1-[6-[3-Fluoro-4-(trifluoromethoxy) phenyl]pyrimidin-4-yl]piperidine-4-carboxamide

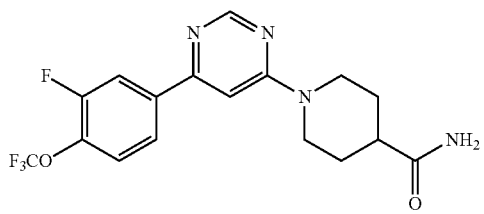 [SMILES: NC(=O)C1CCN(c2cc(-c3ccc(OC(F)(F)F)c(F)c3)ncn2)CC1]

The title compound was prepared in a manner analogous to Example 1, using (3-fluoro-4-(trifluoromethoxy)phenyl) boronic acid instead of (4-(trifluoromethoxy)phenyl)boronic acid in Step B. MS (ESI): mass calcd. for $C_{17}H_{16}F_4N_4O_2$, 384.1; m/z found, 385.2 [M+H]+. 1H NMR (400 MHz, DMSO-$d_6$) δ ppm 8.58 (d, J=1.0 Hz, 1H), 8.30 (dd, J=12.1, 2.1 Hz, 1H), 8.16 (ddd, J=8.6, 2.2, 1.2 Hz, 1H), 7.73-7.67 (m, 1H), 7.44 (d, J=1.3 Hz, 1H), 7.33 (s, 1H), 6.83 (s, 1H), 4.57 (d, J=12.1 Hz, 2H), 3.00 (td, J=13.1, 2.7 Hz, 2H), 2.44 (ddt, J=11.3, 7.8, 4.2 Hz, 1H), 1.81 (dd, J=13.2, 3.7 Hz, 2H), 1.50 (qd, J=11.8, 4.0 Hz, 2H).

Example 32: 1-[5-Methyl-6-[4-(trifluoromethoxy) phenyl]pyrimidin-4-yl]piperidine-4-carboxamide

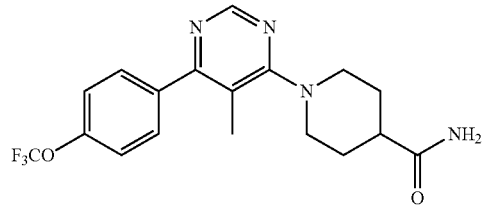 [SMILES: Cc1c(-c2ccc(OC(F)(F)F)cc2)ncnc1N1CCC(C(N)=O)CC1]

The title compound was prepared in a manner analogous to Example 1, using 4,6-dichloro-5-methylpyrimidine instead of 4,6-dichloropyrimidine in Step A. MS (ESI): mass calcd. for $C_{18}H_{19}F_3N_4O_2$, 380.1; m/z found, 381.2 [M+H]+. 1H NMR (500 MHz, DMSO-$d_6$) δ ppm 8.58 (s, 1H), 7.81-7.76 (m, 2H), 7.49-7.45 (m, 2H), 7.31 (s, 1H), 6.81 (s, 1H), 3.90 (d, J=13.1 Hz, 2H), 2.92 (t, J=12.2 Hz, 2H), 2.40-2.32 (m, 1H), 2.17 (s, 3H), 1.85-1.77 (m, 2H), 1.66 (dt, J=12.4, 8.7 Hz, 2H).

Example 33: 1-[6-[3-Fluoro-4-(trifluoromethoxy) phenyl]-2-methyl-pyrimidin-4-yl]piperidine-4-carboxamide

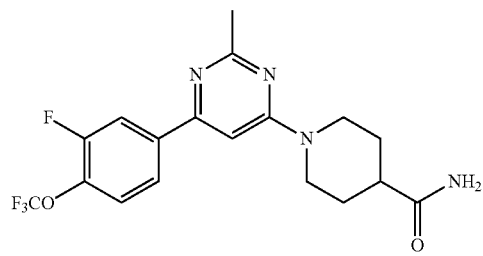 [SMILES: Cc1nc(-c2ccc(OC(F)(F)F)c(F)c2)cc(N2CCC(C(N)=O)CC2)n1]

The title compound was prepared in a manner analogous to Example 1, using 4,6-dichloro-2-methylpyrimidine instead of 4,6-dichloropyrimidine in Step A; and using (3-fluoro-4-(trifluoromethoxy)phenyl)boronic acid instead of (4-(trifluoromethoxy)phenyl)boronic acid in Step B. MS (ESI): mass calcd. for $C_{18}H_{18}F_4N_4O_2$, 398.1; m/z found, 399.2 [M+H]+. 1H NMR (500 MHz, DMSO-$d_6$) δ ppm 8.27 (dd, J=12.0, 2.1 Hz, 1H), 8.13 (dt, J=8.8, 1.6 Hz, 1H), 7.67 (t, J=8.0 Hz, 1H), 7.31 (s, 1H), 7.25 (s, 1H), 6.81 (s, 1H), 4.62-4.48 (m, 2H), 2.96 (t, J=12.8 Hz, 2H), 2.47-2.38 (m, 4H), 1.79 (d, J=13.0 Hz, 2H), 1.54-1.43 (m, 2H).

Example 34: 1-[6-[3-Fluoro-4-(2,2,2-trifluoroethoxy)phenyl]pyrimidin-4-yl]piperidine-4-carboxamide

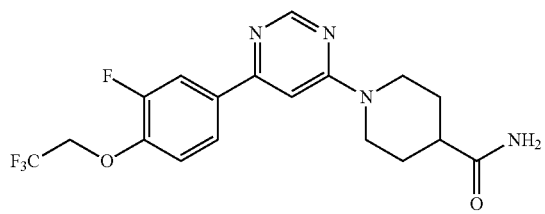 [SMILES: NC(=O)C1CCN(c2cc(-c3ccc(OCC(F)(F)F)c(F)c3)ncn2)CC1]

The title compound was prepared in a manner analogous to Example 1, using (3-fluoro-4-(2,2,2-trifluoroethoxy)phenyl)boronic acid instead of (4-(trifluoromethoxy)phenyl) boronic acid in Step B. MS (ESI): mass calcd. for $C_{18}H_{18}F_4N_4O_2$, 398.1; m/z found, 399.2 [M+H]$^+$. $^1$H NMR (500 MHz, DMSO-d$_6$) δ ppm 8.53 (d, J=1.0 Hz, 1H), 8.12 (dd, J=13.0, 2.1 Hz, 1H), 8.08-8.03 (m, 1H), 7.40 (t, J=8.8 Hz, 1H), 7.34 (d, J=1.2 Hz, 1H), 7.31 (s, 1H), 6.81 (s, 1H), 4.95 (q, J=8.8 Hz, 2H), 4.59-4.50 (m, 2H), 2.97 (t, J=12.7 Hz, 2H), 2.47-2.38 (m, 1H), 1.79 (d, J=13.1 Hz, 2H), 1.49 (d, J=10.4 Hz, 2H).

Example 35: 1-[2-Cyclopropyl-6-[4-(trifluoromethoxy)phenyl]pyrimidin-4-yl]piperidine-4-carboxamide

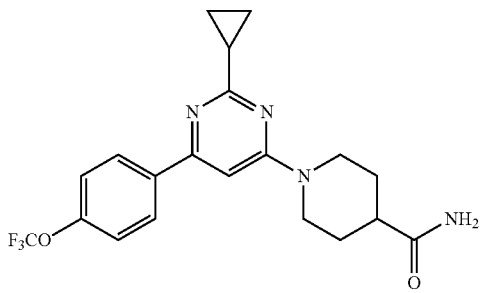 [SMILES: NC(=O)C1CCN(c2cc(-c3ccc(OC(F)(F)F)cc3)nc(C3CC3)n2)CC1]

The title compound was prepared in a manner analogous to Example 1, using 4,6-dichloro-2-cyclopropylpyrimidine instead of 4,6-dichloropyrimidine in Step A. MS (ESI): mass calcd. for $C_{20}H_{21}F_3N_4O_2$, 406.2; m/z found, 407.2 [M+H]$^+$. $^1$H NMR (500 MHz, DMSO-d$_6$) δ ppm 8.28-8.21 (m, 2H), 7.48-7.42 (m, 2H), 7.30 (s, 1H), 7.13 (s, 1H), 6.81 (s, 1H), 4.59-4.46 (m, 2H), 2.93 (t, J=12.6 Hz, 2H), 2.46-2.34 (m, 1H), 2.07-1.97 (m, 1H), 1.78 (d, J=12.7 Hz, 2H), 1.48 (qd, J=12.6, 4.1 Hz, 2H), 0.99 (dt, J=5.6, 2.8 Hz, 2H), 0.92 (ddd, J=8.0, 6.4, 3.5 Hz, 2H).

Example 36: 1-[2,5-Dimethyl-6-[4-(trifluoromethoxy)phenyl]pyrimidin-4-yl]piperidine-4-carboxamide

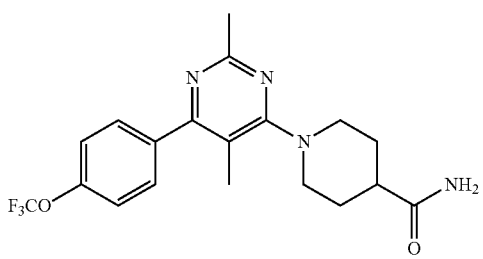 [SMILES: Cc1nc(-c2ccc(OC(F)(F)F)cc2)c(C)c(N2CCC(C(N)=O)CC2)n1]

The title compound was prepared in a manner analogous to Example 1, using 4,6-dichloro-2,5-dimethylpyrimidine instead of 4,6-dichloropyrimidine in Step A. MS (ESI): mass calcd. for $C_{19}H_{21}F_3N_4O_2$, 394.2; m/z found, 395.2 [M+H]$^+$. $^1$H NMR (500 MHz, DMSO-d$_6$) δ ppm 7.77-7.72 (m, 2H), 7.48-7.44 (m, 2H), 7.31 (s, 1H), 6.81 (s, 1H), 3.87 (d, J=13.1 Hz, 2H), 2.87 (t, J=12.2 Hz, 2H), 2.45 (s, 3H), 2.38-2.30 (m, 1H), 2.12 (s, 3H), 1.81 (d, J=12.8 Hz, 2H), 1.65 (q, J=13.2, 12.7 Hz, 2H).

Example 37: 1-[6-[3-Chloro-4-(trifluoromethoxy)phenyl]pyrimidin-4-yl]piperidine-4-carboxamide

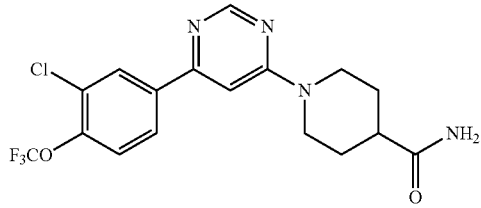 [SMILES: NC(=O)C1CCN(c2cc(-c3ccc(OC(F)(F)F)c(Cl)c3)ncn2)CC1]

The title compound was prepared in a manner analogous to Example 1, using (3-chloro-4-(trifluoromethoxy)phenyl) boronic acid instead of (4-(trifluoromethoxy)phenyl)boronic acid in Step B. MS (ESI): mass calcd. for $C_{17}H_{16}ClF_3N_4O_2$, 400.1; m/z found, 401.2 [M+H]$^+$. $^1$H NMR (500 MHz, DMSO-d$_6$) δ ppm 8.58 (d, J=1.0 Hz, 1H), 8.49 (d, J=2.2 Hz, 1H), 8.28 (dd, J=8.7, 2.2 Hz, 1H), 7.71-7.66 (m, 1H), 7.45 (d, J=1.2 Hz, 1H), 7.32 (s, 1H), 6.82 (s, 1H), 4.63-4.50 (m, 2H), 3.00 (t, J=12.8 Hz, 2H), 2.49-2.39 (m, 1H), 1.80 (d, J=12.7 Hz, 2H), 1.57-1.44 (m, 2H).

Example 38: 1-[6-[3-Methyl-4-(trifluoromethoxy)phenyl]pyrimidin-4-yl]piperidine-4-carboxamide

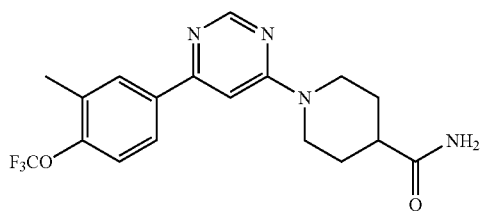 [SMILES: Cc1cc(-c2cc(N3CCC(C(N)=O)CC3)ncn2)ccc1OC(F)(F)F]

The title compound was prepared in a manner analogous to Example 1, using (3-methyl-4-(trifluoromethoxy)phenyl) boronic acid instead of (4-(trifluoromethoxy)phenyl)boronic acid in Step B. MS (ESI): mass calcd. for $C_{18}H_{19}F_3N_4O_2$, 380.1; m/z found, 381.2 [M+H]$^+$. $^1$H NMR (500 MHz, DMSO-d$_6$) δ ppm 8.56 (d, J=1.0 Hz, 1H), 8.20 (dd, J=2.2, 0.9 Hz, 1H), 8.10 (dd, J=8.6, 2.2 Hz, 1H), 7.41 (dd, J=8.8, 1.7 Hz, 1H), 7.35 (d, J=1.2 Hz, 1H), 7.32 (s, 1H), 6.82 (s, 1H), 4.55 (s, 2H), 2.99 (t, J=12.7 Hz, 2H), 2.48-2.39 (m, 1H), 2.36 (s, 3H), 1.84-1.75 (m, 2H), 1.55-1.44 (m, 2H).

Example 39: 1-[6-[3-Methoxy-4-(trifluoromethoxy)phenyl]pyrimidin-4-yl]piperidine-4-carboxamide

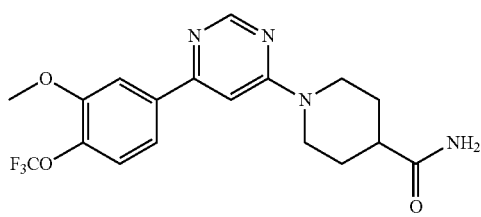 [SMILES: COc1cc(-c2cc(N3CCC(C(N)=O)CC3)ncn2)ccc1OC(F)(F)F]

The title compound was prepared in a manner analogous to Example 1, using (3-methoxy-4-(trifluoromethoxy)phenyl)boronic acid instead of (4-(trifluoromethoxy)phenyl) boronic acid in Step B. MS (ESI): mass calcd. for $C_{18}H_{19}F_3N_4O_3$, 396.1; m/z found, 397.2 [M+H]$^+$. $^1$H NMR (500 MHz, DMSO-$d_6$) δ ppm 8.58 (d, J=1.0 Hz, 1H), 7.92 (d, J=2.0 Hz, 1H), 7.82 (dd, J=8.5, 2.0 Hz, 1H), 7.46 (dd, J=8.5, 1.4 Hz, 1H), 7.37 (d, J=1.2 Hz, 1H), 7.32 (s, 1H), 6.82 (s, 1H), 4.55 (s, 2H), 3.97 (s, 3H), 2.99 (t, J=12.6 Hz, 2H), 2.48-2.39 (m, 1H), 1.81 (d, J=13.2 Hz, 2H), 1.51 (q, J=11.3, 10.8 Hz, 2H).

Example 40: 1-[2-Ethyl-6-[4-(trifluoromethoxy) phenyl]pyrimidin-4-yl]piperidine-4-carboxamide

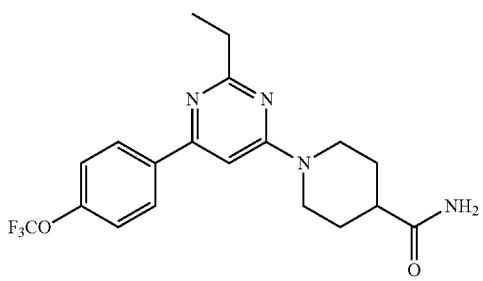 [SMILES: CCc1nc(-c2ccc(OC(F)(F)F)cc2)cc(N2CCC(C(N)=O)CC2)n1]

The title compound was prepared in a manner analogous to Example 1, using 4,6-dichloro-2-ethylpyrimidine instead of 4,6-dichloropyrimidine in Step A. MS (ESI): mass calcd. for $C_{19}H_{21}F_3N_4O_2$, 394.2; m/z found, 395.2 [M+H]$^+$. $^1$H NMR (500 MHz, DMSO-$d_6$) 5 ppm 8.58 (d, J=1.0 Hz, 1H), 7.92 (d, J=2.0 Hz, 1H), 7.82 (dd, J=8.5, 2.0 Hz, 1H), 7.46 (dd, J=8.5, 1.4 Hz, 1H), 7.37 (d, J=1.2 Hz, 1H), 7.32 (s, 1H), 6.82 (s, 1H), 4.55 (s, 2H), 3.97 (s, 3H), 2.99 (t, J=12.6 Hz, 2H), 2.48-2.39 (m, 1H), 1.81 (d, J=13.2 Hz, 2H), 1.51 (q, J=11.3, 10.8 Hz, 2H).

Example 41: 1-[2-Methoxy-6-[4-(trifluoromethoxy) phenyl]pyrimidin-4-yl]piperidine-4-carboxamide

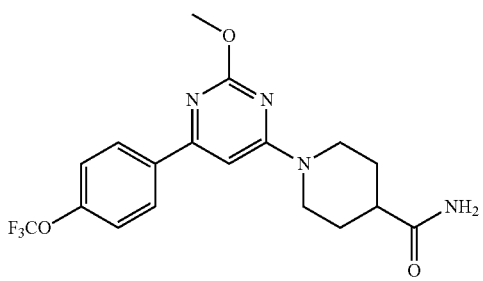 [SMILES: COc1nc(-c2ccc(OC(F)(F)F)cc2)cc(N2CCC(C(N)=O)CC2)n1]

The title compound was prepared in a manner analogous to Example 1, using 4,6-dichloro-2-methoxypyrimidine instead of 4,6-dichloropyrimidine in Step A. MS (ESI): mass calcd. for $C_{18}H_{19}F_3N_4O_3$, 396.1; m/z found, 397.2 [M+H]$^+$. $^1$H NMR (500 MHz, DMSO-$d_6$) δ ppm 8.29-8.24 (m, 2H), 7.47 (d, J=8.4 Hz, 2H), 7.31 (s, 1H), 7.08 (s, 1H), 6.82 (s, 1H), 4.55-4.43 (m, 2H), 3.88 (s, 3H), 3.04-2.92 (m, 2H), 2.45-2.34 (m, 1H), 1.79 (d, J=13.2 Hz, 2H), 1.57-1.42 (m, 2H).

Example 42: N-[1-[6-[4-(Difluoromethyl)phenyl] pyrimidin-4-yl]-4-piperidyl]acetamide

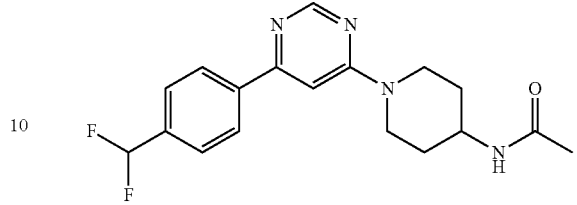

The title compound was prepared in a manner analogous to Example 3, using 4,6-dichloropyrimidine instead of 4,6-dichloro-2-methylpyrimidine in Step A; and using (4-(difluoromethyl)phenyl)boronic acid instead of (3-chloro-4-(trifluoromethoxy)phenyl)boronic acid in Step B. MS (ESI): mass calcd. for $C_{18}H_{20}F_2N_4O$, 346.2; m/z found, 347.2 [M+H]$^+$. $^1$H NMR (400 MHz, DMSO-$d_6$) δ ppm 8.60 (d, J=1.0 Hz, 1H), 8.31 (d, J=8.0 Hz, 2H), 7.83 (d, J=7.6 Hz, 1H), 7.73-7.65 (m, 2H), 7.42 (d, J=1.3 Hz, 1H), 7.11 (t, J=55.8 Hz, 1H), 4.45 (d, J=12.9 Hz, 2H), 3.95-3.80 (m, 1H), 3.14 (ddd, J=13.9, 11.4, 2.8 Hz, 2H), 1.88-1.75 (m, 5H), 1.40-1.26 (m, 2H).

Example 43: N-[1-[6-[3-Methyl-4-(trifluoromethyl) phenyl]pyrimidin-4-yl]-4-piperidyl]acetamide

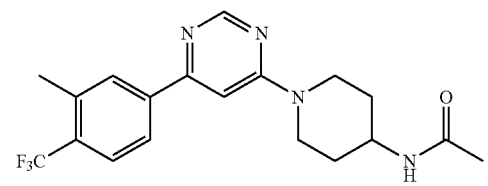 [SMILES: CC(=O)NC1CCN(c2cc(-c3ccc(C(F)(F)F)c(C)c3)ncn2)CC1]

The title compound was prepared in a manner analogous to Example 3, using 4,6-dichloropyrimidine instead of 4,6-dichloro-2-methylpyrimidine in Step A; and using (3-methyl-4-(trifluoromethyl)phenyl)boronic acid instead of (3-chloro-4-(trifluoromethoxy)phenyl)boronic acid in Step B. MS (ESI): mass calcd. for $C_{19}H_{21}F_3N_4O$, 378.2; m/z found, 379.2 [M+H]$^+$. $^1$H NMR (400 MHz, DMSO-$d_6$) δ ppm 8.57 (d, J=1.0 Hz, 1H), 8.21 (s, 1H), 8.14 (d, J=8.2 Hz, 1H), 7.80 (d, J=7.6 Hz, 1H), 7.75 (d, J=8.3 Hz, 1H), 7.42 (d, J=1.2 Hz, 1H), 4.47-4.37 (m, 2H), 3.18-3.07 (m, 2H), 2.53-2.50 (m, 3H), 1.85-1.75 (m, 5H), 1.31 (q, J=10.6 Hz, 2H), 3.92-3.81 (m, 1H).

Example 44: N-[1-[6-[3-Fluoro-4-(trifluoromethoxy)phenyl]-2-methyl-pyrimidin-4-yl]-4-piperidyl]acetamide

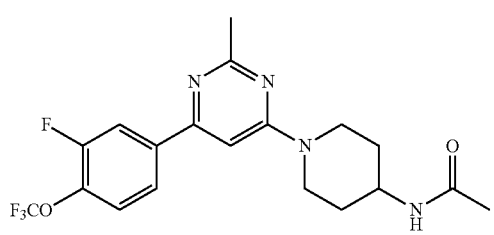 [SMILES: CC(=O)NC1CCN(c2cc(-c3ccc(OC(F)(F)F)c(F)c3)nc(C)n2)CC1]

The title compound was prepared in a manner analogous to Example 3, using (3-fluoro-4-(trifluoromethoxy)phenyl)boronic acid instead of (3-chloro-4-(trifluoromethoxy)phenyl)boronic acid in Step B. MS (ESI): mass calcd. for $C_{19}H_{20}F_4N_4O_2$, 412.2; m/z found, 413.2 [M+H]⁺. ¹H NMR (500 MHz, DMSO-$d_6$) δ ppm 8.27 (dd, J=12.0, 2.1 Hz, 1H), 8.13 (dt, J=9.1, 1.3 Hz, 1H), 7.81 (d, J=7.6 Hz, 1H), 7.67 (t, J=8.3 Hz, 1H), 7.27 (s, 1H), 4.44 (d, J=12.4 Hz, 2H), 3.92-3.81 (m, 1H), 3.11 (ddd, J=13.7, 11.4, 2.8 Hz, 2H), 2.45 (s, 3H), 1.86-1.77 (m, 5H), 1.38-1.26 (m, 2H).

Example 45: N-[1-[6-[3-Chloro-4-(trifluoromethoxy)phenyl]pyrimidin-4-yl]-4-piperidyl]acetamide

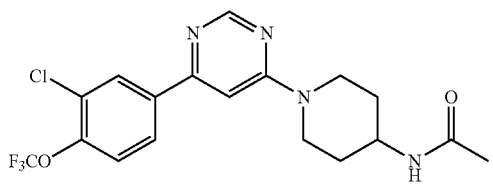 [SMILES: CC(=O)NC1CCN(c2cc(-c3ccc(OC(F)(F)F)c(Cl)c3)ncn2)CC1]

The title compound was prepared in a manner analogous to Example 3, using 4,6-dichloropyrimidine instead of 4,6-dichloro-2-methylpyrimidine in Step A. MS (ESI): mass calcd. for $C_{18}H_{18}ClF_3N_4O_2$, 414.1; m/z found, 415.1 [M+H]⁺. ¹H NMR (500 MHz, DMSO-$d_6$) δ ppm 8.59-8.56 (m, 1H), 8.48 (d, J=2.1 Hz, 1H), 8.28 (dd, J=8.7, 2.2 Hz, 1H), 7.82 (d, J=7.6 Hz, 1H), 7.69 (dd, J=8.6, 1.7 Hz, 1H), 7.46 (d, J=1.3 Hz, 1H), 4.45 (d, J=12.4 Hz, 2H), 3.93-3.82 (m, 1H), 3.15 (ddd, J=13.9, 11.4, 2.9 Hz, 2H), 1.88-1.77 (m, 5H), 1.38-1.27 (m, 2H).

Example 46: 1-[6-[3-Fluoro-4-(trifluoromethoxy)phenyl]-2-methyl-pyrimidin-4-yl]-N-(2-hydroxyethyl)piperidine-4-carboxamide

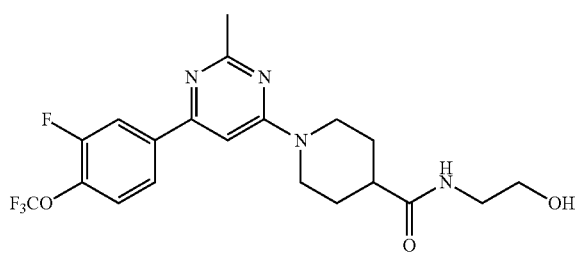

The title compound was prepared in a manner analogous to Example 3, using N-(2-hydroxyethyl)piperidine-4-carboxamide instead of N-(piperidin-4-yl)acetamide in Step A; and (3-fluoro-4-(trifluoromethoxy)phenyl)boronic acid instead of (3-chloro-4-(trifluoromethoxy)phenyl)boronic acid in Step B. MS (ESI): mass calcd. for $C_{20}H_{22}F_4N_4O_3$, 442.2; m/z found, 443.2 [M+H]⁺. ¹H NMR (500 MHz, DMSO-$d_6$) δ ppm 8.26 (dd, J=12.0, 2.1 Hz, 1H), 8.13 (dt, J=8.7, 1.4 Hz, 1H), 7.80 (t, J=5.7 Hz, 1H), 7.66 (t, J=8.3 Hz, 1H), 7.24 (s, 1H), 4.67-4.50 (m, 3H), 3.39 (t, J=6.6 Hz, 2H), 3.11 (q, J=6.0 Hz, 2H), 2.95 (t, J=12.2 Hz, 2H), 2.49-2.41 (m, 4H), 1.81-1.72 (m, 2H), 1.57-1.43 (m, 2H).

Example 47: 1-[6-[3-Chloro-4-(trifluoromethoxy)phenyl]pyrimidin-4-yl]-N-(2-hydroxyethyl)piperidine-4-carboxamide

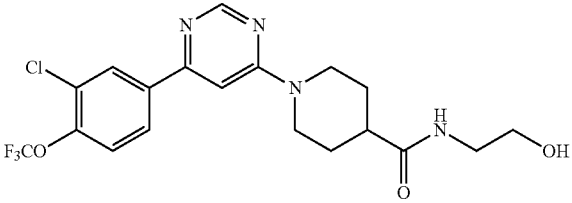 [SMILES: O=C(NCCO)C1CCN(c2cc(-c3ccc(OC(F)(F)F)c(Cl)c3)ncn2)CC1]

The title compound was prepared in a manner analogous to Example 3, using N-(2-hydroxyethyl)piperidine-4-carboxamide instead of N-(piperidin-4-yl)acetamide and 4,6-dichloropyrimidine instead of 4,6-dichloro-2-methylpyrimidine in Step A. MS (ESI): mass calcd. for $C_{19}H_{20}ClF_3N_4O_3$, 444.1; m/z found, 445.2 [M+H]⁺. ¹H NMR (400 MHz, DMSO-$d_6$) δ ppm 8.58 (d, J=1.1 Hz, 1H), 8.49 (d, J=2.2 Hz, 1H), 8.29 (dd, J=8.6, 2.2 Hz, 1H), 7.83 (t, J=5.7 Hz, 1H), 7.69 (dq, J=8.6, 1.5 Hz, 1H), 7.45 (d, J=1.5 Hz, 1H), 4.67-4.52 (m, 3H), 3.44-3.34 (m, 2H), 3.11 (q, J=6.1 Hz, 2H), 2.99 (t, J=12.8 Hz, 2H), 2.48-2.44 (m, 1H), 1.78 (d, J=13.1 Hz, 2H), 1.59-1.45 (m, 2H).

Example 48: 1-[6-[3-Chloro-4-(trifluoromethoxy)phenyl]-2-methyl-pyrimidin-4-yl]-N-(2-hydroxyethyl)piperidine-4-carboxamide

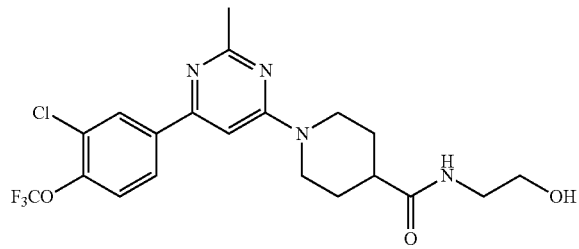 [SMILES: Cc1nc(-c2ccc(OC(F)(F)F)c(Cl)c2)cc(N2CCC(C(=O)NCCO)CC2)n1]

The title compound was prepared in a manner analogous to Example 3, using N-(2-hydroxyethyl)piperidine-4-carboxamide instead of N-(piperidin-4-yl)acetamide in Step A. MS (ESI): mass calcd. for $C_{20}H_{22}ClF_3N_4O_3$, 458.1; m/z found, 459.2 [M+H]⁺. ¹H NMR (500 MHz, DMSO-$d_6$) δ ppm 8.45 (d, J=2.1 Hz, 1H), 8.26 (dd, J=8.7, 2.2 Hz, 1H), 7.80 (t, J=5.6 Hz, 1H), 7.67 (dq, J=8.7, 1.5 Hz, 1H), 7.26 (s, 1H), 4.64-4.52 (m, 3H), 3.39 (q, J=6.0 Hz, 2H), 3.11 (q, J=6.0 Hz, 2H), 2.95 (t, J=12.6 Hz, 2H), 2.48-2.41 (m, 4H), 1.82-1.72 (m, 2H), 1.51 (qd, J=12.4, 4.1 Hz, 2H).

Example 49: N-[1-[2-Methyl-6-[3-methyl-4-(trifluoromethoxy)phenyl]pyrimidin-4-yl]-4-piperidyl]acetamide

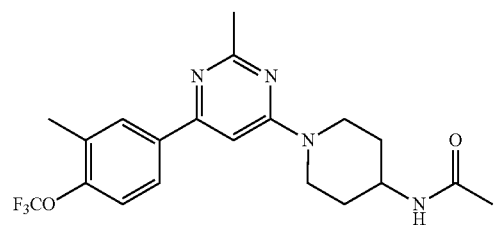

The title compound was prepared in a manner analogous to Example 3, using (3-methyl-4-(trifluoromethoxy)phenyl)boronic acid instead of (3-chloro-4-(trifluoromethoxy)phenyl)boronic acid in Step B. MS (ESI): mass calcd. for $C_{20}H_{23}F_3N_4O_2$, 408.2; m/z found, 409.2 [M+H]$^+$. $^1$H NMR (500 MHz, DMSO-d$_6$) δ ppm 8.16 (dd, J=2.3, 1.0 Hz, 1H), 8.10-8.06 (m, 1H), 7.81 (d, J=7.6 Hz, 1H), 7.42-7.37 (m, 1H), 7.18 (s, 1H), 4.43 (d, J=12.6 Hz, 2H), 3.92-3.80 (m, 1H), 3.09 (ddd, J=13.9, 11.4, 2.8 Hz, 2H), 2.44 (s, 3H), 2.36 (s, 3H), 1.86-1.78 (m, 5H), 1.37-1.27 (m, 2H).

Example 50: N-[1-[6-[3-Methyl-4-(trifluoromethoxy)phenyl]pyrimidin-4-yl]-4-piperidyl]acetamide

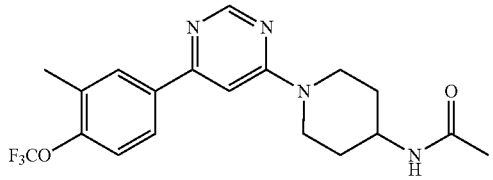

The title compound was prepared in a manner analogous to Example 3, using 4,6-dichloropyrimidine instead of 4,6-dichloro-2-methylpyrimidine in Step A; and (3-methyl-4-(trifluoromethoxy)phenyl)boronic acid instead of (3-chloro-4-(trifluoromethoxy)phenyl)boronic acid in Step B. MS (ESI): mass calcd. for $C_{19}H_{21}F_3N_4O_2$, 394.2; m/z found, 395.2 [M+H]$^+$. $^1$H NMR (500 MHz, DMSO-d$_6$) δ ppm 8.58-8.55 (m, 1H), 8.20 (d, J=2.2 Hz, 1H), 8.10 (dd, J=8.6, 2.3 Hz, 1H), 7.82 (d, J=7.6 Hz, 1H), 7.41 (dd, J=8.8, 1.7 Hz, 1H), 7.38-7.35 (m, 1H), 4.43 (d, J=13.3 Hz, 2H), 3.93-3.83 (m, 1H), 3.13 (ddd, J=13.7, 11.4, 2.8 Hz, 2H), 2.37 (s, 3H), 1.88-1.77 (m, 5H), 1.39-1.27 (m, 2H).

Example 51: N-methyl-N-[1-[6-[3-methyl-4-(trifluoromethoxy)phenyl]pyrimidin-4-yl]-4-piperidyl]acetamide

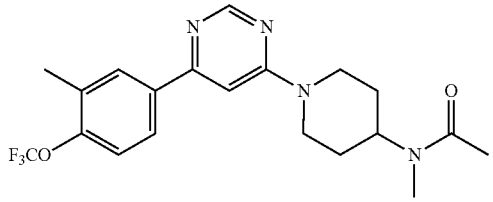 [SMILES: CC(=O)N(C)C1CCN(c2cc(-c3ccc(OC(F)(F)F)c(C)c3)ncn2)CC1]

To a solution of N-[1-[6-[3-methyl-4-(trifluoromethoxy)phenyl]pyrimidin-4-yl]-4-piperidyl]acetamide (Example 50, 30 mg, 0.08 mmol) and iodomethane (7.2 μL, 0.11 mmol) in DMF (1 mL) cooled at 0° C. was added NaH (60% dispersion in mineral oil) (4.5 mg, 0.11 mmol). The reaction mixture was warmed to room temperature and stirred overnight. An additional portion of NaH (4.5 mg, 0.11 mmol) and iodomethane (7.2 μL, 0.11 mmol) was added and the reaction mixture was stirred at room temperature for 4 hours then overnight at 60° C. Water was added and the aqueous layer was extracted twice with EtOAc. The combined organic layers were dried over MgSO$_4$, filtered and evaporated. Purification by basic prep HPLC (Agilent, Waters XBridge C18 5 um 50×100 mm column, 5-90% MeCN/20 mM NH$_4$OH over 15 min, 80 mL/min) gave the title compound (18 mg, 58%). MS (ESI): mass calcd. for $C_{20}H_{23}F_3N_4O_2$, 408.2; m/z found, 409.2 [M+H]$^+$. $^1$H NMR (400 MHz, DMSO-d$_6$) δ ppm 8.57 (t, J=1.3 Hz, 1H), 8.21 (dd, J=2.3, 0.9 Hz, 1H), 8.12 (dd, J=8.6, 2.4 Hz, 1H), 7.44-7.37 (m, 2H), 4.71 (d, J=12.9 Hz, 2H), 4.66-4.55 (m, 0.6H), 4.04-3.92 (m, 0.4H), 3.07-2.92 (m, 2H), 2.78 (s, 1.8H), 2.63 (s, 1.2H), 2.37 (s, 3H), 2.11 (s, 1.2H), 2.00 (s, 1.8H), 1.78-1.54 (m, 4H).

Example 52: N-(2-Hydroxyethyl)-1-[2-methyl-6-[3-methyl-4-(trifluoromethoxy)phenyl]pyrimidin-4-yl]piperidine-4-carboxamide

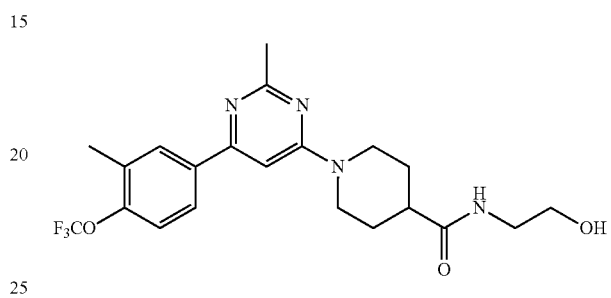

The title compound was prepared in a manner analogous to Example 3, using N-(2-hydroxyethyl)piperidine-4-carboxamide instead of N-(piperidin-4-yl)acetamide in Step A; and (3-methyl-4-(trifluoromethoxy)phenyl)boronic acid instead of (3-chloro-4-(trifluoromethoxy)phenyl)boronic acid in Step B. MS (ESI): mass calcd. for $C_{21}H_{25}F_3N_4O_3$, 438.2; m/z found, 439.2 [M+H]$^+$. $^1$H NMR (500 MHz, DMSO-d$_6$) δ ppm 8.17-8.14 (m, 1H), 8.07 (ddd, J=8.6, 2.2, 0.8 Hz, 1H), 7.80 (t, J=5.6 Hz, 1H), 7.39 (dq, J=8.6, 1.6 Hz, 1H), 7.16 (s, 1H), 4.62 (t, J=5.5 Hz, 1H), 4.55 (d, J=12.7 Hz, 2H), 3.39 (q, J=5.8 Hz, 2H), 3.11 (q, J=6.0 Hz, 2H), 2.94 (td, J=13.0, 2.8 Hz, 2H), 2.44 (sm, 4H), 2.36 (s, 3H), 1.81-1.73 (m, 2H), 1.57-1.46 (m, 2H).

Example 53: N-(2-Hydroxyethyl)-1-[6-[3-methyl-4-(trifluoromethoxy)phenyl]pyrimidin-4-yl]piperidine-4-carboxamide

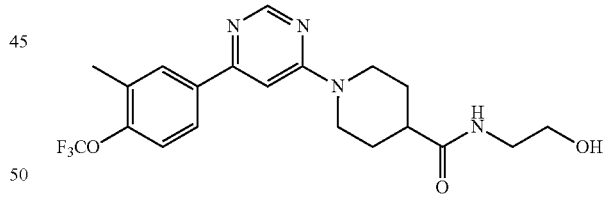

The title compound was prepared in a manner analogous to Example 3, using 4,6-dichloropyrimidine instead of 4,6-dichloro-2-methylpyrimidine and N-(2-hydroxyethyl)piperidine-4-carboxamide instead of N-(piperidin-4-yl)acetamide in Step A; and using (3-methyl-4-(trifluoromethoxy)phenyl)boronic acid instead of (3-chloro-4-(trifluoromethoxy)phenyl)boronic acid in Step B. MS (ESI): mass calcd. for $C_{20}H_{23}F_3N_4O_3$, 424.2; m/z found, 425.2 [M+H]$^+$. $^1$H NMR (500 MHz, DMSO-d$_6$) δ ppm 8.56 (d, J=1.1 Hz, 1H), 8.21-8.18 (m, 1H), 8.10 (dd, J=8.6, 2.3 Hz, 1H), 7.81 (t, J=5.5 Hz, 1H), 7.41 (dq, J=8.7, 1.6 Hz, 1H), 7.34 (d, J=1.3 Hz, 1H), 4.68-4.59 (m, 1H), 4.55 (d, J=12.6 Hz, 2H), 3.39 (t, J=6.2 Hz, 2H), 3.11 (q, J=6.0 Hz, 2H), 2.98 (td, J=13.1, 12.1, 2.7 Hz, 2H), 2.48-2.43 (m, 1H), 2.37 (s, 3H), 1.78 (dd, J=13.7, 3.6 Hz, 2H), 1.53 (qd, J=12.3, 4.0 Hz, 2H).

Example 54: N-[1-[6-[4-(1,1-Difluoroethyl)phenyl]pyrimidin-4-yl]-4-piperidyl]acetamide

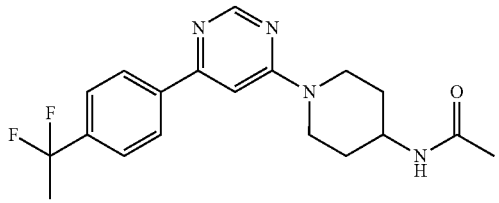 [SMILES: CC(=O)NC1CCN(c2cc(-c3ccc(C(C)(F)F)cc3)ncn2)CC1]

The title compound was prepared in a manner analogous to Example 3, using 4,6-dichloropyrimidine instead of 4,6-dichloro-2-methylpyrimidine in Step A; and 2-(4-(1,1-difluoroethyl)phenyl)-4,4,5,5-tetramethyl-1,3,2-dioxaborolane instead of (3-chloro-4-(trifluoromethoxy)phenyl)boronic acid in Step B. MS (ESI): mass calcd. for $C_{19}H_{22}F_2N_4O$, 360.2; m/z found, 361.2 [M+H]$^+$. $^1$H NMR (400 MHz, DMSO-d$_6$) δ ppm 8.59 (d, J=1.0 Hz, 1H), 8.30-8.25 (m, 2H), 7.83 (d, J=7.6 Hz, 1H), 7.70-7.65 (m, 2H), 7.41 (d, J=1.2 Hz, 1H), 4.44 (d, J=13.1 Hz, 2H), 3.93-3.82 (m, 1H), 3.14 (ddd, J=13.8, 11.1, 2.6 Hz, 2H), 2.01 (t, J=18.9 Hz, 3H), 1.88-1.77 (m, 5H), 1.39-1.27 (m, 2H).

Example 55: N-[1-[6-[3-Fluoro-4-(trifluoromethyl)phenyl]pyrimidin-4-yl]-4-piperidyl]acetamide

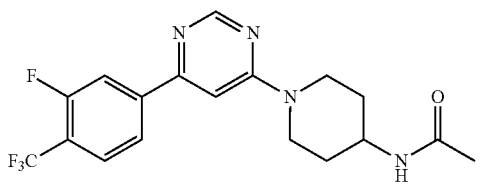 [SMILES: CC(=O)NC1CCN(c2cc(-c3ccc(C(F)(F)F)c(F)c3)ncn2)CC1]

The title compound was prepared in a manner analogous to Example 3, using 4,6-dichloropyrimidine instead of 4,6-dichloro-2-methylpyrimidine in Step A; and using (3-fluoro-4-(trifluoromethyl)phenyl)boronic acid instead of (3-chloro-4-(trifluoromethoxy)phenyl)boronic acid in Step B. MS (ESI): mass calcd. for $C_{18}H_{18}F_4N_4O$, 382.1; m/z found, 383.2 [M+H]$^+$. $^1$H NMR (400 MHz, DMSO-d$_6$) δ ppm 8.61 (d, J=1.0 Hz, 1H), 8.30 (d, J=12.5 Hz, 1H), 8.25 (d, J=8.2 Hz, 1H), 7.92 (t, J=7.9 Hz, 1H), 7.83 (d, J=7.6 Hz, 1H), 7.52 (d, J=1.2 Hz, 1H), 4.46 (d, J=12.2 Hz, 2H), 3.96-3.83 (m, 1H), 3.16 (t, J=12.4 Hz, 2H), 1.89-1.77 (m, 5H), 1.34 (q, J=10.3 Hz, 2H).

Example 56: N-[1-[6-(3-Fluoro-4-methoxy-phenyl)pyrimidin-4-yl]-4-piperidyl]acetamide

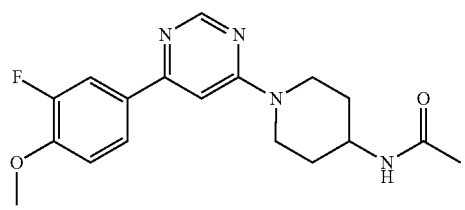 [SMILES: COc1ccc(-c2cc(N3CCC(NC(C)=O)CC3)ncn2)cc1F]

The title compound was prepared in a manner analogous to Example 3, using 4,6-dichloropyrimidine instead of 4,6-dichloro-2-methylpyrimidine in Step A; and using (3-fluoro-4-methoxyphenyl)boronic acid instead of (3-chloro-4-(trifluoromethoxy)phenyl)boronic acid in Step B. MS (ESI): mass calcd. for $C_{18}H_{21}FN_4O_2$, 344.2; m/z found, 345.2 [M+H]$^+$. $^1$H NMR (400 MHz, DMSO-d$_6$) (ppm 8.53 (d, J=1.0 Hz, 1H), 8.08-8.02 (m, 2H), 7.82 (d, J=7.7 Hz, 1H), 7.32 (d, J=1.2 Hz, 1H), 7.26 (t, J=8.9 Hz, 1H), 4.44 (d, J=13.0 Hz, 2H), 3.94-3.82 (m, 4H), 3.11 (ddd, J=14.0, 11.4, 2.8 Hz, 2H), 1.87-1.77 (m, 5H), 1.40-1.24 (m, 2H).

Example 57: N-[1-[6-(3-Chloro-4-methoxy-phenyl)pyrimidin-4-yl]-4-piperidyl]acetamide

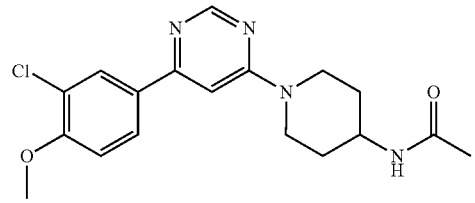 [SMILES: COc1ccc(-c2cc(N3CCC(NC(C)=O)CC3)ncn2)cc1Cl]

The title compound was prepared in a manner analogous to Example 3, using 4,6-dichloropyrimidine instead of 4,6-dichloro-2-methylpyrimidine in Step A; and using (3-chloro-4-methoxyphenyl)boronic acid instead of (3-chloro-4-(trifluoromethoxy)phenyl)boronic acid in Step B. MS (ESI): mass calcd. for $C_{18}H_{21}ClN_4O_2$, 360.1; m/z found, 361.2 [M+H]$^+$. $^1$H NMR (500 MHz, DMSO-d$_6$) δ ppm 8.54-8.50 (m, 1H), 8.28 (dd, J=2.2, 0.7 Hz, 1H), 8.17 (dd, J=8.7, 2.1 Hz, 1H), 7.81 (d, J=7.6 Hz, 1H), 7.33 (s, 1H), 7.24 (d, J=8.7 Hz, 1H), 4.44 (d, J=13.2 Hz, 2H), 3.93 (s, 3H), 3.91-3.82 (m, 1H), 3.11 (ddd, J=14.1, 11.6, 2.9 Hz, 2H), 1.86-1.76 (m, 5H), 1.32 (qd, J=11.2, 3.9 Hz, 2H).

Example 58: N-[1-[6-[3-Chloro-4-(trifluoromethyl)phenyl]pyrimidin-4-yl]-4-piperidyl]acetamide

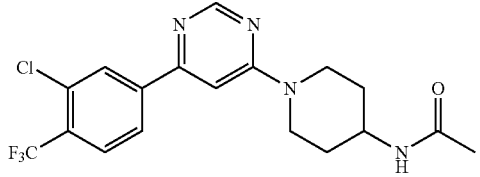 [SMILES: CC(=O)NC1CCN(c2cc(-c3ccc(C(F)(F)F)c(Cl)c3)ncn2)CC1]

The title compound was prepared in a manner analogous to Example 3, using 4,6-dichloropyrimidine instead of 4,6-dichloro-2-methylpyrimidine in Step A; and using (3-chloro-4-(trifluoromethyl)phenyl)boronic acid instead of (3-chloro-4-(trifluoromethoxy)phenyl)boronic acid in Step B. MS (ESI): mass calcd. for $C_{18}H_{18}ClF_3N_4O$, 398.1; m/z found, 399.1 [M+H]$^+$. $^1$H NMR (500 MHz, DMSO-d$_6$) δ ppm 8.61 (d, J=1.0 Hz, 1H), 8.51 (d, J=1.6 Hz, 1H), 8.38-8.32 (m, 1H), 7.98 (d, J=8.3 Hz, 1H), 7.82 (d, J=7.6 Hz, 1H), 7.53 (d, J=1.2 Hz, 1H), 4.53-4.38 (m, 2H), 3.95-3.83 (m, 1H), 3.21-3.10 (m, 2H), 1.88-1.78 (m, 5H), 1.40-1.26 (m, 2H).

Example 59: N-[1-[6-(4-Chloro-3-fluoro-phenyl)pyrimidin-4-yl]-4-piperidyl]acetamide

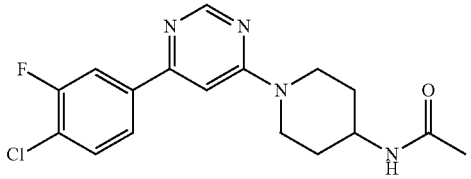 [SMILES: CC(=O)NC1CCN(c2cc(-c3ccc(Cl)c(F)c3)ncn2)CC1]

The title compound was prepared in a manner analogous to Example 3, using 4,6-dichloropyrimidine instead of 4,6-dichloro-2-methylpyrimidine in Step A; and using (4-chloro-3-fluorophenyl)boronic acid instead of (3-chloro-4-(trifluoromethoxy)phenyl)boronic acid in Step B. MS (ESI): mass calcd. for $C_{17}H_{18}ClFN_4O$, 348.1; m/z found, 349.2 [M+H]$^+$. $^1$H NMR (500 MHz, DMSO-d$_6$) δ ppm 8.57 (d, J=1.1 Hz, 1H), 8.22 (dd, J=11.0, 2.0 Hz, 1H), 8.09 (ddd, J=8.5, 1.9, 0.8 Hz, 1H), 7.81 (d, J=7.5 Hz, 1H), 7.74-7.68 (m, 1H), 7.43 (d, J=1.3 Hz, 1H), 4.44 (d, J=13.0 Hz, 2H), 3.93-3.83 (m, 1H), 3.14 (ddd, J=13.8, 11.0, 2.5 Hz, 2H), 1.87-1.77 (m, 5H), 1.38-1.26 (m, 2H).

Example 60: N-[1-[6-(3-Chloro-4-methyl-phenyl)pyrimidin-4-yl]-4-piperidyl]acetamide

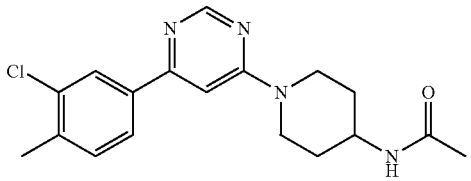 [SMILES: CC(=O)NC1CCN(c2cc(-c3ccc(C)c(Cl)c3)ncn2)CC1]

The title compound was prepared in a manner analogous to Example 3, using 4,6-dichloropyrimidine instead of 4,6-dichloro-2-methylpyrimidine in Step A; and using (3-chloro-4-methylphenyl)boronic acid instead of (3-chloro-4-(trifluoromethoxy)phenyl)boronic acid in Step B. MS (ESI): mass calcd. for $C_{18}H_{21}ClN_4O$, 344.1; m/z found, 345.1 [M+H]$^+$. $^1$H NMR (500 MHz, DMSO-d$_6$) δ ppm 8.55 (d, J=1.1 Hz, 1H), 8.23 (d, J=1.8 Hz, 1H), 8.07 (dd, J=8.0, 1.8 Hz, 1H), 7.81 (d, J=7.6 Hz, 1H), 7.47 (dd, J=8.0, 0.9 Hz, 1H), 7.38 (d, J=1.2 Hz, 1H), 4.44 (d, J=13.3 Hz, 2H), 3.92-3.83 (m, 1H), 3.12 (ddd, J=13.9, 11.5, 2.8 Hz, 2H), 2.39 (s, 3H), 1.86-1.77 (m, 5H), 1.38-1.26 (m, 2H).

Example 61: N-[1-[6-(4-Chloro-3-methyl-phenyl)pyrimidin-4-yl]-4-piperidyl]acetamide

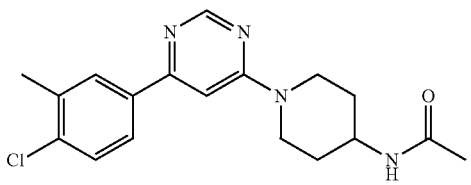 [SMILES: CC(=O)NC1CCN(c2cc(-c3ccc(Cl)c(C)c3)ncn2)CC1]

The title compound was prepared in a manner analogous to Example 3, using 4,6-dichloropyrimidine instead of 4,6-dichloro-2-methylpyrimidine in Step A; and (4-chloro-3-methylphenyl)boronic acid instead of (3-chloro-4-(trifluoromethoxy)phenyl)boronic acid in Step B. MS (ESI): mass calcd. for $C_{18}H_{21}ClN_4O$, 344.1; m/z found, 345.1 [M+H]$^+$. $^1$H NMR (500 MHz, DMSO-d$_6$) δ ppm 8.55 (d, J=1.1 Hz, 1H), 8.19-8.16 (m, 1H), 8.02 (dd, J=8.2, 2.2 Hz, 1H), 7.81 (d, J=7.6 Hz, 1H), 7.52 (d, J=8.4 Hz, 1H), 7.35 (d, J=1.2 Hz, 1H), 4.43 (d, J=13.4 Hz, 2H), 3.92-3.82 (m, 1H), 3.13 (ddd, J=13.9, 11.3, 2.8 Hz, 2H), 2.42 (s, 3H), 1.86-1.77 (m, 5H), 1.41-1.26 (m, 2H).

Example 62: N-[1-[6-[3-Chloro-4-(hydroxymethyl)phenyl]pyrimidin-4-yl]-4-piperidyl]acetamide

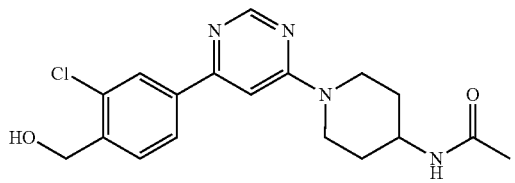 [SMILES: CC(=O)NC1CCN(c2cc(-c3ccc(CO)c(Cl)c3)ncn2)CC1]

The title compound was prepared in a manner analogous to Example 3, using 4,6-dichloropyrimidine instead of 4,6-dichloro-2-methylpyrimidine in Step A; and (3-chloro-4-(hydroxymethyl)phenyl)boronic acid instead of (3-chloro-4-(trifluoromethoxy)phenyl)boronic acid in Step B. MS (ESI): mass calcd. for $C_{18}H_{21}ClN_4O_2$, 360.1; m/z found, 361.2 [M+H]$^+$. $^1$H NMR (500 MHz, DMSO-d$_6$) δ ppm 8.57-8.52 (m, 1H), 8.23-8.20 (m, 1H), 8.20-8.15 (m, 1H), 7.81 (d, J=7.7 Hz, 1H), 7.65 (d, J=8.1 Hz, 1H), 7.40 (s, 1H), 5.47 (t, J=5.3 Hz, 1H), 4.67-4.57 (m, 2H), 4.45 (d, J=13.7 Hz, 2H), 3.94-3.80 (m, 1H), 3.17-3.07 (m, 2H), 1.87-1.77 (m, 5H), 1.38-1.25 (m, 2H).

Example 63: N-[1-[6-(3,4-Dichlorophenyl)pyrimidin-4-yl]-4-piperidyl]acetamide

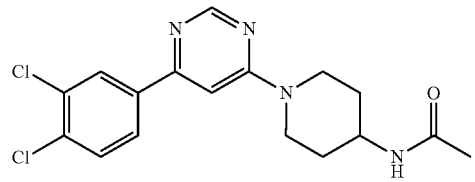

The title compound was prepared in a manner analogous to Example 3, using 4,6-dichloropyrimidine instead of 4,6-dichloro-2-methylpyrimidine in Step A; and (3,4-dichlorophenyl)boronic acid instead of (3-chloro-4-(trifluoromethoxy)phenyl)boronic acid in Step B. MS (ESI): mass calcd. for $C_{17}H_{18}Cl_2N_4O$, 364.1; m/z found, 365.1 [M+H]$^+$. $^1$H NMR (500 MHz, DMSO-d$_6$) δ ppm 8.57 (d, J=1.0 Hz, 1H), 8.45 (d, J=2.0 Hz, 1H), 8.19 (dd, J=8.4, 2.1 Hz, 1H), 7.81 (d, J=7.5 Hz, 1H), 7.76 (d, J=8.5 Hz, 1H), 7.45 (d, J=1.2 Hz, 1H), 4.45 (d, J=13.7 Hz, 2H), 3.94-3.81 (m, 1H), 3.14 (ddd, J=13.8, 11.5, 2.8 Hz, 2H), 1.87-1.77 (m, 5H), 1.40-1.25 (m, 2H).

Example 64: N-[1-[6-(3-Fluoro-4-methyl-phenyl)pyrimidin-4-yl]-4-piperidyl]acetamide

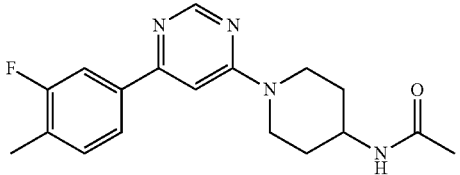 [SMILES: CC(=O)NC1CCN(c2cc(-c3ccc(C)c(F)c3)ncn2)CC1]

The title compound was prepared in a manner analogous to Example 3, using 4,6-dichloropyrimidine instead of 4,6-dichloro-2-methylpyrimidine in Step A: and (3-fluoro-4-methylphenyl)boronic acid instead of (3-chloro-4-(trifluoromethoxy)phenyl)boronic acid in Step B. MS (ESI): mass calcd. for $C_{18}H_{21}FN_4O$, 328.2; m/z found, 329.2 $[M+H]^+$. $^1H$ NMR (500 MHz, DMSO-$d_6$) δ ppm 8.55 (d, J=1.1 Hz, 1H), 7.97-7.93 (m, 2H), 7.81 (d, J=7.6 Hz, 1H), 7.40 (t, J=7.9 Hz, 1H), 7.36 (d, J=1.2 Hz, 1H), 4.43 (d, J=13.3 Hz, 2H), 3.93-3.81 (m, 1H), 3.12 (ddd, J=13.8, 11.3, 2.8 Hz, 2H), 2.32-2.25 (m, 3H), 1.85-1.78 (m, 5H), 1.38-1.26 (m, 2H).

Example 65: N-[1-[6-[4-(Difluoromethoxy)-3-fluoro-phenyl]pyrimidin-4-yl]-4-piperidyl]acetamide

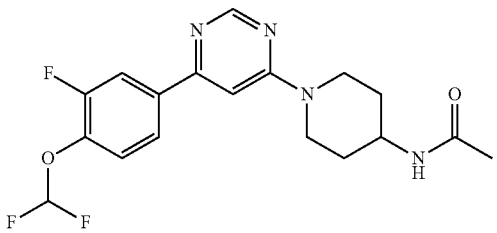 [SMILES: CC(=O)NC1CCN(c2cc(-c3ccc(OC(F)F)c(F)c3)ncn2)CC1]

The title compound was prepared in a manner analogous to Example 3, using 4,6-dichloropyrimidine instead of 4,6-dichloro-2-methylpyrimidine in Step A; and using 2-(4-(difluoromethoxy)-3-fluorophenyl)-4,4,5,5-tetramethyl-1,3,2-dioxaborolane instead of (3-chloro-4-(trifluoromethoxy)phenyl)boronic acid in Step B. MS (ESI): mass calcd. for $C_{18}H_{19}F_3N_4O_2$, 380.1; m/z found, 381.1 $[M+H]^+$. $^1H$ NMR (500 MHz, DMSO-$d_6$) (ppm 8.57 (d, J=1.0 Hz, 1H), 8.21 (dd, J=12.3, 2.1 Hz, 1H), 8.10 (ddd, J=8.6, 2.1, 1.1 Hz, 1H), 7.81 (d, J=7.6 Hz, 1H), 7.51-7.47 (m, 1H), 7.47-7.19 (m, 2H), 4.44 (d, J=13.5 Hz, 2H), 3.95-3.80 (m, 1H), 3.14 (ddd, J=13.9, 11.4, 2.9 Hz, 2H), 1.86-1.76 (m, 5H), 1.40-1.26 (m, 2H).

Example 66: N-[1-[6-[3-(Hydroxymethyl)-4-(trifluoromethoxy)phenyl]pyrimidin-4-yl]-4-piperidyl]acetamide

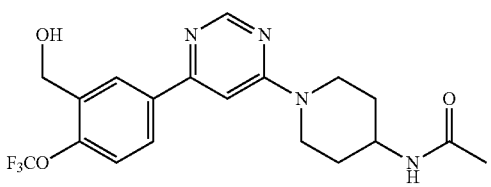 [SMILES: CC(=O)NC1CCN(c2cc(-c3ccc(OC(F)(F)F)c(CO)c3)ncn2)CC1]

The title compound was prepared in a manner analogous to Example 3, using 4,6-dichloropyrimidine instead of 4,6-dichloro-2-methylpyrimidine in Step A; and (3-(hydroxymethyl)-4-(trifluoromethoxy)phenyl)boronic acid instead of (3-chloro-4-(trifluoromethoxy)phenyl)boronic acid in Step B. MS (ESI): mass calcd. for $C_{19}H_{21}F_3N_4O_3$, 410.2; m/z found, 411.2 $[M+H]^+$. $^1H$ NMR (400 MHz, DMSO-$d_6$) δ ppm 8.59 (d, J=1.0 Hz, 1H), 8.39 (d, J=2.3 Hz, 1H), 8.17 (dd, J=8.6, 2.4 Hz, 1H), 7.83 (d, J=7.6 Hz, 1H), 7.42 (dq, J=8.6, 1.7 Hz, 1H), 7.36 (d, J=1.3 Hz, 1H), 5.48-5.40 (m, 1H), 4.67-4.60 (m, 2H), 4.43 (d, J=13.2 Hz, 2H), 3.95-3.81 (m, 1H), 3.14 (ddd, J=13.8, 11.3, 2.8 Hz, 2H), 1.89-1.76 (m, 5H), 1.42-1.26 (m, 2H).

Example 67: N-[1-[6-[3,5-Difluoro-4-(trifluoromethoxy)phenyl]pyrimidin-4-yl]-4-piperidyl]acetamide

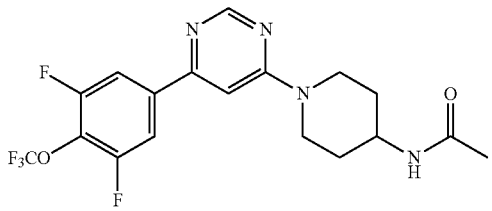 [SMILES: CC(=O)NC1CCN(c2cc(-c3cc(F)c(OC(F)(F)F)c(F)c3)ncn2)CC1]

The title compound was prepared in a manner analogous to Example 3, using 4,6-dichloropyrimidine instead of 4,6-dichloro-2-methylpyrimidine in Step A: and using (3,5-difluoro-4-(trifluoromethoxy)phenyl)boronic acid instead of (3-chloro-4-(trifluoromethoxy)phenyl)boronic acid in Step B. MS (ESI): mass calcd. for $C_{18}H_{17}F_5N_4O_2$, 416.1; m/z found, 417.2 $[M+H]^+$. $^1H$ NMR (400 MHz, DMSO-$d_6$) δ ppm 8.60 (d, J=1.0 Hz, 1H), 8.25-8.19 (m, 2H), 7.83 (d, J=7.6 Hz, 1H), 7.50 (d, J=1.3 Hz, 1H), 4.45 (d, J=12.9 Hz, 2H), 3.95-3.82 (m, 1H), 3.16 (ddd, J=14.1, 11.4, 2.8 Hz, 2H), 1.89-1.77 (m, 5H), 1.40-1.25 (m, 2H).

Example 68: N-[1-[2-Methyl-6-[4-(trifluoromethoxy)phenyl]pyrimidin-4-yl]-4-piperidyl]acetamide

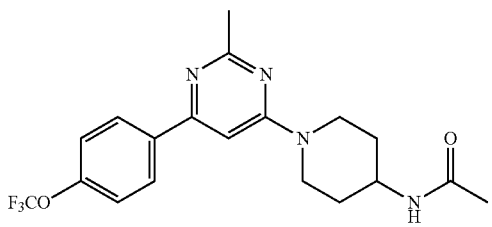 [SMILES: CC(=O)NC1CCN(c2cc(-c3ccc(OC(F)(F)F)cc3)nc(C)n2)CC1]

The title compound was prepared in a manner analogous to Example 3, using (4-(trifluoromethoxy)phenyl)boronic acid instead of (3-chloro-4-(trifluoromethoxy)phenyl)boronic acid in Step B. MS (ESI): mass calcd. for $C_{19}H_{21}F_3N_4O_2$, 394.2; m/z found, 395.2 $[M+H]^+$. $^1H$ NMR (400 MHz, DMSO-$d_6$) δ ppm 8.30-8.24 (m, 2H), 7.82 (d, J=7.6 Hz, 1H), 7.49-7.43 (m, 2H), 7.21 (s, 1H), 4.44 (d, J=12.7 Hz, 2H), 3.93-3.80 (m, 1H), 3.10 (ddd, J=13.9, 11.5, 2.7 Hz, 2H), 2.45 (s, 3H), 1.86-1.78 (m, 5H), 1.40-1.24 (m, 2H).

Example 69: (trans)-N-[3-Fluoro-1-[2-methyl-6-[3-methyl-4-(trifluoromethoxy)phenyl]pyrimidin-4-yl]-4-piperidyl]acetamide

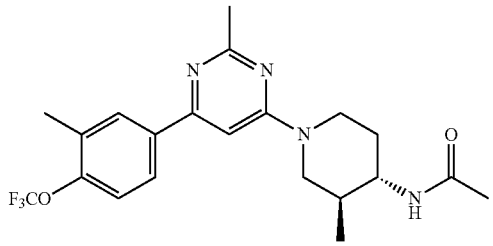 [SMILES: CC(=O)N[C@H]1CCN(c2cc(-c3ccc(OC(F)(F)F)c(C)c3)nc(C)n2)C[C@@H]1C]

The title compound was prepared analogous to Example 4 using (3-methyl-4-(trifluoromethoxy)phenyl)boronic acid instead of (4-(trifluoromethoxy)phenyl)boronic acid in Step C. MS (ESI): mass calcd. for $C_{20}H_{22}F_4N_4O_2$, 426.2; m/z found, 427.2 [M+H]. $^1$H NMR (400 MHz, DMSO-$d_6$) δ ppm 8.19 (dd, J=2.1, 0.9 Hz, 1H), 8.11 (dd, J=8.5, 2.2 Hz, 1H), 8.03 (d, J=8.2 Hz, 1H), 7.41 (dq, J=8.7, 1.6 Hz, 1H), 7.28 (s, 1H), 4.59-4.42 (m, 2H), 4.40-4.30 (m, 1H), 4.23 (d, J=13.2 Hz, 1H), 4.13-4.00 (m, 1H), 3.44 (ddd, J=13.1, 8.6, 6.0 Hz, 1H), 2.47 (s, 3H), 2.37 (s, 3H), 1.92 (dd, J=17.3, 5.7 Hz, 1H), 1.85 (s, 3H), 1.47-1.36 (m, 1H).

Example 70: N-[1-[6-[4-(Trifluoromethoxy)-3-(trifluoromethyl)phenyl]pyrimidin-4-yl]-4-piperidyl]acetamide

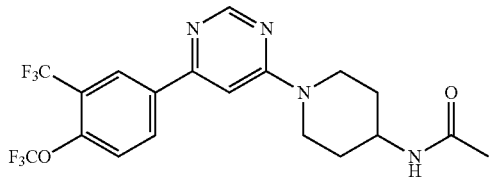 [SMILES: CC(=O)NC1CCN(c2cc(-c3ccc(OC(F)(F)F)c(C(F)(F)F)c3)ncn2)CC1]

The title compound was prepared in a manner analogous to Example 3, using 4,6-dichloropyrimidine instead of (4,6-dichloropyrimidin-2-yl)methanol in Step A; and using 4,4,5,5-tetramethyl-2-(4-(trifluoromethoxy)-3-(trifluoromethyl)phenyl)-1,3,2-dioxaborolane (Intermediate 1) instead of and (3-chloro-4-(trifluoromethoxy)phenyl)boronic acid. MS (ESI): mass calcd. for $C_{19}H_{18}F_6N_4O_2$, 448.1; m/z found, 449.2 [M+H]$^+$. $^1$H NMR (400 MHz, DMSO-$d_6$) δ ppm 8.65-8.60 (m, 3H), 7.86-7.77 (m, 2H), 7.53 (d, J=1.3 Hz, 1H), 4.47 (d, J=12.8 Hz, 2H), 3.95-3.82 (m, 1H), 3.21-3.09 (m, 2H), 1.89-1.78 (m, 5H), 1.40-1.26 (m, 2H).

Example 71: N-Methyl-1-[6-[4-(trifluoromethoxy)phenyl]pyrimidin-4-yl]piperidine-4-carboxamide

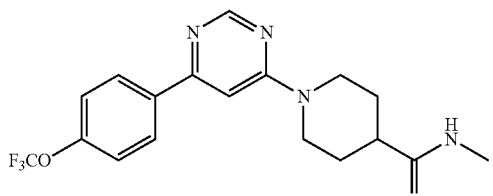

The title compound was prepared in a manner analogous to Example 5, using 4,6-dichloropyrimidine instead of (4,6-dichloropyrimidin-2-yl)methanol and (4-(trifluoromethoxy)phenyl)boronic acid instead of (3-fluoro-4-(trifluoromethoxy)phenyl)boronic acid in Step A; and using N-methylpiperidine-4-carboxamide instead of N-(piperidin-4-yl)acetamide in Step B. MS (ESI): mass calcd. for $C_{18}H_{19}F_3N_4O_2$, 380.1; m/z found, 381.2 [M+H]$^+$. $^1$H NMR (500 MHz, Chloroform-d) δ ppm 8.67 (s, 1H), 8.01 (d, J=8.4 Hz, 2H), 7.31 (d, J=8.1 Hz, 2H), 6.86 (s, 1H), 5.58 (s, 1H), 4.52 (d, J=13.7 Hz, 2H), 3.06 (t, J=12.4 Hz, 2H), 2.83 (d, J=4.8 Hz, 3H), 2.49-2.35 (m, 1H), 2.05-1.90 (m, 2H), 1.85-1.71 (m, 2H).

Example 72: N-(2-Hydroxyethyl)-1-[6-[4-(trifluoromethoxy)phenyl]pyrimidin-4-yl]piperidine-4-carboxamide

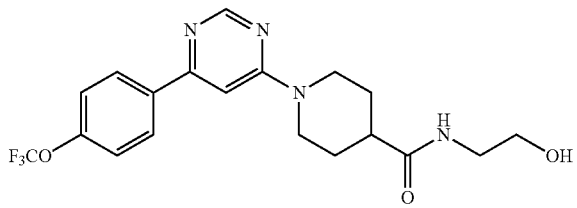 [SMILES: O=C(NCCO)C1CCN(c2cc(-c3ccc(OC(F)(F)F)cc3)ncn2)CC1]

The title compound was prepared in a manner analogous to Example 5, using 4,6-dichloropyrimidine instead of (4,6-dichloropyrimidin-2-yl)methanol and (4-(trifluoromethoxy)phenyl)boronic acid instead of (3-fluoro-4-(trifluoromethoxy)phenyl)boronic acid in Step A; and using N-(2-hydroxyethyl)piperidine-4-carboxamide instead of N-(piperidin-4-yl)acetamide in Step B. MS (ESI): mass calcd. for $C_{19}H_{21}F_3N_4O_3$, 410.2; m/z found, 411.2 [M+H]$^+$. $^1$H NMR (500 MHz, Chloroform-d) δ ppm 8.67 (d, J=1.1 Hz, 1H), 8.03 (d, J=8.8 Hz, 2H), 7.36-7.30 (m, 2H), 6.86 (d, J=1.1 Hz, 1H), 6.21 (s, 1H), 4.54 (d, J=13.3 Hz, 2H), 3.84-3.66 (m, 2H), 3.51-3.37 (m, 2H), 3.13 (t, J=12.6 Hz, 2H), 2.56-2.43 (m, 1H), 2.06-1.96 (m, 2H), 1.90-1.76 (m, 2H).

Example 73: 4-[4-(1H-Imidazol-4-yl)-1-piperidyl]-6-[4-(trifluoromethoxy)phenyl]pyrimidine

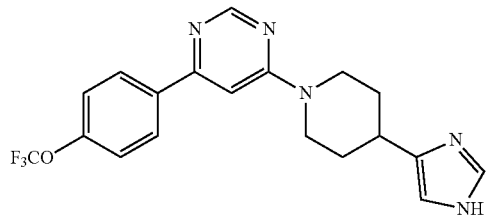 [SMILES: FC(F)(F)Oc1ccc(-c2cc(N3CCC(c4c[nH]cn4)CC3)ncn2)cc1]

The title compound was prepared in a manner analogous to Example 5, using 4,6-dichloropyrimidine instead of (4,6-dichloropyrimidin-2-yl)methanol and (4-(trifluoromethoxy)phenyl)boronic acid instead of (3-fluoro-4-(trifluoromethoxy)phenyl)boronic acid in Step A; and using 4-(1H-imidazol-4-yl)piperidine instead of N-(piperidin-4-yl)acetamide in Step B. MS (ESI): mass calcd. for $C_{19}H_{18}F_3N_5O$, 389.1; m/z found, 390.2 [M+H]$^+$. $^1$H NMR (400 MHz, Chloroform-d) δ ppm 8.66 (d, J=1.1 Hz, 1H), 8.03-7.95 (m, 2H), 7.57 (d, J=1.2 Hz, 1H), 7.32-7.27 (m, 2H), 6.87 (d, J=1.2 Hz, 1H), 6.79-6.72 (m, 1H), 4.54 (d, J=13.3 Hz, 2H), 3.17-3.05 (m, 2H), 3.01-2.89 (m, 1H), 2.22-2.07 (m, 2H), 1.77-1.59 (m, 2H).

Example 74: N-(2-Hydroxyethyl)-1-[2-methyl-6-[4-(trifluoromethoxy)phenyl]pyrimidin-4-yl]piperidine-4-carboxamide

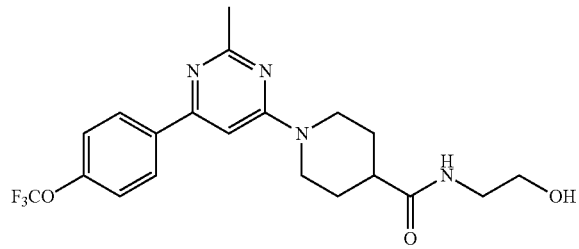 [SMILES: Cc1nc(-c2ccc(OC(F)(F)F)cc2)cc(N2CCC(C(=O)NCCO)CC2)n1]

The title compound was prepared in a manner analogous to Example 5, using 4,6-dichloro-2-methylpyrimidine instead of (4,6-dichloropyrimidin-2-yl)methanol and (4-(trifluoromethoxy)phenyl)boronic acid instead of (3-fluoro-4-(trifluoromethoxy)phenyl)boronic acid in Step A; and using N-(2-hydroxyethyl)piperidine-4-carboxamide instead of N-(piperidin-4-yl)acetamide in Step B. MS (ESI): mass calcd. for $C_{20}H_{23}F_3N_4O_3$, 424.2; m/z found, 425.2 [M+H]$^+$. $^1$H NMR (500 MHz, Chloroform-d) δ ppm 7.96 (d, J=8.3 Hz, 2H), 7.28 (d, J=8.6 Hz, 2H), 6.67 (s, 1H), 6.00 (s, 1H), 4.55 (d, J=13.2 Hz, 2H), 3.77-3.70 (m, 2H), 3.47-3.39 (m, 2H), 3.04-2.93 (m, 2H), 2.57 (s, 3H), 2.50-2.38 (m, 2H), 2.02-1.91 (m, 2H), 1.83-1.70 (m, 2H).

Example 75: 4-[4-(1H-Imidazol-4-yl)-1-piperidyl]-2-methyl-6-[4-(trifluoromethoxy)phenyl]pyrimidine

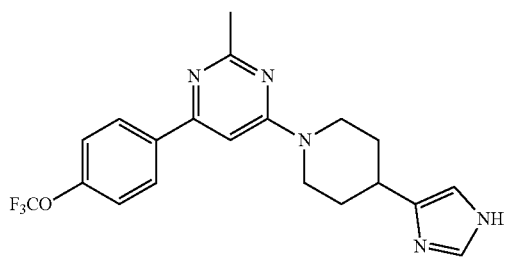 [SMILES: Cc1nc(-c2ccc(OC(F)(F)F)cc2)cc(N2CCC(c3c[nH]cn3)CC2)n1]

The title compound was prepared in a manner analogous to Example 5, using 4,6-dichloro-2-methylpyrimidine instead of (4,6-dichloropyrimidin-2-yl)methanol and (4-(trifluoromethoxy)phenyl)boronic instead of (3-fluoro-4-(trifluoromethoxy)phenyl)boronic acid in Step A; and using 4-(1H-imidazol-4-yl)piperidine instead of N-(piperidin-4-yl)acetamide in Step B. MS (ESI): mass calcd. for $C_{20}H_{20}F_3N_5O$, 403.2; m/z found, 404.2 [M+H]$^+$. $^1$H NMR (500 MHz, Chloroform-d) δ ppm 8.00-7.93 (m, 2H), 7.58 (d, J=1.2 Hz, 1H), 7.30-7.27 (m, 2H), 6.77 (s, 1H), 6.69 (s, 1H), 4.57 (d, J=13.3 Hz, 2H), 3.12-3.03 (m, 2H), 2.99-2.87 (m, 1H), 2.58 (s, 3H), 2.19-2.05 (m, 2H), 1.75-1.61 (m, 2H).

Example 76: 1-[6-[3-Fluoro-4-(trifluoromethoxy)phenyl]pyrimidin-4-yl]-N-(2-hydroxyethyl)piperidine-4-carboxamide

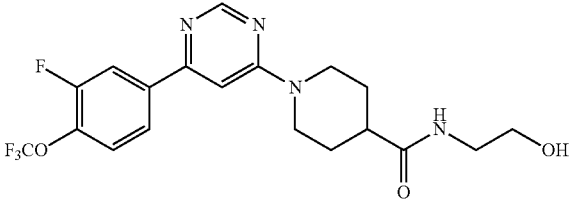 [SMILES: O=C(NCCO)C1CCN(c2cc(-c3ccc(OC(F)(F)F)c(F)c3)ncn2)CC1]

The title compound was prepared in a manner analogous to Example 5, using 4,6-dichloropyrimidine instead of (4,6-dichloropyrimidin-2-yl)methanol in Step A; and using N-(2-hydroxyethyl)piperidine-4-carboxamide instead of N-(piperidin-4-yl)acetamide in Step B. MS (ESI): mass calcd. for $C_{19}H_{20}F_4N_4O_3$, 428.1; m/z found, 429.2 [M+H]$^+$. $^1$H NMR (500 MHz, Chloroform-d) δ ppm 8.66 (s, 1H), 7.85 (d, J=11.2 Hz, 1H), 7.77 (d, J=8.6 Hz, 1H), 7.39 (t, J=8.1 Hz, 1H), 6.84 (s, 1H), 5.99 (s, 1H), 4.53 (d, J=13.4 Hz, 2H), 3.79-3.70 (m, 2H), 3.51-3.41 (m, 2H), 3.06 (t, J=12.6 Hz, 2H), 2.52-2.41 (m, 1H), 2.33 (s, 1H), 2.04-1.92 (m, 2H), 1.86-1.71 (m, 2H).

Example 77: 4-[3-Fluoro-4-(trifluoromethoxy)phenyl]-6-[4-(1H-imidazol-4-yl)-1-piperidyl]pyrimidine

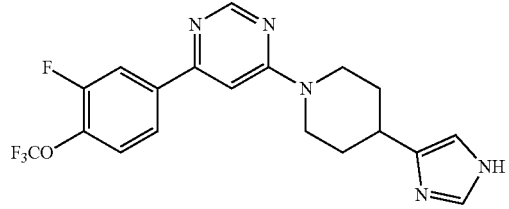 [SMILES: Fc1cc(-c2cc(N3CCC(c4c[nH]cn4)CC3)ncn2)ccc1OC(F)(F)F]

The title compound was prepared in a manner analogous to Example 5, using 4,6-dichloropyrimidine instead of (4,6-dichloropyrimidin-2-yl)methanol in Step A; and using 4-(1H-imidazol-4-yl)piperidine instead of N-(piperidin-4-yl)acetamide in Step B. MS (ESI): mass calcd. for $C_{19}H_{17}F_4N_5O$, 407.1; m/z found, 408.1 [M+H]$^+$. $^1$H NMR (500 MHz, Chloroform-d) δ ppm 8.66 (d, J=1.1 Hz, 1H), 7.85 (dd, J=11.1, 2.1 Hz, 1H), 7.76 (ddd, J=8.5, 2.1, 1.2 Hz, 1H), 7.59 (d, J=1.2 Hz, 1H), 7.44-7.35 (m, 1H), 6.86 (d, J=1.2 Hz, 1H), 6.78 (s, 1H), 4.55 (d, J=13.3 Hz, 2H), 3.21-3.06 (m, 2H), 3.02-2.89 (m, 1H), 2.23-2.10 (m, 2H), 1.78-1.64 (m, 2H).

Example 78: 2-[1-[6-[4-(Trifluoromethoxy)phenyl]pyrimidin-4-yl]-4-piperidyl]acetamide

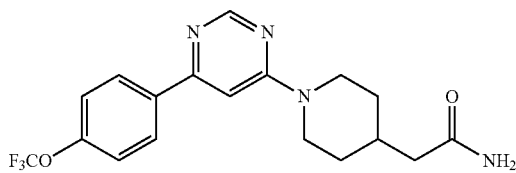 [SMILES: NC(=O)CC1CCN(c2cc(-c3ccc(OC(F)(F)F)cc3)ncn2)CC1]

The title compound was prepared in a manner analogous to Example 5, using 4,6-dichloropyrimidine instead of (4,6-dichloropyrimidin-2-yl)methanol and (4-(trifluoromethoxy)phenyl)boronic acid instead of (3-fluoro-4-(trifluoromethoxy)phenyl)boronic acid in Step A; and using 2-(piperidin-4-yl)acetamide instead of N-(piperidin-4-yl)acetamide Step B. MS (ESI): mass calcd. for $C_{18}H_{19}F_3N_4O_2$, 380.1; m/z found, 381.2 [M+H]+. $^1$H NMR (500 MHz, Chloroform-d) δ ppm 8.66 (d, J=1.1 Hz, 1H), 8.00 (d, J=8.7 Hz, 2H), 7.30 (d, J=8.3 Hz, 2H), 6.85 (s, 1H), 5.37 (d, J=21.1 Hz, 2H), 4.51 (s, 2H), 2.98 (t, J=12.8 Hz, 2H), 2.19 (s, 3H), 2.01-1.81 (m, 2H), 1.37-1.19 (m, 2H).

Example 79: N-[1-[6-[4-(Trifluoromethoxy)phenyl]pyrimidin-4-yl]-4-piperidyl]acetamide

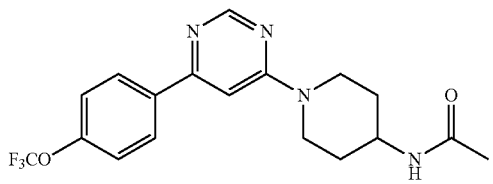 [SMILES: CC(=O)NC1CCN(c2cc(-c3ccc(OC(F)(F)F)cc3)ncn2)CC1]

The title compound was prepared in a manner analogous to Example 5, using 4,6-dichloropyrimidine instead of (4,6-dichloropyrimidin-2-yl)methanol and (4-(trifluoromethoxy)phenyl)boronic acid instead of (3-fluoro-4-(trifluoromethoxy)phenyl)boronic acid in Step A. MS (ESI): mass calcd. for $C_{18}H_{19}F_3N_4O_2$, 380.1; m/z found, 381.2 [M+H]+. $^1$H NMR (500 MHz, Chloroform-d) δ ppm 8.67 (d, J=1.1 Hz, 1H), 8.03-7.95 (m, 2H), 7.33-7.27 (m, 2H), 6.87 (d, J=1.2 Hz, 1H), 5.42 (d, J=8.0 Hz, 1H), 4.46 (d, J=13.6 Hz, 2H), 4.14-4.05 (m, 1H), 3.15-3.01 (m, 2H), 2.14-2.04 (m, 2H), 1.99 (s, 3H), 1.47-1.32 (m, 2H).

Example 80: 4-[4-(1H-Imidazol-2-yl)-1-piperidyl]-6-[4-(trifluoromethoxy)phenyl]pyrimidine

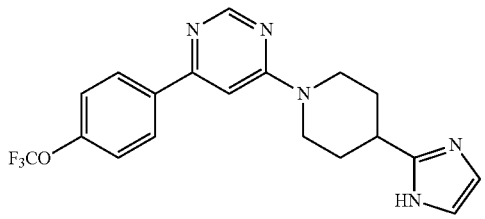 [SMILES: FC(F)(F)Oc1ccc(-c2cc(N3CCC(c4ncc[nH]4)CC3)ncn2)cc1]

The title compound was prepared in a manner analogous to Example 5, using 4,6-dichloropyrimidine instead of 4,6-dichloropyrimidin-2-yl)methanol and (4-(trifluoromethoxy)phenyl)boronic acid instead of (3-fluoro-4-(trifluoromethoxy)phenyl)boronic acid in Step A; and using 4-(1H-imidazol-2-yl)piperidine instead of N-(piperidin-4-yl)acetamide in Step B. MS (ESI): mass calcd. for $C_{19}H_{18}F_3N_5O$, 389.1; m/z found, 390.1 [M+H]+. $^1$H NMR (400 MHz, Chloroform-d) δ ppm 8.66 (s, 1H), 8.02-7.95 (m, 2H), 7.29 (d, J=8.4 Hz, 2H), 6.96 (s, 2H), 6.86 (s, 1H), 4.53 (d, J=13.4 Hz, 2H), 3.19-2.99 (m, 3H), 2.19-2.09 (m, 2H), 1.93-1.75 (m, 2H).

Example 81: N-[[1-[6-[4-(Trifluoromethoxy)phenyl]pyrimidin-4-yl]-4-piperidyl]methyl]acetamide

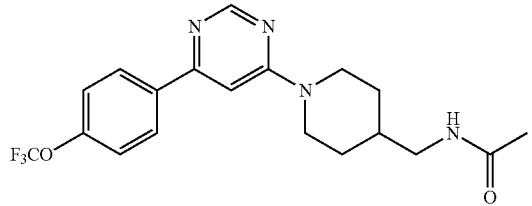 [SMILES: CC(=O)NCC1CCN(c2cc(-c3ccc(OC(F)(F)F)cc3)ncn2)CC1]

The title compound was prepared in a manner analogous to Example 5, using 4,6-dichloropyrimidine instead of (4,6-dichloropyrimidin-2-yl)methanol, and (4-(trifluoromethoxy)phenyl)boronic acid instead of (3-fluoro-4-(trifluoromethoxy)phenyl)boronic acid in Step A; and using N-(piperidin-4-ylmethyl)acetamide instead of N-(piperidin-4-yl)acetamide in Step B. MS (ESI): mass calcd. for $C_{19}H_{21}F_3N_4O_2$, 394.2; m/z found, 395.2 [M+H]+. $^1$H NMR (400 MHz, Chloroform-d) δ ppm 8.64 (d, J=1.1 Hz, 1H), 8.06-7.88 (m, 2H), 7.35-7.27 (m, 2H), 6.83 (d, J=1.2 Hz, 1H), 5.78-5.64 (m, 1H), 4.50 (d, J=13.2 Hz, 2H), 3.17 (t, J=6.3 Hz, 2H), 3.01-2.83 (m, 2H), 1.99 (s, 3H), 1.92-1.75 (m, 3H), 1.31-1.11 (m, 2H).

Example 82: 8-[6-[3-Fluoro-4-(trifluoromethoxy)phenyl]pyrimidin-4-yl]-4,8-diazaspiro[4.5]decan-3-one

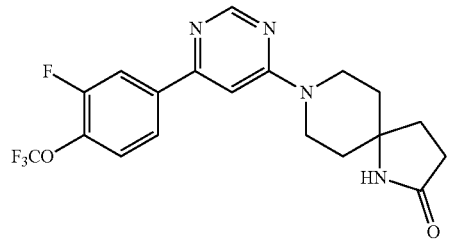 [SMILES: O=C1CCC2(CCN(c3cc(-c4ccc(OC(F)(F)F)c(F)c4)ncn3)CC2)N1]

The title compound was prepared in a manner analogous to Example 5, using 4,6-dichloropyrimidine instead of (4,6-dichloropyrimidin-2-yl)methanol in Step A; and 1,8-diazaspiro[4.5]decan-2-one hydrochloride instead of N-(piperidin-4-yl)acetamide in Step B. MS (ESI): mass calcd. for $C_{19}H_{18}F_4N_4O_2$, 410.1; m/z found, 411.1 [M+H]+. $^1$H NMR (400 MHz, Chloroform-d) δ ppm 8.66 (d, J=1.1 Hz, 1H), 7.85 (dd, J=11.1, 2.1 Hz, 1H), 7.79-7.74 (m, 1H), 7.47 (s, 1H), 7.42-7.36 (m, 1H), 6.85 (d, J=1.2 Hz, 1H), 3.92-3.71 (m, 4H), 2.51-2.42 (m, 2H), 2.08-2.00 (m, 2H), 1.84-1.73 (m, 4H).

Example 83: 1-[6-[3-Fluoro-4-(trifluoromethoxy)phenyl]-2-methyl-pyrimidin-4-yl]piperidin-4-ol

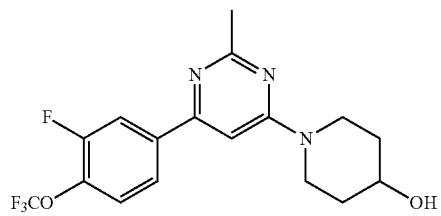 [SMILES: Cc1nc(-c2ccc(OC(F)(F)F)c(F)c2)cc(N2CCC(O)CC2)n1]

The title compound was prepared in a manner analogous to Example 5, using 4,6-dichloro-2-methylpyrimidine instead of (4,6-dichloropyrimidin-2-yl)methanol in Step A; and using piperidin-4-ol instead of N-(piperidin-4-yl)acetamide in Step B. MS (ESI): mass calcd. for C$_{17}$H$_{17}$F$_4$N$_3$O$_2$, 371.1; m/z found, 372.1 [M+H]$^+$. $^1$H NMR (500 MHz, Chloroform-d) δ ppm 7.82 (dd, J=11.1, 2.1 Hz, 1H), 7.72 (ddd, J=8.6, 2.1, 1.2 Hz, 1H), 7.36 (ddt, J=8.8, 7.5, 1.3 Hz, 1H), 6.65 (s, 1H), 4.21-4.12 (m, 2H), 4.02-3.96 (m, 1H), 3.40-3.32 (m, 2H), 2.56 (s, 3H), 2.01-1.92 (m, 2H), 1.84 (s, 1H), 1.63-1.53 (m, 2H).

Example 84: N-Methyl-1-[6-[4-(trifluoromethoxy)phenyl]pyrimidin-4-yl]azetidine-3-carboxamide

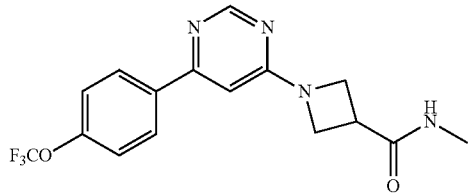 [SMILES: CNC(=O)C1CN(c2cc(-c3ccc(OC(F)(F)F)cc3)ncn2)C1]

The title compound was prepared in a manner analogous to Example 6, Steps A-C; using azetidine-3-carboxylic acid for pyrrolidine-3-carboxylic acid in Step B. MS (ESI): mass calcd. for C$_{16}$H$_{15}$F$_3$N$_4$O$_2$, 352.1; m/z found, 353.1 [M+H]$^+$. $^1$H NMR (500 MHz, Chloroform-d) δ ppm 8.66 (d, J=1.2 Hz, 1H), 8.07-7.94 (m, 2H), 7.33-7.27 (m, 2H), 6.52 (d, J=1.2 Hz, 1H), 5.69 (s, 1H), 4.38-4.23 (m, 4H), 3.47-3.39 (m, 1H), 2.88 (d, J=4.8 Hz, 3H).

Example 85: (*R/*R)—N-[3-Fluoro-1-[6-[3-fluoro-4-(trifluoromethoxy)phenyl]-2-methyl-pyrimidin-4-yl]-4-piperidyl]acetamide

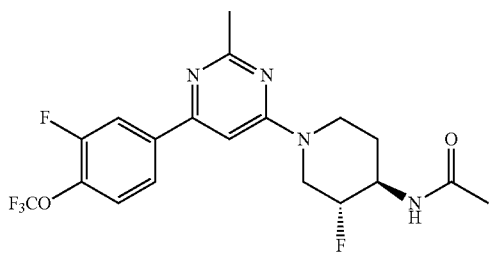 [SMILES: CC(=O)N[C@@H]1CCN(c2cc(-c3ccc(OC(F)(F)F)c(F)c3)nc(C)n2)C[C@H]1F]

(Trans)-N-[3-Fluoro-1-[6-[3-fluoro-4-(trifluoromethoxy)phenyl]-2-methyl-pyrimidin-4-yl]-4-piperidyl]acetamide (Example 7) was separated via SFC chiral separation (Stationary phase: Chiralpak IF 5 μm 250×21 mm, Mobile phase: 15% methanol, 85% CO$_2$, 2 mL/min, 150 Bar, retention time: 4.36 min at 254 nM) to afford the tile compound (20 mg, 30%). MS (ESI): mass calcd. for C$_{19}$H$_{19}$F$_5$N$_4$O$_2$, 430.1; m/z found, 431.1 [M+H]$^+$. $^1$H NMR (500 MHz, Chloroform-d)(ppm 7.84 (dd, J=11.1, 2.1 Hz, 1H), 7.73 (ddd, J=8.5, 2.1, 1.2 Hz, 1H), 7.39-7.34 (m, 1H), 6.69 (s, 1H), 5.67 (d, J=7.5 Hz, 1H), 4.81-4.73 (m, 1H), 4.38 (dtd, J=49.0, 9.2, 4.8 Hz, 1H), 4.27-4.16 (m, 2H), 3.21-3.13 (m, 2H), 2.57 (s, 3H), 2.31-2.23 (m, 1H), 2.03 (s, 3H), 1.55-1.43 (m, 1H).

Example 86: (*S/*S)—N-[3-Fluoro-1-[6-[3-fluoro-4-(trifluoromethoxy)phenyl]-2-methyl-pyrimidin-4-yl]-4-piperidyl]acetamide

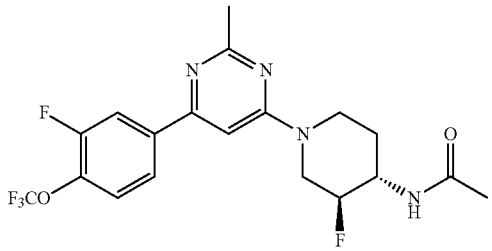 [SMILES: CC(=O)N[C@H]1CCN(c2cc(-c3ccc(OC(F)(F)F)c(F)c3)nc(C)n2)C[C@@H]1F]

(Trans)-N-[3-Fluoro-1-[6-[3-fluoro-4-(trifluoromethoxy)phenyl]-2-methyl-pyrimidin-4-yl]-4-piperidyl]acetamide (Example 7) was separated via SFC chiral separation (Stationary phase: Chiralpak IF 5 μm 250×21 mm, Mobile phase: 15% methanol, 85% CO$_2$, 2 mL/min, 150 Bar, retention time: 5.87 min at 254 nM) to afford the tile compound (27 mg, 41%). MS (ESI): mass calcd. for C$_{19}$H$_{19}$F$_5$N$_4$O$_2$, 430.1; m/z found, 431.1 [M+H]$^+$. $^1$H NMR (500 MHz, Chloroform-d) δ ppm 7.84 (dd, J=11.1, 2.1 Hz, 1H), 7.73 (ddd, J=8.6, 2.2, 1.2 Hz, 1H), 7.40-7.34 (m, 1H), 6.69 (s, 1H), 5.67 (d, J=7.6 Hz, 1H), 4.82-4.72 (m, 1H), 4.38 (dtd, J=49.0, 9.2, 4.8 Hz, 1H), 4.27-4.15 (m, 2H), 3.22-3.11 (m, 2H), 2.57 (s, 3H), 2.31-2.22 (m, 1H), 2.03 (s, 3H), 1.54-1.43 (m, 1H).

Example 87: (trans)-N-[3-Fluoro-1-[6-[3-fluoro-4-(trifluoromethoxy)phenyl]pyrimidin-4-yl]-4-piperidyl]acetamide

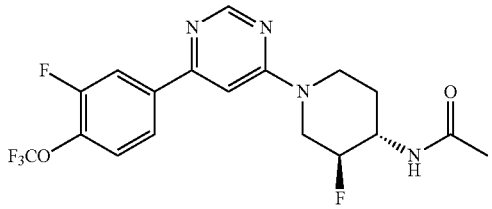

The title compound was prepared in a manner analogous to Example 7, using 4,6-dichloropyrimidine instead of 4,6-dichloro-2-methylpyrimidine in Step A. MS (ESI): mass calcd. for C$_{18}$H$_{17}$F$_5$N$_4$O$_2$, 416.1; m/z found, 417.1 [M+H]$^+$. $^1$H NMR (500 MHz, Chloroform-d) δ ppm 8.70 (d, J=1.1 Hz, 1H), 7.87 (dd, J=11.1, 2.1 Hz, 1H), 7.78 (ddd, J=8.6, 2.2, 1.3 Hz, 1H), 7.40 (ddd, J=8.7, 7.6, 1.4 Hz, 1H), 6.89 (d, J=1.2 Hz, 1H), 5.49 (d, J=7.5 Hz, 1H), 4.78-4.69 (m, 1H), 4.41 (dtd, J=48.8, 9.1, 4.7 Hz, 1H), 4.28-4.17 (m, 2H), 3.29-3.20 (m, 2H), 2.36-2.28 (m, 1H), 2.04 (s, 3H), 1.53-1.48 (m, 1H).

Example 88: (*S/*S)—N-[3-Fluoro-1-[6-[3-fluoro-4-(trifluoromethoxy)phenyl]pyrimidin-4-yl]-4-piperidyl]acetamide

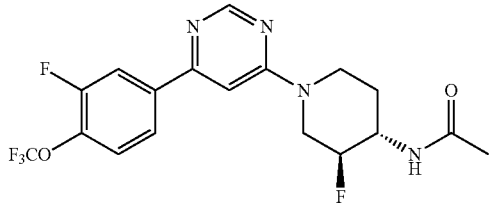 [SMILES: CC(=O)N[C@H]1CCN(c2cc(-c3ccc(OC(F)(F)F)c(F)c3)ncn2)C[C@@H]1F]

(trans)-N-[3-Fluoro-1-[6-[3-fluoro-4-(trifluoromethoxy)phenyl]pyrimidin-4-yl]-4-piperidyl]acetamide (Example 87) was separated via SFC chiral separation (Stationary phase: Chiralpak IC 5 μm 250×21.2 mm, Mobile phase: 82% $CO_2$, 18% iPOH (0.3% $iPrNH_2$), 2 mL/min, 150 Bar, retention time: 1.07 min at 250 nM) to afford the tile compound (42 mg, 34%). MS (ESI): mass calcd. for $C_{18}H_{17}F_5N_4O_2$, 416.1; m/z found, 417.1 $[M+H]^+$. $^1$H NMR (500 MHz, Chloroform-d) δ ppm 8.69 (d, J=1.1 Hz, 1H), 7.87 (dd, J=11.1, 2.1 Hz, 1H), 7.77 (ddd, J=8.6, 2.2, 1.3 Hz, 1H), 7.43-7.37 (m, 1H), 6.88 (d, J=1.2 Hz, 1H), 5.61 (d, J=7.5 Hz, 1H), 4.72 (s, 1H), 4.41 (dtd, J=48.8, 9.1, 4.7 Hz, 1H), 4.27-4.17 (m, 2H), 3.28-3.18 (m, 2H), 2.34-2.26 (m, 1H), 2.03 (s, 3H), 1.57-1.46 (m, 1H).

Example 89: (*R/*R)—N-[3-Fluoro-4-(trifluoromethoxy)phenyl]pyrimidin-4-yl]-4-piperidyl]acetamide

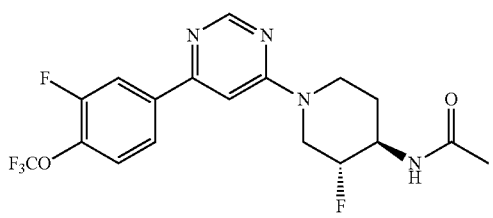

(trans)-N-[3-Fluoro-1-[6-[3-fluoro-4-(trifluoromethoxy)phenyl]pyrimidin-4-yl]-4-piperidyl]acetamide (Example 87) was separated via SFC chiral separation (Stationary phase: Chiralpak IC 5 μm 250×21.2 mm, Mobile phase: 82% $CO_2$, 18% iPOH (0.3% $iPrNH_2$), 2 mL/min, 150 Bar, retention time: 1.30 min at 250 nM) to afford the tile compound (29 mg, 23%). MS (ESI): mass calcd. for $C_{18}H_{17}F_5N_4O_2$, 416.1; m/z found, 417.1 $[M+H]^+$. $^1$H NMR (500 MHz, Chloroform-d) δ ppm 8.69 (d, J=1.1 Hz, 1H), 7.87 (dd, J=11.1, 2.1 Hz, 1H), 7.77 (ddd, J=8.5, 2.1, 1.2 Hz, 1H), 7.42-7.37 (m, 1H), 6.88 (d, J=1.2 Hz, 1H), 5.58 (d, J=7.5 Hz, 1H), 4.77-4.68 (m, 1H), 4.41 (dtd, J=48.9, 9.1, 4.7 Hz, 1H), 4.27-4.16 (m, 2H), 3.28-3.19 (m, 2H), 2.35-2.26 (m, 1H), 2.03 (s, 3H), 1.56-1.46 (m, 1H).

Example 90: (trans)-N-[3-Fluoro-1-[6-[3-methyl-4-(trifluoromethoxy)phenyl]pyrimidin-4-yl]-4-piperidyl]acetamide

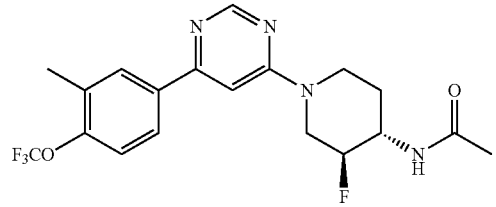 [SMILES: CC(=O)N[C@H]1CCN(c2cc(-c3ccc(OC(F)(F)F)c(C)c3)ncn2)C[C@@H]1F]

The title compound was prepared in a manner analogous to Example 7, using 4,6-dichloropyrimidine instead of 4,6-dichloro-2-methylpyrimidine in Step A; and (3-methyl-4-(trifluoromethoxy)phenyl)boronic acid instead of (3-fluoro-4-(trifluoromethoxy)phenyl)boronic acid in Step C. MS (ESI): mass calcd. for $C_{19}H_{20}F_4N_4O_2$, 412.2; m/z found, 413.1 $[M+H]^+$. $^1$H NMR (500 MHz, Chloroform-d) δ ppm 8.70 (d, J=1.1 Hz, 1H), 7.89 (dd, J=2.3, 0.9 Hz, 1H), 7.81-7.76 (m, 1H), 7.32-7.27 (m, 1H), 6.89 (d, J=1.2 Hz, 1H), 5.51 (d, J=7.5 Hz, 1H), 4.80-4.71 (m, 1H), 4.40 (dtd, J=48.9, 9.2, 4.7 Hz, 1H), 4.30-4.17 (m, 2H), 3.27-3.17 (m, 2H), 2.39 (s, 3H), 2.35-2.27 (m, 1H), 2.04 (s, 3H), 1.55-1.45 (m, 1H).

Example 91: (*S/*S)—N-[3-Fluoro-1-[6-[3-methyl-4-(trifluoromethoxy)phenyl]pyrimidin-4-yl]-4-piperidyl]acetamide

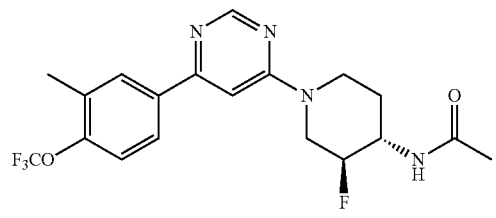 [SMILES: CC(=O)N[C@H]1CCN(c2cc(-c3ccc(OC(F)(F)F)c(C)c3)ncn2)C[C@@H]1F]

(Trans)-N-[3-Fluoro-1-[6-[3-methyl-4-(trifluoromethoxy)phenyl]pyrimidin-4-yl]-4-piperidyl]acetamide (Example 90) was separated via SFC chiral separation (Stationary phase: Chiralpak AD-H 5 μm 250×30 mm, Mobile phase: 82% $CO_2$, 18% MeOH (0.3% $iPrNH_2$), 2 mL/min, 150 Bar, retention time: 1.44 min at 250 nM) to afford the tile compound (24 mg, 20%). MS (ESI): mass calcd. for $C_{19}H_{20}F_4N_4O_2$, 412.2; m/z found, 413.1 $[M+H]^+$. $^1$H NMR (500 MHz, Chloroform-d) δ ppm 8.69 (d, J=1.1 Hz, 1H), 7.90-7.87 (m, 1H), 7.79 (dd, J=8.5, 2.3 Hz, 1H), 7.31-7.27 (m, 1H), 6.89 (d, J=1.2 Hz, 1H), 5.61 (d, J=7.5 Hz, 1H), 4.77-4.69 (m, 1H), 4.40 (dtd, J=48.9, 9.2, 4.7 Hz, 1H), 4.29-4.16 (m, 2H), 3.26-3.16 (m, 2H), 2.39 (s, 3H), 2.33-2.26 (m, 1H), 2.03 (s, 3H), 1.56-1.45 (m, 1H).

Example 92: (*R/*R)—N-[3-Fluoro-1-[6-[3-methyl-4-(trifluoromethoxy)phenyl]pyrimidin-4-yl]-4-piperidyl]acetamide

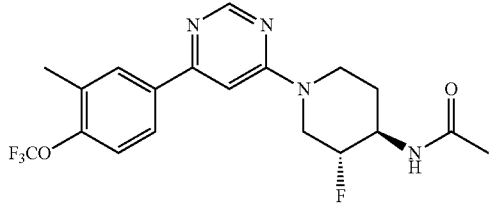 [SMILES: CC(=O)N[C@@H]1CCN(c2cc(-c3ccc(OC(F)(F)F)c(C)c3)ncn2)C[C@H]1F]

(trans)-N-[3-Fluoro-1-[6-[3-methyl-4-(trifluoromethoxy)phenyl]pyrimidin-4-yl]-4-piperidyl]acetamide (Example 90) was separated via SFC chiral separation (Stationary phase: Chiralpak AD-H 5 μm 250×30 mm, Mobile phase: 82% CO$_2$, 18% MeOH (0.3% iPrNH$_2$), 2 mL/min, 150 Bar, retention time: 1.98 min at 250 nM) to afford the tile compound (35 mg, 29%). MS (ESI): mass calcd. for C$_{19}$H$_{20}$F$_4$N$_4$O$_2$, 412.2; m/z found, 413.1 [M+H]$^+$. $^1$H NMR (500 MHz, Chloroform-d) δ ppm 8.69 (d, J=1.2 Hz, 1H), 7.89 (d, J=2.3 Hz, 1H), 7.79 (dd, J=8.6, 2.3 Hz, 1H), 7.31-7.27 (m, 1H), 6.89 (d, J=1.2 Hz, 1H), 5.64 (d, J=7.5 Hz, 1H), 4.77-4.69 (m, 1H), 4.39 (dtd, J=48.9, 9.2, 4.7 Hz, 1H), 4.29-4.17 (m, 2H), 3.25-3.17 (m, 2H), 2.39 (s, 3H), 2.33-2.24 (m, 1H), 2.03 (s, 3H), 1.56-1.45 (m, 1H).

Example 93: (trans)-N-[1-[6-[3-Chloro-4-(trifluoromethoxy)phenyl]pyrimidin-4-yl]-3-fluoro-4-piperidyl]acetamide

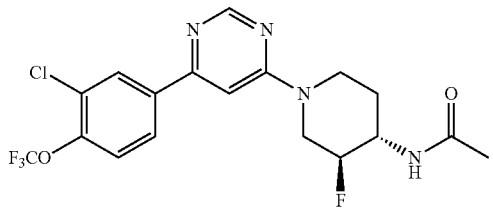 [SMILES: CC(=O)N[C@H]1CCN(c2cc(-c3ccc(OC(F)(F)F)c(Cl)c3)ncn2)C[C@@H]1F]

The title compound was prepared in a manner analogous to Example 7, using 4,6-dichloropyrimidine instead of 4,6-dichloro-2-methylpyrimidine in Step A; and (3-chloro-4-(trifluoromethoxy)phenyl)boronic acid instead of (3-fluoro-4-(trifluoromethoxy)phenyl)boronic acid in Step C. MS (ESI): mass calcd. for C$_{18}$H$_{17}$ClF$_4$N$_4$O$_2$, 432.1; m/z found, 433.1 [M+H]$^+$. $^1$H NMR (500 MHz, Chloroform-d) δ ppm 8.70 (d, J=1.1 Hz, 1H), 8.11 (d, J=2.2 Hz, 1H), 7.91 (dd, J=8.6, 2.2 Hz, 1H), 7.44-7.40 (m, 1H), 6.89 (d, J=1.2 Hz, 1H), 5.51 (d, J=7.5 Hz, 1H), 4.78-4.70 (m, 1H), 4.41 (dtd, J=48.8, 9.1, 4.7 Hz, 1H), 4.28-4.19 (m, 2H), 3.28-3.20 (m, 2H), 2.36-2.28 (m, 1H), 2.04 (s, 3H), 1.54-1.47 (m, 1H).

Example 94: (*S/*S)—N-[1-[6-[3-Chloro-4-(trifluoromethoxy)phenyl]pyrimidin-4-yl]-3-fluoro-4-piperidyl]acetamide

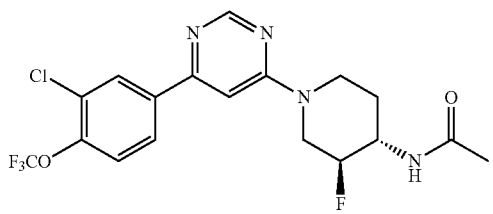 [SMILES: CC(=O)N[C@H]1CCN(c2cc(-c3ccc(OC(F)(F)F)c(Cl)c3)ncn2)C[C@@H]1F]

(trans)-N-[1-[6-[3-Chloro-4-(trifluoromethoxy)phenyl]pyrimidin-4-yl]-3-fluoro-4-piperidyl]acetamide (Example 93) was separated via SFC chiral separation (Stationary phase: Chiralpak AD-H 5 μm 250×30 mm, Mobile phase: 80% CO$_2$, 18% MeOH (0.3% iPrNH$_2$), 2 mL/min, 150 Bar, retention time: 1.71 min at 250 nM) to afford the tile compound (33 mg, 26%). MS (ESI): mass calcd. for C$_{18}$H$_{17}$ClF$_4$N$_4$O$_2$, 432.1; m/z found, 433.1 [M+H]$^+$. $^1$H NMR (500 MHz, Chloroform-d) δ ppm 8.69 (d, J=1.2 Hz, 1H), 8.11 (d, J=2.2 Hz, 1H), 7.90 (dd, J=8.6, 2.2 Hz, 1H), 7.43-7.39 (m, 1H), 6.88 (d, J=1.2 Hz, 1H), 5.62 (d, J=7.5 Hz, 1H), 4.77-4.68 (m, 1H), 4.41 (dtd, J=48.8, 9.1, 4.7 Hz, 1H), 4.27-4.17 (m, 2H), 3.28-3.19 (m, 2H), 2.34-2.26 (m, 1H), 2.03 (s, 3H), 1.56-1.46 (m, 1H).

Example 95: (*R/*R)—N-[1-[6-[3-Chloro-4-(trifluoromethoxy)phenyl]pyrimidin-4-yl]-3-fluoro-4-piperidyl]acetamide

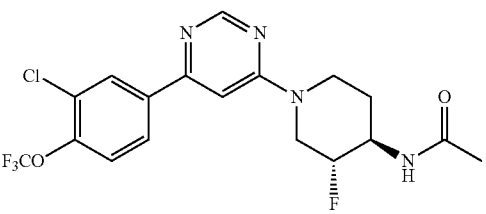

(trans)-N-[1-[6-[3-Chloro-4-(trifluoromethoxy)phenyl]pyrimidin-4-yl]-3-fluoro-4-piperidyl]acetamide (Example 93) was separated via SFC chiral separation (Stationary phase: Chiralpak AD-H 5 μm 250×30 mm, Mobile phase: 80% CO$_2$, 18% MeOH (0.3% iPrNH$_2$), 2 mL/min, 150 Bar, retention time: 2.28 min at 250 nM) to afford the tile compound (49 mg, 38%). MS (ESI): mass calcd. for C$_{18}$H$_{17}$ClF$_4$N$_4$O$_2$, 432.1; m/z found, 433.1 [M+H]$^+$. $^1$H NMR (500 MHz, Chloroform-d) δ ppm 8.69 (d, J=1.1 Hz, 1H), 8.11 (d, J=2.2 Hz, 1H), 7.90 (dd, J=8.6, 2.2 Hz, 1H), 7.43-7.39 (m, 1H), 6.88 (d, J=1.2 Hz, 1H), 5.61 (d, J=7.5 Hz, 1H), 4.77-4.67 (m, 1H), 4.41 (dtd, J=48.9, 9.1, 4.7 Hz, 1H), 4.28-4.17 (m, 2H), 3.29-3.19 (m, 2H), 2.34-2.26 (m, 1H), 2.03 (s, 3H), 1.56-1.46 (m, 1H).

Example 96: (cis)-N-[3-Fluoro-1-[6-[3-fluoro-4-(trifluoromethoxy)phenyl]pyrimidin-4-yl]-4-piperidyl]acetamide

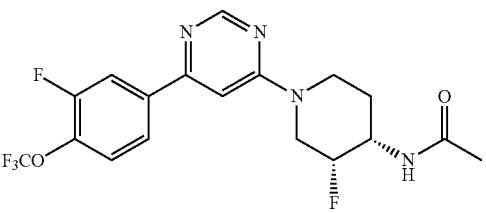 [SMILES: CC(=O)N[C@H]1CCN(c2cc(-c3ccc(OC(F)(F)F)c(F)c3)ncn2)C[C@H]1F]

The title compound was prepared in a manner analogous to Example 7, using 4,6-dichloropyrimidine instead of 4,6-dichloro-2-methylpyrimidine in Step A; using tert-butyl ((3,4-cis)-3-fluoropiperidin-4-yl)carbamate instead of tert-butyl ((3,4-trans)-3-fluoropiperidin-4-yl)carbamate in Step B. MS (ESI): mass calcd. for C$_{18}$H$_{17}$F$_5$N$_4$O$_2$, 416.1; m/z found, 417.1 [M+H]$^+$. $^1$H NMR (500 MHz, Chloroform-d)

δ ppm 8.68 (d, J=1.2 Hz, 1H), 7.86 (dd, J=11.1, 2.1 Hz, 1H), 7.78 (ddd, J=8.6, 2.2, 1.3 Hz, 1H), 7.43-7.36 (m, 1H), 6.89 (d, J=1.2 Hz, 1H), 5.74 (d, J=8.9 Hz, 1H), 5.01-4.79 (m, 2H), 4.69-4.61 (m, 1H), 4.36-4.22 (m, 1H), 3.26-3.11 (m, 1H), 3.09-3.01 (m, 1H), 2.04 (s, 3H), 1.98-1.89 (m, 1H), 1.87-1.77 (m, 1H).

Example 97: (*R/*S)—N-[3-Fluoro-1-[6-[3-fluoro-4-(trifluoromethoxy)phenyl]pyrimidin-4-yl]-4-piperidyl]acetamide

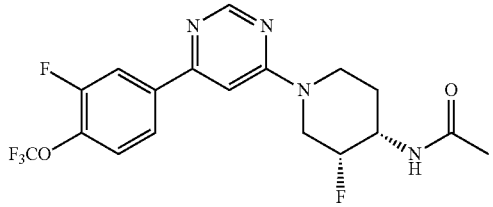 [SMILES: CC(=O)N[C@H]1CCN(c2cc(-c3ccc(OC(F)(F)F)c(F)c3)ncn2)C[C@H]1F]

(cis)-N-[3-Fluoro-1-[6-[3-fluoro-4-(trifluoromethoxy)phenyl]pyrimidin-4-yl]-4-piperidyl]acetamide (Example 96) was separated via SFC chiral separation (Stationary phase: Chiralpak AD-H 5 μm 250×21 mm, Mobile phase: 15% methanol, 85% $CO_2$, 2 mL/min, 150 Bar, retention time: 5.48 min at 254 nM) to afford the tile compound (31 mg, 21%). MS (ESI): mass calcd. for $C_{18}H_{17}F_5N_4O_2$, 416.1; m/z found, 417.1 $[M+H]^+$. $^1H$ NMR (400 MHz, Chloroform-d) δ ppm 8.68 (s, 1H), 7.91-7.71 (m, 2H), 7.45-7.33 (m, 1H), 6.89 (s, 1H), 5.78 (d, J=8.4 Hz, 1H), 5.03-4.73 (m, 2H), 4.70-4.58 (m, 1H), 4.42-4.16 (m, 1H), 3.28-2.95 (m, 2H), 2.14-1.72 (m, 5H).

Example 98: (*S/*R)—N-[3-Fluoro-1-[6-[3-fluoro-4-(trifluoromethoxy)phenyl]pyrimidin-4-yl]-4-piperidyl]acetamide

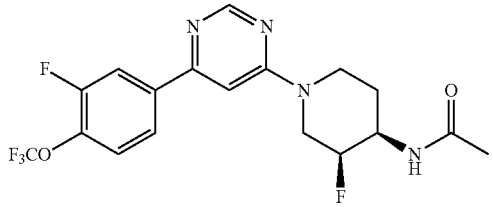

(cis)-N-[3-Fluoro-1-[6-[3-fluoro-4-(trifluoromethoxy)phenyl]pyrimidin-4-yl]-4-piperidyl]acetamide (Example 96) was separated via SFC chiral separation (Stationary phase: Chiralpak AD-H 5 μm 250×21 mm, Mobile phase: 15% methanol, 85% $CO_2$, 2 mL/min, 150 Bar, retention time: 7.15 min at 254 nM) to afford the tile compound (41 mg, 28%). MS (ESI): mass calcd. for $C_{18}H_{17}F_5N_4O_2$, 416.1; m/z found, 417.1 $[M+H]^+$. $^1H$ NMR (400 MHz, Chloroform-d) δ ppm 8.68 (d, J=1.1 Hz, 1H), 7.86 (dd, J=11.1, 2.1 Hz, 1H), 7.77 (ddd, J=8.6, 2.1, 1.2 Hz, 1H), 7.43-7.36 (m, 1H), 6.89 (d, J=1.3 Hz, 1H), 5.75 (d, J=8.8 Hz, 1H), 5.02-4.76 (m, 2H), 4.65 (d, J=13.9 Hz, 1H), 4.38-4.20 (m, 1H), 3.26-3.09 (m, 1H), 3.08-2.99 (m, 1H), 2.04 (s, 3H), 1.99-1.89 (m, 1H), 1.88-1.73 (m, 1H).

Example 99: N-[1-[6-[3-fluoro-4-(trifluoromethoxy)phenyl]-2-methyl-pyrimidin-4-yl]-4-methyl-4-piperidyl]acetamide

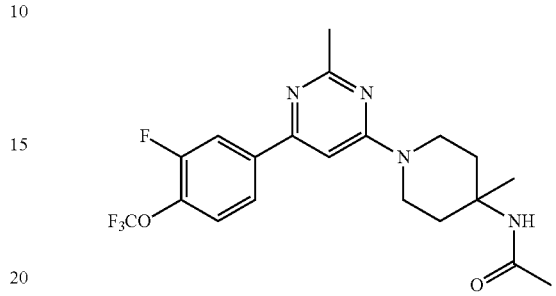

The title compound was prepared in a manner analogous to Example 7, using tert-butyl (4-methylpiperidin-4-yl)carbamate instead of tert-butyl ((3,4-trans)-3-fluoropiperidin-4-yl)carbamate in Step B. MS (ESI): mass calcd. for $C_{20}H_{22}F_4N_4O_2$, 426.2; m/z found, 427.2 $[M+H]^+$. $^1H$ NMR (500 MHz, Chloroform-d) δ ppm 7.84 (dd, J=11.1, 2.1 Hz, 1H), 7.75-7.71 (m, 1H), 7.40-7.33 (m, 1H), 6.65 (s, 1H), 5.22 (s, 1H), 3.97 (d, J=12.9 Hz, 2H), 3.47-3.40 (m, 2H), 2.56 (s, 3H), 2.23-2.16 (m, 2H), 1.99 (s, 3H), 1.74-1.66 (m, 2H), 1.46 (s, 3H).

Example 100: N-[1-[6-[3-Fluoro-4-(trifluoromethoxy)phenyl]-2-methyl-pyrimidin-4-yl]-4-piperidyl]methanesulfonamide

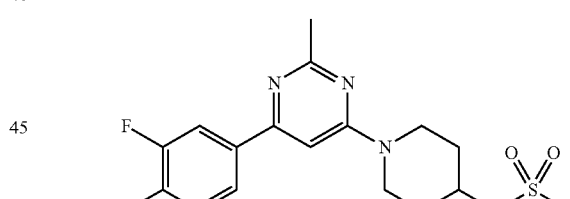

The title compound was prepared in a manner analogous to Example 5, using 4,6-dichloro-2-methylpyrimidine instead of (4,6-dichloropyrimidin-2-yl)methanol in Step A; and using N-(piperidin-4-yl)methanesulfonamide instead of N-(piperidin-4-yl)acetamide in Step B. MS (ESI): mass calcd. for $C_{18}H_{20}F_4N_4O_3S$, 448.1; m/z found, 449.1 $[M+H]^+$. $^1H$ NMR (500 MHz, Chloroform-d) δ ppm 7.84 (dd, J=11.1, 2.1 Hz, 1H), 7.73 (ddd, J=8.6, 2.1, 1.2 Hz, 1H), 7.40-7.33 (m, 1H), 6.66 (s, 1H), 4.44 (d, J=13.7 Hz, 2H), 4.37 (d, J=7.5 Hz, 1H), 3.69-3.59 (m, 1H), 3.15-3.07 (m, 2H), 3.03 (s, 3H), 2.57 (s, 3H), 2.17-2.10 (m, 2H), 1.58-1.48 (m, 2H).

Example 101: 4-[3-Fluoro-4-(trifluoromethoxy)phenyl]-2-methyl-6-[4-(1H-pyrazol-5-yl)-1-piperidyl]pyrimidine

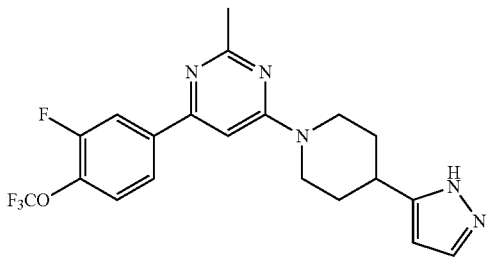 [SMILES: Cc1nc(-c2ccc(OC(F)(F)F)c(F)c2)cc(N2CCC(c3ccn[nH]3)CC2)n1]

The title compound was prepared in a manner analogous to Example 5, using 4,6-dichloro-2-methylpyrimidine instead of (4,6-dichloropyrimidin-2-yl)methanol in Step A; and using 4-(1H-pyrazol-5-yl)piperidine instead of N-(piperidin-4-yl)acetamide in Step B. MS (ESI): mass calcd. for $C_{20}H_{19}F_4N_5O$, 421.2; m/z found, 422.1 [M+H]$^+$. $^1$H NMR (500 MHz, Chloroform-d) δ ppm 7.84 (dd, J=11.2, 2.1 Hz, 1H), 7.77-7.72 (m, 1H), 7.51 (s, 1H), 7.40-7.34 (m, 1H), 6.68 (s, 1H), 6.15 (s, 1H), 4.58 (d, J=13.3 Hz, 2H), 3.15-3.00 (m, 3H), 2.57 (s, 3H), 2.15-2.06 (m, 2H), 1.81-1.70 (m, 2H).

Example 102: 1-[1-[6-[3-Fluoro-4-(trifluoromethoxy)phenyl]pyrimidin-4-yl]-4-piperidyl]ethanone

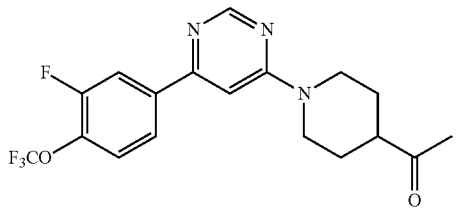 [SMILES: CC(=O)C1CCN(c2cc(-c3ccc(OC(F)(F)F)c(F)c3)ncn2)CC1]

The title compound was prepared in a manner analogous to Example 5, using 4,6-dichloropyrimidine instead of (4,6-dichloropyrimidin-2-yl)methanol in Step A; and 1-(piperidin-4-yl)ethan-1-one instead of N-(piperidin-4-yl)acetamide in Step B. MS (ESI): mass calcd. for $C_{18}H_{17}F_4N_3O_2$, 383.1; m/z found, 384.1 [M+H]$^+$. $^1$H NMR (500 MHz, Chloroform-d) δ ppm 8.65 (d, J=1.2 Hz, 1H), 7.85 (dd, J=11.2, 2.1 Hz, 1H), 7.76 (ddd, J=8.6, 2.2, 1.3 Hz, 1H), 7.41-7.36 (m, 1H), 6.83 (d, J=1.2 Hz, 1H), 4.45 (d, J=13.4 Hz, 2H), 3.14-3.06 (m, 2H), 2.70-2.61 (m, 1H), 2.20 (s, 3H), 2.04-1.96 (m, 2H), 1.71-1.61 (m, 2H).

Example 103: 1-[1-[6-[3-Fluoro-4-(trifluoromethoxy)phenyl]pyrimidin-4-yl]-4-piperidyl]propan-2-one

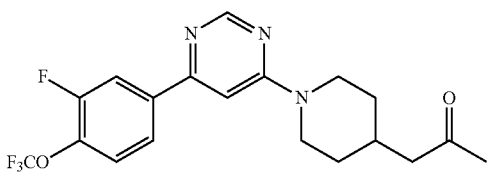

The title compound was prepared in a manner analogous to Example 5, using 4,6-dichloropyrimidine instead of (4,6-dichloropyrimidin-2-yl)methanol in Step A; and using 1-(piperidin-4-yl)propan-2-one (Intermediate 4) instead of N-(piperidin-4-yl)acetamide in Step B. MS (ESI): mass calcd. for $C_{19}H_{19}F_4N_3O_2$, 397.1; m/z found, 398.1 [M+H]$^+$. $^1$H NMR (500 MHz, Chloroform-d) δ ppm 8.64 (d, J=1.2 Hz, 1H), 7.84 (dd, J=11.1, 2.1 Hz, 1H), 7.76 (ddd, J=8.6, 2.2, 1.3 Hz, 1H), 7.41-7.34 (m, 1H), 6.81 (d, J=1.2 Hz, 1H), 4.47 (d, J=13.5 Hz, 2H), 3.03-2.94 (m, 2H), 2.41 (d, J=6.7 Hz, 2H), 2.23-2.13 (m, 4H), 1.88-1.80 (m, 2H), 1.27-1.17 (m, 2H).

Example 104: N-[[1-[6-[3-Fluoro-4-(trifluoromethoxy)phenyl]pyrimidin-4-yl]azetidin-3-yl]methyl]acetamide

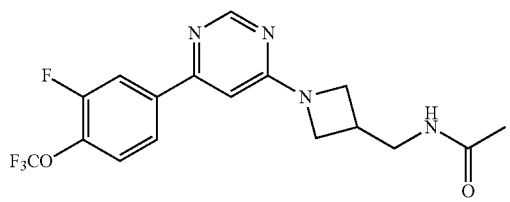 [SMILES: CC(=O)NCC1CN(c2cc(-c3ccc(OC(F)(F)F)c(F)c3)ncn2)C1]

The title compound was prepared in a manner analogous to Example 7, using 4,6-dichloropyrimidine instead of 4,6-dichloro-2-methylpyrimidine in Step A; and using tert-butyl (azetidin-3-ylmethyl)carbamate instead of tert-butyl ((3,4-trans)-3-fluoropiperidin-4-yl)carbamate in Step B. MS (ESI): mass calcd. for $C_{17}H_{16}F_4N_4O_2$, 384.1; m/z found, 385.1 [M+H]$^+$. $^1$H NMR (500 MHz, Chloroform-d) δ ppm 8.65 (d, J=1.2 Hz, 1H), 7.87 (dd, J=11.2, 2.1 Hz, 1H), 7.77 (ddd, J=8.6, 2.2, 1.3 Hz, 1H), 7.41-7.36 (m, 1H), 6.48 (d, J=1.2 Hz, 1H), 5.70-5.63 (m, 1H), 4.23 (t, J=8.5 Hz, 2H), 3.88 (dd, J=8.9, 5.2 Hz, 2H), 3.58 (t, J=6.5 Hz, 2H), 3.07-2.98 (m, 1H), 2.02 (s, 3H).

Example 105: (racemic)-N-[[1-[6-[3-Fluoro-4-(trifluoromethoxy)phenyl]pyrimidin-4-yl]pyrrolidin-3-yl]methyl]acetamide

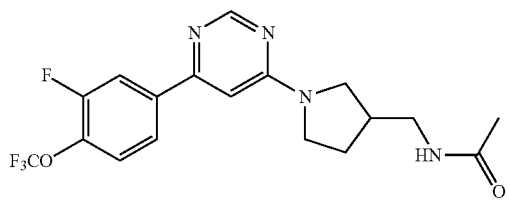 [SMILES: CC(=O)NCC1CCN(c2cc(-c3ccc(OC(F)(F)F)c(F)c3)ncn2)C1]

The title compound was prepared in a manner analogous to Example 7, using 4,6-dichloropyrimidine instead of 4,6-dichloro-2-methylpyrimidine in Step A; and tert-butyl (pyrrolidin-3-ylmethyl)carbamate instead of tert-butyl ((3,4-trans)-3-fluoropiperidin-4-yl)carbamate in Step B. MS (ESI): mass calcd. for $C_{18}H_{18}F_4N_4O_2$, 398.1; m/z found, 399.1 [M+H]$^+$. $^1$H NMR (500 MHz, Chloroform-d) δ ppm 8.64 (d, J=1.1 Hz, 1H), 7.86 (dd, J=11.1, 2.1 Hz, 1H), 7.81-7.73 (m, 1H), 7.41-7.34 (m, 1H), 6.58 (d, J=1.2 Hz, 1H), 5.80-5.74 (m, 1H), 3.94-3.11 (m, 6H), 2.66-2.55 (m, 1H), 2.25-2.14 (m, 1H), 2.07-1.96 (m, 4H).

Example 106: (racemic)-N-[1-[6-[3-Fluoro-4-(trifluoromethoxy)phenyl]pyrimidin-4-yl]pyrrolidin-3-yl]acetamide

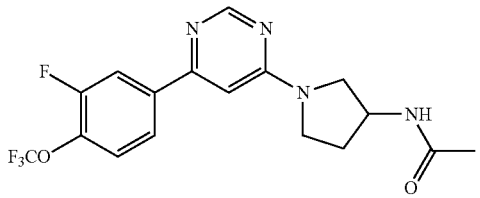 [SMILES: CC(=O)NC1CCN(c2cc(-c3ccc(OC(F)(F)F)c(F)c3)ncn2)C1]

The title compound was prepared in a manner analogous to Example 7, using 4,6-dichloropyrimidine instead of 4,6-dichloro-2-methylpyrimidine in Step A; and using tert-butyl pyrrolidin-3-ylcarbamate instead of tert-butyl ((3,4-trans)-3-fluoropiperidin-4-yl)carbamate in Step B. MS (ESI): mass calcd. for $C_{17}H_{16}F_4N_4O_2$, 384.1; m/z found, 385.1 [M+H]$^+$. $^1$H NMR (500 MHz, Chloroform-d) δ ppm 8.68 (d, J=1.2 Hz, 1H), 7.88 (dd, J=11.1, 2.1 Hz, 1H), 7.83-7.73 (m, 1H), 7.44-7.35 (m, 1H), 6.62 (d, J=1.2 Hz, 1H), 5.60 (s, 1H), 4.70-4.57 (m, 1H), 3.91-3.82 (m, 1H), 3.79-3.59 (m, 2H), 3.56-3.38 (m, 1H), 2.43-2.31 (m, 1H), 2.12-1.96 (m, 4H).

Example 107: (racemic)-N-[1-[6-[3-Fluoro-4-(trifluoromethoxy)phenyl]pyrimidin-4-yl]-3-piperidyl]acetamide

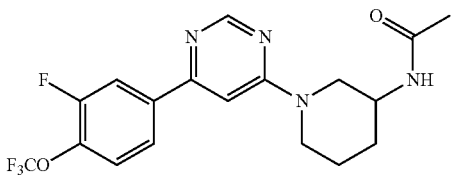 [SMILES: CC(=O)NC1CCCN(c2cc(-c3ccc(OC(F)(F)F)c(F)c3)ncn2)C1]

The title compound was prepared in a manner analogous to Example 7, using 4,6-dichloropyrimidine instead of 4,6-dichloro-2-methylpyrimidine in Step A; and using tert-butyl piperidin-3-ylcarbamate instead of tert-butyl ((3,4-trans)-3-fluoropiperidin-4-yl)carbamate in Step B. MS (ESI): mass calcd. for $C_{18}H_{18}F_4N_4O_2$, 398.1; m/z found, 399.1 [M+H]$^+$. $^1$H NMR (500 MHz, Chloroform-d) δ ppm 8.64 (d, J=1.2 Hz, 1H), 7.89 (dd, J=11.2, 2.1 Hz, 1H), 7.78 (ddd, J=8.6, 2.2, 1.3 Hz, 1H), 7.41-7.35 (m, 1H), 6.95 (d, J=1.2 Hz, 1H), 5.68-5.62 (m, 1H), 4.03-3.92 (m, 2H), 3.56-3.43 (m, 2H), 2.03-1.93 (m, 4H), 1.87-1.74 (m, 2H), 1.73-1.62 (m, 2H).

Example 108: (racemic)-N-[1-[6-[3-Fluoro-4-(trifluoromethoxy)phenyl]pyrimidin-4-yl]azepan-4-yl]acetamide

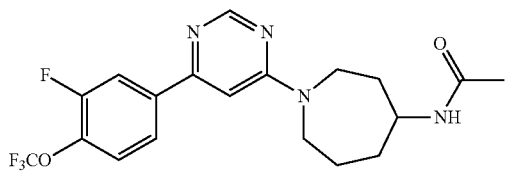 [SMILES: CC(=O)NC1CCCN(c2cc(-c3ccc(OC(F)(F)F)c(F)c3)ncn2)CC1]

The title compound was prepared in a manner analogous to Example 7, using 4,6-dichloropyrimidine instead of 4,6-dichloro-2-methylpyrimidine in Step A; and using tert-butyl azepan-4-ylcarbamate instead of tert-butyl ((3,4-trans)-3-fluoropiperidin-4-yl)carbamate in Step B. MS (ESI): mass calcd. for $C_{19}H_{20}F_4N_4O_2$, 412.2; m/z found, 413.1 [M+H]$^+$. $^1$H NMR (500 MHz, Chloroform-d) δ ppm 8.67 (d, J=1.2 Hz, 1H), 7.86 (dd, J=11.1, 2.1 Hz, 1H), 7.77 (ddd, J=8.5, 2.1, 1.2 Hz, 1H), 7.42-7.36 (m, 1H), 6.73 (d, J=1.2 Hz, 1H), 5.34 (d, J=8.0 Hz, 1H), 4.06-3.96 (m, 1H), 3.81-3.57 (m, 2H), 3.50-3.42 (m, 1H), 2.27-2.17 (m, 1H), 2.07-1.82 (m, 6H), 1.75-1.65 (m, 1H), 1.53-1.45 (m, 2H).

Example 109: (trans)-N-[3-Fluoro-1-[6-[4-(trifluoromethoxy)phenyl]pyrimidin-4-yl]-4-piperidyl]acetamide

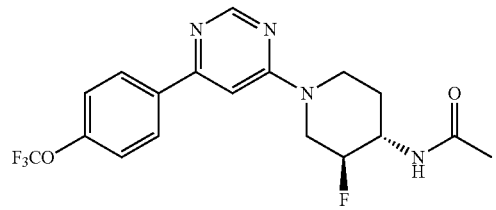 [SMILES: CC(=O)N[C@H]1CCN(c2cc(-c3ccc(OC(F)(F)F)cc3)ncn2)C[C@@H]1F]

The title compound was prepared in a manner analogous to Example 7, using 4,6-dichloropyrimidine instead of 4,6-dichloro-2-methylpyrimidine and using (4-(trifluoromethoxy)phenyl)boronic acid instead of (3-fluoro-4-(trifluoromethoxy)phenyl)boronic acid in Step A. MS (ESI): mass calcd. for $C_{18}H_{18}F_4N_4O_2$, 398.1; m/z found, 399.1 [M+H]$^+$. $^1$H NMR (400 MHz, Chloroform-d) δ ppm 8.69 (d, J=1.1 Hz, 1H), 8.04-7.98 (m, 2H), 7.34-7.28 (m, 2H), 6.90 (d, J=1.2 Hz, 1H), 5.68 (d, J=7.5 Hz, 1H), 4.78-4.68 (m, 1H), 4.49-4.29 (m, 1H), 4.28-4.17 (m, 2H), 3.26-3.16 (m, 2H), 2.33-2.24 (m, 1H), 2.03 (s, 3H), 1.56-1.43 (m, 1H).

Example 110: (racemic)-N-[1-[6-[3-Fluoro-4-(trifluoromethoxy)phenyl]pyrimidin-4-yl]-3-methyl-4-piperidyl]acetamide

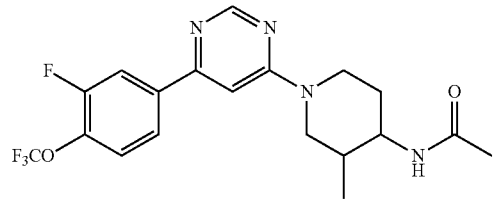 [SMILES: CC(=O)NC1CCN(c2cc(-c3ccc(OC(F)(F)F)c(F)c3)ncn2)CC1C]

The title compound was prepared in a manner analogous to Example 7, using 4,6-dichloropyrimidine instead of 4,6-dichloro-2-methylpyrimidine in Step A; and using tert-butyl (3-methylpiperidin-4-yl)carbamate instead of tert-butyl ((3,4-trans)-3-fluoropiperidin-4-yl)carbamate in Step B. MS (ESI): mass calcd. for $C_{19}H_{20}F_4N_4O_2$, 412.2; m/z found, 413.1 [M+H]$^+$. $^1$H NMR (500 MHz, Chloroform-d) δ ppm 8.66 (d, J=6.0 Hz, 1H), 7.92-7.84 (m, 1H), 7.81-7.74 (m, 1H), 7.42-7.34 (m, 1H), 6.84 (d, J=1.2 Hz, 1H), 5.38 (s, 0.5H), 5.14 (d, J=8.9 Hz, 0.5H), 4.57-4.40 (m, 1H), 4.31-4.22 (m, 0.5H), 4.15-4.02 (m, 0.5H), 3.90-3.76 (m, 1H), 3.62-3.53 (m, 0.5H), 3.49-3.39 (m, 0.5H), 3.13-3.00 (m, 0.5H), 2.72 (dd, J=13.6, 11.0 Hz, 0.5H), 2.30-2.22 (m, 0.5H), 2.16-2.09 (m, 0.5H), 2.03-1.99 (m, 3H), 1.85-1.71 (m, 1H), 1.60-1.35 (m, 1H), 1.09-0.93 (m, 3H).

Example 111: (racemic)-N-[1-[6-[3-Fluoro-4-(trifluoromethoxy)phenyl]pyrimidin-4-yl]-2-methyl-4-piperidyl]acetamide

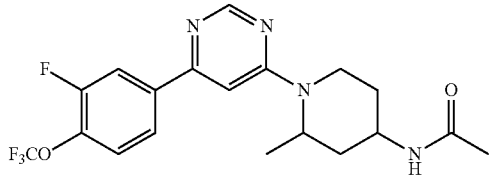

The title compound was prepared in a manner analogous to Example 7, using 4,6-dichloropyrimidine instead of 4,6-dichloro-2-methylpyrimidine in Step A; and using tert-butyl (2-methylpiperidin-4-yl)carbamate instead of tert-butyl ((3,4-trans)-3-fluoropiperidin-4-yl)carbamate in Step B. MS (ESI): mass calcd. for $C_{19}H_{20}F_4N_4O_2$, 412.2; m/z found, 413.1 [M+H]$^+$. $^1$H NMR (400 MHz, Chloroform-d) δ ppm 8.66 (d, J=1.1 Hz, 0.6H), 8.65 (d, J=1.1 Hz, 0.4H), 7.84 (ddd, J=11.1, 2.1, 0.7 Hz, 1H), 7.79-7.72 (m, 1H), 7.43-7.35 (m, 1H), 6.81 (d, J=1.1 Hz, 0.6H), 6.74 (d, J=1.2 Hz, 0.4H), 5.56 (d, J=7.0 Hz, 0.4H), 5.33 (d, J=7.9 Hz, 0.6H), 4.92 (s, 0.6H), 4.54-4.23 (m, 2H), 4.06 (dt, J=13.6, 6.9 Hz, 0.4H), 3.30-3.09 (m, 1H), 2.22-2.09 (m, 1.4H), 2.03-1.93 (m, 4H), 1.84-1.76 (m, 0.4H), 1.61-1.51 (m, 0.6H), 1.37-1.26 (m, 3.6H).

Example 112: 2,2-Difluoro-N-[1-[6-[3-fluoro-4-(trifluoromethoxy)phenyl]pyrimidin-4-yl]-4-piperidyl]acetamide

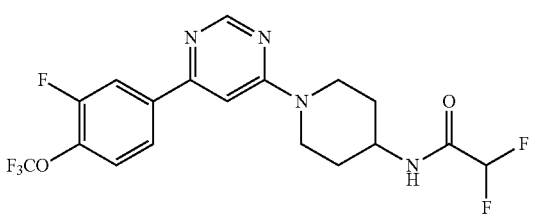 [SMILES: O=C(NC1CCN(c2cc(-c3ccc(OC(F)(F)F)c(F)c3)ncn2)CC1)C(F)F]

The title compound was prepared in a manner analogous to Example 8, using 2,2-difluoroacetic acid instead of cyclopropanecarboxylic acid in Step C. MS (ESI): mass calcd. for $C_{18}H_{16}F_6N_4O_2$, 434.1; m/z found, 435.1 [M+H]$^+$. $^1$H NMR (400 MHz, Chloroform-d) δ ppm 8.67 (d, J=1.1 Hz, 1H), 7.85 (dd, J=11.1, 2.1 Hz, 1H), 7.77 (ddd, J=8.6, 2.1, 1.3 Hz, 1H), 7.42-7.35 (m, 1H), 6.86 (d, J=1.2 Hz, 1H), 6.23 (d, J=7.8 Hz, 1H), 5.89 (t, J=54.3 Hz, 1H), 4.51 (d, J=13.7 Hz, 2H), 4.21-4.09 (m, 1H), 3.18-3.06 (m, 2H), 2.18-2.08 (m, 2H), 1.58-1.45 (m, 1H).

Example 113: 1-[2-[6-[3-Fluoro-4-(trifluoromethoxy)phenyl]pyrimidin-4-yl]-2,6-diazaspiro[3.3]heptan-6-yl]ethanone

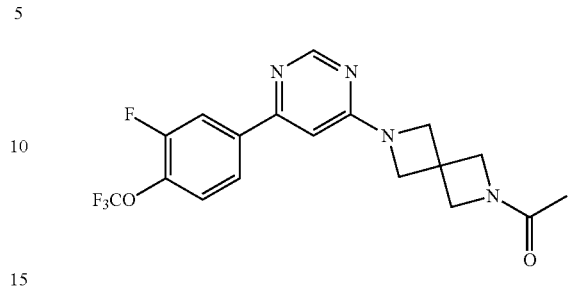

The title compound was prepared in a manner analogous to Example 7, using 4,6-dichloropyrimidine instead of 4,6-dichloro-2-methylpyrimidine in Step A; and using tert-butyl 2,6-diazaspiro[3.3]heptane-2-carboxylate oxalate instead of tert-butyl ((3,4-trans)-3-fluoropiperidin-4-yl)carbamate in Step B. MS (ESI): mass calcd. for $C_{18}H_{16}F_4N_4O_2$, 396.1; m/z found, 397.1 [M+H]$^+$. $^1$H NMR (500 MHz, Chloroform-d) δ ppm 8.66 (d, J=1.2 Hz, 1H), 7.86 (dd, J=11.1, 2.1 Hz, 1H), 7.80-7.75 (m, 1H), 7.42-7.35 (m, 1H), 6.50 (d, J=1.2 Hz, 1H), 4.35 (s, 2H), 4.30 (d, J=2.2 Hz, 4H), 4.22 (s, 2H), 1.90 (s, 3H).

Example 114: N-[4-[[6-[3-Fluoro-4-(trifluoromethoxy)phenyl]pyrimidin-4-yl]amino]cyclohexyl]acetamide

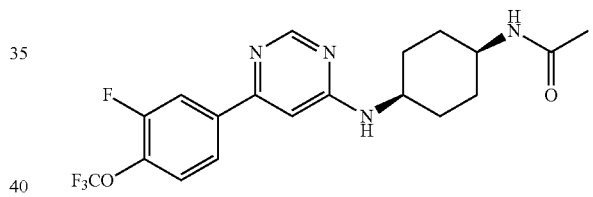

The title compound was prepared in a manner analogous to Example 7, using 4,6-dichloropyrimidine instead of 4,6-dichloro-2-methylpyrimidine in Step A; and using tert-butyl ((1,4-cis)-4-aminocyclohexyl)carbamate instead of tert-butyl ((3,4-trans)-3-fluoropiperidin-4-yl)carbamate in Step B. MS (ESI): mass calcd. for $C_{19}H_{20}F_4N_4O_2$, 412.2; m/z found, 413.1 [M+H]$^+$. $^1$H NMR (400 MHz, Chloroform-d) δ ppm 8.62 (d, J=1.1 Hz, 1H), 7.85 (dd, J=11.1, 2.1 Hz, 1H), 7.78-7.73 (m, 1H), 7.43-7.35 (m, 1H), 6.63 (s, 1H), 5.46 (d, J=7.6 Hz, 1H), 5.13 (s, 1H), 4.02-3.88 (m, 2H), 1.99 (s, 3H), 1.94-1.81 (m, 3H), 1.79-1.67 (m, 3H), 1.65-1.53 (m, 2H).

Example 115: N-[1-[6-[3-Fluoro-4-(trifluoromethoxy)phenyl]pyrimidin-4-yl]-4-piperidyl]propanamide

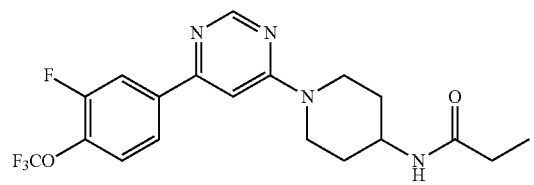 [SMILES: CCC(=O)NC1CCN(c2cc(-c3ccc(OC(F)(F)F)c(F)c3)ncn2)CC1]

The title compound was prepared in a manner analogous to Example 8, using propionic acid instead of cyclopropanecarboxylic acid in Step C. MS (ESI): mass calcd. for $C_{19}H_{20}F_4N_4O_2$, 412.2; m/z found, 413.1 [M+H]$^+$. $^1$H NMR (400 MHz, Chloroform-d) δ ppm 8.66 (d, J=1.1 Hz, 1H), 7.85 (dd, J=11.1, 2.1 Hz, 1H), 7.77 (ddd, J=8.6, 2.1, 1.3 Hz, 1H), 7.43-7.35 (m, 1H), 6.85 (d, J=1.2 Hz, 1H), 5.33 (d, J=7.9 Hz, 1H), 4.47 (d, J=13.6 Hz, 2H), 4.18-4.04 (m, 1H), 3.17-3.06 (m, 2H), 2.20 (q, J=7.6 Hz, 2H), 2.14-2.05 (m, 2H), 1.48-1.34 (m, 2H), 1.16 (t, J=7.6 Hz, 3H).

Example 116: N-[1-[6-[3-Fluoro-4-(trifluoromethoxy)phenyl]pyrimidin-4-yl]-4-piperidyl]-3-hydroxy-propanamide

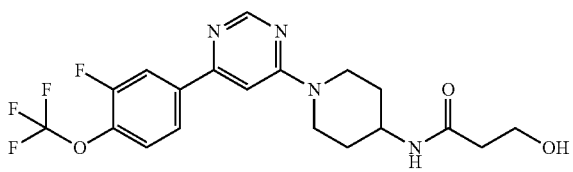 [SMILES: O=C(CCO)NC1CCN(c2cc(-c3ccc(OC(F)(F)F)c(F)c3)ncn2)CC1]

The title compound was prepared in a manner analogous to Example 8, using 3-hydroxypropanoic acid instead of cyclopropanecarboxylic acid in Step C. MS (ESI): mass calcd. for $C_{19}H_{20}F_4N_4O_3$, 428.1; m/z found, 429.1 [M+H]$^+$. $^1$H NMR (400 MHz, Chloroform-d) δ ppm 8.67 (d, J=1.1 Hz, 1H), 7.86 (dd, J=11.1, 2.1 Hz, 1H), 7.77 (ddd, J=8.6, 2.1, 1.3 Hz, 1H), 7.43-7.35 (m, 1H), 6.85 (d, J=1.2 Hz, 1H), 5.76 (d, J=7.9 Hz, 1H), 4.46 (d, J=13.6 Hz, 2H), 4.20-4.05 (m, 1H), 3.94-3.84 (m, 2H), 3.13 (ddd, J=14.1, 11.8, 2.8 Hz, 2H), 2.83-2.73 (m, 1H), 2.47-2.40 (m, 2H), 2.15-2.06 (m, 2H), 1.50-1.37 (m, 2H).

Example 117: (trans)-3-Amino-N-[3-fluoro-1-[6-[3-fluoro-4-(trifluoromethoxy)phenyl]pyrimidin-4-yl]-4-piperidyl]propanamide

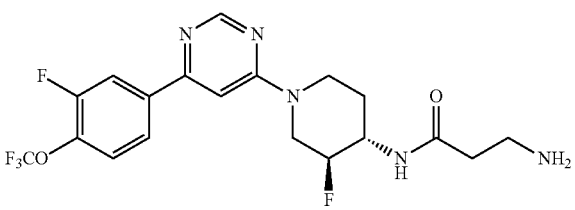 [SMILES: NCCC(=O)N[C@H]1CCN(c2cc(-c3ccc(OC(F)(F)F)c(F)c3)ncn2)C[C@@H]1F]

The title compound was prepared in a manner analogous to Example 9, using tert-butyl ((3,4-trans)-3-fluoropiperidin-4-yl)carbamate instead of tert-butyl piperidin-4-ylcarbamate in Step A. $^1$H NMR (400 MHz, Methanol-d$_4$) δ ppm 8.73 (s, 1H), 7.99 (dd, J=11.0, 2.2 Hz, 1H), 7.85 (ddd, J=8.7, 2.3, 1.3 Hz, 1H), 7.71-7.64 (m, 1H), 7.46 (s, 1H), 4.71-4.50 (m, 2H), 4.33-4.21 (m, 2H), 3.95-3.85 (m, 1H), 3.84-3.71 (m, 1H), 3.24-3.18 (m, 2H), 2.71-2.65 (m, 2H), 2.24-2.13 (m, 1H), 1.76-1.64 (m, 1H), 1.40-1.35 (m, 2H), 1.29 (s, 1H). MS (ESI): mass calcd. for $C_{19}H_{20}F_5N_5O_2$, 445.2; m/z found, 446.1 [M+H]$^+$.

Example 118: N-[3-[[6-[3-Fluoro-4-(trifluoromethoxy)phenyl]pyrimidin-4-yl]amino]propyl]acetamide

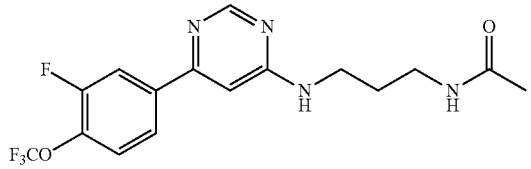 [SMILES: CC(=O)NCCCNc1cc(-c2ccc(OC(F)(F)F)c(F)c2)ncn1]

The title compound was prepared in a manner analogous to Example 7, using 4,6-dichloropyrimidine instead of 4,6-dichloro-2-methylpyrimidine in Step A; and using tert-butyl (3-aminopropyl)carbamate instead of tert-butyl ((3,4-trans)-3-fluoropiperidin-4-yl)carbamate in Step B. MS (ESI): mass calcd. for $C_{16}H_{16}F_4N_4O_2$, 372.1; m/z found, 373.1 [M+H]$^+$. H NMR (500 MHz, Chloroform-d) δ ppm 8.60 (s, 1H), 7.84 (dd, J=11.2, 2.1 Hz, 1H), 7.73 (ddd, J=8.6, 2.2, 1.2 Hz, 1H), 7.39-7.33 (m, 1H), 6.68 (d, J=1.2 Hz, 1H), 6.19 (s, 1H), 6.04-5.97 (m, 1H), 3.54-3.46 (m, 2H), 3.35 (q, J=6.3 Hz, 2H), 2.02 (s, 3H), 1.81-1.72 (m, 2H).

Example 119: (racemic)-N-[3-[[6-[3-Fluoro-4-(trifluoromethoxy)phenyl]pyrimidin-4-yl]amino]-2-methyl-propyl]acetamide

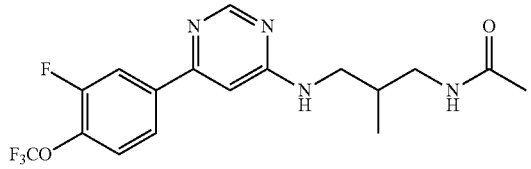

The title compound was prepared in a manner analogous to Example 7, using 4,6-dichloropyrimidine instead of 4,6-dichloro-2-methylpyrimidine in Step A; and using tert-butyl (3-amino-2-methylpropyl)carbamate instead of tert-butyl ((3,4-trans)-3-fluoropiperidin-4-yl)carbamate in Step B. MS (ESI): mass calcd. for $C_{17}H_{18}F_4N_4O_2$, 386.1; m/z found, 387.1 [M+H]$^+$. $^1$H NMR (400 MHz, Chloroform-d) δ ppm 8.60 (d, J=1.1 Hz, 1H), 7.85 (dd, J=11.2, 2.1 Hz, 1H), 7.74 (ddd, J=8.6, 2.2, 1.3 Hz, 1H), 7.41-7.33 (m, 1H), 6.70 (d, J=1.2 Hz, 1H), 6.28-6.06 (m, 2H), 3.56 (s, 1H), 3.46-3.36 (m, 1H), 3.26-3.16 (m, 1H), 3.13-3.04 (m, 1H), 2.05 (s, 3H), 2.02-1.91 (m, 1H), 0.97 (d, J=6.9 Hz, 3H).

Example 120: (*R)—N-[3-[[6-[3-Fluoro-4-(trifluoromethoxy)phenyl]pyrimidin-4-yl]amino]-2-methyl-propyl]acetamide

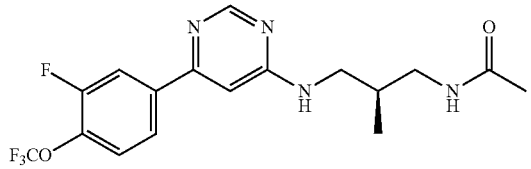 [SMILES: CC(=O)NC[C@@H](C)CNc1cc(-c2ccc(OC(F)(F)F)c(F)c2)ncn1]

(racemic)-N-[3-[[6-[3-Fluoro-4-(trifluoromethoxy)phenyl]pyrimidin-4-yl]amino]-2-methyl-propyl]acetamide (Example 119) was separated via SFC chiral separation (Stationary phase: Lux-Amylose-2 5 µm 250×21.2 mm, Mobile phase: 2% MeOH, 90% $CO_2$, 8% EtOH, 2 mL/min, 150 Bar, retention time: 1.52 min at 245 nM) to afford the tile compound (11 mg, 29%). MS (ESI): mass calcd. for $C_{17}H_{18}F_4N_4O_2$, 386.1; m/z found, 387.0 [M+H]$^+$. $^1$H NMR (400 MHz, Chloroform-d) δ ppm 8.61 (s, 1H), 7.86 (dd, J=11.2, 2.1 Hz, 1H), 7.75 (ddd, J=8.6, 2.2, 1.3 Hz, 1H), 7.42-7.34 (m, 1H), 6.70 (s, 1H), 6.15-6.04 (m, 2H), 3.56 (s, 1H), 3.47-3.37 (m, 1H), 3.27-3.16 (m, 1H), 3.14-3.05 (m, 1H), 2.06 (s, 3H), 2.02-1.91 (m, 1H), 0.98 (d, J=6.9 Hz, 3H).

Example 121: (*S)—N-[3-[[6-[3-Fluoro-4-(trifluoromethoxy)phenyl]pyrimidin-4-yl]amino]-2-methyl-propyl]acetamide

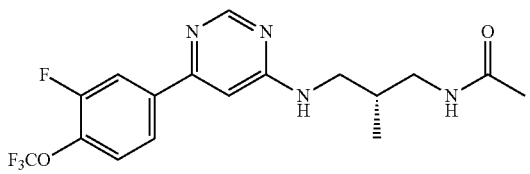 [SMILES: CC(=O)NC[C@H](C)CNc1cc(-c2ccc(OC(F)(F)F)c(F)c2)ncn1]

(racemic)-N-[3-[[6-[3-Fluoro-4-(trifluoromethoxy)phenyl]pyrimidin-4-yl]amino]-2-methyl-propyl]acetamide (Example 119) was separated via SFC chiral separation (Stationary phase: Lux-Amylose-2 5 µm 250×21.2 mm, Mobile phase: 2% MeOH, 90% $CO_2$, 8% EtOH, 2 mL/min, 150 Bar, retention time: 1.95 min at 245 nM) to afford the tile compound (8 mg, 21%). MS (ESI): mass calcd. for $C_{17}H_{18}F_4N_4O_2$, 386.1; m/z found, 387.0 [M+H]$^+$. $^1$H NMR (400 MHz, Chloroform-d) δ ppm 8.61 (s, 1H), 7.86 (dd, J=11.2, 2.1 Hz, 1H), 7.75 (ddd, J=8.6, 2.1, 1.3 Hz, 1H), 7.41-7.35 (m, 1H), 6.70 (d, J=1.2 Hz, 1H), 6.15-6.03 (m, 2H), 3.55 (s, 1H), 3.47-3.38 (m, 1H), 3.26-3.16 (m, 1H), 3.15-3.05 (m, 1H), 2.06 (s, 3H), 2.02-1.94 (m, 1H), 0.98 (d, J=6.9 Hz, 3H).

Example 122: 1-[2-[3-Fluoro-4-(trifluoromethoxy)phenyl]-4-pyridyl]piperidin-4-ol

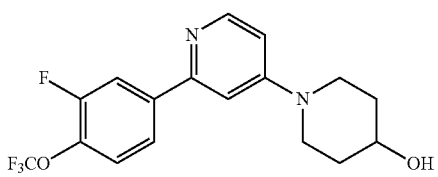 [SMILES: OC1CCN(c2ccnc(-c3ccc(OC(F)(F)F)c(F)c3)c2)CC1]

The title compound was prepared in a manner analogous to Example 11, using 4-fluoro-2-(3-fluoro-4-(trifluoromethoxy)phenyl)pyridine (product from Step A) and using piperidin-4-ol instead of N-(piperidin-4-yl)acetamide in Step B. MS (ESI): mass calcd. for $C_{17}H_{16}F_4N_2O_2$, 356.1; m/z found, 357.1 [M+H]$^+$. $^1$H NMR (500 MHz, Chloroform-d) δ ppm 8.30 (d, J=6.0 Hz, 1H), 7.77 (dd, J=11.3, 2.1 Hz, 1H), 7.70-7.63 (m, 1H), 7.38-7.32 (m, 1H), 7.01 (d, J=2.5 Hz, 1H), 6.66 (dd, J=6.0, 2.5 Hz, 1H), 3.99-3.91 (m, 1H), 3.80-3.72 (m, 2H), 3.21-3.12 (m, 2H), 2.35 (s, 1H), 2.00-1.92 (m, 2H), 1.66-1.57 (m, 2H).

Example 123: N-[1-[2-[4-(Trifluoromethoxy)phenyl]-4-pyridyl]-4-piperidyl]acetamide

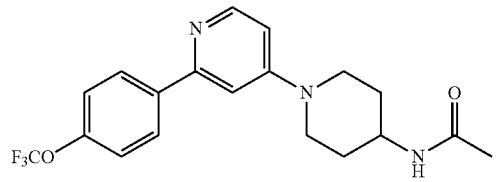 [SMILES: CC(=O)NC1CCN(c2ccnc(-c3ccc(OC(F)(F)F)cc3)c2)CC1]

The title compound was prepared in a manner analogous to Example 11, using (4-(trifluoromethoxy)phenyl)boronic acid instead of (3-fluoro-4-(trifluoromethoxy)phenyl)boronic acid in Step A. MS (ESI): mass calcd. for $C_{19}H_{20}F_3N_3O_2$, 379.2; m/z found, 380.4 [M+H]$^+$. $^1$H NMR (300 MHz, DMSO-$d_6$) δ ppm 8.24 (d, J=5.9 Hz, 1H), 8.22-8.14 (m, 2H), 7.81 (d, J=7.7 Hz, 1H), 7.47-7.39 (m, 2H), 7.35 (d, J=2.4 Hz, 1H), 6.83 (dd, J=6.0, 2.4 Hz, 1H), 4.07-3.92 (m, 2H), 3.91-3.74 (m, 1H), 3.12-2.95 (m, 2H), 1.87-1.70 (m, 2H), 1.79 (s, 3H), 1.47-1.28 (m, 2H).

Example 124: N-[1-[2-[3-Methyl-4-(trifluoromethoxy)phenyl]-4-pyridyl]-4-piperidyl]acetamide

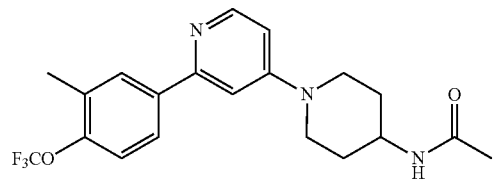 [SMILES: CC(=O)NC1CCN(c2ccnc(-c3ccc(OC(F)(F)F)c(C)c3)c2)CC1]

The title compound was prepared in a manner analogous to Example 11, using (3-methyl-4-(trifluoromethoxy)phenyl)boronic acid instead of (3-fluoro-4-(trifluoromethoxy)phenyl)boronic acid in Step A. MS (ESI): mass calcd. for $C_{20}H_{22}F_3N_3O_2$, 393.2; m/z found, 394.2 [M+H]$^+$. $^1$H NMR (300 MHz, DMSO-$d_6$) δ ppm 8.23 (d, J=5.9 Hz, 1H), 8.13-8.06 (m, 1H), 8.00 (dd, J=8.6, 2.3 Hz, 1H), 7.82 (d, J=7.6 Hz, 1H), 7.40-7.30 (m, 2H), 6.82 (dd, J=6.0, 2.4 Hz, 1H), 4.07-3.94 (m, 2H), 3.91-3.73 (m, 1H), 3.10-2.94 (m, 2H), 2.35 (s, 3H), 1.86-1.78 (m, 2H), 1.79 (s, 3H), 1.49-1.28 (m, 2H).

Example 125: N-[1-[2-[4-(Difluoromethoxy)-3-methyl-phenyl]-4-pyridyl]-4-piperidyl]acetamide

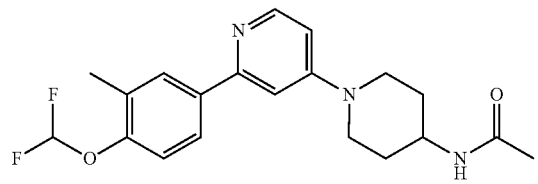 [SMILES: CC(=O)NC1CCN(c2ccnc(-c3ccc(OC(F)F)c(C)c3)c2)CC1]

The title compound was prepared in a manner analogous to Example 11, using (4-(difluoromethoxy)-3-methylphenyl)boronic acid instead of (3-fluoro-4-(trifluoromethoxy)phenyl)boronic acid in Step A. MS (ESI): mass calcd. for $C_{20}H_{23}F_2N_3O_2$, 375.2; m/z found, 376.2 [M+H]⁺. ¹H NMR (500 MHz, DMSO-d₆) b ppm 8.22 (d, J=5.9 Hz, 1H), 8.04-8.00 (m, 1H), 7.96-7.92 (m, 1H), 7.80 (d, J=7.7 Hz, 1H), 7.30 (d, J=2.5 Hz, 1H), 7.23 (t, J=74.2 Hz, 1H), 7.19 (d, J=8.5 Hz, 1H), 6.79 (dd, J=6.0, 2.5 Hz, 1H), 4.03-3.94 (m, 2H), 3.89-3.77 (m, 1H), 3.07-2.97 (m, 2H), 2.30 (s, 3H), 1.84-1.78 (m, 2H), 1.79 (s, 3H), 1.45-1.33 (m, 2H).

Example 126: 1-[2-[3-Fluoro-4-(trifluoromethoxy)phenyl]-4-pyridyl]piperidine-4-carboxamide

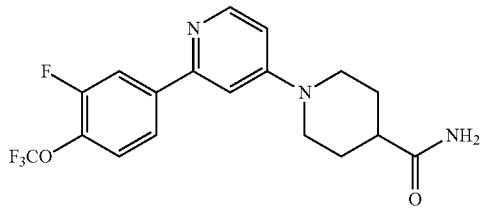 [SMILES: NC(=O)C1CCN(c2ccnc(-c3ccc(OC(F)(F)F)c(F)c3)c2)CC1]

The title compound was prepared in a manner analogous to Example 11, using 4-fluoro-2-(3-fluoro-4-(trifluoromethoxy)phenyl)pyridine (Example 11, product from Step A) and using piperidine-4-carboxamide instead of N-(piperidin-4-yl)acetamide in Step B. MS (ESI): mass calcd. for $C_{18}H_{17}F_4N_3O_2$, 383.1; m/z found, 384.1 [M+H]⁺. ¹H NMR (500 MHz, Methanol-d₄) δ ppm 8.20 (d, J=6.1 Hz, 1H), 7.84 (dd, J=11.6, 2.2 Hz, 1H), 7.77-7.73 (m, 1H), 7.52-7.46 (m, 1H), 7.22 (d, J=2.6 Hz, 1H), 6.85 (dd, J=6.2, 2.6 Hz, 1H), 4.17-4.10 (m, 2H), 3.04-2.96 (m, 2H), 2.58-2.50 (m, 1H), 1.95-1.88 (m, 2H), 1.80-1.71 (m, 2H).

Example 127: 1-[1-[2-[3-Fluoro-4-(trifluoromethoxy)phenyl]-4-pyridyl]-4-piperidyl]propan-2-one

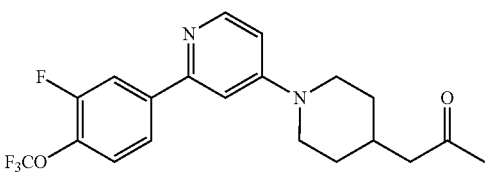 [SMILES: CC(=O)CC1CCN(c2ccnc(-c3ccc(OC(F)(F)F)c(F)c3)c2)CC1]

The title compound was prepared in a manner analogous to Example 11, using 4-fluoro-2-(3-fluoro-4-(trifluoromethoxy)phenyl)pyridine (product from Step A) and using 1-(piperidin-4-yl)propan-2-one (Intermediate 4) instead of N-(piperidin-4-yl)acetamide in Step B. MS (ESI): mass calcd. for $C_{20}H_{20}F_4N_2O_2$, 396.1; m/z found, 397.2 [M+H]⁺. ¹H NMR (500 MHz, Chloroform-d) δ ppm 8.30 (d, J=5.9 Hz, 1H), 7.78 (dd, J=11.4, 2.1 Hz, 1H), 7.72-7.66 (m, 1H), 7.37-7.31 (m, 1H), 7.00 (d, J=2.5 Hz, 1H), 6.64 (dd, J=6.0, 2.6 Hz, 1H), 3.95-3.87 (m, 2H), 2.98-2.89 (m, 2H), 2.40 (d, J=6.7 Hz, 2H), 2.17-2.07 (m, 4H), 1.85-1.77 (m, 2H), 1.33-1.21 (m, 2H).

Example 128: 2-[1-[2-[3-Fluoro-4-(trifluoromethoxy)phenyl]-4-pyridyl]-4-piperidyl]acetamide

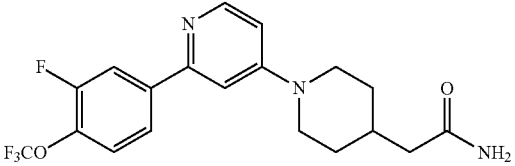 [SMILES: NC(=O)CC1CCN(c2ccnc(-c3ccc(OC(F)(F)F)c(F)c3)c2)CC1]

The title compound was prepared in a manner analogous to Example 11, using 4-fluoro-2-(3-fluoro-4-(trifluoromethoxy)phenyl)pyridine (product from Step A) and using 2-(piperidin-4-yl)acetamide instead of N-(piperidin-4-yl)acetamide in Step B. MS (ESI): mass calcd. for $C_{19}H_{19}F_4N_3O_2$, 397.1; m/z found, 398.1 [M+H]⁺. ¹H NMR (500 MHz, Chloroform-d) δ ppm 8.32 (d, J=6.0 Hz, 1H), 7.79 (dd, J=11.4, 2.1 Hz, 1H), 7.70 (ddd, J=8.5, 2.1, 1.2 Hz, 1H), 7.39-7.33 (m, 1H), 7.01 (d, J=2.5 Hz, 1H), 6.66 (dd, J=6.0, 2.5 Hz, 1H), 5.42 (s, 2H), 3.99-3.92 (m, 2H), 3.00-2.92 (m, 2H), 2.20-2.09 (m, 3H), 1.93-1.86 (m, 2H), 1.39-1.28 (m, 2H).

Example 129: 2-[3-Fluoro-4-(trifluoromethoxy)phenyl]-4-[4-(1H-pyrazol-5-yl)-1-piperidyl]pyridine

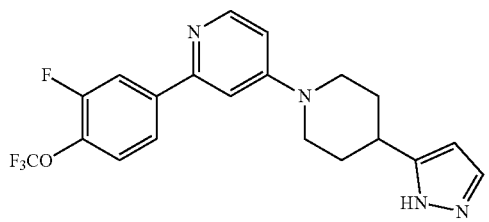 [SMILES: Fc1cc(-c2cc(N3CCC(c4ccn[nH]4)CC3)ccn2)ccc1OC(F)(F)F]

The title compound was prepared in a manner analogous to Example 11, using 4-fluoro-2-(3-fluoro-4-(trifluoromethoxy)phenyl)pyridine (product from Step A) and using 4-(1H-pyrazol-5-yl)piperidine instead of N-(piperidin-4-yl)acetamide in Step B. MS (ESI): mass calcd. for $C_{20}H_{18}F_4N_4O$, 406.1; m/z found, 407.1 [M+H]⁺. ¹H NMR (500 MHz, Methanol-d₄) δ ppm 8.19 (d, J=6.2 Hz, 1H), 7.83 (dd, J=11.6, 2.1 Hz, 1H), 7.75 (ddd, J=8.6, 2.1, 1.2 Hz, 1H), 7.52-7.45 (m, 2H), 7.23 (d, J=2.5 Hz, 1H), 6.85 (dd, J=6.2, 2.6 Hz, 1H), 6.15 (d, J=2.1 Hz, 1H), 4.20-4.11 (m, 2H), 3.13-3.03 (m, 2H), 3.04-2.95 (m, 1H), 2.09-2.01 (m, 2H), 1.83-1.70 (m, 2H).

Example 130: 2-[3-Fluoro-4-(trifluoromethoxy)phenyl]-4-[4-(1H-imidazol-4-yl)-1-piperidyl]pyridine

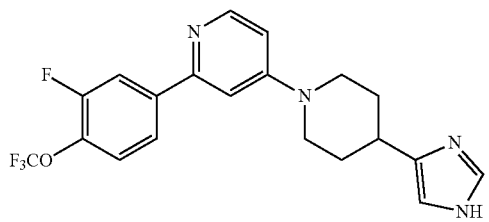 [SMILES: Fc1cc(-c2cc(N3CCC(c4c[nH]cn4)CC3)ccn2)ccc1OC(F)(F)F]

The title compound was prepared in a manner analogous to Example 11, using 4-fluoro-2-(3-fluoro-4-(trifluoromethoxy)phenyl)pyridine (product from Step A) and using 4-(1H-imidazol-4-yl)piperidine instead of N-(piperidin-4-yl)acetamide in Step B. MS (ESI): mass calcd. for C$_{20}$H$_{18}$F$_4$N$_4$O, 406.1; m/z found, 407.1 [M+H]$^+$. $^1$H NMR (500 MHz, Methanol-d$_4$) δ ppm 8.19 (d, J=6.1 Hz, 1H), 7.83 (dd, J=11.6, 2.1 Hz, 1H), 7.75 (ddd, J=8.6, 2.2, 1.2 Hz, 1H), 7.58 (d, J=1.2 Hz, 1H), 7.51-7.46 (m, 1H), 7.22 (d, J=2.5 Hz, 1H), 6.85 (dd, J=6.2, 2.6 Hz, 1H), 6.82 (s, 1H), 4.18-4.11 (m, 2H), 3.11-3.03 (m, 2H), 2.93-2.85 (m, 1H), 2.10-2.04 (m, 2H), 1.77-1.65 (m, 2H).

Example 131: 2-[3-Fluoro-4-(trifluoromethoxy)phenyl]-4-[4-(1H-imidazol-2-yl)-1-piperidyl]pyridine

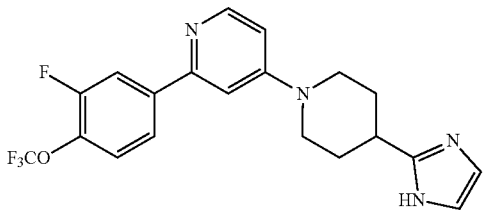 [SMILES: Fc1cc(-c2cc(N3CCC(c4ncc[nH]4)CC3)ccn2)ccc1OC(F)(F)F]

The title compound was prepared in a manner analogous to Example 11, using 4-fluoro-2-(3-fluoro-4-(trifluoromethoxy)phenyl)pyridine (product from Step A) and using 4-(1H-imidazol-2-yl)piperidine hydrochloride instead of N-(piperidin-4-yl)acetamide in Step B. MS (ESI): mass calcd. for C$_{20}$H$_{18}$F$_4$N$_4$O, 406.1; m/z found, 407.1 [M+H]$^+$. $^1$H NMR (500 MHz, Methanol-d$_4$) δ ppm 8.20 (d, J=6.2 Hz, 1H), 7.84 (dd, J=11.6, 2.1 Hz, 1H), 7.78-7.74 (m, 1H), 7.52-7.46 (m, 1H), 7.24 (d, J=2.6 Hz, 1H), 6.92 (s, 2H), 6.87 (dd, J=6.1, 2.6 Hz, 1H), 4.22-4.14 (m, 2H), 3.14-3.02 (m, 3H), 2.10-2.01 (m, 2H), 1.91-1.79 (m, 2H).

Example 132: 2-[3-Fluoro-4-(trifluoromethoxy)phenyl]-4-[4-(1H-pyrazol-4-yl)-1-piperidyl]pyridine

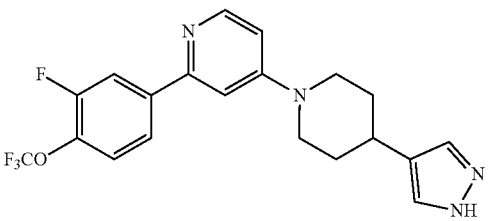 [SMILES: Fc1cc(-c2cc(N3CCC(c4cn[nH]c4)CC3)ccn2)ccc1OC(F)(F)F]

The title compound was prepared in a manner analogous to Example 11, using 4-fluoro-2-(3-fluoro-4-(trifluoromethoxy)phenyl)pyridine (product from Step A) and using 4-(1H-pyrazol-4-yl)piperidine instead of N-(piperidin-4-yl)acetamide in Step B. MS (ESI): mass calcd. for C$_{20}$H$_{18}$F$_4$N$_4$O, 406.1; m/z found, 407.0 [M+H]$^+$. $^1$H NMR (500 MHz, Chloroform-d) δ ppm 8.34 (d, J=6.0 Hz, 1H), 7.80 (dd, J=11.3, 2.1 Hz, 1H), 7.71 (ddd, J=8.6, 2.2, 1.2 Hz, 1H), 7.45 (s, 2H), 7.39-7.33 (m, 1H), 7.05 (d, J=2.5 Hz, 1H), 6.70 (dd, J=6.0, 2.5 Hz, 1H), 4.05-3.98 (m, 2H), 3.10-3.00 (m, 2H), 2.88-2.79 (m, 1H), 2.10-2.02 (m, 2H), 1.76-1.66 (m, 2H).

Example 133: 8-[2-[3-Fluoro-4-(trifluoromethoxy)phenyl]-4-pyridyl]-4,8-diazaspiro[4.5]decan-3-one

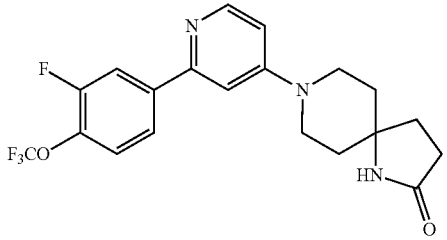 [SMILES: O=C1CCC2(CCN(c3ccnc(-c4ccc(OC(F)(F)F)c(F)c4)c3)CC2)N1]

The title compound was prepared in a manner analogous to Example 11, using 4-fluoro-2-(3-fluoro-4-(trifluoromethoxy)phenyl)pyridine (product from Step A) and using 1,8-diazaspiro[4.5]decan-2-one hydrochloride instead of N-(piperidin-4-yl)acetamide in Step B. MS (ESI): mass calcd. for C$_{20}$H$_{19}$F$_4$N$_3$O$_2$, 409.1; m/z found, 410.1 [M+H]$^+$. $^1$H NMR (500 MHz, Methanol-d$_4$) δ ppm 8.21 (d, J=6.1 Hz, 1H), 7.84 (dd, J=11.6, 2.1 Hz, 1H), 7.76 (ddd, J=8.6, 2.2, 1.2 Hz, 1H), 7.53-7.46 (m, 1H), 7.25 (d, J=2.6 Hz, 1H), 6.87 (dd, J=6.2, 2.6 Hz, 1H), 3.77-3.69 (m, 2H), 3.49-3.42 (m, 2H), 2.43 (dd, J=8.6, 7.5 Hz, 2H), 2.08 (dd, J=8.6, 7.5 Hz, 2H), 1.84-1.78 (m, 4H).

Example 134: N-[1-[2-[3-Fluoro-4-(trifluoromethoxy)phenyl]-4-pyridyl]-4-piperidyl]methanesulfonamide

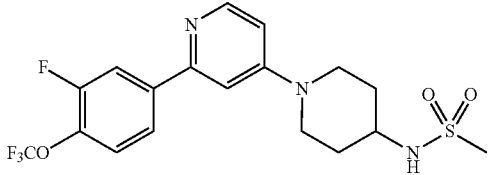 [SMILES: CS(=O)(=O)NC1CCN(c2ccnc(-c3ccc(OC(F)(F)F)c(F)c3)c2)CC1]

The title compound was prepared in a manner analogous to Example 11, using 4-fluoro-2-(3-fluoro-4-(trifluoromethoxy)phenyl)pyridine (product from Step A) and using N-(piperidin-4-yl)methanesulfonamide instead of N-(piperidin-4-yl)acetamide in Step B. MS (ESI): mass calcd. for C$_{18}$H$_{19}$F$_4$N$_3$O$_3$S, 433.1; m/z found, 434.1 [M+H]$^+$. $^1$H NMR (500 MHz, Chloroform-d) δ ppm 8.34 (d, J=5.9 Hz, 1H), 7.78 (dd, J=11.3, 2.1 Hz, 1H), 7.69 (ddd, J=8.5, 2.1, 1.2 Hz, 1H), 7.38-7.33 (m, 1H), 7.00 (d, J=2.5 Hz, 1H), 6.65 (dd, J=6.0, 2.5 Hz, 1H), 4.68 (d, J=7.5 Hz, 1H), 3.92-3.85 (m, 2H), 3.64-3.54 (m, 1H), 3.06 (ddd, J=14.1, 12.0, 2.8 Hz, 2H), 3.01 (s, 3H), 2.16-2.08 (m, 2H), 1.65-1.55 (m, 2H).

Example 135: N-[1-[2-[4-(Difluoromethoxy)phenyl]-4-pyridyl]-4-piperidyl]acetamide

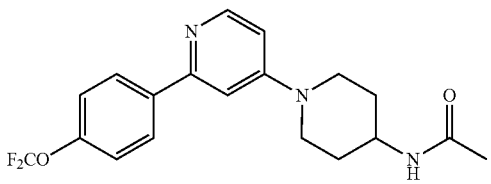

The title compound was prepared in a manner analogous to Example 12, using (4-(difluoromethoxy)phenyl)boronic acid instead of (3-(difluoromethoxy)-4-fluorophenyl)boronic acid in Step B. MS (ESI): mass calcd. for $C_{19}H_{21}F_2N_3O_2$, 361.2; m/z found, 362.2 [M+H]$^+$. $^1$H NMR (500 MHz, Methanol-d$_4$) δ ppm 8.17 (d, J=6.1 Hz, 1H), 7.89-7.84 (m, 2H), 7.25-7.20 (m, 2H), 7.16 (d, J=2.6 Hz, 1H), 6.89 (t, J=74.0 Hz, 1H), 6.83 (dd, J=6.2, 2.6 Hz, 1H), 4.09-4.02 (m, 2H), 3.98-3.90 (m, 1H), 3.13-3.04 (m, 2H), 1.99-1.95 (m, 2H), 1.93 (s, 3H), 1.57-1.47 (m, 2H).

Example 136: N-[1-[2-[4-(Difluoromethoxy)-3-fluoro-phenyl]-4-pyridyl]-4-piperidyl]acetamide

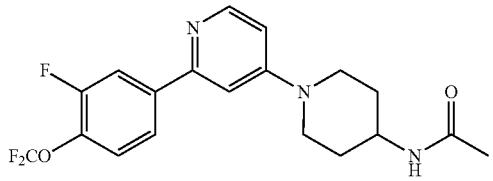

The title compound was prepared in a manner analogous to Example 12, using 2-(4-(difluoromethoxy)-3-fluorophenyl)-4,4,5,5-tetramethyl-1,3,2-dioxaborolane instead of (3-(difluoromethoxy)-4-fluorophenyl)boronic acid in Step B. MS (ESI): mass calcd. for $C_{19}H_{20}F_3N_3O_2$, 379.2; m/z found, 380.1 [M+H]$^+$. $^1$H NMR (400 MHz, Methanol-d$_4$) δ ppm 8.13 (d, J=7.4 Hz, 1H), 7.83 (dd, J=11.1, 2.3 Hz, 1H), 7.70-7.66 (m, 1H), 7.57-7.51 (m, 1H), 7.40-7.34 (m, 1H), 7.23-7.15 (m, 1H), 7.01 (t, J=72.7 Hz, 1H), 4.31 (d, J=14.0 Hz, 2H), 4.11-4.00 (m, 1H), 3.47-3.36 (m, 2H), 2.13-2.04 (m, 2H), 1.95 (s, 3H), 1.64-1.51 (m, 2H).

Example 137: N-[1-[2-[3-(Difluoromethyl)-4-fluoro-phenyl]-4-pyridyl]-4-piperidyl]acetamide

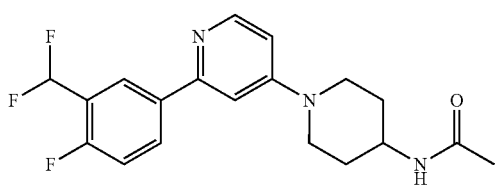 [SMILES: CC(=O)NC1CCN(c2ccnc(-c3ccc(F)c(C(F)F)c3)c2)CC1]

The title compound was prepared in a manner analogous to Example 12, using 2-(3-(difluoromethyl)-4-fluorophenyl)-4,4,5,5-tetramethyl-1,3,2-dioxaborolane (Intermediate 2) instead of (3-(difluoromethoxy)-4-fluorophenyl)boronic acid in Step B. MS (ESI): mass calcd. for $C_{19}H_{20}F_3N_3O$, 363.2; m/z found, 364.1 [M+H]$^+$. $^1$H NMR (400 MHz, Methanol-d$_4$) δ ppm 8.14-8.07 (m, 2H), 8.06-8.00 (m, 1H), 7.54-7.47 (m, 1H), 7.38 (d, J=2.9 Hz, 1H), 7.20 (dd, J=7.5, 2.9 Hz, 1H), 7.10 (t, J=54.7 Hz, 1H), 4.31 (d, J=14.0 Hz, 2H), 4.11-4.01 (m, 1H), 3.47-3.36 (m, 2H), 2.13-2.04 (m, 2H), 1.95 (s, 3H), 1.64-1.51 (m, 2H).

Example 138: N-[1-[2-(p-Tolyl)-4-pyridyl]-4-piperidyl]acetamide

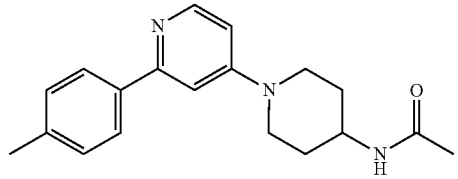 [SMILES: CC(=O)NC1CCN(c2ccnc(-c3ccc(C)cc3)c2)CC1]

The title compound was prepared in a manner analogous to Example 14, using N-(1-(2-chloropyridin-4-yl)piperidin-4-yl)acetamide (Example 12, product from Step A) and using p-tolylboronic acid instead of (3,5-difluoro-4-(trifluoromethoxy)phenyl)boronic acid. MS (ESI): mass calcd. for $C_{19}H_{23}N_3O$, 309.2; m/z found, 310.2 [M+H]$^+$. $^1$H NMR (400 MHz, DMSO-d$_6$) δ ppm 8.26 (d, J=5.9 Hz, 1H), 8.14 (dt, J=7.8, 1.2 Hz, 1H), 8.09-8.06 (m, 1H), 7.81 (d, J=7.7 Hz, 1H), 7.58 (t, J=8.0 Hz, 1H), 7.43-7.36 (m, 2H), 6.85 (dd, J=5.9, 2.3 Hz, 1H), 4.02 (d, J=13.5 Hz, 2H), 3.90-3.77 (m, 1H), 3.08-2.97 (m, 2H), 2.34 (s, 3H) 1.86-1.77 (m, 5H), 1.45-1.32 (m, 2H).

Example 139: N-[1-[2-[4-(1,1-Difluoroethyl)phenyl]-4-pyridyl]-4-piperidyl]acetamide

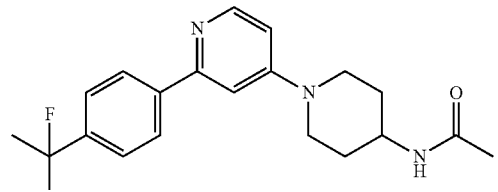

The title compound was prepared in a manner analogous to Example 13, using N-(1-(2-chloropyridin-4-yl)piperidin-4-yl)acetamide (Example 12, product from Step A); and using 2-(4-(1,1-difluoroethyl)phenyl)-4,4,5,5-tetramethyl-1,3,2-dioxaborolane instead of (4-(difluoromethyl)phenyl)boronic acid. MS (ESI): mass calcd. for $C_{20}H_{23}F_2N_3O$, 359.2; m/z found, 360.2 [M+H]$^+$. $^1$H NMR (400 MHz, DMSO-d$_6$) δ ppm 8.26 (d, J=5.9 Hz, 1H), 8.20-8.14 (m, 2H), 7.81 (d, J=7.8 Hz, 1H), 7.63 (dd, J=7.0, 1.6 Hz, 2H), 7.37 (d, J=2.5 Hz, 1H), 6.84 (dd, J=6.0, 2.4 Hz, 1H), 4.01 (dt, J=12.9, 3.8 Hz, 2H), 3.89-3.78 (m, 1H), 3.03 (ddd, J=13.4, 11.3, 2.6 Hz, 2H), 2.01 (t, J=18.8 Hz, 3H), 1.86-1.76 (m, 5H), 1.47-1.33 (m, 2H).

Example 140: N-[1-[2-[4-(Trifluoromethyl)phenyl]-4-pyridyl]-4-piperidyl]acetamide

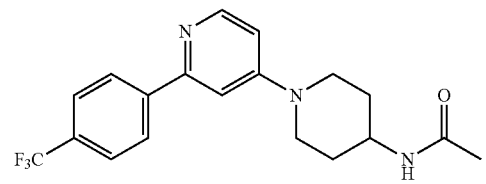 [SMILES: CC(=O)NC1CCN(c2ccnc(-c3ccc(C(F)(F)F)cc3)c2)CC1]

The title compound was prepared in a manner analogous to Example 13, using N-(1-(2-chloropyridin-4-yl)piperidin-4-yl)acetamide (Example 12, product from Step A); and using (4-(trifluoromethyl)phenyl)boronic acid instead of (4-(difluoromethyl)phenyl)boronic acid. MS (ESI): mass calcd. for C₁₉H₂₀F₃N₃O, 363.2; m/z found, 364.2 [M+H]⁺. ¹H NMR (400 MHz, DMSO-d₆) δ ppm 8.32-8.26 (m, 3H), 7.84-7.77 (m, 3H), 7.43 (d, J=2.4 Hz, 1H), 6.87 (dd, J=6.0, 2.5 Hz, 1H), 4.06-3.98 (m, 2H), 3.90-3.78 (m, 1H), 3.05 (ddd, J=13.7, 11.4, 2.8 Hz, 2H), 1.85-1.77 (m, 5H), 1.45-1.33 (m, 2H).

Example 141: N-[1-[2-[3-Chloro-4-(trifluoromethoxy)phenyl]-4-pyridyl]-4-piperidyl]acetamide

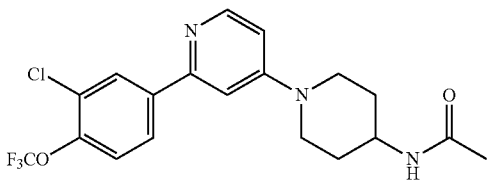

The title compound was prepared in a manner analogous to Example 13, using N-(1-(2-chloropyridin-4-yl)piperidin-4-yl)acetamide (Example 12, product from Step A); and using (3-chloro-4-(trifluoromethoxy)phenyl)boronic acid instead of (4-(difluoromethyl)phenyl)boronic acid. MS (ESI): mass calcd. for C₁₉H₁₉ClF₃N₃O₂, 413.1; m/z found, 414.1 [M+H]⁺. ¹H NMR (400 MHz, DMSO-d₆) δ ppm 8.38 (d, J=2.2 Hz, 1H), 8.25 (d, J=5.9 Hz, 1H), 8.20 (dd, J=8.7, 2.2 Hz, 1H), 7.82 (d, J=7.7 Hz, 1H), 7.63 (dq, J=8.7, 1.4 Hz, 1H), 7.44 (d, J=2.4 Hz, 1H), 6.86 (dd, J=6.1, 2.4 Hz, 1H), 4.03 (d, J=13.4 Hz, 2H), 3.89-3.78 (m, 1H), 3.04 (t, J=12.4 Hz, 2H), 1.85-1.77 (m, 5H), 1.44-1.32 (m, 2H).

Example 142: N-[1-[2-[2-Fluoro-4-(trifluoromethoxy)phenyl]-4-pyridyl]-4-piperidyl]acetamide

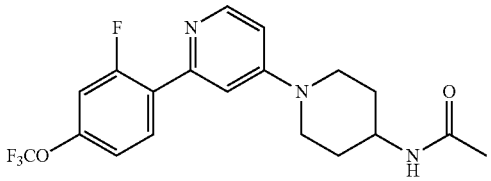 [SMILES: CC(=O)NC1CCN(c2ccnc(-c3ccc(OC(F)(F)F)cc3F)c2)CC1]

The title compound was prepared in a manner analogous to Example 13, using N-(1-(2-chloropyridin-4-yl)piperidin-4-yl)acetamide (Example 12, product from Step A); and using (2-fluoro-4-(trifluoromethoxy)phenyl)boronic acid instead of (4-(difluoromethyl)phenyl)boronic acid. MS (ESI): mass calcd. for C₁₉H₁₉F₄N₃O₂, 397.1; m/z found, 398.2 [M+H]⁺. ¹H NMR (400 MHz, DMSO-d₆) δ ppm 8.27 (d, J=6.0 Hz, 1H), 7.94 (t, J=8.7 Hz, 1H), 7.81 (d, J=7.7 Hz, 1H), 7.51-7.45 (m, 1H), 7.37-7.31 (m, 1H), 7.16 (t, J=2.0 Hz, 1H), 6.88 (dd, J=6.1, 2.5 Hz, 1H), 3.91 (d, J=13.6 Hz, 2H), 3.87-3.77 (m, 1H), 3.03 (ddd, J=13.8, 11.5, 2.7 Hz, 2H), 1.84-1.76 (m, 5H), 1.44-1.31 (m, 2H).

Example 143: N-[1-[2-[3-Fluoro-4-(2,2,2-trifluoroethoxy)phenyl]-4-pyridyl]-4-piperidyl]acetamide

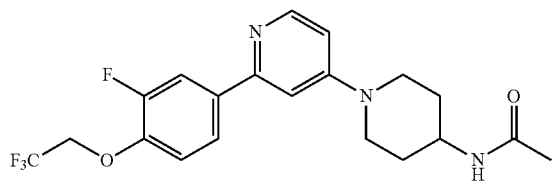 [SMILES: CC(=O)NC1CCN(c2ccnc(-c3ccc(OCC(F)(F)F)c(F)c3)c2)CC1]

The title compound was prepared in a manner analogous to Example 13, using N-(1-(2-chloropyridin-4-yl)piperidin-4-yl)acetamide (Example 12, product from Step A); and using (3-fluoro-4-(2,2,2-trifluoroethoxy)phenyl)boronic acid instead of (4-(difluoromethyl)phenyl)boronic acid. MS (ESI): mass calcd. for C₂₀H₂₁F₄N₃O₂, 411.2; m/z found, 412.2 [M+H]⁺. ¹H NMR (400 MHz, DMSO-d₆) δ ppm 8.21 (d, J=5.9 Hz, 1H), 8.02 (dd, J=13.1, 2.1 Hz, 1H), 7.94 (dt, J=8.7, 1.5 Hz, 1H), 7.81 (d, J=7.6 Hz, 1H), 7.38-7.32 (m, 2H), 6.79 (dd, J=6.0, 2.4 Hz, 1H), 4.92 (q, J=8.8 Hz, 2H), 4.01 (d, J=13.7 Hz, 2H), 3.87-3.76 (m, 1H), 3.02 (t, J=12.3 Hz, 2H), 1.85-1.73 (m, 5H), 1.45-1.30 (m, 2H).

Example 144: N-[1-[2-(4-Chloro-3-fluoro-phenyl)-4-pyridyl]-4-piperidyl]acetamide

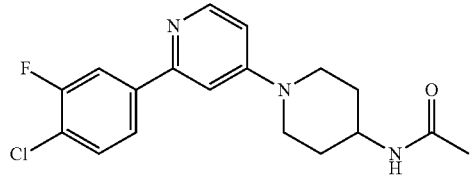 [SMILES: CC(=O)NC1CCN(c2ccnc(-c3ccc(Cl)c(F)c3)c2)CC1]

The title compound was prepared in a manner analogous to Example 13, using N-(1-(2-chloropyridin-4-yl)piperidin-4-yl)acetamide (Example 12, product from Step A); and using (4-chloro-3-fluorophenyl)boronic acid instead of (4-(difluoromethyl)phenyl)boronic acid. MS (ESI): mass calcd. for C₁₈H₁₉ClFN₃O, 347.1; m/z found, 348.2 [M+H]⁺. ¹H NMR (500 MHz, DMSO-d₆) δ ppm 8.24 (d, J=5.9 Hz, 1H), 8.13 (dd, J=11.3, 2.0 Hz, 1H), 8.03-7.99 (m, 1H), 7.82 (d, J=7.7 Hz, 1H), 7.65 (t, J=8.2 Hz, 1H), 7.41 (d, J=2.5 Hz, 1H), 6.84 (dd, J=6.0, 2.4 Hz, 1H), 4.06-3.98 (m, 2H), 3.88-3.77 (m, 1H), 3.03 (ddd, J=13.9, 11.5, 2.8 Hz, 2H), 1.84-1.76 (m, 5H), 1.43-1.29 (m, 2H).

Example 145: N-[1-[2-(3-Fluoro-4-methoxy-phenyl)-4-pyridyl]-4-piperidyl]acetamide

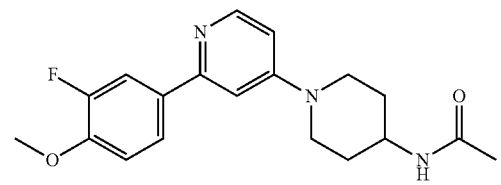 [SMILES: COc1ccc(-c2cc(N3CCC(NC(C)=O)CC3)ccn2)cc1F]

The title compound was prepared in a manner analogous to Example 14, using N-(1-(2-chloropyridin-4-yl)piperidin-4-yl)acetamide (Example 12, product from Step A) and using (3-fluoro-4-methoxyphenyl)boronic acid instead of (3,5-difluoro-4-(trifluoromethoxy)phenyl)boronic acid. MS (ESI): mass calcd. for $C_{19}H_{22}FN_3O_2$, 343.2; m/z found, 344.2 $[M+H]^+$. $^1$H NMR (400 MHz, DMSO-$d_6$) δ ppm 8.20 (d, J=5.9 Hz, 1H), 7.97-7.88 (m, 2H), 7.81 (d, J=7.7 Hz, 1H), 7.30 (d, J=2.4 Hz, 1H), 7.21 (t, J=8.9 Hz, 1H), 6.77 (dd, J=6.0, 2.4 Hz, 1H), 4.00 (dt, J=13.2, 3.8 Hz, 2H), 3.89 (s, 3H), 3.87-3.77 (m, 1H), 3.01 (ddd, J=13.7, 11.4, 2.8 Hz, 2H), 1.85-1.74 (m, 5H), 1.44-1.31 (m, 2H).

Example 146: N-[1-[2-[3-Fluoro-4-(trifluoromethyl)phenyl]-4-pyridyl]-4-piperidyl]acetamide

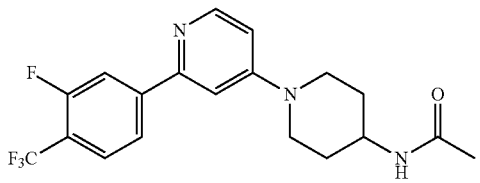 [SMILES: CC(=O)NC1CCN(c2ccnc(-c3ccc(C(F)(F)F)c(F)c3)c2)CC1]

The title compound was prepared in a manner analogous to Example 14, using N-(1-(2-chloropyridin-4-yl)piperidin-4-yl)acetamide (Example 12, product from Step A) and using (3-fluoro-4-(trifluoromethyl)phenyl)boronic acid instead of (3,5-difluoro-4-(trifluoromethoxy)phenyl)boronic acid. MS (ESI): mass calcd. for $C_{19}H_{19}F_4N_3O$, 381.1; m/z found, 382.2 $[M+H]^+$. $^1$H NMR (400 MHz, DMSO-$d_6$) δ ppm 8.28 (d, J=5.9 Hz, 1H), 8.24-8.15 (m, 2H), 7.87-7.79 (m, 2H), 7.50 (d, J=2.4 Hz, 1H), 6.89 (dd, J=6.0, 2.4 Hz, 1H), 4.04 (dt, J=13.6, 3.9 Hz, 2H), 3.92-3.77 (m, 1H), 3.05 (ddd, J=13.9, 11.6, 2.8 Hz, 2H), 1.86-1.75 (m, 5H), 1.39 (qd, J=11.3, 3.7 Hz, 2H).

Example 147: N-[1-[2-(4-Acetyl-3-fluoro-phenyl)-4-pyridyl]-4-piperidyl]acetamide

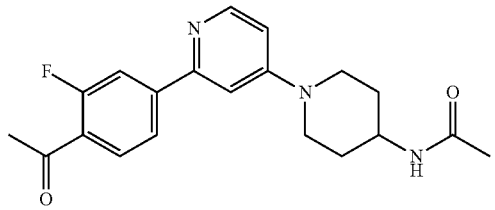 [SMILES: CC(=O)NC1CCN(c2ccnc(-c3ccc(C(C)=O)c(F)c3)c2)CC1]

The title compound was prepared in a manner analogous to Example 14, using N-(1-(2-chloropyridin-4-yl)piperidin-4-yl)acetamide (Example 12, product from Step A) and using (4-acetyl-3-fluorophenyl)boronic acid instead of (3,5-difluoro-4-(trifluoromethoxy)phenyl)boronic acid. MS (ESI): mass calcd. for $C_{20}H_{22}FN_3O_2$, 355.2; m/z found, 356.2 $[M+H]^+$. $^1$H NMR (500 MHz, Methanol-$d_4$) δ ppm 8.22 (d, J=6.1 Hz, 1H), 7.94 (t, J=7.9 Hz, 1H), 7.81-7.74 (m, 2H), 7.29 (d, J=2.6 Hz, 1H), 6.88 (dd, J=6.2, 2.6 Hz, 1H), 4.08 (d, J=13.4 Hz, 2H), 3.99-3.89 (m, 1H), 3.10 (ddd, J=13.7, 11.8, 2.7 Hz, 2H), 2.65 (d, J=4.4 Hz, 3H), 1.98 (dd, J=12.9, 3.6 Hz, 2H), 1.93 (s, 3H), 1.52 (qd, J=11.9, 3.9 Hz, 2H).

Example 148: N-[1-[2-[3-Fluoro-4-(trifluoromethoxy)phenyl]-5-methyl-4-pyridyl]-4-piperidyl]acetamide

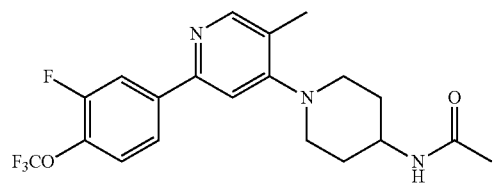 [SMILES: CC(=O)NC1CCN(c2cc(-c3ccc(OC(F)(F)F)c(F)c3)ncc2C)CC1]

The title compound was prepared in a manner analogous to Example 15, using 2-chloro-4-iodo-5-methylpyridine instead of 2-chloro-5-fluoro-4-iodopyridine in Step A. MS (ESI): mass calcd. for $C_{20}H_{21}F_4N_3O_2$, 411.2; m/z found, 412.1 $[M+H]^+$. $^1$H NMR (400 MHz, Chloroform-d) δ ppm 8.34 (s, 1H), 7.80 (dd, J=11.3, 2.1 Hz, 1H), 7.72-7.68 (m, 1H), 7.39-7.33 (m, 1H), 7.16 (s, 1H), 5.46 (d, J=8.0 Hz, 1H), 4.07-3.94 (m, 1H), 3.38-3.28 (m, 2H), 2.94-2.83 (m, 2H), 2.27 (s, 3H), 2.15-2.06 (m, 2H), 2.01 (s, 3H), 1.66-1.55 (m, 2H).

Example 149: N-[1-[2-[3-Fluoro-4-(trifluoromethoxy)phenyl]-5-methoxy-4-pyridyl]-4-piperidyl]acetamide

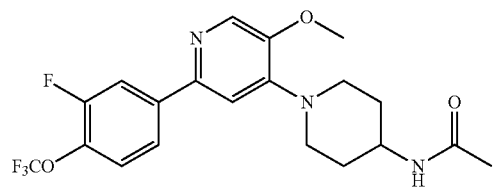 [SMILES: COc1cnc(-c2ccc(OC(F)(F)F)c(F)c2)cc1N1CCC(NC(C)=O)CC1]

The title compound was prepared in a manner analogous to Example 15, using 2-chloro-4-iodo-5-methoxypyridine instead of 2-chloro-5-fluoro-4-iodopyridine in Step A. MS (ESI): mass calcd. for $C_{20}H_{21}F_4N_3O_3$, 427.2; m/z found, 428.1 $[M+H]^+$. $^1$H NMR (500 MHz, Chloroform-d) δ ppm 8.16 (s, 1H), 7.77 (dd, J=11.4, 2.1 Hz, 1H), 7.66 (ddd, J=8.6, 2.1, 1.2 Hz, 1H), 7.38-7.32 (m, 1H), 7.11 (s, 1H), 5.41 (d, J=8.0 Hz, 1H), 4.04-3.94 (m, 4H), 3.75-3.69 (m, 2H), 2.91-2.84 (m, 2H), 2.12-2.05 (m, 2H), 2.00 (s, 3H), 1.66-1.57 (m, 2H).

Example 150: N-[1-[2-[4-(Difluoromethoxy)phenyl]-6-methyl-4-pyridyl]-4-piperidyl]acetamide

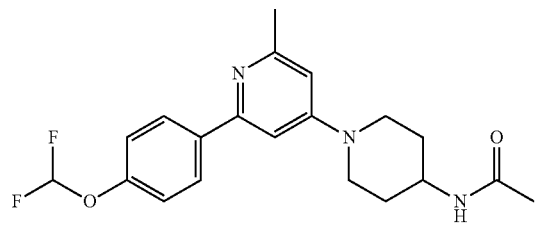 [SMILES: CC(=O)NC1CCN(c2cc(C)nc(-c3ccc(OC(F)F)cc3)c2)CC1]

The title compound was prepared in a manner analogous to Example 20, using 2,4-dichloro-6-methylpyridine instead of 4,6-dichloropyridine-2-carbonitrile and using (4-(difluoromethoxy)phenyl)boronic acid instead of (3-fluoro-4-(trifluoromethoxy)phenyl)boronic acid in Step A. MS (ESI): mass calcd. for $C_{20}H_{23}F_2N_3O_2$, 375.2; m/z found, 376.1 [M+H]$^+$. $^1$H NMR (400 MHz, DMSO-d$_6$) δ ppm 8.14-8.08 (m, 2H), 7.82 (d, J=7.6 Hz, 1H), 7.49-7.10 (m, 1H), 7.25-7.20 (m, 2H), 6.70 (d, J=2.1 Hz, 1H), 3.98 (dt, J=13.5, 3.7 Hz, 2H), 3.87-3.75 (m, 1H), 2.99 (t, J=11.8 Hz, 2H), 2.39 (s, 3H), 1.84-1.75 (m, 5H), 1.37 (q, J=10.1 Hz, 2H), 7.18-7.13 (m, 1H).

Example 151: N-[1-[2-[4-(1,1-Difluoroethyl)phenyl]-6-methyl-4-pyridyl]-4-piperidyl]acetamide

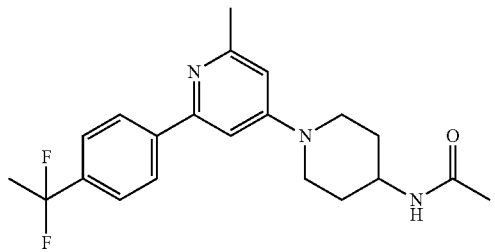 [SMILES: CC(=O)NC1CCN(c2cc(C)nc(-c3ccc(C(C)(F)F)cc3)c2)CC1]

The title compound was prepared in a manner analogous to Example 20, using 2,4-dichloro-6-methylpyridine instead of 4,6-dichloropyridine-2-carbonitrile and using 2-(4-(1,1-difluoroethyl)phenyl)-4,4,5,5-tetramethyl-1,3,2-dioxaborolane instead of (3-fluoro-4-(trifluoromethoxy)phenyl)boronic acid in Step A. MS (ESI): mass calcd. for $C_{21}H_{25}F_2N_3O$, 373.2; m/z found, 374.2 [M+H]$^+$. $^1$H NMR (500 MHz, DMSO-d$_6$) δ ppm 8.15 (dd, J=7.2, 1.4 Hz, 2H), 7.81 (d, J=7.7 Hz, 1H), 7.61 (dd, J=7.0, 1.6 Hz, 2H), 7.21 (d, J=2.2 Hz, 1H), 6.73 (d, J=2.2 Hz, 1H), 3.98 (dt, J=13.5, 3.8 Hz, 2H), 3.87-3.77 (m, 1H), 3.00 (ddd, J=13.7, 11.5, 2.7 Hz, 2H), 2.41 (s, 3H), 2.00 (t, J=18.8 Hz, 3H), 1.83-1.75 (m, 5H), 1.43-1.32 (m, 2H).

Example 152: N-[1-[2-[4-(Difluoromethoxy)-3-fluoro-phenyl]-6-methyl-4-pyridyl]-4-piperidyl]acetamide

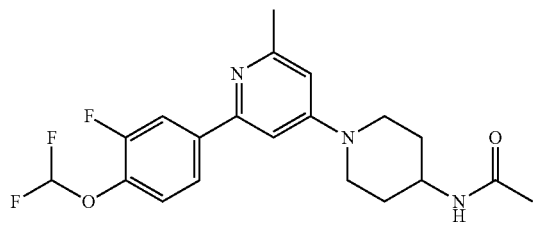 [SMILES: CC(=O)NC1CCN(c2cc(C)nc(-c3ccc(OC(F)F)c(F)c3)c2)CC1]

The title compound was prepared in a manner analogous to Example 20, using 2,4-dichloro-6-methylpyridine instead of 4,6-dichloropyridine-2-carbonitrile and using 2-(4-(difluoromethoxy)-3-fluorophenyl)-4,4,5,5-tetramethyl-1,3,2-dioxaborolane instead of (3-fluoro-4-(trifluoromethoxy)phenyl)boronic acid in Step A. MS (ESI): mass calcd. for $C_{20}H_{22}F_3N_3O_2$, 393.2; m/z found, 393.9 [M+H]$^+$. $^1$H NMR (400 MHz, DMSO-d$_6$) δ ppm 8.09 (dd, J=12.5, 2.1 Hz, 1H), 7.98 (ddd, J=8.6, 2.1, 1.1 Hz, 1H), 7.82 (d, J=7.7 Hz, 1H), 7.41 (t, J=8.5 Hz, 1H), 7.31 (t, J=73.2 Hz, 1H), 7.23 (d, J=2.2 Hz, 1H), 6.73 (d, J=2.1 Hz, 1H), 4.00 (dt, J=13.6, 3.8 Hz, 2H), 3.88-3.74 (m, 1H), 3.00 (ddd, J=13.7, 11.5, 2.7 Hz, 2H), 2.40 (s, 3H), 1.84-1.74 (m, 5H), 1.43-1.30 (m, 2H).

Example 153: N-[1-[2-(Fluoromethyl)-6-[3-fluoro-4-(trifluoromethoxy)phenyl]-4-pyridyl]-4-piperidyl]acetamide

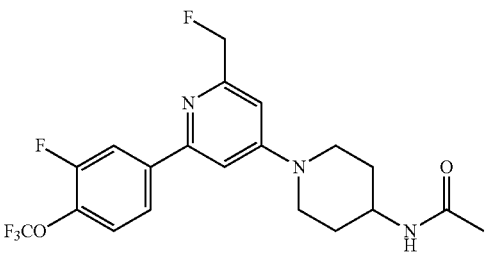 [SMILES: CC(=O)NC1CCN(c2cc(CF)nc(-c3ccc(OC(F)(F)F)c(F)c3)c2)CC1]

The title compound was prepared in a manner analogous to Example 20, using 2,4-dichloro-6-(fluoromethyl)pyridine instead of 4,6-dichloropyridine-2-carbonitrile in Step A. MS (ESI): mass calcd. for $C_{20}H_{20}F_5N_3O_2$, 429.1; m/z found, 430.2 [M+H]$^+$. $^1$H NMR (500 MHz, DMSO-d$_6$) δ ppm 8.20 (dd, J=12.2, 2.1 Hz, 1H), 8.07 (ddd, J=8.8, 2.2, 1.1 Hz, 1H), 7.82 (d, J=7.7 Hz, 1H), 7.66-7.61 (m, 1H), 7.41 (d, J=2.3 Hz, 1H), 6.95 (d, J=2.2 Hz, 1H), 5.39 (d, J=47.2 Hz, 2H), 4.06 (d, J=13.6 Hz, 2H), 3.84 (ddt, J=14.9, 10.6, 5.5 Hz, 1H), 3.12-3.02 (m, 2H), 1.86-1.76 (m, 5H), 1.44-1.32 (m, 2H).

Example 154: N-[1-[2-(Difluoromethyl)-6-[3-fluoro-4-(trifluoromethoxy)phenyl]-4-pyridyl]-4-piperidyl]acetamide

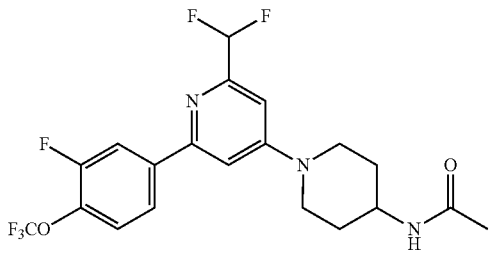 [SMILES: CC(=O)NC1CCN(c2cc(-c3ccc(OC(F)(F)F)c(F)c3)nc(C(F)F)c2)CC1]

The title compound was prepared in a manner analogous to Example 20, using 2,4-dichloro-6-(difluoromethyl)pyridine instead of 4,6-dichloropyridine-2-carbonitrile in Step A. MS (ESI): mass calcd. for $C_{20}H_{19}F_6N_3O_2$, 447.1; m/z found, 448.2 [M+H]$^+$. $^1$H NMR (500 MHz, DMSO-d$_6$) δ ppm 8.23 (dd, J=12.1, 2.2 Hz, 1H), 8.09 (ddd, J=8.6, 2.2, 1.1 Hz, 1H), 7.82 (d, J=7.7 Hz, 1H), 7.67 (t, J=8.3 Hz, 1H), 7.53 (d, J=2.3 Hz, 1H), 7.10 (d, J=2.2 Hz, 1H), 6.83 (t, J=55.2 Hz, 1H), 4.09 (d, J=13.5 Hz, 2H), 3.92-3.78 (m, 1H), 3.12 (ddd, J=13.9, 11.5, 2.7 Hz, 2H), 1.87-1.77 (m, 5H), 1.44-1.32 (m, 2H).

Example 155: N-[1-[2-[3-Fluoro-4-(trifluoromethoxy)phenyl]-6-(hydroxymethyl)-4-pyridyl]-4-piperidyl]acetamide

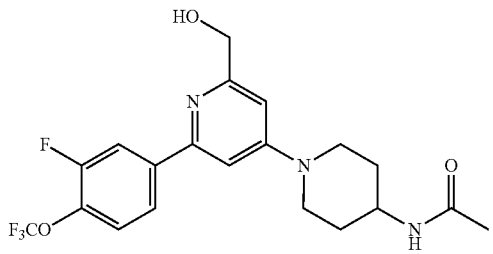 [SMILES: CC(=O)NC1CCN(c2cc(CO)nc(-c3ccc(OC(F)(F)F)c(F)c3)c2)CC1]

The title compound was prepared in a manner analogous to Example 20, using (4,6-dichloropyridin-2-yl)methanol instead of 4,6-dichloropyridine-2-carbonitrile in Step A. MS (ESI): mass calcd. for $C_{20}H_{21}F_4N_3O_3$, 427.2; m/z found, 428.2 [M+H]$^+$. $^1$H NMR (400 MHz, DMSO-d$_6$) δ ppm 8.20 (dd, J=12.2, 2.1 Hz, 1H), 8.06 (ddd, J=8.7, 2.2, 1.1 Hz, 1H), 7.82 (d, J=7.7 Hz, 1H), 7.62 (td, J=8.4, 1.4 Hz, 1H), 7.32 (d, J=2.3 Hz, 1H), 6.92 (d, J=2.2 Hz, 1H), 5.30 (t, J=5.9 Hz, 1H), 4.50 (d, J=5.8 Hz, 2H), 4.02 (d, J=13.5 Hz, 2H), 3.91-3.78 (m, 1H), 3.10-2.98 (m, 2H), 1.88-1.77 (m, 5H), 1.46-1.30 (m, 2H).

Example 156: N-[1-[2-(3-Fluoro-4-isopropoxy-phenyl)-6-(hydroxymethyl)-4-pyridyl]-4-piperidyl]acetamide

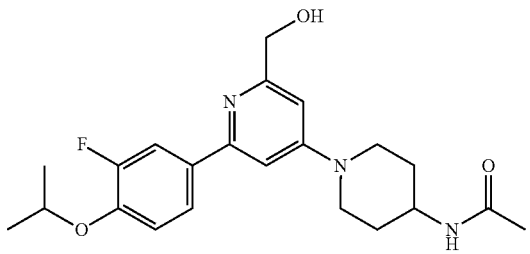 [SMILES: CC(=O)NC1CCN(c2cc(CO)nc(-c3ccc(OC(C)C)c(F)c3)c2)CC1]

The title compound was prepared in a manner analogous to Example 20, using (3-fluoro-4-isopropoxyphenyl)boronic acid instead of (3-fluoro-4-(trifluoromethoxy)phenyl)boronic acid and (4,6-dichloropyridin-2-yl)methanol instead of 4,6-dichloropyridine-2-carbonitrile in Step A. MS (ESI): mass calcd. for $C_{22}H_{28}FN_3O_3$, 401.2; m/z found, 402.2 [M+H]$^+$. $^1$H NMR (400 MHz, DMSO-d$_6$) δ ppm 7.93 (dd, J=13.3, 2.2 Hz, 1H), 7.86 (ddd, J=8.6, 2.2, 1.0 Hz, 1H), 7.81 (d, J=7.7 Hz, 1H), 7.23-7.16 (m, 2H), 6.84 (d, J=2.2 Hz, 1H), 5.24 (t, J=5.9 Hz, 1H), 4.69 (hept, J=6.0 Hz, 1H), 4.48 (d, J=5.9 Hz, 2H), 3.99 (d, J=13.5 Hz, 2H), 3.89-3.76 (m, 1H), 3.02 (t, J=12.0 Hz, 2H), 1.85-1.76 (m, 5H), 1.46-1.33 (m, 2H), 1.32 (d, J=6.0 Hz, 6H).

Example 157: N-[1-[2-(4-Ethoxy-3-fluoro-phenyl)-6-(hydroxymethyl)-4-pyridyl]-4-piperidyl]acetamide

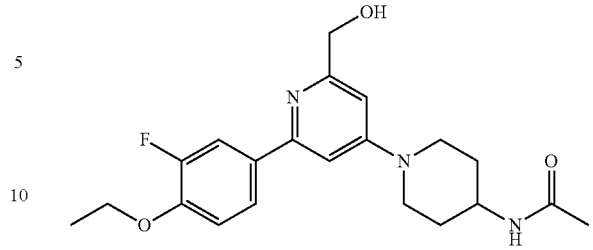

The title compound was prepared in a manner analogous to Example 20, using (4-ethoxy-3-fluorophenyl)boronic acid instead of (3-fluoro-4-(trifluoromethoxy)phenyl)boronic acid and (4,6-dichloropyridin-2-yl)methanol instead of 4,6-dichloropyridine-2-carbonitrile in Step A. MS (ESI): mass calcd. for $C_{21}H_{26}FN_3O_3$, 387.2; m/z found, 388.2 [M+H]$^+$. $^1$H NMR (400 MHz, DMSO-d$_6$) δ ppm 7.94 (dd, J=13.4, 2.2 Hz, 1H), 7.88 (ddd, J=8.6, 2.2, 1.0 Hz, 1H), 7.81 (d, J=7.7 Hz, 1H), 7.22-7.15 (m, 2H), 6.84 (d, J=2.2 Hz, 1H), 5.24 (t, J=5.9 Hz, 1H), 4.48 (d, J=5.9 Hz, 2H), 4.16 (q, J=7.0 Hz, 2H), 3.99 (d, J=13.4 Hz, 2H), 3.90-3.76 (m, 1H), 3.02 (t, J=12.1 Hz, 2H), 1.86-1.74 (m, 5H), 1.45-1.32 (m, 5H).

Example 158: N-[1-[2-[3-Fluoro-4-(trifluoromethoxy)phenyl]-6-methoxy-4-pyridyl]-4-piperidyl]acetamide

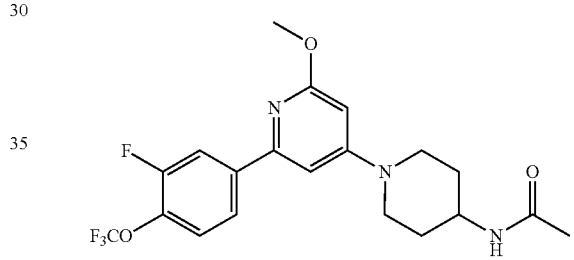

The title compound was prepared in a manner analogous to Example 20, using 2,4-dichloro-6-methoxypyridine instead of 4,6-dichloropyridine-2-carbonitrile in Step A. MS (ESI): mass calcd. for $C_{20}H_{21}F_4N_3O_3$, 427.2; m/z found, 428.0 [M+H]$^+$. $^1$H NMR (400 MHz, DMSO-d$_6$) δ ppm 8.22 (dd, J=12.3, 2.1 Hz, 1H), 8.08 (ddd, J=8.7, 2.1, 1.1 Hz, 1H), 7.81 (d, J=7.6 Hz, 1H), 7.67-7.62 (m, 1H), 7.22 (d, J=2.0 Hz, 1H), 6.16 (d, J=1.9 Hz, 1H), 3.97 (d, J=13.4 Hz, 2H), 3.89 (s, 3H), 3.86-3.75 (m, 1H), 3.00 (t, J=12.4 Hz, 2H), 1.83-1.73 (m, 5H), 1.37 (q, J=10.2 Hz, 2H).

Example 159: N-[1-[2-[3-Fluoro-4-(trifluoromethoxy)phenyl]-6-hydroxy-4-pyridyl]-4-piperidyl]acetamide

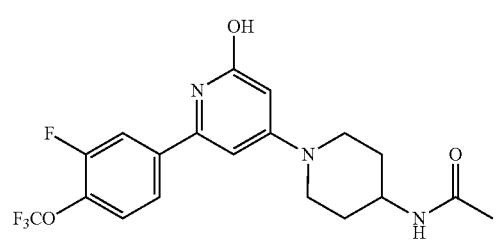 [SMILES: CC(=O)NC1CCN(c2cc(O)nc(-c3ccc(OC(F)(F)F)c(F)c3)c2)CC1]

N-[1-[2-[3-Fluoro-4-(trifluoromethoxy)phenyl]-6-methoxy-4-pyridyl]-4-piperidyl]acetamide (Example 158, 25 mg, 0.059 mmol) was combined with pyridine hydrochloride (135 mg, 1.17 mmol) in a round bottom flask. The solids were heated with a heat gun for 5 minutes until solids melted forming a solution that was able to be stirred. The reaction mixture was allowed to cool to room temperature overnight. Purification by basic prep HPLC (Agilent, Waters XBridge C18 5 um 50×100 mm column, 5-90% MeCN/20 mM NH$_4$OH over 15 min, 80 mL/min) gave the title compound (24 mg, 73%). MS (ESI): mass calcd. for C$_{19}$H$_{19}$F$_4$N$_3$O$_3$, 413.1; m/z found, 414.2 [M+H]$^+$. $^1$H NMR (400 MHz, DMSO-d$_6$) δ ppm 10.91 (s, 1H), 7.97 (dd, J=11.7, 2.2 Hz, 1H), 7.83 (d, J=7.7 Hz, 1H), 7.75 (d, J=8.8 Hz, 1H), 7.70-7.61 (m, 1H), 6.54 (s, 1H), 5.57 (s, 1H), 3.87 (d, J=13.3 Hz, 2H), 3.84-3.74 (m, 1H), 2.97 (t, J=12.4 Hz, 2H), 1.82-1.72 (m, 5H), 1.43-1.28 (m, 2H).

Example 160: N-[1-[2-(Difluoromethoxy)-6-[3-fluoro-4-(trifluoromethoxy)phenyl]-4-pyridyl]-4-piperidyl]acetamide

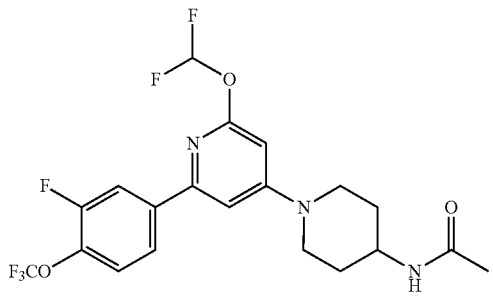 [SMILES: CC(=O)NC1CCN(c2cc(OC(F)F)nc(-c3ccc(OC(F)(F)F)c(F)c3)c2)CC1]

To a solution of N-[1-[2-[3-fluoro-4-(trifluoromethoxy)phenyl]-6-hydroxy-4-pyridyl]-4-piperidyl]acetamide (Example 159, 100 mg, 0.24 mmol) in acetonitrile (4 mL) cooled at 0° C. was added NaH (60% dispersion in mineral oil) (26 mg, 0.65 mmol). The reaction mixture was stirred for 5 minutes then 2,2-difluoro-2-(fluorosulfonyl)acetic acid (44 μL, 0.41 mmol) was added. The ice bath was then removed and the reaction mixture was warmed up to room temperature and stirred for 16 hours. Water was added and volatiles were evaporated. To the residue was added water and EtOAc. The aqueous layer was extracted twice with EtOAc. The combined organic layers were washed a saturated aqueous solution of NaCl, dried over MgSO4, filtered and evaporated. Purification via silica gel chromatography (0-15% MeOH in DCM) gave the title compound (15 mg, 14%). MS (ESI): mass calcd. for C$_{20}$H$_{19}$F$_6$N$_3$O$_3$, 463.1; m/z found, 464.2 [M+H]$^+$. $^1$H NMR (500 MHz, DMSO-d$_6$) δ ppm 8.27 (dd, J=12.2, 2.1 Hz, 1H), 8.08 (ddd, J=8.6, 2.2, 1.1 Hz, 1H), 7.91 (t, J=73.4 Hz, 1H), 7.81 (d, J=7.7 Hz, 1H), 7.67-7.62 (m, 1H), 7.36 (d, J=2.0 Hz, 1H), 6.43 (d, J=2.0 Hz, 1H), 4.04 (d, J=13.7 Hz, 2H), 3.90-3.79 (m, 1H), 3.09 (t, J=12.1 Hz, 2H), 1.85-1.75 (m, 5H), 1.36 (q, J=10.1 Hz, 2H).

Example 161: (cis)-N-[3-Fluoro-1-[2-[3-fluoro-4-(trifluoromethoxy)phenyl]-4-pyridyl]-4-piperidyl]acetamide

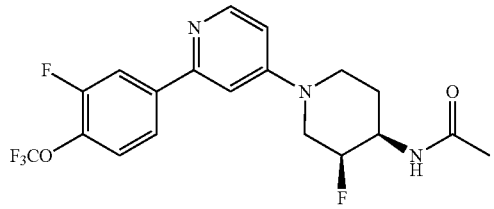 [SMILES: CC(=O)N[C@@H]1CCN(c2ccnc(-c3ccc(OC(F)(F)F)c(F)c3)c2)C[C@@H]1F]

The title compound was prepared in a manner analogous to Example 16, using tert-butyl ((3,4-cis)-3-fluoropiperidin-4-yl)carbamate instead of tert-butyl ((3,4-trans)-3-fluoropiperidin-4-yl)carbamate in Step A. MS (ESI): mass calcd. for C$_{19}$H$_{18}$F$_5$N$_3$O$_2$, 415.1; m/z found, 416.1 [M+H]$^+$. $^1$H NMR (500 MHz, Methanol-d$_4$) δ ppm 8.20 (d, J=6.1 Hz, 1H), 7.84 (dd, J=11.6, 2.2 Hz, 1H), 7.79-7.74 (m, 1H), 7.53-7.47 (m, 1H), 7.25 (d, J=2.6 Hz, 1H), 6.88 (dd, J=6.1, 2.6 Hz, 1H), 4.79 (s, 1H), 4.50-4.40 (m, 1H), 4.25-4.06 (m, 2H), 3.30-3.18 (m, 1H), 3.15-3.06 (m, 1H), 1.98 (s, 3H), 1.96-1.87 (m, 1H), 1.84-1.75 (m, 1H).

Example 162: (*R/*R)—N-[3-Fluoro-1-[2-[3-fluoro-4-(trifluoromethoxy)phenyl]-4-pyridyl]-4-piperidyl]acetamide

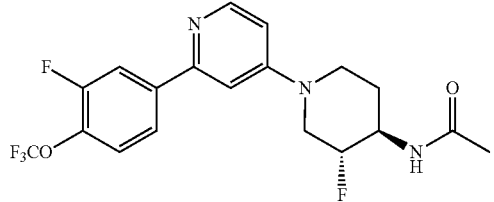 [SMILES: CC(=O)N[C@@H]1CCN(c2ccnc(-c3ccc(OC(F)(F)F)c(F)c3)c2)C[C@H]1F]

(trans)-N-[3-Fluoro-1-[2-[3-fluoro-4-(trifluoromethoxy)phenyl]-4-pyridyl]-4-piperidyl]acetamide (Example 16) was separated via SFC chiral separation (Stationary phase: Whelk O1 SS 5 μm 250×21 mm, Mobile phase: 25% isopropanol with 0.2% isopropylamine, 75% CO$_2$, 2 mL/min, 150 Bar, retention time: 15.31 min at 254 nM) to afford the tile compound (8 mg, 13%). MS (ESI): mass calcd. for C$_{19}$H$_{18}$F$_5$N$_3$O$_2$, 415.1; m/z found, 416.1 [M+H]$^+$. $^1$H NMR (400 MHz, Chloroform-d) δ ppm 8.38 (d, J=5.9 Hz, 1H), 7.80 (dd, J=11.3, 2.1 Hz, 1H), 7.70 (ddd, J=8.6, 2.1, 1.2 Hz, 1H), 7.41-7.33 (m, 1H), 7.04 (d, J=2.5 Hz, 1H), 6.69 (dd, J=5.9, 2.5 Hz, 1H), 5.61 (d, J=7.6 Hz, 1H), 4.55-4.34 (m, 1H), 4.25-4.12 (m, 2H), 3.87-3.78 (m, 1H), 3.18-3.03 (m, 2H), 2.35-2.24 (m, 1H), 2.04 (s, 3H), 1.63-1.50 (m, 1H).

Example 163: (*S/*S)—N-[3-Fluoro-1-[2-[3-fluoro-4-(trifluoromethoxy)phenyl]-4-pyridyl]-4-piperidyl]acetamide

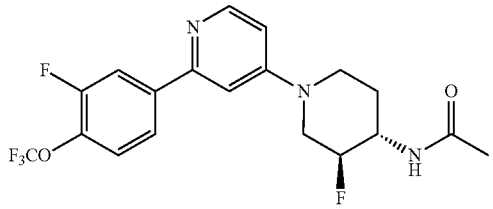 [SMILES: CC(=O)N[C@H]1CCN(c2ccnc(-c3ccc(OC(F)(F)F)c(F)c3)c2)C[C@@H]1F]

(trans)-N-[3-Fluoro-1-[2-[3-fluoro-4-(trifluoromethoxy)phenyl]-4-pyridyl]-4-piperidyl]acetamide (Example 16) was separated via SFC chiral separation (Stationary phase: Whelk O1 SS 5 μm 250×21 mm, Mobile phase: 25% isopropanol with 0.2% isopropylamine, 75% $CO_2$, 2 mL/min, 150 Bar, retention time: 17.91 min at 254 nM) to afford the tile compound (11 mg, 17%). MS (ESI): mass calcd. for $C_{19}H_{18}F_5N_3O_2$, 415.1; m/z found, 416.1 $[M+H]^+$. $^1$H NMR (500 MHz, Chloroform-d) δ ppm 8.37 (d, J=5.9 Hz, 1H), 7.80 (dd, J=11.3, 2.2 Hz, 1H), 7.72-7.68 (m, 1H), 7.40-7.34 (m, 1H), 7.04 (d, J=2.6 Hz, 1H), 6.69 (dd, J=5.9, 2.5 Hz, 1H), 5.63 (d, J=7.6 Hz, 1H), 4.54-4.35 (m, 1H), 4.24-4.11 (m, 2H), 3.87-3.78 (m, 1H), 3.17-3.04 (m, 2H), 2.34-2.25 (m, 1H), 2.03 (s, 3H), 1.62-1.51 (m, 1H).

Example 164: (*S/*S)—N-[3-Fluoro-1-[5-fluoro-2-[3-fluoro-4-(trifluoromethoxy)phenyl]-4-pyridyl]-4-piperidyl]acetamide

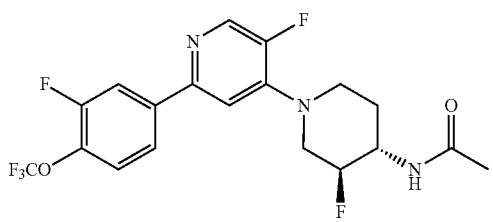 [SMILES: CC(=O)N[C@H]1CCN(c2cc(-c3ccc(OC(F)(F)F)c(F)c3)ncc2F)C[C@@H]1F]

(racemic) N-[3-Fluoro-1-[5-fluoro-2-[3-fluoro-4-(trifluoromethoxy)phenyl]-4-pyridyl]-4-piperidyl]acetamide (Example 17) product from Step C before separation: was separated via SFC chiral separation (Stationary phase: Chiralpak IF 5 μm 250×21 mm, Mobile phase: 18% methanol, 82% $CO_2$, 2 mL/min, 150 Bar, retention time: 4.38 min at 254 nM) to afford the tile compound (14 mg, 29%). MS (ESI): mass calcd. for $C_{19}H_{17}F_6N_3O_2$, 433.1; m/z found, 434.1 $[M+H]^+$. $^1$H NMR (500 MHz, Chloroform-d) δ ppm 8.31 (d, J=4.7 Hz, 1H), 7.77 (dd, J=11.2, 2.1 Hz, 1H), 7.66 (ddd, J=8.6, 2.2, 1.2 Hz, 1H), 7.40-7.34 (m, 1H), 7.11 (d, J=7.1 Hz, 1H), 5.62 (d, J=7.7 Hz, 1H), 4.53 (dtd, J=49.4, 9.4, 4.8 Hz, 1H), 4.21-4.11 (m, 1H), 4.07-4.00 (m, 1H), 3.72-3.65 (m, 1H), 3.11-3.00 (m, 2H), 2.35-2.27 (m, 1H), 2.05 (s, 3H), 1.71-1.60 (m, 1H).

Example 165: (trans)-N-[1-[2-[3-Fluoro-4-(trifluoromethoxy)phenyl]-4-pyridyl]-3-hydroxy-4-piperidyl]acetamide

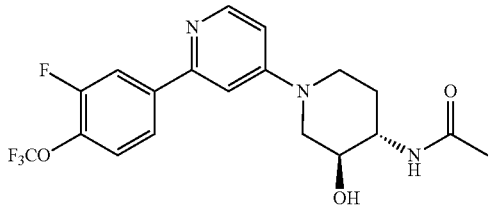 [SMILES: CC(=O)N[C@H]1CCN(c2ccnc(-c3ccc(OC(F)(F)F)c(F)c3)c2)C[C@@H]1O]

The title compound was prepared in a manner analogous to Example 22, using 4-fluoro-2-(3-fluoro-4-(trifluoromethoxy)phenyl)pyridine (Example 11, product from Step A) and using tert-butyl ((3,4-trans)-3-hydroxypiperidin-4-yl)carbamate instead of tert-butyl 2,6-diazaspiro[3.3]heptane-2-carboxylate oxalate in Step A. MS (ESI): mass calcd. for $C_{19}H_{19}F_4N_3O_3$, 413.1; m/z found, 414.1 $[M+H]^+$. $^1$H NMR (400 MHz, Methanol-d$_4$) δ ppm 8.22 (d, J=6.1 Hz, 1H), 7.85 (dd, J=11.6, 2.1 Hz, 1H), 7.77 (ddd, J=8.6, 2.2, 1.2 Hz, 1H), 7.55-7.47 (m, 1H), 7.24 (d, J=2.6 Hz, 1H), 6.87 (dd, J=6.2, 2.6 Hz, 1H), 4.18-4.10 (m, 1H), 4.09-3.99 (m, 1H), 3.85 (s, 1H), 3.56-3.47 (m, 1H), 3.12-3.02 (m, 1H), 2.91 (dd, J=13.2, 10.1 Hz, 1H), 2.07-1.99 (m, 1H), 1.97 (s, 3H), 1.57-1.44 (m, 1H).

Example 166: (racemic)-N-[1-[2-[3-Fluoro-4-(trifluoromethoxy)phenyl]-4-pyridyl]-3-methyl-4-piperidyl]acetamide

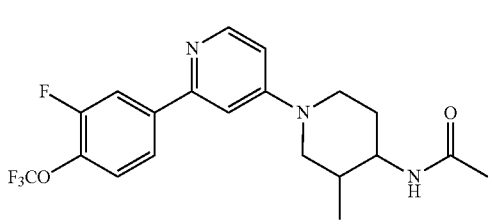 [SMILES: CC(=O)NC1CCN(c2ccnc(-c3ccc(OC(F)(F)F)c(F)c3)c2)CC1C]

The title compound was prepared in a manner analogous to Example 22, using 4-fluoro-2-(3-fluoro-4-(trifluoromethoxy)phenyl)pyridine (Example 11, product from Step A) and using tert-butyl (3-methylpiperidin-4-yl)carbamate instead of tert-butyl 2,6-diazaspiro[3.3]heptane-2-carboxylate oxalate in Step A. MS (ESI): mass calcd. for $C_{20}H_{21}F_4N_3O_2$, 411.2; m/z found, 412.2 $[M+H]^+$. $^1$H NMR (500 MHz, Methanol-d$_4$) δ ppm 8.21-8.16 (m, 1H), 7.87-7.80 (m, 1H), 7.77-7.73 (m, 1H), 7.51-7.46 (m, 1H), 7.23-7.19 (m, 1H), 6.87-6.82 (m, 1H), 4.17-4.04 (m, 1.6H), 3.69-3.60 (m, 1H), 3.54-3.38 (m, 1H), 3.01 (td, J=13.1, 2.7 Hz, 0.6H), 2.69 (dd, J=13.5, 11.3 Hz, 0.6H), 2.20-2.11 (m, 0.4H), 2.02-1.90 (m, 3.6H), 1.87-1.72 (m, 1H), 1.68-1.57 (m, 0.6H), 1.53-1.43 (m, 0.6H), 1.03-0.92 (m, 3H).

Example 167: (trans)-N-[1-[2-[3-Fluoro-4-(trifluoromethoxy)phenyl]-4-pyridyl]-3-methyl-4-piperidyl]acetamide

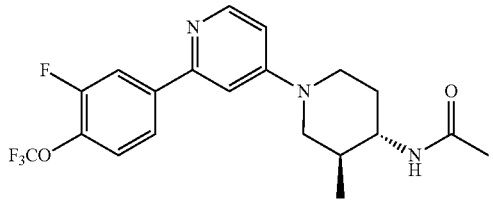 [SMILES: CC(=O)N[C@H]1CCN(c2ccnc(-c3ccc(OC(F)(F)F)c(F)c3)c2)C[C@@H]1C]

(racemic)-N-[1-[2-[3-Fluoro-4-(trifluoromethoxy)phenyl]-4-pyridyl]-3-methyl-4-piperidyl]acetamide (Example 166) was separated via SFC chiral separation (Stationary phase: Whelk O1 SS 5 µm 250×21 mm, Mobile phase: 20% isopropanol, 80% $CO_2$, 2 mL/min, 150 Bar, retention time: 20.09 min at 254 nM) to afford the tile compound (7 mg, 11%). MS (ESI): mass calcd. for $C_{20}H_{21}F_4N_3O_2$, 411.2; m/z found, 412.1 $[M+H]^+$. $^1H$ NMR (400 MHz, Methanol-$d_4$) δ ppm 8.20 (d, J=6.2 Hz, 1H), 7.85 (dd, J=11.6, 2.1 Hz, 1H), 7.79-7.74 (m, 1H), 7.54-7.46 (m, 1H), 7.23 (d, J=2.5 Hz, 1H), 6.87 (dd, J=6.2, 2.5 Hz, 1H), 4.18-4.05 (m, 2H), 3.70-3.60 (m, 1H), 3.09-2.99 (m, 1H), 2.76-2.68 (m, 1H), 1.99-1.91 (m, 4H), 1.70-1.59 (m, 1H), 1.55-1.42 (m, 1H), 1.00 (d, J=6.5 Hz, 3H).

Example 168: (cis)-N-[1-[2-[3-Fluoro-4-(trifluoromethoxy)phenyl]-4-pyridyl]-3-methyl-4-piperidyl]acetamide

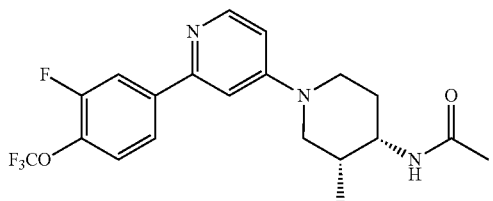

(racemic)-N-[1-[2-[3-Fluoro-4-(trifluoromethoxy)phenyl]-4-pyridyl]-3-methyl-4-piperidyl]acetamide (Example 166) was separated via SFC chiral separation (Stationary phase: Whelk O1 SS 5 µm 250×21 mm, Mobile phase: 20% isopropanol, 80% $CO_2$, 2 mL/min, 150 Bar, retention time: 26.42 min at 254 nM) to afford the tile compound (12 mg, 18%). MS (ESI): mass calcd. for $C_{20}H_{21}F_4N_3O_2$, 411.2; m/z found, 412.1 $[M+H]^+$. $^1H$ NMR (400 MHz, Methanol-$d_4$) δ ppm 8.18 (d, J=6.2 Hz, 1H), 7.84 (dd, J=11.6, 2.1 Hz, 1H), 7.79-7.73 (m, 1H), 7.54-7.46 (m, 1H), 7.22 (d, J=2.5 Hz, 1H), 6.87 (dd, J=6.3, 2.6 Hz, 1H), 4.19-4.11 (m, 1H), 3.72-3.63 (m, 1H), 3.57-3.40 (m, 3H), 2.22-2.11 (m, 1H), 2.00 (d, J=1.6 Hz, 3H), 1.88-1.72 (m, 2H), 0.96 (d, J=7.0 Hz, 3H).

Example 169: N-[[1-[2-[3-Fluoro-4-(trifluoromethoxy)phenyl]-4-pyridyl]azetidin-3-yl]methyl]acetamide

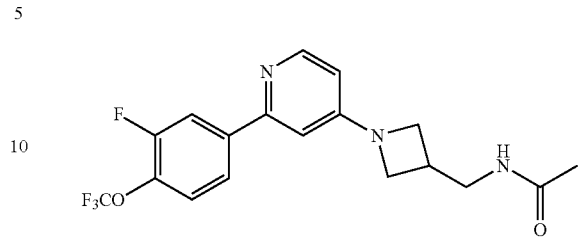

The title compound was prepared in a manner analogous to Example 22, using 4-fluoro-2-(3-fluoro-4-(trifluoromethoxy)phenyl)pyridine (Example 11, product from Step A) and using tert-butyl (azetidin-3-ylmethyl)carbamate instead of tert-butyl 2,6-diazaspiro[3.3]heptane-2-carboxylate oxalate in Step A. MS (ESI): mass calcd. for $C_{18}H_{17}F_4N_3O_2$, 383.1; m/z found, 384.1 $[M+H]^+$. $^1H$ NMR (500 MHz, Methanol-$d_4$) δ ppm 8.15 (d, J=5.8 Hz, 1H), 7.81 (dd, J=11.6, 2.1 Hz, 1H), 7.73 (ddd, J=8.5, 2.1, 1.2 Hz, 1H), 7.51-7.46 (m, 1H), 6.73 (d, J=2.2 Hz, 1H), 6.36 (dd, J=5.8, 2.3 Hz, 1H), 4.09 (t, J=8.1 Hz, 2H), 3.75 (dd, J=8.2, 5.1 Hz, 2H), 3.47 (d, J=7.0 Hz, 2H), 3.02-2.92 (m, 1H), 1.95 (s, 3H).

Example 170: (racemic)-N-[[1-[2-[3-Fluoro-4-(trifluoromethoxy)phenyl]-4-pyridyl]pyrrolidin-3-yl]methyl]acetamide

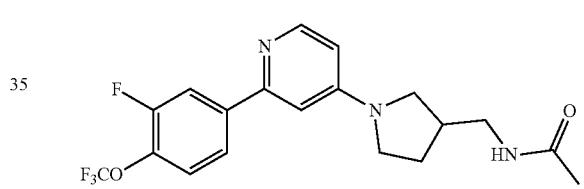

The title compound was prepared in a manner analogous to Example 22, using 4-fluoro-2-(3-fluoro-4-(trifluoromethoxy)phenyl)pyridine (Example 11, product from Step A) and using tert-butyl (pyrrolidin-3-ylmethyl)carbamate instead of tert-butyl 2,6-diazaspiro[3.3]heptane-2-carboxylate oxalate in Step A. MS (ESI): mass calcd. for $C_{19}H_{19}F_4N_3O_2$, 397.1; m/z found, 398.1 $[M+H]^+$. $^1H$ NMR (400 MHz, Chloroform-d) δ ppm 8.23 (d, J=5.8 Hz, 1H), 7.75 (dd, J=11.4, 2.1 Hz, 1H), 7.70-7.64 (m, 1H), 7.36-7.28 (m, 1H), 6.65 (d, J=2.3 Hz, 1H), 6.32 (dd, J=5.9, 2.3 Hz, 1H), 6.23-6.16 (m, 1H), 3.50-3.20 (m, 5H), 3.07 (dd, J=9.8, 6.8 Hz, 1H), 2.62-2.51 (m, 1H), 2.19-2.08 (m, 1H), 1.99 (s, 3H), 1.84-1.71 (m, 1H).

Example 171: (racemic)-N-[1-[2-[3-Fluoro-4-(trifluoromethoxy)phenyl]-4-pyridyl]-3-piperidyl]acetamide

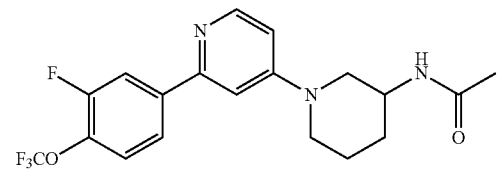 [SMILES: CC(=O)NC1CCCN(c2ccnc(-c3ccc(OC(F)(F)F)c(F)c3)c2)C1]

The title compound was prepared in a manner analogous to Example 22, using 4-fluoro-2-(3-fluoro-4-(trifluoromethoxy)phenyl)pyridine (Example 11, product from Step A) and using tert-butyl piperidin-3-ylcarbamate instead of tert-butyl 2,6-diazaspiro[3.3]heptane-2-carboxylate oxalate in Step A. MS (ESI): mass calcd. for $C_{19}H_{19}F_4N_3O_2$, 397.1; m/z found, 398.1 [M+H]+. 1H NMR (500 MHz, Chloroform-d) δ ppm 8.32 (d, J=5.9 Hz, 1H), 7.83 (dd, J=11.4, 2.1 Hz, 1H), 7.73 (ddd, J=8.6, 2.2, 1.2 Hz, 1H), 7.39-7.33 (m, 1H), 7.11 (d, J=2.5 Hz, 1H), 6.69 (dd, J=6.0, 2.5 Hz, 1H), 5.66 (d, J=7.4 Hz, 1H), 4.08-3.99 (m, 1H), 3.84-3.78 (m, 1H), 3.59-3.51 (m, 1H), 3.27-3.19 (m, 1H), 3.08 (dd, J=12.9, 7.9 Hz, 1H), 1.98 (s, 3H), 1.97-1.92 (m, 1H), 1.83-1.76 (m, 1H), 1.75-1.66 (m, 1H), 1.64-1.54 (m, 1H).

Example 172: (racemic)-N-[1-[2-[3-Fluoro-4-(trifluoromethoxy)phenyl]-4-pyridyl]-3,3-dimethyl-4-piperidyl]acetamide

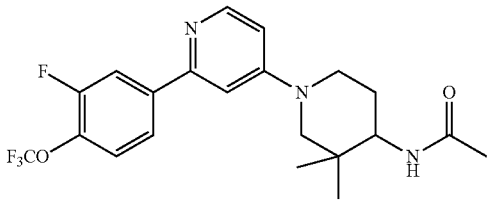 [SMILES: CC(=O)NC1CCN(c2ccnc(-c3ccc(OC(F)(F)F)c(F)c3)c2)CC1(C)C]

The title compound was prepared in a manner analogous to Example 22, using 4-fluoro-2-(3-fluoro-4-(trifluoromethoxy)phenyl)pyridine (Example 11, product from Step A) and using tert-butyl (3,3-dimethylpiperidin-4-yl)carbamate instead of tert-butyl 2,6-diazaspiro[3.3]heptane-2-carboxylate oxalate in Step A. MS (ESI): mass calcd. for $C_{21}H_{23}F_4N_3O_2$, 425.2; m/z found, 426.2 [M+H]+. 1H NMR (500 MHz, Methanol-d4) δ ppm 8.16 (d, J=6.2 Hz, 1H), 7.83 (dd, J=11.7, 2.1 Hz, 1H), 7.75 (ddd, J=8.6, 2.1, 1.2 Hz, 1H), 7.52-7.46 (m, 1H), 7.19 (d, J=2.6 Hz, 1H), 6.84 (dd, J=6.2, 2.6 Hz, 1H), 4.11-4.04 (m, 1H), 3.92-3.86 (m, 1H), 3.78 (dd, J=13.5, 2.4 Hz, 1H), 3.10-3.01 (m, 1H), 2.86 (d, J=13.5 Hz, 1H), 1.99 (s, 3H), 1.77-1.68 (m, 2H), 0.95 (d, J=23.7 Hz, 6H).

Example 173: N-[[1-[2-[3-Fluoro-4-(trifluoromethoxy)phenyl]-4-pyridyl]-4-piperidyl]methyl]acetamide

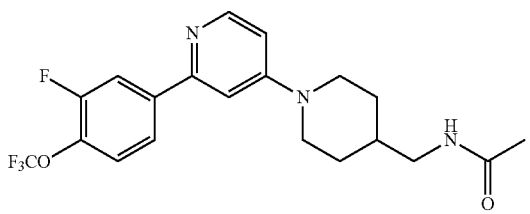 [SMILES: CC(=O)NCC1CCN(c2ccnc(-c3ccc(OC(F)(F)F)c(F)c3)c2)CC1]

The title compound was prepared in a manner analogous to Example 22, using 4-fluoro-2-(3-fluoro-4-(trifluoromethoxy)phenyl)pyridine (Example 11, product from Step A) and using tert-butyl (piperidin-4-ylmethyl)carbamate instead of tert-butyl 2,6-diazaspiro[3.3]heptane-2-carboxylate oxalate in Step A. MS (ESI): mass calcd. for $C_{20}H_{21}F_4N_3O_2$, 411.2; m/z found, 412.1 [M+H]+. 1H NMR (600 MHz, Chloroform-d) δ ppm 8.31 (d, J=5.9 Hz, 1H), 7.78 (dd, J=11.3, 2.1 Hz, 1H), 7.69 (ddd, J=8.5, 2.1, 1.2 Hz, 1H), 7.38-7.32 (m, 1H), 7.00 (d, J=2.5 Hz, 1H), 6.64 (dd, J=6.0, 2.5 Hz, 1H), 5.66 (s, 1H), 4.00-3.90 (m, 2H), 3.18 (t, J=6.3 Hz, 2H), 2.95-2.83 (m, 2H), 1.99 (s, 3H), 1.85-1.75 (m, 3H), 1.37-1.25 (m, 2H).

Example 174: (racemic)-N-[[1-[2-[3-Fluoro-4-(trifluoromethoxy)phenyl]-4-pyridyl]-3-piperidyl]methyl]acetamide

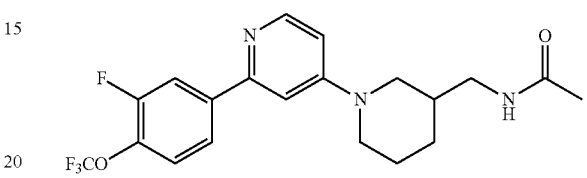

The title compound was prepared in a manner analogous to Example 22, using 4-fluoro-2-(3-fluoro-4-(trifluoromethoxy)phenyl)pyridine (Example 11, product from Step A) and using tert-butyl (piperidin-3-ylmethyl)carbamate instead of tert-butyl 2,6-diazaspiro[3.3]heptane-2-carboxylate oxalate in Step A. MS (ESI): mass calcd. for $C_{20}H_{21}F_4N_3O_2$, 411.2; m/z found, 412.1 [M+H]+. 1H NMR (500 MHz, Chloroform-d) δ ppm 8.26 (d, J=6.0 Hz, 1H), 7.75 (dd, J=11.4, 2.1 Hz, 1H), 7.66 (ddd, J=8.5, 2.1, 1.2 Hz, 1H), 7.36-7.30 (m, 1H), 6.97 (d, J=2.5 Hz, 1H), 6.60 (dd, J=6.0, 2.5 Hz, 1H), 6.15-6.09 (m, 1H), 3.83-3.74 (m, 2H), 3.25-3.11 (m, 2H), 2.94-2.86 (m, 1H), 2.67 (dd, J=13.0, 10.2 Hz, 1H), 1.99 (s, 3H), 1.88-1.74 (m, 3H), 1.61-1.51 (m, 1H), 1.28-1.18 (m, 1H).

Example 175: 1-[2-[2-[3-(Difluoromethyl)-4-fluorophenyl]-4-pyridyl]-2,6-diazaspiro[3.3]heptan-6-yl]ethanone

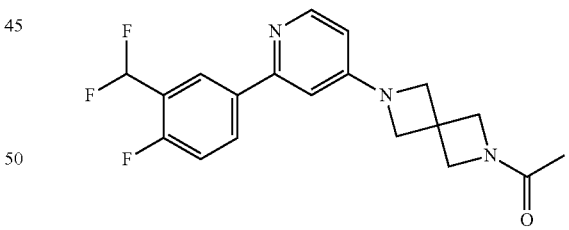

The title compound was prepared in a manner analogous to Example 23, using 1-(6-(2-chloropyridin-4-yl)-2,6-diazaspiro[3.3]heptan-2-yl)ethan-1-one and 2-(3-(difluoromethyl)-4-fluorophenyl)-4,4,5,5-tetramethyl-1,3,2-dioxaborolane (Intermediate 2) instead of 2-(4-(difluoromethoxy)-3-fluorophenyl)-4,4,5,5-tetramethyl-1,3,2-dioxaborolane in Step C. MS (ESI): mass calcd. for $C_{19}H_{18}F_3N_3O$, 361.1; m/z found, 362.2 [M+H]+. 1H NMR (400 MHz, Methanol-d4) δ ppm 8.19 (d, J=5.8 Hz, 1H), 8.13-8.07 (m, 1H), 8.07-8.00 (m, 1H), 7.38-7.31 (m, 1H), 7.06 (t, J=54.7 Hz, 1H), 6.77 (d, J=2.3 Hz, 1H), 6.43 (dd, J=5.8, 2.3 Hz, 1H), 4.45 (s, 2H), 4.26-4.17 (m, 6H), 1.90 (s, 3H).

Example 176: 1-[2-[2-[4-(Trifluoromethoxy)phenyl]-4-pyridyl]-2,6-diazaspiro[3.3]heptan-6-yl]ethanone

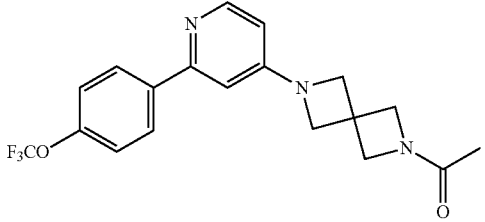 [SMILES: CC(=O)N1CC2(C1)CN(c1ccnc(-c3ccc(OC(F)(F)F)cc3)c1)C2]

The title compound was prepared in a manner analogous to Example 23, using 1-(6-(2-chloropyridin-4-yl)-2,6-diazaspiro[3.3]heptan-2-yl)ethan-1-one and (4-(trifluoromethoxy)phenyl)boronic acid instead of 2-(4-(difluoromethoxy)-3-fluorophenyl)-4,4,5,5-tetramethyl-1,3,2-dioxaborolane in Step C. MS (ESI): mass calcd. for $C_{19}H_{18}F_3N_3O_2$, 377.1; m/z found, 378.2 [M+H]$^+$. $^1$H NMR (400 MHz, Methanol-d$_4$) δ ppm 8.19 (d, J=5.8 Hz, 1H), 8.13-8.07 (m, 1H), 8.07-8.00 (m, 1H), 7.38-7.31 (m, 1H), 7.06 (t, J=54.7 Hz, 1H), 6.77 (d, J=2.3 Hz, 1H), 6.43 (dd, J=5.8, 2.3 Hz, 1H), 4.45 (s, 2H), 4.26-4.17 (m, 6H), 1.90 (s, 3H).

Example 177: 1-[2-[[2-[3-Fluoro-4-(trifluoromethoxy)phenyl]-4-pyridyl]amino]-6-azaspiro[3.3]heptan-6-yl]ethanone

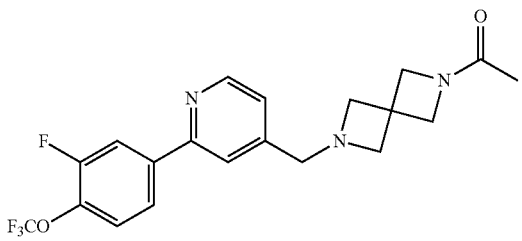 [SMILES: CC(=O)N1CC2(CN(Cc3ccnc(-c4ccc(OC(F)(F)F)c(F)c4)c3)C2)C1]

The title compound was prepared in a manner analogous to Example 23, using tert-butyl 6-amino-2-azaspiro[3.3]heptane-2-carboxylate hydrochloride instead of tert-butyl 2,6-diazaspiro[3.3]heptane-2-carboxylate oxalate in Step A; and using (3-fluoro-4-(trifluoromethoxy)phenyl)boronic acid instead of 2-(4-(difluoromethoxy)-3-fluorophenyl)-4,4,5,5-tetramethyl-1,3,2-dioxaborolane in Step C. MS (ESI): mass calcd. for $C_{20}H_{19}F_4N_3O_2$, 409.1; m/z found, 410.2 [M+H]$^+$. $^1$H NMR (400 MHz, DMSO-d$_6$) δ ppm 8.14 (d, J=5.6 Hz, 1H), 8.05 (dt, J=12.1, 2.3 Hz, 1H), 7.92 (d, J=8.6 Hz, 1H), 7.67-7.60 (m, 1H), 7.00-6.91 (m, 2H), 6.50-6.43 (m, 1H), 4.20 (s, 1H), 4.11-4.05 (m, 1H), 3.99-3.90 (m, 2H), 3.79 (s, 1H), 2.73-2.62 (m, 2H), 2.11-2.01 (m, 2H), 1.77-1.71 (m, 3H).

Example 178: N-[6-[2-[3-Fluoro-4-(trifluoromethoxy)phenyl]-4-pyridyl]-6-azaspiro[3.3]heptan-2-yl]acetamide

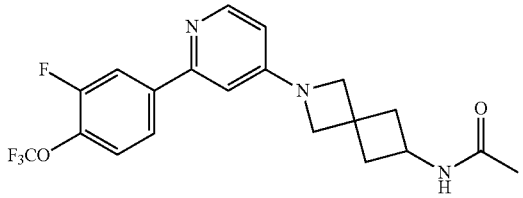 [SMILES: CC(=O)NC1CC2(C1)CN(c1ccnc(-c3ccc(OC(F)(F)F)c(F)c3)c1)C2]

The title compound was prepared in a manner analogous to Example 23, Steps A and D, using N-(2-azaspiro[3.3]heptan-6-yl)acetamide instead of tert-butyl 2,6-diazaspiro[3.3]heptane-2-carboxylate oxalate in Step A; 3-fluoro-4-(trifluoromethoxy)phenyl)boronic acid instead of 2-(4-(difluoromethoxy)-3-fluorophenyl)-4,4,5,5-tetramethyl-1,3,2-dioxaborolane in Step D. MS (ESI): mass calcd. for $C_{20}H_{19}F_4N_3O_2$, 409.1; m/z found, 410.2 [M+H]$^+$. $^1$H NMR (400 MHz, DMSO-d$_6$) δ ppm 8.22 (d, J=5.6 Hz, 1H), 8.16-8.08 (m, 2H), 8.00 (ddd, J=8.6, 2.1, 1.1 Hz, 1H), 7.67-7.60 (m, 1H), 6.95-6.91 (m, 1H), 6.35 (dd, J=5.6, 2.1 Hz, 1H), 4.10 (q, J=7.8 Hz, 1H), 4.04 (s, 2H), 3.93 (s, 2H), 2.54-2.52 (m, 2H), 2.12 (td, J=8.9, 3.0 Hz, 2H), 1.78 (s, 3H).

Example 179: N-[3-[[2-[3-Fluoro-4-(trifluoromethoxy)phenyl]-4-pyridyl]amino]cyclobutyl]acetamide

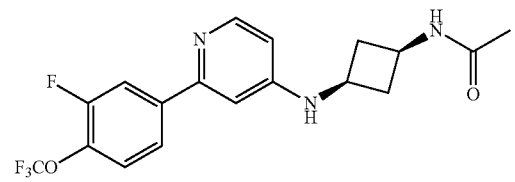

The title compound was prepared in a manner analogous to Example 22, using 4-fluoro-2-(3-fluoro-4-(trifluoromethoxy)phenyl)pyridine (Example 11, product from Step A) and using tert-butyl ((1,3-cis)-3-aminocyclobutyl)carbamate instead of tert-butyl 2,6-diazaspiro[3.3]heptane-2-carboxylate oxalate in Step A. MS (ESI): mass calcd. for $C_{18}H_{17}F_4N_3O_2$, 383.1; m/z found, 384.1 [M+H]$^+$. $^1$H NMR (500 MHz, Chloroform-d) δ ppm 8.29 (d, J=5.7 Hz, 1H), 7.80 (dd, J=11.3, 2.1 Hz, 1H), 7.73-7.66 (m, 1H), 7.41-7.34 (m, 1H), 6.77 (d, J=2.2 Hz, 1H), 6.42 (dd, J=5.8, 2.3 Hz, 1H), 5.75-5.59 (m, 1H), 4.72-4.58 (m, 1H), 4.32-4.16 (m, 1H), 3.87-3.69 (m, 1H), 3.09-2.93 (m, 2H), 1.99 (s, 3H), 1.93-1.82 (m, 2H).

Example 180: (trans)-N-[3-[[2-[3-Fluoro-4-(trifluoromethoxy)phenyl]-4-pyridyl]amino]cyclopentyl]acetamide

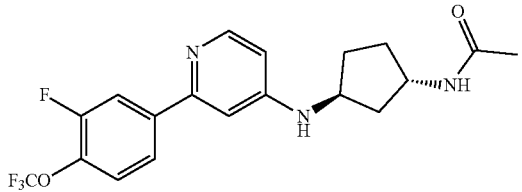 [SMILES: CC(=O)N[C@H]1CC[C@H](Nc2ccnc(-c3ccc(OC(F)(F)F)c(F)c3)c2)C1]

The title compound was prepared in a manner analogous to Example 22, using 4-fluoro-2-(3-fluoro-4-(trifluoromethoxy)phenyl)pyridine (Example 11, product from Step A) and using tert-butyl ((1,3-trans)-3-aminocyclopentyl)carbamate instead of tert-butyl 2,6-diazaspiro[3.3]heptane-2-carboxylate oxalate in Step A. MS (ESI): mass calcd. for $C_{19}H_{19}F_4N_3O_2$, 397.1; m/z found, 398.2 [M+H]$^+$. $^1$H NMR (300 MHz, DMSO-$d_6$) δ ppm 8.13 (d, J=5.7 Hz, 1H), 8.03 (dd, J=12.1, 2.1 Hz, 1H), 7.95-7.82 (m, 2H), 7.69-7.57 (m, 1H), 7.02 (d, J=2.1 Hz, 1H), 6.77 (d, J=6.8 Hz, 1H), 6.51 (dd, J=5.8, 2.1 Hz, 1H), 4.26-4.10 (m, 1H), 4.10-3.92 (m, 1H), 2.23-2.08 (m, 1H), 2.08-1.90 (m, 1H), 1.86-1.70 (m, 2H), 1.79 (s, 3H), 1.56-1.29 (m, 2H).

Example 181: (cis)-N-[3-[[2-[3-Fluoro-4-(trifluoromethoxy)phenyl]-4-pyridyl]amino]cyclopentyl] acetamide

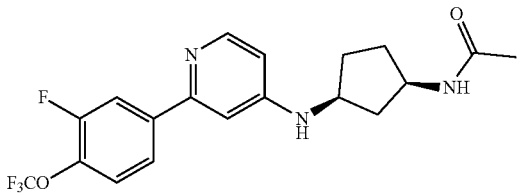 [SMILES: CC(=O)N[C@@H]1CC[C@H](Nc2ccnc(-c3ccc(OC(F)(F)F)c(F)c3)c2)C1]

The title compound was prepared in a manner analogous to Example 22, using 4-fluoro-2-(3-fluoro-4-(trifluoromethoxy)phenyl)pyridine (Example 11, product from Step A) and using tert-butyl ((1,3-cis)-3-aminocyclopentyl)carbamate instead of tert-butyl 2,6-diazaspiro[3.3]heptane-2-carboxylate oxalate in Step A. MS (ESI): mass calcd. for $C_{19}H_{19}F_4N_3O_2$, 397.1; m/z found, 398.1 [M+H]$^+$. $^1$H NMR (300 MHz, DMSO-$d_6$) δ ppm 8.12 (d, J=5.7 Hz, 1H), 8.05 (dd, J=12.2, 2.1 Hz, 1H), 7.97-7.83 (m, 2H), 7.70-7.56 (m, 1H), 7.05 (d, J=2.2 Hz, 1H), 6.74 (d, J=6.8 Hz, 1H), 6.51 (dd, J=5.8, 2.1 Hz, 1H), 4.13-3.93 (m, 1H), 3.97-3.77 (m, 1H), 2.50-2.30 (m, 1H), 2.11-1.79 (m, 2H), 1.79 (s, 3H), 1.65-1.44 (m, 2H), 1.40-1.20 (m, 1H).

Example 182: (trans)-N-[3-[[2-[3-Fluoro-4-(trifluoromethoxy)phenyl]-4-pyridyl]amino]cyclohexyl] acetamide

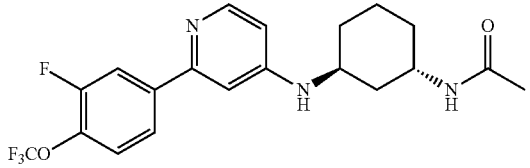 [SMILES: CC(=O)N[C@H]1CCC[C@H](Nc2ccnc(-c3ccc(OC(F)(F)F)c(F)c3)c2)C1]

The title compound was prepared in a manner analogous to Example 22, using 4-fluoro-2-(3-fluoro-4-(trifluoromethoxy)phenyl)pyridine (Example 11, product from Step A) and using tert-butyl ((1,3-trans)-3-aminocyclohexyl)carbamate instead of tert-butyl 2,6-diazaspiro[3.3]heptane-2-carboxylate oxalate in Step A. MS (ESI): mass calcd. for $C_{20}H_{21}F_4N_3O_2$, 411.2; m/z found, 412.1 [M+H]$^+$. $^1$H NMR (500 MHz, Chloroform-d) δ ppm 8.26 (d, J=5.7 Hz, 1H), 7.79 (dd, J=11.4, 2.1 Hz, 1H), 7.72-7.67 (m, 1H), 7.39-7.32 (m, 1H), 6.79 (d, J=2.3 Hz, 1H), 6.43 (dd, J=5.8, 2.3 Hz, 1H), 5.41 (d, J=7.7 Hz, 1H), 4.49 (s, 1H), 4.19-4.09 (m, 1H), 3.81 (s, 1H), 2.00 (s, 3H), 1.95-1.86 (m, 2H), 1.83-1.62 (m, 5H), 1.42-1.32 (m, 1H).

Example 183: (cis)-N-[3-[[2-[3-Fluoro-4-(trifluoromethoxy)phenyl]-4-pyridyl]amino]cyclohexyl] acetamide

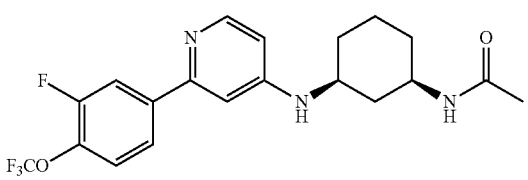 [SMILES: CC(=O)N[C@@H]1CCC[C@H](Nc2ccnc(-c3ccc(OC(F)(F)F)c(F)c3)c2)C1]

The title compound was prepared in a manner analogous to Example 22, using 4-fluoro-2-(3-fluoro-4-(trifluoromethoxy)phenyl)pyridine (Example 11, product from Step A) and using tert-butyl ((1,3-cis)-3-aminocyclohexyl)carbamate instead of tert-butyl 2,6-diazaspiro[3.3]heptane-2-carboxylate oxalate in Step A. MS (ESI): mass calcd. for $C_{20}H_{21}F_4N_3O_2$, 411.2; m/z found, 412.2 [M+H]$^+$. $^1$H NMR (300 MHz, DMSO-$d_6$) δ ppm 8.10 (d, J=5.7 Hz, 1H), 8.06 (dd, J=12.4, 2.3 Hz, 1H), 7.99-7.86 (m, 1H), 7.77 (d, J=7.8 Hz, 1H), 7.68-7.57 (m, 1H), 7.08 (d, J=2.1 Hz, 1H), 6.62-6.45 (m, 2H), 3.79-3.62 (m, 1H), 3.64-3.44 (m, 1H), 2.13-1.97 (m, 1H), 1.98-1.85 (m, 1H), 1.85-1.66 (m, 2H), 1.77 (s, 3H), 1.53-1.30 (m, 1H), 1.21-0.91 (m, 3H).

Example 184: N-[4-[[2-[3-Fluoro-4-(trifluoromethoxy)phenyl]-4-pyridyl]amino]cyclohexyl] acetamide

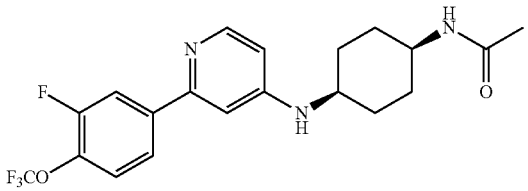 [SMILES: CC(=O)N[C@H]1CC[C@@H](Nc2ccnc(-c3ccc(OC(F)(F)F)c(F)c3)c2)CC1]

The title compound was prepared in a manner analogous to Example 22, using 4-fluoro-2-(3-fluoro-4-(trifluoromethoxy)phenyl)pyridine (Example 11, product from Step A) and using tert-butyl ((1,4-cis)-4-aminocyclohexyl)carbamate instead of tert-butyl 2,6-diazaspiro[3.3]heptane-2-carboxylate oxalate in Step A. MS (ESI): mass calcd. for $C_{20}H_{21}F_4N_3O_2$, 411.2; m/z found, 412.1 [M+H]$^+$. $^1$H NMR (500 MHz, Chloroform-d) δ ppm 8.27 (d, J=5.8 Hz, 1H), 7.77 (dd, J=11.4, 2.1 Hz, 1H), 7.68 (ddd, J=8.6, 2.2, 1.2 Hz, 1H), 7.38-7.32 (m, 1H), 6.78 (d, J=2.2 Hz, 1H), 6.43 (dd, J=5.7, 2.3 Hz, 1H), 5.47 (d, J=7.6 Hz, 1H), 4.30 (d, J=7.1 Hz, 1H), 4.00-3.91 (m, 1H), 3.67-3.59 (m, 1H), 1.99 (s, 3H), 1.91-1.79 (m, 4H), 1.76-1.67 (m, 2H), 1.64-1.54 (m, 2H).

Example 185: N-[4-[[2-[3-Fluoro-4-(trifluoromethoxy)phenyl]-4-pyridyl]amino]cyclohexyl]acetamide

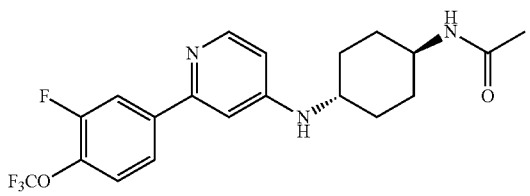 [SMILES: CC(=O)N[C@H]1CC[C@H](Nc2ccnc(-c3ccc(OC(F)(F)F)c(F)c3)c2)CC1]

The title compound was prepared in a manner analogous to Example 22, using 4-fluoro-2-(3-fluoro-4-(trifluoromethoxy)phenyl)pyridine (Example 11, product from Step A) and using tert-butyl ((1,4-trans)-4-aminocyclohexyl)carbamate instead of tert-butyl 2,6-diazaspiro[3.3]heptane-2-carboxylate oxalate in Step A. MS (ESI): mass calcd. for $C_{20}H_{21}F_4N_3O_2$, 411.2; m/z found, 412.1 [M+H]$^+$. $^1$H NMR (400 MHz, Chloroform-d) δ ppm 8.25 (d, J=5.7 Hz, 1H), 7.77 (dd, J=11.4, 2.1 Hz, 1H), 7.68 (ddd, J=8.6, 2.1, 1.2 Hz, 1H), 7.38-7.31 (m, 1H), 6.75 (d, J=2.2 Hz, 1H), 6.41 (dd, J=5.8, 2.3 Hz, 1H), 5.36 (d, J=8.1 Hz, 1H), 4.20 (d, J=7.9 Hz, 1H), 3.88-3.76 (m, 1H), 3.42-3.29 (m, 1H), 2.22-2.05 (m, 4H), 1.98 (s, 3H), 1.42-1.21 (m, 4H).

Example 186: 1-[3-[[[2-[3-Fluoro-4-(trifluoromethoxy)phenyl]-4-pyridyl]amino]methyl]azetidin-1-yl]ethanone

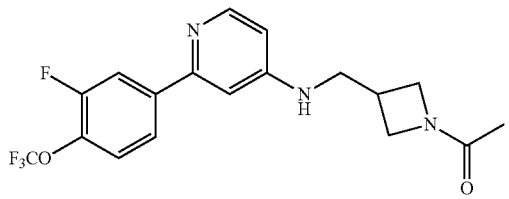 [SMILES: CC(=O)N1CC(CNc2ccnc(-c3ccc(OC(F)(F)F)c(F)c3)c2)C1]

The title compound was prepared in a manner analogous to Example 22, using 4-fluoro-2-(3-fluoro-4-(trifluoromethoxy)phenyl)pyridine (Example 11, product from Step A) and using tert-butyl 3-(aminomethyl)azetidine-1-carboxylate instead of tert-butyl 2,6-diazaspiro[3.3]heptane-2-carboxylate oxalate in Step A. MS (ESI): mass calcd. for $C_{18}H_{17}F_4N_3O_2$, 383.1; m/z found, 384.1 [M+H]$^+$. $^1$H NMR (500 MHz, Chloroform-d) δ ppm 8.24 (d, J=5.7 Hz, 1H), 7.74 (dd, J=11.4, 2.1 Hz, 1H), 7.66 (ddd, J=8.6, 2.2, 1.2 Hz, 1H), 7.37-7.28 (m, 1H), 6.80 (d, J=2.2 Hz, 1H), 6.43 (dd, J=5.7, 2.3 Hz, 1H), 5.05 (t, J=5.7 Hz, 1H), 4.23 (t, J=8.4 Hz, 1H), 4.13-4.06 (m, 1H), 3.84 (dd, J=8.6, 5.1 Hz, 1H), 3.73 (dd, J=10.0, 5.2 Hz, 1H), 3.44-3.39 (m, 2H), 2.89 (ddt, J=9.9, 7.9, 3.8 Hz, 1H), 1.84 (s, 3H).

Example 187: N-[1-[[[2-[3-Fluoro-4-(trifluoromethoxy)phenyl]-4-pyridyl]amino]methyl]-3-bicyclo[1.1.1]pentanyl]acetamide

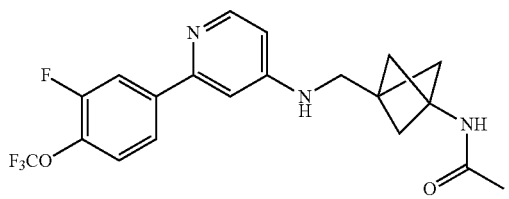 [SMILES: CC(=O)NC12CC(CNc3ccnc(-c4ccc(OC(F)(F)F)c(F)c4)c3)(C1)C2]

To a solution of 4-fluoro-2-(3-fluoro-4-(trifluoromethoxy)phenyl)pyridine (Example 11, product of Step A) (43 mg, 0.15 mmol) and N-(3-(aminomethyl)bicyclo[1.1.1]pentan-1-yl)acetamide trifluoroacetic salt (Intermediate 3) (46 mg, 0.17 mmol) in 1-butanol (0.8 mL) was added DIPEA (80 μL, 0.47 mmol). The reaction mixture was then heated to 130° C. for 5 days. Solvent was evaporated and purification by basic prep HPLC (Agilent, Waters XBridge C18 5 um 50×100 mm column, 5-90% MeCN/20 mM NH$_4$OH over 15 min, 80 mL/min) gave the title compound (25 mg, 64%). MS (ESI): mass calcd. for $C_{20}H_{19}F_4N_3O_2$, 409.1; m/z found, 410.2 [M+H]$^+$. $^1$H NMR (500 MHz, Methanol-d$_4$) δ ppm 6.79 (d, J=6.0 Hz, 1H), 6.48 (dd, J=11.6, 2.1 Hz, 1H), 6.21 (td, J=8.7, 8.2, 1.3 Hz, 1H), 5.67 (d, J=2.3 Hz, 1H), 5.32-5.27 (m, 1H), 2.12 (s, 2H), 0.73 (s, 6H), 0.57 (s, 3H), 6.43-6.39 (m, 1H).

Example 188: N-[2-[[2-[3-Fluoro-4-(trifluoromethoxy)phenyl]-4-pyridyl]amino]ethyl]acetamide

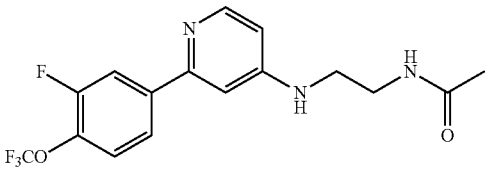 [SMILES: CC(=O)NCCNc1ccnc(-c2ccc(OC(F)(F)F)c(F)c2)c1]

The title compound was prepared in a manner analogous to Example 22, using 4-fluoro-2-(3-fluoro-4-(trifluoromethoxy)phenyl)pyridine (Example 11, product from Step A) and using tert-butyl (2-aminoethyl)carbamate instead of tert-butyl 2,6-diazaspiro[3.3]heptane-2-carboxylate oxalate in Step A. MS (ESI): mass calcd. for $C_{16}H_{15}F_4N_3O_2$, 357.1; m/z found, 358.1 [M+H]$^+$. $^1$H NMR (500 MHz, Chloroform-d) δ ppm 8.25 (d, J=5.7 Hz, 1H), 7.80 (dd, J=11.4, 2.1 Hz, 1H), 7.69 (ddd, J=8.5, 2.1, 1.2 Hz, 1H), 7.37-7.30 (m, 1H), 6.82 (d, J=2.3 Hz, 1H), 6.42 (dd, J=5.7, 2.3 Hz, 1H), 6.05-5.99 (m, 1H), 5.22-5.16 (m, 1H), 3.54 (q, J=5.9 Hz, 2H), 3.33 (q, J=5.5 Hz, 2H), 2.01 (s, 3H).

Example 189: N-[3-[[2-[3-Fluoro-4-(trifluoromethoxy)phenyl]-4-pyridyl]amino]propyl]acetamide

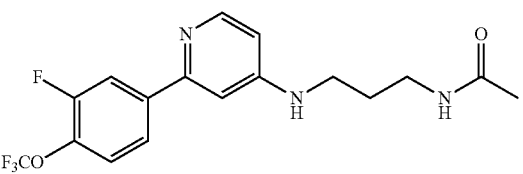 [SMILES: CC(=O)NCCCNc1ccnc(-c2ccc(OC(F)(F)F)c(F)c2)c1]

The title compound was prepared in a manner analogous to Example 22, using 4-fluoro-2-(3-fluoro-4-(trifluoromethoxy)phenyl)pyridine (Example 11, product from Step A) and using tert-butyl (3-aminopropyl)carbamate instead of tert-butyl 2,6-diazaspiro[3.3]heptane-2-carboxylate oxalate in Step A. MS (ESI): mass calcd. for $C_{17}H_{17}F_4N_3O_2$, 371.1; m/z found, 372.1 [M+H]$^+$. $^1$H NMR (600 MHz, Chloroform-d) δ ppm 8.23 (d, J=5.7 Hz, 1H), 7.78 (dd, J=11.4, 2.1 Hz, 1H), 7.67 (ddd, J=8.6, 2.2, 1.2 Hz, 1H), 7.36-7.31 (m, 1H), 6.80 (d, J=2.3 Hz, 1H), 6.43 (dd, J=5.7, 2.3 Hz, 1H), 5.84 (s, 1H), 5.20-5.13 (m, 1H), 3.36 (q, J=6.4 Hz, 2H), 3.24 (q, J=6.2 Hz, 2H), 2.00 (s, 3H), 1.77 (p, J=6.4 Hz, 2H).

Example 190: N-[3-[[2-[3-Fluoro-4-(trifluoromethoxy)phenyl]-4-pyridyl]-methylamino]propyl]acetamide

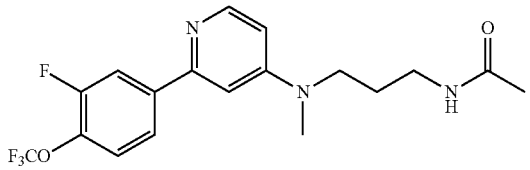 [SMILES: CC(=O)NCCCN(C)c1ccnc(-c2ccc(OC(F)(F)F)c(F)c2)c1]

The title compound was prepared in a manner analogous to Example 22, using 4-fluoro-2-(3-fluoro-4-(trifluoromethoxy)phenyl)pyridine (Example 11, product from Step A) and using tert-butyl (3-(methylamino)propyl)carbamate instead of tert-butyl 2,6-diazaspiro[3.3]heptane-2-carboxylate oxalate in Step A. MS (ESI): mass calcd. for $C_{18}H_{19}F_4N_3O_2$, 385.1; m/z found, 386.1 $[M+H]^+$. $^1$H NMR (500 MHz, Chloroform-d) δ ppm 8.26 (d, J=6.0 Hz, 1H), 7.77 (dd, J=11.4, 2.1 Hz, 1H), 7.68 (ddd, J=8.5, 2.2, 1.2 Hz, 1H), 7.41-7.30 (m, 1H), 6.80 (s, 1H), 6.47 (dd, J=6.0, 2.5 Hz, 1H), 5.81 (s, 1H), 3.44 (t, J=7.4 Hz, 2H), 3.29 (q, J=6.7 Hz, 2H), 3.02 (s, 3H), 1.96 (s, 3H), 1.89-1.76 (m, 2H).

Example 191: (racemic)-N-[3-[[2-[3-Fluoro-4-(trifluoromethoxy)phenyl]-4-pyridyl]amino]butyl]acetamide

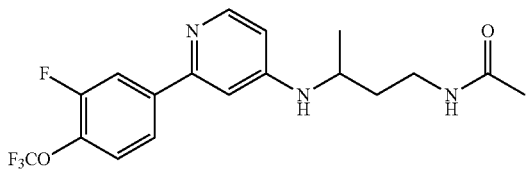 [SMILES: CC(=O)NCCC(C)Nc1ccnc(-c2ccc(OC(F)(F)F)c(F)c2)c1]

The title compound was prepared in a manner analogous to Example 22, using 4-fluoro-2-(3-fluoro-4-(trifluoromethoxy)phenyl)pyridine (Example 11, product from Step A) and using tert-butyl (3-aminobutyl)carbamate instead of tert-butyl 2,6-diazaspiro[3.3]heptane-2-carboxylate oxalate in Step A. MS (ESI): mass calcd. for $C_{18}H_{19}F_4N_3O_2$, 385.1; m/z found, 386.1 $[M+H]^+$. $^1$H NMR (400 MHz, Chloroform-d) δ ppm 8.24 (d, J=5.5 Hz, 1H), 7.77 (dd, J=11.4, 2.1 Hz, 1H), 7.71-7.64 (m, 1H), 7.39-7.30 (m, 1H), 6.78 (d, J=2.3 Hz, 1H), 6.41 (dd, J=5.8, 2.2 Hz, 1H), 5.75 (s, 1H), 4.48 (d, J=8.2 Hz, 1H), 3.72-3.60 (m, 1H), 3.48-3.36 (m, 1H), 3.32-3.22 (m, 1H), 1.96 (s, 3H), 1.83-1.70 (m, 2H), 1.26 (d, J=6.4 Hz, 3H).

Example 192: (racemic)-N-[3-[[2-[3-Fluoro-4-(trifluoromethoxy)phenyl]-4-pyridyl]amino]-2-methyl-propyl]acetamide

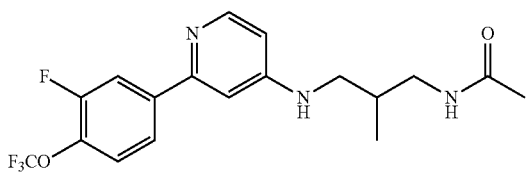 [SMILES: CC(=O)NCC(C)CNc1ccnc(-c2ccc(OC(F)(F)F)c(F)c2)c1]

The title compound was prepared in a manner analogous to Example 22, using 4-fluoro-2-(3-fluoro-4-(trifluoromethoxy)phenyl)pyridine (Example 11, product from Step A) and using tert-butyl (3-amino-2-methylpropyl)carbamate instead of tert-butyl 2,6-diazaspiro[3.3]heptane-2-carboxylate oxalate in Step A. MS (ESI): mass calcd. for $C_{18}H_{19}F_4N_3O_2$, 385.1; m/z found, 386.1 $[M+H]^+$. $^1$H NMR (400 MHz, Chloroform-d) δ ppm 8.21 (d, J=5.7 Hz, 1H), 7.77 (dd, J=11.4, 2.1 Hz, 1H), 7.66 (ddd, J=8.6, 2.1, 1.2 Hz, 1H), 7.37-7.29 (m, 1H), 6.80 (d, J=2.2 Hz, 1H), 6.42 (dd, J=5.8, 2.3 Hz, 1H), 5.99-5.92 (m, 1H), 5.52-5.45 (m, 1H), 3.41-3.31 (m, 1H), 3.21-3.09 (m, 2H), 3.03-2.94 (m, 1H), 2.01 (s, 3H), 1.99-1.90 (m, 1H), 0.96 (d, J=6.9 Hz, 3H).

Example 193: (*R)—N-[3-[[2-[3-Fluoro-4-(trifluoromethoxy)phenyl]-4-pyridyl]amino]-2-methyl-propyl]acetamide

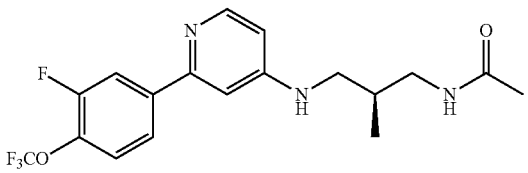

(racemic)-N-[3-[[2-[3-Fluoro-4-(trifluoromethoxy)phenyl]-4-pyridyl]amino]-2-methyl-propyl]acetamide (Example 192) was separated via SFC chiral separation (Stationary phase: Chiralpak AD-H 5 μm 250×30 mm, Mobile phase: 90% $CO_2$, 10% MeOH (0.3% $iPrNH_2$), 2 mL/min, 150 Bar, retention time: 1.02 min at 245 nM) to afford the tile compound (10 mg, 21%). MS (ESI): mass calcd. for $C_{18}H_{19}F_4N_3O_2$, 385.1; m/z found, 386.1 $[M+H]^+$. $^1$H NMR (500 MHz, Chloroform-d) δ ppm 8.24 (d, J=5.7 Hz, 1H), 7.78 (dd, J=11.4, 2.1 Hz, 1H), 7.71-7.66 (m, 1H), 7.37-7.32 (m, 1H), 6.81 (d, J=2.3 Hz, 1H), 6.44 (dd, J=5.8, 2.3 Hz, 1H), 5.77-5.70 (m, 1H), 5.51-5.46 (m, 1H), 3.43-3.36 (m, 1H), 3.21-3.13 (m, 2H), 3.04-2.97 (m, 1H), 2.04 (s, 3H), 2.02-1.93 (m, 1H), 0.99 (d, J=7.0 Hz, 3H).

Example 194: (*S)—N-[3-[[2-[3-Fluoro-4-(trifluoromethoxy)phenyl]-4-pyridyl]amino]-2-methyl-propyl]acetamide

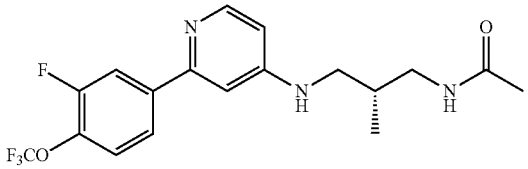 [SMILES: CC(=O)NC[C@H](C)CNc1ccnc(-c2ccc(OC(F)(F)F)c(F)c2)c1]

(racemic)-N-[3-[[2-[3-Fluoro-4-(trifluoromethoxy)phenyl]-4-pyridyl]amino]-2-methyl-propyl]acetamide (Example 192) was separated via SFC chiral separation (Stationary phase: Chiralpak AD-H 5 μm 250×30 mm, Mobile phase: 90% $CO_2$, 10% MeOH (0.3% $iPrNH_2$), 2 mL/min, 150 Bar, retention time: 1.25 min at 245 nM) to afford the tile compound (11 mg, 23%). MS (ESI): mass calcd. for $C_{18}H_{19}F_4N_3O_2$, 385.1; m/z found, 386.1 $[M+H]^+$. $^1$H NMR (500 MHz, Chloroform-d) δ ppm 8.24 (d, J=5.7 Hz, 1H), 7.79 (dd, J=11.4, 2.1 Hz, 1H), 7.73-7.64 (m, 1H), 7.39-7.31

(m, 1H), 6.82 (d, J=2.3 Hz, 1H), 6.44 (dd, J=5.7, 2.3 Hz, 1H), 5.77-5.69 (m, 1H), 5.51-5.39 (m, 1H), 3.45-3.34 (m, 1H), 3.23-3.10 (m, 2H), 3.05-2.94 (m, 1H), 2.04 (s, 3H), 2.00-1.93 (m, 1H), 0.99 (d, J=6.9 Hz, 3H).

Example 195: (racemic)-N-[3-[[2-[3-Fluoro-4-(trifluoromethoxy)phenyl]-4-pyridyl]amino]-1-methylpropyl]acetamide

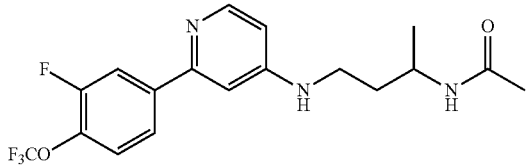 [SMILES: CC(=O)NC(C)CCNc1ccnc(-c2ccc(OC(F)(F)F)c(F)c2)c1]

The title compound was prepared in a manner analogous to Example 22, using 4-fluoro-2-(3-fluoro-4-(trifluoromethoxy)phenyl)pyridine (Example 11, product from Step A) and using tert-butyl (4-aminobutan-2-yl)carbamate instead of tert-butyl 2,6-diazaspiro[3.3]heptane-2-carboxylate oxalate in Step A. MS (ESI): mass calcd. for $C_{18}H_{19}F_4N_3O_2$, 385.1; m/z found, 386.1 [M+H]$^+$. $^1$H NMR (500 MHz, Chloroform-d) δ ppm 8.23 (d, J=5.7 Hz, 1H), 7.79 (dd, J=11.4, 2.1 Hz, 1H), 7.68 (ddd, J=8.6, 2.1, 1.2 Hz, 1H), 7.37-7.31 (m, 1H), 6.81 (dd, J=2.2, 0.5 Hz, 1H), 6.43 (dd, J=5.7, 2.3 Hz, 1H), 5.45 (d, J=8.6 Hz, 1H), 5.41-5.36 (m, 1H), 4.18-4.07 (m, 1H), 3.39-3.31 (m, 1H), 3.18-3.08 (m, 1H), 2.01 (s, 3H), 1.88-1.79 (m, 1H), 1.55-1.45 (m, 1H), 1.19 (d, J=6.7 Hz, 3H).

Example 196: N-[3-[[2-[3-Fluoro-4-(trifluoromethoxy)phenyl]-4-pyridyl]amino]-2,2-dimethylpropyl]acetamide

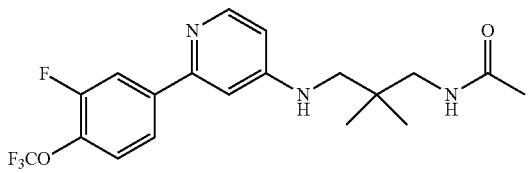 [SMILES: CC(=O)NCC(C)(C)CNc1ccnc(-c2ccc(OC(F)(F)F)c(F)c2)c1]

The title compound was prepared in a manner analogous to Example 22, using 4-fluoro-2-(3-fluoro-4-(trifluoromethoxy)phenyl)pyridine (Example 11, product from Step A) and using tert-butyl (3-amino-2,2-dimethylpropyl)carbamate instead of tert-butyl 2,6-diazaspiro[3.3]heptane-2-carboxylate oxalate in Step A. MS (ESI): mass calcd. for $C_{19}H_{21}F_4N_3O_2$, 399.2; m/z found, 400.1 [M+H]$^+$. $^1$H NMR (500 MHz, Chloroform-d) δ ppm 8.20 (d, J=5.8 Hz, 1H), 7.78 (dd, J=11.4, 2.1 Hz, 1H), 7.68 (ddd, J=8.6, 2.2, 1.2 Hz, 1H), 7.36-7.30 (m, 1H), 6.83 (d, J=2.3 Hz, 1H), 6.45 (dd, J=5.8, 2.3 Hz, 1H), 5.93-5.81 (m, 2H), 3.14 (d, J=7.0 Hz, 2H), 2.95 (d, J=6.9 Hz, 2H), 2.05 (s, 3H), 0.94 (s, 6H).

Example 197: N-[4-[[2-[3-Fluoro-4-(trifluoromethoxy)phenyl]-4-pyridyl]amino]butyl]acetamide

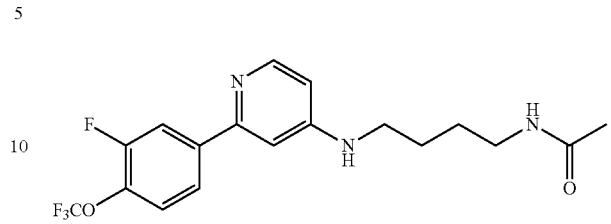

The title compound was prepared in a manner analogous to Example 22, using 4-fluoro-2-(3-fluoro-4-(trifluoromethoxy)phenyl)pyridine (Example 11, product from Step A) and using tert-butyl (4-aminobutyl)carbamate instead of tert-butyl 2,6-diazaspiro[3.3]heptane-2-carboxylate oxalate in Step A. MS (ESI): mass calcd. for $C_{18}H_{19}F_4N_3O_2$, 385.1; m/z found, 386.1 [M+H]$^+$. $^1$H NMR (400 MHz, Chloroform-d) δ ppm 8.24 (d, J=5.7 Hz, 1H), 7.78 (dd, J=11.4, 2.1 Hz, 1H), 7.69 (ddd, J=8.6, 2.2, 1.2 Hz, 1H), 7.38-7.30 (m, 1H), 6.79 (d, J=2.2 Hz, 1H), 6.42 (dd, J=5.8, 2.3 Hz, 1H), 5.68 (s, 1H), 4.66 (t, J=5.5 Hz, 1H), 3.30 (q, J=6.6 Hz, 2H), 3.23 (q, J=6.4 Hz, 2H), 1.98 (s, 3H), 1.72-1.57 (m, 4H).

Example 198: N-[3-[[2-[3-Fluoro-4-(trifluoromethoxy)phenyl]-4-pyridyl]oxy]propyl]acetamide

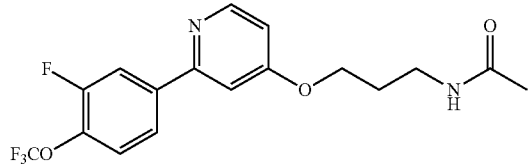 [SMILES: CC(=O)NCCCOc1ccnc(-c2ccc(OC(F)(F)F)c(F)c2)c1]

The title compound was prepared in a manner analogous to Example 24, using 4-fluoro-2-(3-fluoro-4-(trifluoromethoxy)phenyl)pyridine (Example 11, product from Step A) and using tert-butyl (3-hydroxypropyl)carbamate instead of tert-butyl ((1,4-cis)-4-hydroxycyclohexyl)carbamate in Step A. MS (ESI): mass calcd. for $C_{17}H_{16}F_4N_2O_3$, 372.1; m/z found, 373.1 [M+H]$^+$. $^1$H NMR (400 MHz, Chloroform-d) δ ppm 8.47 (d, J=5.7 Hz, 1H), 7.82 (dd, J=11.3, 2.1 Hz, 1H), 7.71 (ddd, J=8.6, 2.2, 1.3 Hz, 1H), 7.40-7.32 (m, 1H), 7.15 (d, J=2.4 Hz, 1H), 6.76 (dd, J=5.7, 2.4 Hz, 1H), 6.02-5.94 (m, 1H), 4.11 (t, J=6.0 Hz, 2H), 3.44 (q, J=6.5 Hz, 2H), 2.08-2.00 (m, 2H), 1.97 (s, 3H).

Example 199: N-[3-[[2-[3-Fluoro-4-(trifluoromethoxy)phenyl]-4-pyridyl]oxy]cyclobutyl]acetamide

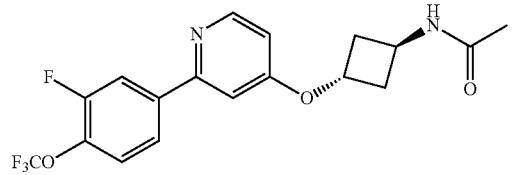 [SMILES: CC(=O)N[C@H]1C[C@H](Oc2ccnc(-c3ccc(OC(F)(F)F)c(F)c3)c2)C1]

The title compound was prepared in a manner analogous to Example 24, using 4-fluoro-2-(3-fluoro-4-(trifluoromethoxy)phenyl)pyridine (Example 11, product from Step A) and using tert-butyl ((1,3-trans)-3-hydroxycyclobutyl)carbamate instead of ((1,4-cis)-4-hydroxycyclohexyl)carbamate in Step A. MS (ESI): mass calcd. for $C_{18}H_{16}F_4N_2O_3$, 384.1; m/z found, 385.1 [M+H]$^+$. $^1$H NMR (400 MHz, Chloroform-d) δ ppm 8.47 (d, J=5.6 Hz, 1H), 7.82 (dd, J=11.3, 2.1 Hz, 1H), 7.71 (ddd, J=8.6, 2.2, 1.2 Hz, 1H), 7.42-7.32 (m, 1H), 7.07 (d, J=2.3 Hz, 1H), 6.64 (dd, J=5.7, 2.4 Hz, 1H), 5.94 (d, J=6.7 Hz, 1H), 4.96-4.85 (m, 1H), 4.63-4.48 (m, 1H), 2.72-2.58 (m, 2H), 2.55-2.43 (m, 2H), 1.99 (s, 3H).

Example 200: N-[3-[[2-[3-Fluoro-4-(trifluoromethoxy)phenyl]-4-pyridyl]oxy]cyclobutyl]acetamide

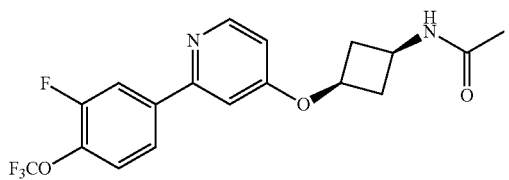 [SMILES: CC(=O)N[C@H]1C[C@@H](Oc2ccnc(-c3ccc(OC(F)(F)F)c(F)c3)c2)C1]

The title compound was prepared in a manner analogous to Example 24, using 4-fluoro-2-(3-fluoro-4-(trifluoromethoxy)phenyl)pyridine (Example 11, product from Step A) and using tert-butyl ((1,3-cis)-3-hydroxycyclobutyl)carbamate instead of ((1,4-cis)-4-hydroxycyclohexyl)carbamate in Step A. MS (ESI): mass calcd. for $C_{18}H_{16}F_4N_2O_3$, 384.1; m/z found, 385.1 [M+H]$^+$. $^1$H NMR (400 MHz, Chloroform-d) δ ppm 8.50 (d, J=5.6 Hz, 1H), 7.83 (dd, J=11.3, 2.2 Hz, 1H), 7.72 (ddd, J=8.5, 2.1, 1.2 Hz, 1H), 7.44-7.32 (m, 1H), 7.10 (d, J=2.3 Hz, 1H), 6.69 (dd, J=5.7, 2.4 Hz, 1H), 5.67 (d, J=7.5 Hz, 1H), 4.59-4.47 (m, 1H), 4.32-4.16 (m, 1H), 3.11-2.98 (m, 2H), 2.16-2.03 (m, 2H), 1.98 (s, 3H).

Example 201: N-(4-(2-(3-Fluoro-4-(trifluoromethoxy)phenyl)pyridin-4-yl)cyclohexyl)acetamide

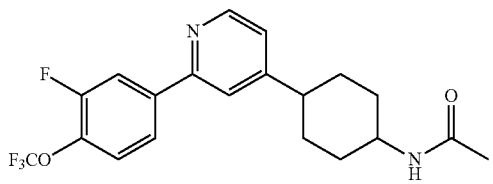

Step A: 4-Bromo-2-(3-fluoro-4-(trifluoromethoxy)phenyl)pyridine

A solution of 2,4-dibromopyridine (700 mg, 2.96 mmol), 3-fluoro-4-(trifluoromethoxy)phenylboronic acid (742 mg, 3.25 mmol), KOH (331 mg, 5.91 mmol), triphenylphosphine (155 mg, 0.59 mmol), and Pd(OAc)$_2$ (33 mg, 0.15 mmol) in MeCN (30 mL) was degassed and placed under atmosphere of nitrogen. The reaction mixture was heated at 70° C. for 18 hours then filtered through Celite® and the solvent was evaporated. Purification via silica gel chromatography (0-15% EtOAc in hexanes) gave the title compound (390 mg, 39%). MS (ESI): mass calcd. for $C_{12}H_6BrF_4NO$, 335.0; m/z found, 335.9 [M+H]$^+$. $^1$H NMR (500 MHz, Chloroform-d) δ ppm 8.53 (dd, J=5.3, 0.6 Hz, 1H), 7.93-7.88 (m, 2H), 7.78 (ddd, J=8.6, 2.1, 1.3 Hz, 1H), 7.48 (dd, J=5.2, 1.8 Hz, 1H), 7.46-7.40 (m, 1H).

Step B: 4-(2-(3-Fluoro-4-(trifluoromethoxy)phenyl)pyridin-4-yl)cyclohexan-1-one

To a 20 mL vial equipped with a stir bar was added [4,4'-bis(1,1-dimethylethyl)-2,2'-bipyridine-N1,N1']bis[3,5-difluoro-2-[5-(trifluoromethyl)-2-pyridinyl-N]phenyl-C] Iridium(III) hexafluorophosphate ((Ir[dF(CF$_3$)ppy]$_2$(dtbpy))PF$_6$) (1.7 mg, 0.0015 mmol), 4-Bromo-2-(3-fluoro-4-(trifluoromethoxy)phenyl)pyridine (50 mg, 0.15 m mmol), 4-bromocyclohexan-1-one (53 mg, 0.30 mmol), tris(trimethylsilyl)silane (37 mg, 0.15 mmol), 2,6-dimethylpyridine (87 μL, 0.74 mmol), To a separate 20 mL vial equipped with a stir bar was added NiCl$_2$ glyme (3.3 mg, 0.015 mmol) and 4,4'-di-tert-butyl-2,2'-bipyridine (4.0 mg, 0.015 mmol). The catalyst vial was purged with nitrogen then to it was added 10 mL of 1,4-dioxane. The resulting suspension was stirred and sonicated for 10 minutes, after which, 1 mL (1 mol % catalyst, 1.5 μmol, 0.01 eq) was syringed into the reaction vial. The reaction was degassed with a stream of nitrogen for five minutes then placed in a photoreactor with stirring overnight. The solvent was removed under reduced pressure. Purification via silica gel chromatography (0-60% EtOAc in hexanes) gave the title compound (17 mg, 33%). The procedure was repeated on the same scale using the same catalyst solution two more times to obtain a total of 55 mg of the title compound to carry forward. MS (ESI): mass calcd. for $C_{18}H_{15}F_4NO_2$, 353.1; m/z found, 345.1 [M+H]$^+$. $^1$H NMR (500 MHz, Chloroform-d) δ ppm 8.57-8.51 (m, 1H), 7.80-7.69 (m, 2H), 7.50 (s, 1H), 7.30 (t, J=8.2 Hz, 1H), 7.16 (s, 1H), 3.08-2.96 (m, 1H), 2.46-2.36 (m, 4H), 2.20-2.11 (m, 2H), 1.94-1.80 (m, 2H).

Step C: 4-(2-(3-Fluoro-4-(trifluoromethoxy)phenyl)pyridin-4-yl)cyclohexan-1-amine To a solution of 4-(2-(3-Fluoro-4-(trifluoromethoxy)phenyl)pyridin-4-yl)cyclohexan-1-one (55 mg, 0.16 mmol) in MeOH (1.6 mL) was added NH4OAc (36 mg, 0.47 mmol) and sodium cyanoborohydride (29 mg, 0.47 mmol). The reaction mixture was stirred at room temperature for 2 hours then the solvent was evaporated. To the residue was added DCM and 1N aqueous solution of NaOH. The aqueous solution was extracted twice with DCM and the combined organic layers were dried over MgSO$_4$, filtered and evaporated to afford the title compound (55 mg, 99%). MS (ESI): mass calcd. for $C_{18}H_{18}F_4N_2O$, 354.1; m/z found, 355.1 [M+H]$^+$.

Step D: N-(4-(2-(3-Fluoro-4-(trifluoromethoxy)phenyl)pyridin-4-yl)cyclohexyl)acetamide 4-(2-(3-Fluoro-4-(trifluoromethoxy)phenyl)pyridin-4-yl)cyclohexan-1-amine (55 mg, 0.15 mmol) was taken up in pyridine (1.5 mL) and acetic anhydride (29 μL, 0.31 mmol) was added followed by 4-dimethylaminopyridine (DMAP) (1 mg, 0.08 mmol). The reaction mixture was stirred at room temperature for 16 hours then the solvent was evaporated. To the residue was added EtOAc and a saturated solution of NaHCO$_3$. The aqueous solution was extracted twice with EtOAc and the combined organic layers were dried over MgSO$_4$, filtered and evaporated. Purification via silica gel chromatography (0-100% EtOAc in hexanes) gave the title compound (20 mg, 32%). MS (ESI): mass calcd. for C$_{20}$H$_{20}$F$_4$N$_2$O$_2$, 396.1; m/z found, 397.2 [M+H]$^+$. $^1$H NMR (600 MHz, Chloroform-d) δ ppm 8.51 (d, J=5.0 Hz, 1H), 7.83-7.78 (m, 1H), 7.71-7.66 (m, 1H), 7.44 (d, J=1.6 Hz, 1H), 7.34-7.28 (m, 1H), 7.04 (dd, J=5.1, 1.7 Hz, 1H), 5.31 (d, J=8.0 Hz, 1H), 3.80 (tdt, J=12.0, 8.1, 4.0 Hz, 1H), 2.49 (tt, J=12.3, 3.5 Hz, 1H), 2.13-2.06 (m, 2H), 1.92 (s, 3H), 1.85-1.79 (m, 1H), 1.62-1.53 (m, 2H), 1.24 (qd, J=12.8, 3.5 Hz, 2H).

Example 202: (R/S)—N-(3-((5-Fluoro-2-(3-fluoro-4-(trifluoromethoxy)phenyl)pyridin-4-yl)amino)-2-methylpropyl)acetamide

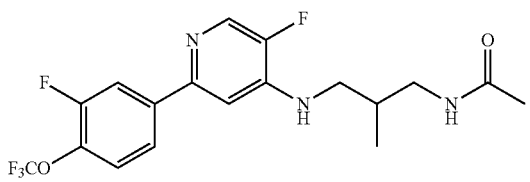 [SMILES: CC(=O)NCC(C)CNc1cc(-c2ccc(OC(F)(F)F)c(F)c2)ncc1F]

The title compound was prepared in a manner analogous to Example 17, using tert-butyl (3-amino-2-methylpropyl)carbamate instead of tert-butyl ((3,4-trans)-3-fluoropiperidin-4-yl)carbamate in Step A. MS (ESI): mass calcd. for C$_{18}$H$_{18}$F$_5$N$_3$O$_2$, 403.1; m/z found, 404.1 [M+H]$^+$. $^1$H NMR (400 MHz, Chloroform-d) δ 8.15 (d, J=3.1 Hz, 1H), 7.73 (dd, J=11.3, 2.2 Hz, 1H), 7.64 (d, J=8.6, 1.6 Hz, 1H), 7.37-7.30 (m, 1H), 6.87 (d, J=6.8 Hz, 1H), 5.91-5.84 (m, 1H), 5.55-5.47 (m, 1H), 3.41-3.32 (m, 1H), 3.25-3.07 (m, 3H), 2.12-1.94 (m, 4H), 1.01 (d, J=6.9 Hz, 3H).

Example 203: N-(3-((5-Fluoro-2-(3-fluoro-4-(trifluoromethoxy)phenyl)pyridin-4-yl)amino)propyl)acetamide

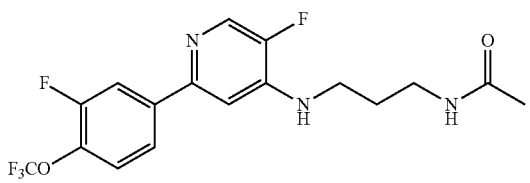 [SMILES: CC(=O)NCCCNc1cc(-c2ccc(OC(F)(F)F)c(F)c2)ncc1F]

The title compound was prepared in a manner analogous to Example 17, using tert-butyl (3-aminopropyl)carbamate instead of tert-butyl ((3,4-trans)-3-fluoropiperidin-4-yl)carbamate in Step A. MS (ESI): mass calcd. for C$_{17}$H$_{16}$F$_5$N$_3$O$_2$, 389.1; m/z found, 390.1 [M+H]$^+$. 1H NMR (400 MHz, Chloroform-d) δ ppm 8.18 (d, J=3.1 Hz, 1H), 7.75 (dd, J=11.3, 2.2 Hz, 1H), 7.69-7.62 (m, 1H), 7.38-7.31 (m, 1H), 6.89 (d, J=6.8 Hz, 1H), 5.70 (s, 1H), 5.18 (s, 1H), 3.40 (q, J=6.4 Hz, 2H), 3.33 (q, J=6.3 Hz, 2H), 2.02 (s, 3H), 1.89-1.79 (m, 2H).

Effects of Test Articles on Cloned Human NR1/NR2B Ion Channels Expressed in Mammalian Cells NMDA receptors are ion channels that are highly permeable to Ca$^{2+}$ ions, rendering it possible to monitor NMDA receptor function using cell-based calcium flux assay. In this assay, co-agonists glutamate and glycine are added to cells heterologously expressing human GluN1/GluN2B NMDA receptors to initiate cellular Ca$^{2+}$ influx. The time course of the changes in intracellular calcium is measured using a fluorescent dye and a FLIPR (Fluorometric Imaging Plate Reader) device.

Twenty four hours before measurements, the expression of the NMDA receptors in the stable cell line is induced with Tet-On inducible system in the presence of a non-selective NMDA receptor blocker. On the day of the experiment, cell culture media is carefully washed and the cells are loaded with Calcium 5 Dye Kit (Molecular Devices) in dye loading buffer containing 137 mM NaCl, 4 mM KCl, 2 mM CaCl$_2$), 0.5 mM MgCl$_2$ (standard assay) or 1.5 mM MgCl$_2$ (HTS assay), 10 mM HEPES and 5 mM D-glucose; pH 7.4. After 1 h incubation at the room temperature, the dye is washed away with the assay buffer (137 mM NaCl (standard assay) or 150 mM (HTS assay), 4 mM KCl (standard assay) or 3 mM (HTS assay), 2 mM CaCl$_2$), 0.01 mM EDTA, 10 mM HEPES and 5 mM D-glucose; pH 7.4) In the FLIPR TETRA reader, various concentrations of the test compounds are added to the cells for 5 min while fluorescence is monitored to detect potential agonist activity. Next, co-agonists, glutamate and glycine are added for another 5 minutes. The concentration of glutamate corresponding to ~EC$_{40}$ (standard assay) or EC$_{40}$ (HTS assay) is used to maximize the assay's signal window and ability to detect NMDA receptor antagonists and negative allosteric modulators. A saturating concentration (10 μM) of glycine is also present in the assay. A non-selective NMDA receptor antagonist, (+)MK-801 is used as a positive control for antagonist activity. The fluorescent signal in the presence of test compounds is quantified and normalized to the signal defined by the appropriate control wells.

TABLE 5

| Ex # | Compound Name | NR2B IC$_{50}$ (mM) standard assay |
|---|---|---|
| 1 | 1-[6-[4-(Trifluoromethoxy)phenyl]pyrimidin-4-yl]piperidine-4-carboxamide; | 1.446 |
| 2 | N-[1-[6-[3-Fluoro-4-(trifluoromethoxy)phenyl]pyrimidin-4-yl]-4-piperidyl]acetamide; | 0.063 |
| 3 | N-[1-[6-[3-Chloro-4-(trifluoromethoxy)phenyl]-2-methyl-pyrimidin-4-yl]-4-piperidyl]acetamide; | 0.284 |
| 4 | (trans)-N-[3-Fluoro-1-[2-methyl-6-[4-(trifluoromethoxy)phenyl]pyrimidin-4-yl]-4-piperidyl]acetamide; | 0.293 |
| 5 | N-[1-[6-[3-Fluoro-4-(trifluoromethoxy)phenyl]-2-(hydroxymethyl)pyrimidin-4-yl]-4-piperidyl]acetamide; | 0.157 |
| 6 | (racemic)-N-Methyl-1-[6-[4-(trifluoromethoxy)phenyl]pyrimidin-4-yl]pyrrolidine-3-carboxamide; | >3 |

TABLE 5-continued

| Ex # | Compound Name | NR2B IC$_{50}$ (mM) standard assay |
|---|---|---|
| 7 | (Trans)-N-[3-Fluoro-1-[6-[3-fluoro-4-(trifluoromethoxy)phenyl]-2-methyl-pyrimidin-4-yl]-4-piperidyl]acetamide; | 0.168 |
| 8 | N-[1-[6-[3-Fluoro-4-(trifluoromethoxy)phenyl]pyrimidin-4-yl]-4-piperidyl]cyclopropanecarboxamide; | 0.497 |
| 9 | 3-Amino-N-[1-[6-[3-fluoro-4-(trifluoromethoxy)phenyl]pyrimidin-4-yl]-4-piperidyl]propanamide; | 0.073 |
| 10 | N-[1-[6-[3-Fluoro-4-(trifluoromethoxy)phenyl]pyrimidin-4-yl]azetidin-3-yl]acetamide; | 0.654 |
| 11 | N-[1-[2-[3-Fluoro-4-(trifluoromethoxy)phenyl]-4-pyridyl]-4-piperidyl]acetamide; | 0.021 |
| 12 | N-[1-[2-[3-(Difluoromethoxy)-4-fluoro-phenyl]-4-pyridyl]-4-piperidyl]acetamide; | >3 |
| 13 | N-[1-[2-[4-(Difluoromethyl)phenyl]-4-pyridyl]-4-piperidyl]acetamide; | 0.310 |
| 14 | N-[1-[2-[3,5-Difluoro-4-(trifluoromethoxy)phenyl]-4-pyridyl]-4-piperidyl]acetamide; | 0.102 |
| 15 | N-[1-[5-Fluoro-2-[3-fluoro-4-(trifluoromethoxy)phenyl]-4-pyridyl]-4-piperidyl]acetamide; | 0.106 |
| 16 | (trans)-N-[3-Fluoro-1-[2-[3-fluoro-4-(trifluoromethoxy)phenyl]-4-pyridyl]-4-piperidyl]acetamide; | 0.051 |
| 17 | (*R/*R)-N-[3-Fluoro-1-[5-fluoro-2-[3-fluoro-4-(trifluoromethoxy)phenyl]-4-pyridyl]-4-piperidyl]acetamide; | 0.255 |
| 18 | (racemic)-N-[1-[2-[3-Fluoro-4-(trifluoromethoxy)phenyl]-4-pyridyl]-2-methyl-4-pipendyl]acetamide; | 3.115 |
| 19 | N-[1-[5-Cyano-2-[4-(trifluoromethoxy)phenyl]-4-pyridyl]-4-pipendyl]acetamide; | 0.257 |
| 20 | N-[1-[2-Cyano-6-[3-fluoro-4-(trifluoromethoxy)phenyl]-4-pyridyl]-4-pipendyl]acetamide; | 0.647 |
| 21 | N-[1-[2-[3-Fluoro-4-(trifluoromethoxy)phenyl]-6-methyl-4-pyridyl]-4-piperidyl]acetamide; | 0.075 |
| 22 | 1-[2-[2-[3-Fluoro-4-(trifluoromethoxy)phenyl]-4-pyridyl]-2,6-diazaspiro[3;3]heptan-6-yl]ethanone; | 0.220 |
| 23 | 1-[2-[2-[4-(Difluoromethoxy)-3-fluoro-phenyl]-4-pyridyl]-2,6-diazaspiro[3;3]heptan-6-yl]ethanone; | 0.487 |
| 24 | N-[4-[[2-[3-Fluoro-4-(trifluoromethoxy)phenyl]-4-pyridyl]oxy]cyclohexyl]acetamide; | 0.244 |
| 25 | (racemic)-N-[3-[[2-[3-Fluoro-4-(trifluoromethoxy)phenyl]-6-(hydroxymethyl)-4-pyridyl]amino]-2-methyl-propyl]acetamide; | 0.233 |
| 26 | 1-[6-[4-(Trifluoromethoxy)phenyl]pyrimidin-4-yl]pipendine-3-carboxamide; | >3 |
| 27 | 1-[6-[4-(Difluoromethoxy)phenyl]pyrimidin-4-yl]pipendine-4-carboxamide; | 2.640 |
| 28 | 1-[2-Methyl-6-[4-(trifluoromethoxy)phenyl]pyrimidin-4-yl]pipendine-4-carboxamide; | 0.820 |
| 29 | 1-[6-[3-(Difluoromethoxy)-4-fluoro-phenyl]pyrimidin-4-yl]pipendine-4-carboxamide; | >3 |
| 30 | 1-[6-[4-(Trifluoromethyl)phenyl]pyrimidin-4-yl]pipendine-4-carboxamide; | 2.150 |
| 31 | 1-[6-[3-Fluoro-4-(trifluoromethoxy)phenyl]pyrimidin-4-yl]pipendine-4-carboxamide; | 0.488 |
| 32 | 1-[5-Methyl-6-[4-(trifluoromethoxy)phenyl]pyrimidin-4-yl]pipendine-4-carboxamide; | >3 |
| 33 | 1-[6-[3-Fluoro-4-(trifluoromethoxy)phenyl]-2-methyl-pyrimidin-4-yl]piperidine-4-carboxamide; | 0.421 |
| 34 | 1-[6-[3-Fluoro-4-(2,2,2-trifluoroethoxy)phenyl]pyrimidin-4-yl]piperidine-4-carboxamide; | >3 |
| 35 | 1-[2-Cyclopropyl-6-[4-(trifluoromethoxy)phenyl]pyrimidin-4-yl]piperidine-4-carboxamide; | 1.450 |
| 36 | 1-[2,5-Dimethyl-6-[4-(trifluoromethoxy)phenyl]pyrimidin-4-yl]piperidine-4-carboxamide; | 4.510 |
| 37 | 1-[6-[3-Chloro-4-(trifluoromethoxy)phenyl]pyrimidin-4-yl]piperidine-4-carboxamide; | 0.327 |
| 38 | 1-[6-[3-Methyl-4-(trifluoromethoxy)phenyl]pyrimidin-4-yl]piperidine-4-carboxamide; | 0.296 |
| 39 | 1-[6-[3-Methoxy-4-(trifluoromethoxy)phenyl]pyrimidin-4-yl]piperidine-4-carboxamide; | 0.874 |
| 40 | 1-[2-Ethyl-6-[4-(trifluoromethoxy)phenyl]pyrimidin-4-yl]piperidine-4-carboxamide; | 0.860 |
| 41 | 1-[2-Methoxy-6-[4-(trifluoromethoxy)phenyl]pyrimidin-4-yl]piperidine-4-carboxamide; | 1.720 |
| 42 | N-[1-[6-[4-(Difluoromethyl)phenyl]pyrimidin-4-yl]-4-piperidyl]acetamide; | 2.420 |
| 43 | N-[1-[6-[3-Methyl-4-(trifluoromethyl)phenyl]pyrimidin-4-yl]-4-piperidyl]acetamide; | 0.412 |
| 44 | N-[1-[6-[3-Fluoro-4-(trifluoromethoxy)phenyl]-2-methyl-pyrimidin-4-yl]-4-piperidyl]acetamide; | 0.155 |

TABLE 5-continued

| Ex # | Compound Name | NR2B IC$_{50}$ (mM) standard assay |
|---|---|---|
| 45 | N-[1-[6-[3-Chloro-4-(trifluoromethoxy)phenyl]pyrimidin-4-yl]-4-piperidyl]acetamide; | 0.071 |
| 46 | 1-[6-[3-Fluoro-4-(trifluoromethoxy)phenyl]-2-methyl-pyrimidin-4-yl]-N-(2-hydroxyethyl)piperidine-4-carboxamide; | 0.420 |
| 47 | 1-[6-[3-Chloro-4-(trifluoromethoxy)phenyl]pyrimidin-4-yl]-N-(2-hydroxyethyl)piperidine-4-carboxamide; | 0.266 |
| 48 | 1-[6-[3-Chloro-4-(trifluoromethoxy)phenyl]-2-methyl-pyrimidin-4-yl]-N-(2-hydroxyethyl)piperidine-4-carboxamide; | 0.474 |
| 49 | N-[1-[2-Methyl-6-[3-methyl-4-(trifluoromethoxy)phenyl]pyrimidin-4-yl]-4-piperidyl]acetamide; | 0.144 |
| 50 | N-[1-[6-[3-Methyl-4-(trifluoromethoxy)phenyl]pyrimidin-4-yl]-4-piperidyl]acetamide; | 0.074 |
| 51 | N-methyl-N-[1-[6-[3-methyl-4-(trifluoromethoxy)phenyl]pyrimidin-4-yl]-4-piperidyl]acetamide; | 3.050 |
| 52 | N-(2-Hydroxyethyl)-1-[2-methyl-6-[3-methyl-4-(trifluoromethoxy)phenyl]pyrimidin-4-yl]piperidine-4-carboxamide; | 0.166 |
| 53 | N-(2-Hydroxyethyl)-1-[6-[3-methyl-4-(trifluoromethoxy)phenyl]pyrimidin-4-yl]piperidine-4-carboxamide; | 0.162 |
| 54 | N-[1-[6-[4-(1,1-Difluoroethyl)phenyl]pyrimidin-4-yl]-4-piperidyl]acetamide; | 0.200 |
| 55 | N-[1-[6-[3-Fluoro-4-(trifluoromethyl)phenyl]pyrimidin-4-yl]-4-piperidyl]acetamide; | 0.379 |
| 56 | N-[1-[6-(3-Fluoro-4-methoxy-phenyl)pyrimidin-4-yl]-4-piperidyl]acetamide; | 2.440 |
| 57 | N-[1-[6-(3-Chloro-4-methoxy-phenyl)pyrimidin-4-yl]-4-piperidyl]acetamide; | 1.260 |
| 58 | N-[1-[6-[3-Chloro-4-(trifluoromethyl)phenyl]pyrimidin-4-yl]-4-piperidyl]acetamide; | 0.252 |
| 59 | N-[1-[6-(4-Chloro-3-fluoro-phenyl)pyrimidin-4-yl]-4-piperidyl]acetamide; | 0.883 |
| 60 | N-[1-[6-(3-Chloro-4-methyl-phenyl)pyrimidin-4-yl]-4-piperidyl]acetamide; | 0.649 |
| 61 | N-[1-[6-(4-Chloro-3-methyl-phenyl)pyrimidin-4-yl]-4-piperidyl]acetamide; | 0.524 |
| 62 | N-[1-[6-[3-Chloro-4-(hydroxymethyl)phenyl]pyrimidin-4-yl]-4-piperidyl]acetamide; | >3 |
| 63 | N-[1-[6-(3,4-Dichlorophenyl)pyrimidin-4-yl]-4-piperidyl]acetamide; | 0.615 |
| 64 | N-[1-[6-(3-Fluoro-4-methyl-phenyl)pyrimidin-4-yl]-4-piperidyl]acetamide; | >3 |
| 65 | N-[1-[6-[4-(Difluoromethoxy)-3-fluoro-phenyl]pyrimidin-4-yl]-4-piperidyl]acetamide; | 0.264 |
| 66 | N-[1-[6-[3-(Hydroxymethyl)-4-(trifluoromethoxy)phenyl]pyrimidin-4-yl]-4-piperidyl]acetamide; | 3.740 |
| 67 | N-[1-[6-[3,5-Difluoro-4-(trifluoromethoxy)phenyl]pyrimidin-4-yl]-4-piperidyl]acetamide; | 0.192 |
| 68 | N-[1-[2-Methyl-6-[4-(trifluoromethoxy)phenyl]pyrimidin-4-yl]-4-piperidyl]acetamide; | 0.209 |
| 69 | (trans)-N-[3-Fluoro-1-[2-methyl-6-[3-methyl-4-(trifluoromethoxy)phenyl]pyrimidin-4-yl]-4-piperidyl]acetamide; | 0.334 |
| 70 | N-[1-[6-[4-(Trifluoromethoxy)-3-(trifluoromethyl)phenyl]pyrimidin-4-yl]-4-piperidyl]acetamide; | 1.080 |
| 71 | N-Methyl-1-[6-[4-(trifluoromethoxy)phenyl]pyrimidin-4-yl]piperidine-4-carboxamide; | 1.060 |
| 72 | N-(2-Hydroxyethyl)-1-[6-[4-(trifluoromethoxy)phenyl]pyrimidin-4-yl]piperidine-4-carboxamide; | 0.660 |
| 73 | 4-[4-(1H-Imidazol-4-yl)-1-piperidyl]-6-[4-(trifluoromethoxy)phenyl]pyrimidine; | 0.374 |
| 74 | N-(2-Hydroxyethyl)-1-[2-methyl-6-[4-(trifluoromethoxy)phenyl]pyrimidin-4-yl]piperidine-4-carboxamide; | 0.459 |
| 75 | 4-[4-(1H-Imidazol-4-yl)-1-piperidyl]-2-methyl-6-[4-(trifluoromethoxy)phenyl]pyrimidine; | 0.315 |
| 76 | 1-[6-[3-Fluoro-4-(trifluoromethoxy)phenyl]pyrimidin-4-yl]-N-(2-hydroxyethyl)piperidine-4-carboxamide; | 0.230 |
| 77 | 4-[3-Fluoro-4-(trifluoromethoxy)phenyl]-6-[4-(1H-imidazol-4-yl)-1-piperidyl]pyrimidine; | 0.246 |
| 78 | 2-[1-[6-[4-(Trifluoromethoxy)phenyl]pyrimidin-4-yl]-4-piperidyl]acetamide; | 1.350 |
| 79 | N-[1-[6-[4-(Trifluoromethoxy)phenyl]pyrimidin-4-yl]-4-piperidyl]acetamide; | 0.152 |
| 80 | 4-[4-(1H-Imidazol-2-yl)-1-piperidyl]-6-[4-(trifluoromethoxy)phenyl]pyrimidine; | 0.224 |
| 81 | N-[[1-[6-[4-(Trifluoromethoxy)phenyl]pyrimidin-4-yl]-4-piperidyl]methyl]acetamide; | 4.220 |
| 82 | 8-[6-[3-Fluoro-4-(trifluoromethoxy)phenyl]pyrimidin-4-yl]-4,8-diazaspiro[4;5]decan-3-one; | 2.540 |

TABLE 5-continued

| Ex # | Compound Name | NR2B IC$_{50}$ (mM) standard assay |
|---|---|---|
| 83 | 1-[6-[3-Fluoro-4-(trifluoromethoxy)phenyl]-2-methyl-pyrimidin-4-yl]piperidin-4-ol; | 1.380 |
| 84 | N-Methyl-1-[6-[4-(trifluoromethoxy)phenyl]pyrimidin-4-yl]azetidine-3-carboxamide; | 1.890 |
| 85 | (*R/*R)-N-[3-Fluoro-1-[6-[3-fluoro-4-(trifluoromethoxy)phenyl]-2-methyl-pyrimidin-4-yl]-4-piperidyl]acetamide; | 0.121 |
| 86 | (*S/*S)-N-[3-Fluoro-1-[6-[3-fluoro-4-(trifluoromethoxy)phenyl]-2-methyl-pyrimidin-4-yl]-4-piperidyl]acetamide; | 0.189 |
| 87 | (trans)-N-[3-Fluoro-1-[6-[3-fluoro-4-(trifluoromethoxy)phenyl]pyrimidin-4-yl]-4-piperidyl]acetamide; | 0.167 |
| 88 | (*S/*S)-N-[3-Fluoro-1-[6-[3-fluoro-4-(trifluoromethoxy)phenyl]pyrimidin-4-yl]-4-piperidyl]acetamide; | 0.415 |
| 89 | (*R/*R)-N-[3-fluoro-1-[6-[3-fluoro-4-(trifluoromethoxy)phenyl]pyrimidin-4-yl]-4-piperidyl]acetamide; | 0.127 |
| 90 | (trans)-N-[3-Fluoro-1-[6-[3-methyl-4-(trifluoromethoxy)phenyl]pyrimidin-4-yl]-4-piperidyl]acetamide; | 0.253 |
| 91 | (*S/*S)-N-[3-Fluoro-1-[6-[3-methyl-4-(trifluoromethoxy)phenyl]pyrimidin-4-yl]-4-piperidyl]acetamide; | 0.385 |
| 92 | (*R/*R)-N-[3-Fluoro-1-[6-[3-methyl-4-(trifluoromethoxy)phenyl]pyrimidin-4-yl]-4-piperidyl]acetamide; | 0.286 |
| 93 | (trans)-N-[1-[6-[3-Chloro-4-(trifluoromethoxy)phenyl]pyrimidin-4-yl]-3-fluoro-4-piperidyl]acetamide; | 0.205 |
| 94 | (*S/*S)-N-[1-[6-[3-Chloro-4-(trifluoromethoxy)phenyl]pyrimidin-4-yl]-3-fluoro-4-piperidyl]acetamide; | 0.116 |
| 95 | (*R/*R)-N-[1-[6-[3-Chloro-4-(trifluoromethoxy)phenyl]pyrimidin-4-yl]-3-fluoro-4-piperidyl]acetamide; | 0.307 |
| 96 | (cis)-N-[3-Fluoro-1-[6-[3-fluoro-4-(trifluoromethoxy)phenyl]pyrimidin-4-yl]-4-piperidyl]acetamide; | 0.148 |
| 97 | (*R/*S)-N-[3-Fluoro-1-[6-[3-fluoro-4-(trifluoromethoxy)phenyl]pyrimidin-4-yl]-4-piperidyl]acetamide; | 0.101 |
| 98 | (*S/*R)-N-[3-Fluoro-1-[6-[3-fluoro-4-(trifluoromethoxy)phenyl]pyrimidin-4-yl]-4-piperidyl]acetamide; | 1.260 |
| 99 | N-[1-[6-[3-fluoro-4-(trifluoromethoxy)phenyl]-2-methyl-pyrimidin-4-yl]-4-methyl-4-piperidyl]acetamide; | >3 |
| 100 | N-[1-[6-[3-Fluoro-4-(trifluoromethoxy)phenyl]-2-methyl-pyrimidin-4-yl]-4-piperidyl]methanesulfonamide; | >3 |
| 101 | 4-[3-Fluoro-4-(trifluoromethoxy)phenyl]-2-methyl-6-[4-(1H-pyrazol-5-yl)-1-piperidyl]pyrimidine; | 0.568 |
| 102 | 1-[1-[6-[3-Fluoro-4-(trifluoromethoxy)phenyl]pyrimidin-4-yl]-4-piperidyl]ethanone; | >3 |
| 103 | 1-[1-[6-[3-Fluoro-4-(trifluorornethoxy)phenyl]pyrimidin-4-yl]-4-piperidyl]propan-2-one; | >3 |
| 104 | N-[[1-[6-[3-Fluoro-4-(trifluoromethoxy)phenyl]pyrimidin-4-yl]azetidin-3-yl]methyl]acetamide; | 0.425 |
| 105 | (racemic)-N-[[1-[6-[3-Fluoro-4-(trifluoromethoxy)phenyl]pyrimidin-4-yl]pyrrolidin-3-yl]methyl]acetamide; | 0.652 |
| 106 | (racemic)-N-[1-[6-[3-Fluoro-4-(trifluoromethoxy)phenyl]pyrimidin-4-yl]pyrrolidin-3-yl]acetamide; | 3.360 |
| 107 | (racemic)-N-[1-[6-[3-Fluoro-4-(trifluoromethoxy)phenyl]pyrimidin-4-yl]-3-piperidyl]acetamide; | >3 |
| 108 | (racemic)-N-[1-[6-[3-Fluoro-4-(trifluoromethoxy)phenyl]pyrimidin-4-yl]azepan-4-yl]acetamide; | 0.845 |
| 109 | (trans)-N-[3-Fluoro-1-[6-[4-(trifluoromethoxy)phenyl]pyrimidin-4-yl]-4-piperidyl]acetamide; | 0.375 |
| 110 | (racemic)-N-[1-[6-[3-Fluoro-4-(trifluoromethoxy)phenyl]pyrimidin-4-yl]-3-methyl-4-piperidyl]acetamide; | 0.217 |
| 111 | (racemic)-N-[1-[6-[3-Fluoro-4-(trifluoromethoxy)phenyl]pyrimidin-4-yl]-2-methyl-4-piperidyl]acetamide; | >3 |
| 112 | 2,2-Difluoro-N-[1-[6-[3-fluoro-4-(trifluoromethoxy)phenyl]pyrimidin-4-yl]-4-piperidyl]acetamide; | 0.827 |
| 113 | 1-[2-[6-[3-Fluoro-4-(trifluoromethoxy)phenyl]pyrimidin-4-yl]-2,6-diazaspiro[3;3]heptan-6-yl]ethanone; | 0.396 |
| 114 | N-[4-[[6-[3-Fluoro-4-(trifluoromethoxy)phenyl]pyrimidin-4-yl]amino]cyclohexyl]acetamide; | 0.286 |
| 115 | N-[1-[6-[3-Fluoro-4-(trifluoromethoxy)phenyl]pyrimidin-4-yl]-4-pipendyl]propanamide; | 0.603 |
| 116 | N-[1-[6-[3-Fluoro-4-(trifluoromethoxy)phenyl]pyrimidin-4-yl]-4-piperidyl]-3-hydroxy-propanamide; | 0.393 |
| 117 | (trans)-3-Amino-N-[3-fluoro-1-[6-[3-fluoro-4-(trifluoromethoxy)phenyl]pyrimidin-4-yl]-4-pipendyl]propanamide; | 0.128 |
| 118 | N-[3-[[6-[3-Fluoro-4-(trifluoromethoxy)phenyl]pyrimidin-4-yl]amino]propyl]acetamide; | 0.377 |
| 119 | (racemic)-N-[3-[[6-[3-Fluoro-4-(trifluoromethoxy)phenyl]pyrimidin-4-yl]amino]-2-methyl-propyl]acetamide; | 0.152 |
| 120 | (*R)-N-[3-[[6-[3-Fluoro-4-(trifluoromethoxy)phenyl]pyrimidin-4-yl]amino]-2-methyl-propyl]acetamide; | 2.090 |

TABLE 5-continued

| Ex # | Compound Name | NR2B IC$_{50}$ (mM) standard assay |
|---|---|---|
| 121 | (*S)-N-[3-[[6-[3-Fluoro-4-(trifluoromethoxy)phenyl]pyrimidin-4-yl]amino]-2-methyl-propyl]acetamide; | 0.141 |
| 122 | 1-[2-[3-Fluoro-4-(trifluoromethoxy)phenyl]-4-pyridyl]piperidin-4-ol; | 0.510 |
| 123 | N-[1-[2-[4-(Trifluoromethoxy)phenyl]-4-pyridyl]-4-pipendyl]acetamide; | 0.023 |
| 124 | N-[1-[2-[3-Methyl-4-(trifluoromethoxy)phenyl]-4-pyridyl]-4-pipendyl]acetamide; | 0.032 |
| 125 | N-[1-[2-[4-(Difluoromethoxy)-3-methyl-phenyl]-4-pyridyl]-4-pipendyl]acetamide; | 0.032 |
| 126 | 1-[2-[3-Fluoro-4-(trifluoromethoxy)phenyl]-4-pyridyl]piperidine-4-carboxamide; | 0.080 |
| 127 | 1-[1-[2-[3-Fluoro-4-(trifluoromethoxy)phenyl]-4-pyridyl]-4-pipendyl]propan-2-one; | 0.277 |
| 128 | 2-[1-[2-[3-Fluoro-4-(trifluoromethoxy)phenyl]-4-pyridyl]-4-pipendyl]acetamide; | 0.058 |
| 129 | 2-[3-Fluoro-4-(trifluoromethoxy)phenyl]-4-[4-(1H-pyrazol-5-yl)-1-piperidyl]pyridine; | 0.374 |
| 130 | 2-[3-Fluoro-4-(trifluoromethoxy)phenyl]-4-[4-(1H-imidazol-4-yl)-1-piperidyl]pyridine; | 0.161 |
| 131 | 2-[3-Fluoro-4-(trifluoromethoxy)phenyl]-4-[4-(1H-imidazol-2-yl)-1-piperidyl]pyridine; | 0.056 |
| 132 | 2-[3-Fluoro-4-(trifluoromethoxy)phenyl]-4-[4-(1H-pyrazol-4-yl)-1-piperidyl]pyridine; | 0.067 |
| 133 | 8-[2-[3-Fluoro-4-(trifluoromethoxy)phenyl]-4-pyridyl]-4,8-diazaspiro[4;5]decan-3-one; | 0.541 |
| 134 | N-[1-[2-[3-Fluoro-4-(trifluoromethoxy)phenyl]-4-pyridyl]-4-piperidyl]methanesulfonamide; | 0.450 |
| 135 | N-[1-[2-[4-(Difluoromethoxy)phenyl]-4-pyridyl]-4-piperidyl]acetamide; | 0.078 |
| 136 | N-[1-[2-[4-(Difluoromethoxy)-3-fluoro-phenyl]-4-pyridyl]-4-piperidyl]acetamide; | 0.038 |
| 137 | N-[1-[2-[3-(Difluoromethyl)-4-fluoro-phenyl]-4-pyridyl]-4-piperidyl]acetamide; | >3 |
| 138 | N-[1-[2-(p-Tolyl)-4-pyridyl]-4-piperidyl]acetamide; | 0.689 |
| 139 | N-[1-[2-[4-(1,1-Difluoroethyl)phenyl]-4-pyridyl]-4-piperidyl]acetamide; | 0.043 |
| 140 | N-[1-[2-[4-(Trifluoromethyl)phenyl]-4-pyridyl]-4-piperidyl]acetamide; | 0.071 |
| 141 | N-[1-[2-[3-Chloro-4-(trifluoromethoxy)phenyl]-4-pyridyl]-4-piperidyl]acetamide; | 0.053 |
| 142 | N-[1-[2-[2-Fluoro-4-(trifluoromethoxy)phenyl]-4-pyridyl]-4-piperidyl]acetamide; | 0.790 |
| 143 | N-[1-[2-[3-Fluoro-4-(2,2,2-trifluoroethoxy)phenyl]-4-pyridyl]-4-piperidyl]acetamide; | 0.428 |
| 144 | N-[1-[2-(4-Chloro-3-fluoro-phenyl)-4-pyridyl]-4-piperidyl]acetamide; | 0.293 |
| 145 | N-[1-[2-(3-Fluoro-4-methoxy-phenyl)-4-pyridyl]-4-piperidyl]acetamide; | 0.132 |
| 146 | N-[1-[2-[3-Fluoro-4-(trifluoromethyl)phenyl]-4-pyridyl]-4-piperidyl]acetamide; | 0.166 |
| 147 | N-[1-[2-(4-Acetyl-3-fluoro-phenyl)-4-pyridyl]-4-piperidyl]acetamide; | 0.855 |
| 148 | N-[1-[2-[3-Fluoro-4-(trifluoromethoxy)phenyl]-5-methyl-4-pyridyl]-4-piperidyl]acetamide; | 0.978 |
| 149 | N-[1-[2-[3-Fluoro-4-(trifluoromethoxy)phenyl]-5-methoxy-4-pyridyl]-4-piperidyl]acetamide; | 0.257 |
| 150 | N-[1-[2-[4-(Difluoromethoxy)phenyl]-6-methyl-4-pyridyl]-4-piperidyl]acetamide; | 0.185 |
| 151 | N-[1-[2-[4-(1,1-Difluoroethyl)phenyl]-6-methyl-4-pyridyl]-4-piperidyl]acetamide; | 0.238 |
| 152 | N-[1-[2-[4-(Difluoromethoxy)-3-fluoro-phenyl]-6-methyl-4-pyridyl]-4-piperidyl]acetamide; | 0.154 |
| 153 | N-[1-[2-(Fluoromethyl)-6-[3-fluoro-4-(trifluoromethoxy)phenyl]-4-pyridyl]-4-piperidyl]acetamide; | 0.105 |
| 154 | N-[1-[2-(Difluoromethyl)-6-[3-fluoro-4-(trifluoromethoxy)phenyl]-4-pyridyl]-4-piperidyl]acetamide; | 0.678 |
| 155 | N-[1-[2-[3-Fluoro-4-(trifluoromethoxy)phenyl]-6-(hydroxymethyl)-4-pyridyl]-4-piperidyl]acetamide; | 0.032 |
| 156 | N-[1-[2-(3-Fluoro-4-isopropoxy-phenyl)-6-(hydroxymethyl)-4-pyridyl]-4-piperidyl]acetamide; | 0.197 |
| 157 | N-[1-[2-(4-Ethoxy-3-fluoro-phenyl)-6-(hydroxymethyl)-4-pyridyl]-4-piperidyl]acetamide; | 0.179 |
| 158 | N-[1-[2-[3-Fluoro-4-(trifluoromethoxy)phenyl]-6-methoxy-4-pyridyl]-4-piperidyl]acetamide; | 0.749 |
| 159 | N-[1-[2-[3-Fluoro-4-(trifluoromethoxy)phenyl]-6-hydroxy-4-pyridyl]-4-piperidyl]acetamide; | 0.248 |

TABLE 5-continued

| Ex # | Compound Name | NR2B IC$_{50}$ (mM) standard assay |
|---|---|---|
| 160 | N-[1-[2-(Difluoromethoxy)-6-[3-fluoro-4-(trifluoromethoxy)phenyl]-4-pyridyl]-4-piperidyl]acetamide; | 1.950 |
| 161 | (cis)-N-[3-Fluoro-1-[2-[3-fluoro-4-(trifluoromethoxy)phenyl]-4-pyridyl]-4-piperidyl]acetamide; | 0.065 |
| 162 | (*R/*R)-N-[3-Fluoro-1-[2-[3-fluoro-4-(trifluoromethoxy)phenyl]-4-pyridyl]-4-piperidyl]acetamide; | 0.025 |
| 163 | (*S/*S)-N-[3-Fluoro-1-[2-[3-fluoro-4-(trifluoromethoxy)phenyl]-4-pyridyl]-4-piperidyl]acetamide; | 0.175 |
| 164 | (*S/*S)-N-[3-Fluoro-1-[5-fluoro-2-[3-fluoro-4-(trifluoromethoxy)phenyl]-4-pyridyl]-4-piperidyl]acetamide; | 0.550 |
| 165 | (trans)-N-[1-[2-[3-Fluoro-4-(trifluoromethoxy)phenyl]-4-pyridyl]-3-hydroxy-4-piperidyl]acetamide; | 0.697 |
| 166 | (racemic)-N-[1-[2-[3-Fluoro-4-(trifluoromethoxy)phenyl]-4-pyridyl]-3-methyl-4-piperidyl]acetamide; | 0.132 |
| 167 | (trans)-N-[1-[2-[3-Fluoro-4-(trifluoromethoxy)phenyl]-4-pyridyl]-3-methyl-4-piperidyl]acetamide; | 0.767 |
| 168 | (cis)-N-[1-[2-[3-Fluoro-4-(trifluoromethoxy)phenyl]-4-pyridyl]-3-methyl-4-piperidyl]acetamide; | 0.173 |
| 169 | N-[[1-[2-[3-Fluoro-4-(trifluoromethoxy)phenyl]-4-pyridyl]azetidin-3-yl]methyl]acetamide; | 0.135 |
| 170 | (racemic)-N-[[1-[2-[3-Fluoro-4-(trifluoromethoxy)phenyl]-4-pyridyl]pyrrolidin-3-yl]methyl]acetamide; | 0.392 |
| 171 | (racemic)-N-[1-[2-[3-Fluoro-4-(trifluoromethoxy)phenyl]-4-pyridyl]-3-piperidyl]acetamide; | 3.840 |
| 172 | (racemic)-N-[1-[2-[3-Fluoro-4-(trifluoromethoxy)phenyl]-4-pyridyl]-3,3-dimethyl-4-piperidyl]acetamide; | 3.390 |
| 173 | N-[[1-[2-[3-Fluoro-4-(trifluoromethoxy)phenyl]-4-pyridyl]-4-piperidyl]methyl]acetamide; | 0.410 |
| 174 | (racemic)-N-[[1-[2-[3-Fluoro-4-(trifluoromethoxy)phenyl]-4-pyridyl]-3-piperidyl]methyl]acetamide; | 2.050 |
| 175 | 1-[2-[2-[3-(Difluoromethyl)-4-fluoro-phenyl]-4-pyridyl]-2,6-diazaspiro[3;3]heptan-6-yl]ethanone; | >3 |
| 176 | 1-[2-[2-[4-(Trifluoromethoxy)phenyl]-4-pyridyl]-2,6-diazaspiro[3;3]heptan-6-yl]ethanone; | 0.605 |
| 177 | 1-[2-[[2-[3-Fluoro-4-(trifluoromethoxy)phenyl]-4-pyridyl]amino]-6-azaspiro[3;3]heptan-6-yl]ethanone; | 0.869 |
| 178 | N-[6-[2-[3-Fluoro-4-(trifluoromethoxy)phenyl]-4-pyridyl]-6-azaspiro[3;3]heptan-2-yl]acetamide; | 0.365 |
| 179 | N-[3-[[2-[3-Fluoro-4-(trifluoromethoxy)phenyl]-4-pyridyl]amino]cyclobutyl]acetamide; | 0.269 |
| 180 | (trans)-N-[3-[[2-[3-Fluoro-4-(trifluoromethoxy)phenyl]-4-pyridyl]amino]cyclopentyl]acetamide; | 0.550 |
| 181 | (cis)-N-[3-[[2-[3-Fluoro-4-(trifluoromethoxy)phenyl]-4-pyridyl]amino]cyclopentyl]acetamide; | 0.273 |
| 182 | (trans)-N-[3-[[2-[3-Fluoro-4-(trifluoromethoxy)phenyl]-4-pyridyl]amino]cyclohexyl]acetamide; | >3 |
| 183 | (cis)-N-[3-[[2-[3-Fluoro-4-(trifluoromethoxy)phenyl]-4-pyridyl]amino]cyclohexyl]acetamide; | 2.040 |
| 184 | N-[4-[[2-[3-Fluoro-4-(trifluoromethoxy)phenyl]-4-pyridyl]amino]cyclohexyl]acetamide; | 0.156 |
| 185 | N-[4-[[2-[3-Fluoro-4-(trifluoromethoxy)phenyl]-4-pyridyl]amino]cyclohexyl]acetamide; | 2.130 |
| 186 | 1-[3-[[[2-[3-Fluoro-4-(trifluoromethoxy)phenyl]-4-pyridyl]amino]methyl]azetidin-1-yl]ethanone; | 0.916 |
| 187 | N-[1-[[[2-[3-Fluoro-4-(trifluoromethoxy)phenyl]-4-pyridyl]amino]methyl-3-bicyclo[1;1;1]pentanyl]acetamide; | 0.639 |
| 188 | N-[2-[[2-[3-Fluoro-4-(trifluoromethoxy)phenyl]-4-pyridyl]amino]ethyl]acetamide; | 1.810 |
| 189 | N-[3-[[2-[3-Fluoro-4-(trifluoromethoxy)phenyl]-4-pyridyl]amino]propyl]acetamide; | 0.160 |
| 190 | N-[3-[[2-[3-Fluoro-4-(trifluoromethoxy)phenyl]-4-pyridyl]-methyl-amino]propyl]acetamide; | 2.660 |
| 191 | (racemic)-N-[3-[[2-[3-Fluoro-4-(trifluoromethoxy)phenyl]-4-pyridyl]amino]butyl]acetamide; | 3.410 |
| 192 | (racemic)-N-[3-[[2-[3-Fluoro-4-(trifluoromethoxy)phenyl]-4-pyridyl]amino]-2-methyl-propyl]acetamide; | 0.128 |
| 193 | (*R)-N-[3-[[2-[3-Fluoro-4-(trifluoromethoxy)phenyl]-4-pyridyl]amino]-2-methyl-propyl]acetamide; | 0.994 |
| 194 | (*S)-N-[3-[[2-[3-Fluoro-4-(trifluoromethoxy)phenyl]-4-pyridyl]amino]-2-methyl-propyl]acetamide; | 0.062 |
| 195 | (racemic)-N-[3-[[2-[3-Fluoro-4-(trifluoromethoxy)phenyl]-4-pyridyl]amino]-1-methyl-propyl]acetamide; | 1.150 |
| 196 | N-[3-[[2-[3-Fluoro-4-(trifluoromethoxy)phenyl]-4-pyridyl]amino]-2,2-dimethyl-propyl]acetamide; | 1.290 |
| 197 | N-[4-[[2-[3-Fluoro-4-(trifluoromethoxy)phenyl]-4-pyridyl]amino]butyl]acetamide; | 0.366 |

TABLE 5-continued

| Ex # | Compound Name | NR2B IC$_{50}$ (mM) standard assay |
|---|---|---|
| 198 | N-[3-[[2-[3-Fluoro-4-(trifluoromethoxy)phenyl]-4-pyridyl]oxy]propyl]acetamide; | 0.137 |
| 199 | N-[3-[[2-[3-Fluoro-4-(trifluoromethoxy)phenyl]-4-pyridyl]oxy]cyclobutyl]acetamide; | 1.370 |
| 200 | N-[3-[[2-[3-Fluoro-4-(trifluoromethoxy)phenyl]-4-pyridyl]oxy]cyclobutyl]acetamide; | 0.209 |
| 201 | N-(4-(2-(3-Fluoro-4-(trifluoromethoxy)phenyl)pyridin-4-yl)cyclohexyl)acetamide; | 2.425 |
| 202 | (R/S)-N-(3-((5-Fluoro-2-(3-fluoro-4-(trifluoromethoxy)phenyl)pyridin-4-yl)amino)-2-methylpropyl)acetamide; and | 0.382 |
| 203 | N-(3-((5-Fluoro-2-(3-fluoro-4-(trifluoromethoxy)phenyl)pyridin-4-yl)amino)propyl)acetamide. | 0.139 |

The present disclosure is exemplified by the specific embodiments below.

1. A compound, or a pharmaceutically acceptable salt, solvate, stereoisomer, isotopic variant, or N-oxide thereof, having the structure of Formula (I):

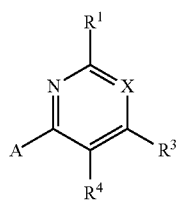

(I)

wherein

R$^1$ is selected from the group consisting of: H, OH, C$_{1-4}$alkyl, CH$_2$OH, CH$_2$F, CHF$_2$, OC$_{1-4}$alkyl, OCHF$_2$, CN, and cyclopropyl;

X is C—R$^2$ or N; wherein R$^2$ is selected from the group consisting of: H, halo, C$_{1-4}$alkyl, OC$_{1-4}$alkyl, and CN;

R$^3$ is:

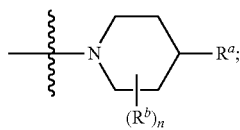

(I)

wherein

R$^a$ is selected from the group consisting of: OH, (C═O)NH$_2$, (C═O)NHCH$_3$, (C═O)NHCH$_2$CH$_2$OH, CH$_2$(C═O)NH$_2$, CH$_2$C(═O)CH$_3$, (C═O)CH$_3$, CH$_2$NH(C═O)CH$_3$, NH(C═O)C$_{1-4}$alkyl, NCH$_3$(C═O)C$_{1-4}$alkyl, NH(C═O)CH$_2$CH$_2$NH$_2$, NH(C═O)CH$_2$CH$_2$OH, NH(C═O)haloC$_{1-4}$alkyl, NH(C═O)cyclopropyl, NHSO$_2$CH$_3$,

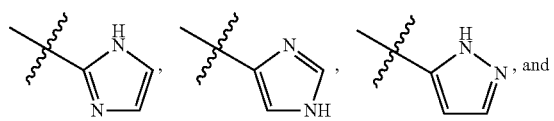
, and

-continued

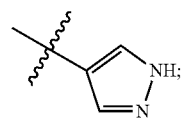

each R$^b$ is independently selected from the group consisting of: H, F, CH$_3$ and OH;

n is 0, 1 or 2;

(b)

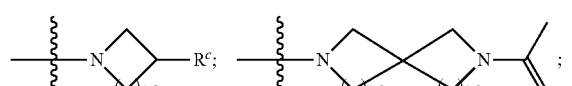

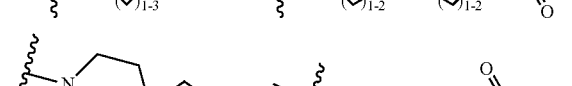

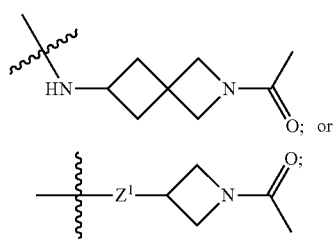

wherein

R$^c$ is selected from the group consisting of: NH(C═O)CH$_3$, CH$_2$NH(C═O)CH$_3$, (C═O)CH$_3$, and (C═O)NHCH$_3$;

Z$^1$ is NHCH$_2$;

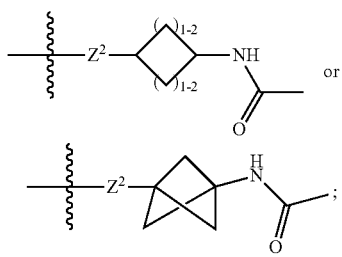

wherein
Z² is NH or CH₂NH; or
(d) Z³—C$_{1-6}$alkyl-NH(C=O)CH₃ or Z³—C$_{4-6}$cycloalkyl-NH(C=O)CH₃;
wherein
Z³ is NH, NCH₃, or O;
R⁴ is H or CH₃; and
A is selected from the group consisting of:

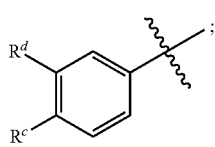

wherein
R$^d$ is selected from the group consisting of: halo, C$_{1-4}$alkyl, CH₂OH, C$_{1-4}$haloalkyl, OC$_{1-4}$alkyl, and OC$_{1-4}$haloalkyl;
R$^e$ is selected from the group consisting of: halo, C$_{1-4}$alkyl, CH₂OH, OC$_{1-4}$alkyl, C$_{1-4}$haloalkyl, OC$_{1-4}$haloalkyl, and (C=O)CH₃;

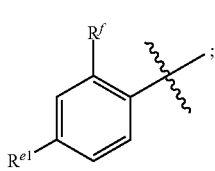

wherein
R$^f$ is H or F;
R$^{e1}$ is selected from the group consisting of: C$_{1-4}$alkyl, C$_{1-4}$haloalkyl, and OC$_{1-4}$haloalkyl; and

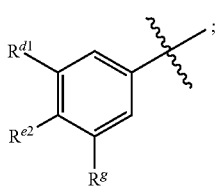

wherein
R$^{d1}$ and R$^{e2}$ are halo; and
R$^g$ is OC$_{1-4}$haloalkyl.

2. The compound of embodiment 1, or a pharmaceutically acceptable salt, solvate, stereoisomer, isotopic variant, or N-oxide thereof, wherein R¹ is H, OH, CH₃, CH₂CH₃, CH₂OH, OCH₃, CH₂F, CHF₂, OCHF₂, CN, or cyclopropyl.

3. The compound of embodiment 1, or a pharmaceutically acceptable salt, solvate, stereoisomer, isotopic variant, or N-oxide thereof, wherein R¹ is H.

4. The compound of any one of embodiments 1 to 3, or a pharmaceutically acceptable salt, solvate, stereoisomer, isotopic variant, or N-oxide thereof, wherein X is C—R² and wherein R² is H, F, CH₃, OCH₃, or CN.

5. The compound of any one of embodiments 1 to 3, or a pharmaceutically acceptable salt, solvate, stereoisomer, isotopic variant, or N-oxide thereof, wherein X is C—R² and wherein R² is H.

6. The compound of any one of embodiments 1 to 3, or a pharmaceutically acceptable salt, solvate, stereoisomer, isotopic variant, or N-oxide thereof, wherein X is N.

7. The compound of any one of embodiments 1 to 6, or a pharmaceutically acceptable salt, solvate, stereoisomer, isotopic variant, or N-oxide thereof, wherein R³ is

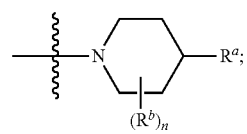

wherein R$^a$ is OH, (C=O)NH₂, (C=O)NHCH₃, (C=O)NHCH₂CH₂OH, CH₂(C=O)NH₂, CH₂C(=O)CH₃, (C=O)CH₃, CH₂NH(C=O)CH₃, NH(C=O)C$_{1-4}$alkyl, NCH₃(C=O)C$_{1-4}$alkyl, NH(C=O)CH₂CH₂NH₂, NH(C=O)CH₂CH₂OH, NH(C=O)haloC$_{1-4}$alkyl, NH(C=O)cyclopropyl, NHSO₂CH₃,

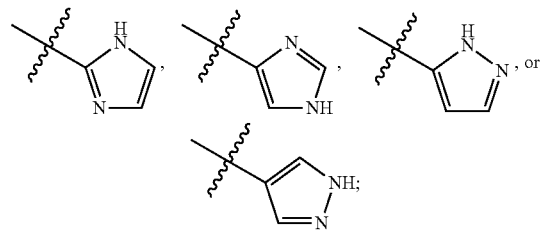

and n is 0.

8. The compound of any one of embodiments 1 to 6, or a pharmaceutically acceptable salt, solvate, stereoisomer, isotopic variant, or N-oxide thereof, wherein R³ is

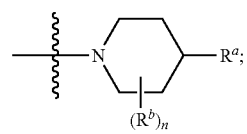

wherein R$^a$ is NH(C=O)C$_{1-4}$alkyl or NH(C=O)CH₂CH₂NH₂;
R$^b$ is F, OH, or CH₃;
and n is 1 or 2.

9. The compound of embodiment 8, or a pharmaceutically acceptable salt, solvate, stereoisomer, isotopic variant, or N-oxide thereof, wherein R$^b$ is F and n is 1.

10. The compound of any one of embodiments 1 to 6, or a pharmaceutically acceptable salt, solvate, stereoisomer, isotopic variant, or N-oxide thereof, wherein $R^3$ is

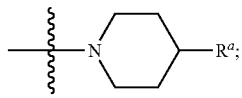

wherein $R^a$ is NH(C=O)$C_{1-4}$alkyl, $CH_2C$(=O)NH$_2$, or C(=O)NH$_2$.

11. The compound of any one of embodiments 1 to 6, or a pharmaceutically acceptable salt, solvate, stereoisomer, isotopic variant, or N-oxide thereof, wherein $R^3$ is

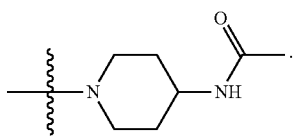

12. The compound of any one of embodiments 1 to 6, or a pharmaceutically acceptable salt, solvate, stereoisomer, isotopic variant, or N-oxide thereof, wherein $R^3$ is

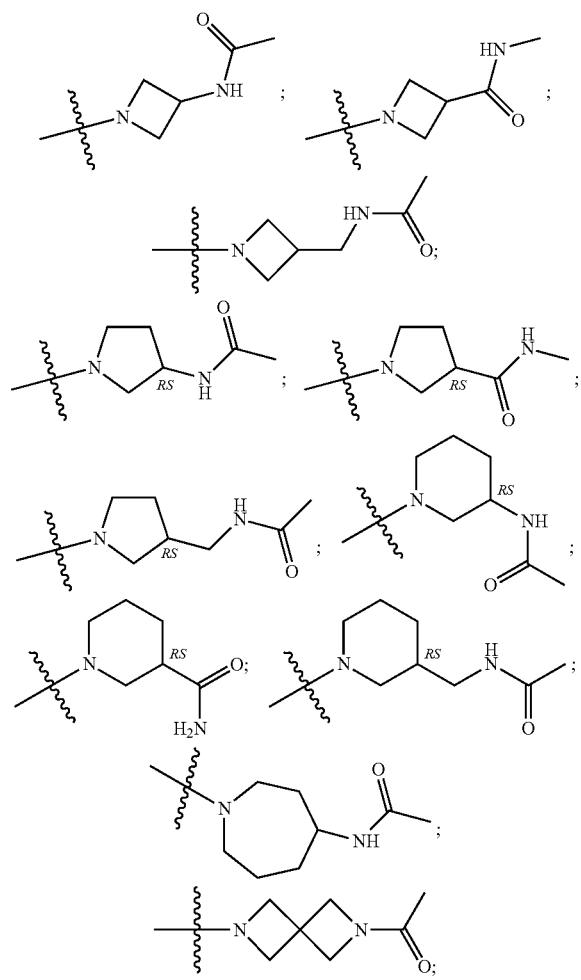

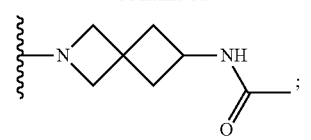

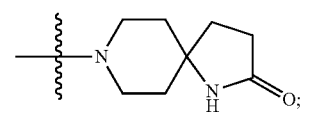

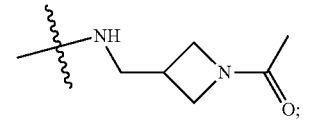

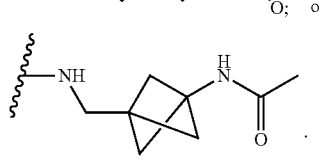

13. The compound of any one of embodiments 1 to 6, or a pharmaceutically acceptable salt, solvate, stereoisomer, isotopic variant, or N-oxide thereof, wherein $R^3$ is

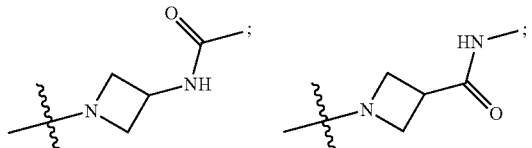

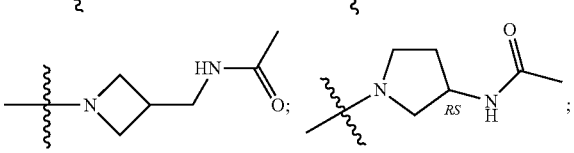

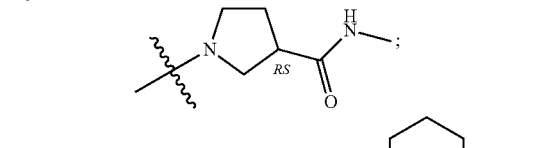

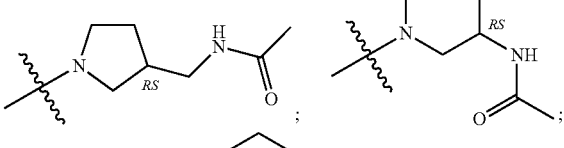

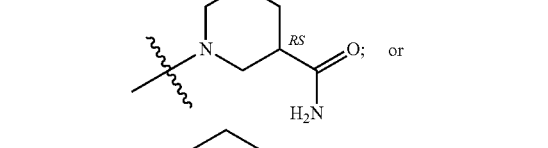

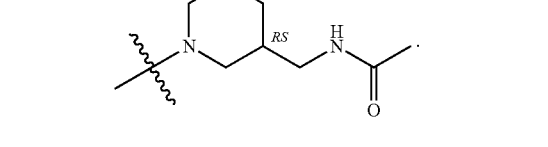

14. The compound of any one of embodiments 1 to 6, or a pharmaceutically acceptable salt, solvate, stereoisomer, isotopic variant, or N-oxide thereof, wherein R³ is
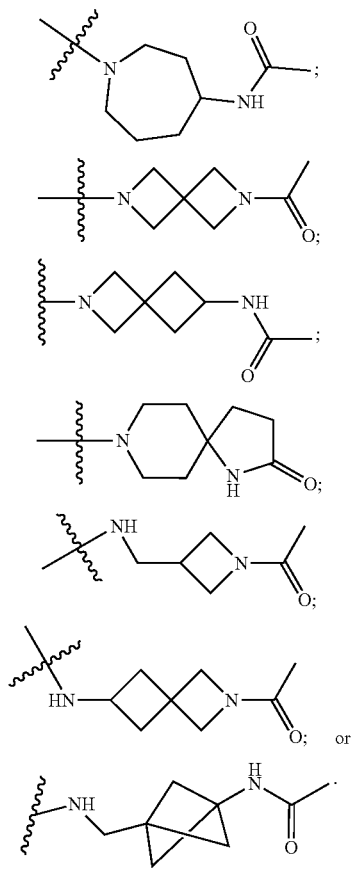
15. The compound of any one of embodiments 1 to 6, or a pharmaceutically acceptable salt, solvate, stereoisomer, isotopic variant, or N-oxide thereof, wherein R³ is
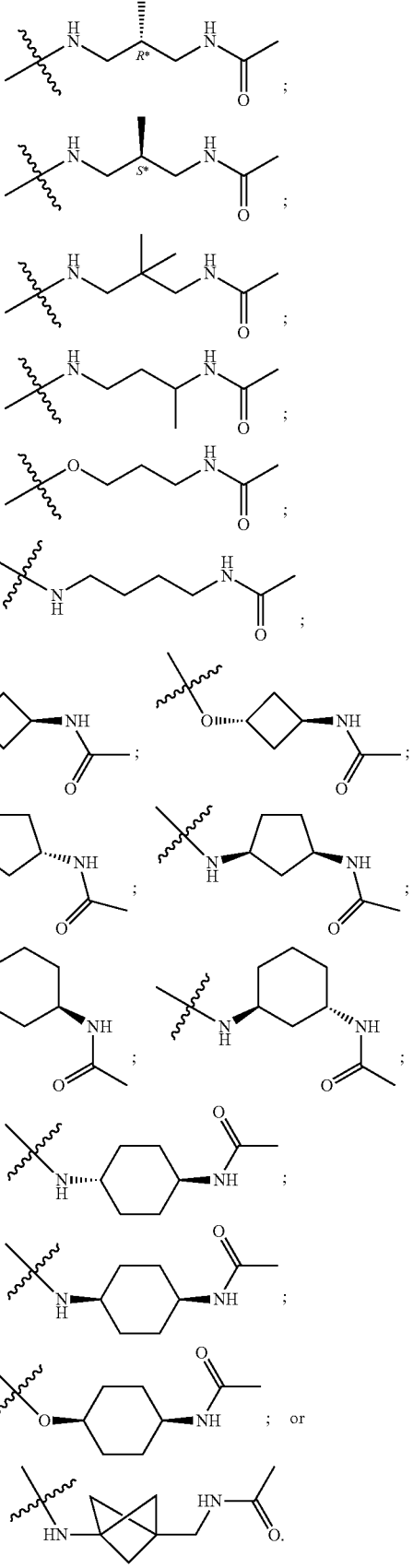

16. The compound of any one of embodiments 1 to 6, or a pharmaceutically acceptable salt, solvate, stereoisomer, isotopic variant, or N-oxide thereof, wherein $R^3$ is

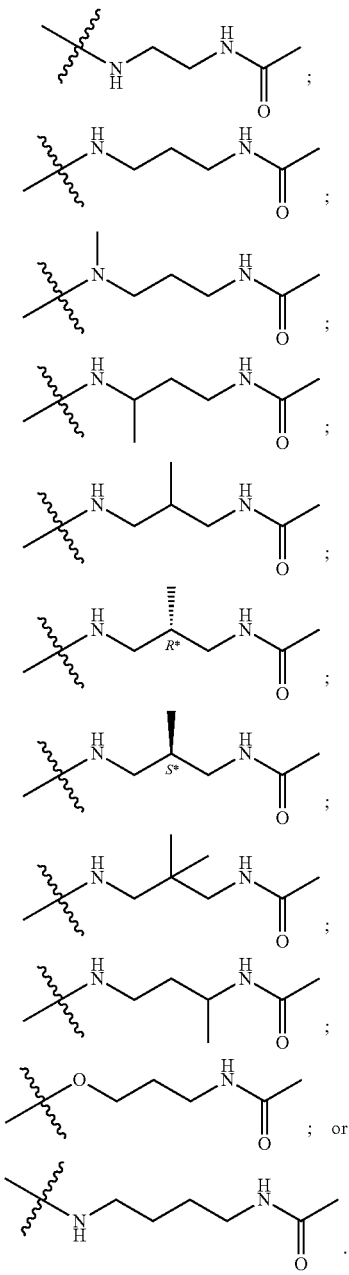

17. The compound of any one of embodiments 1 to 6, or a pharmaceutically acceptable salt, solvate, stereoisomer, isotopic variant, or N-oxide thereof, wherein $R^3$ is

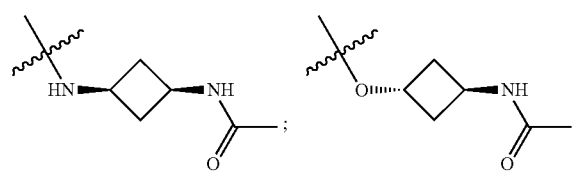

-continued

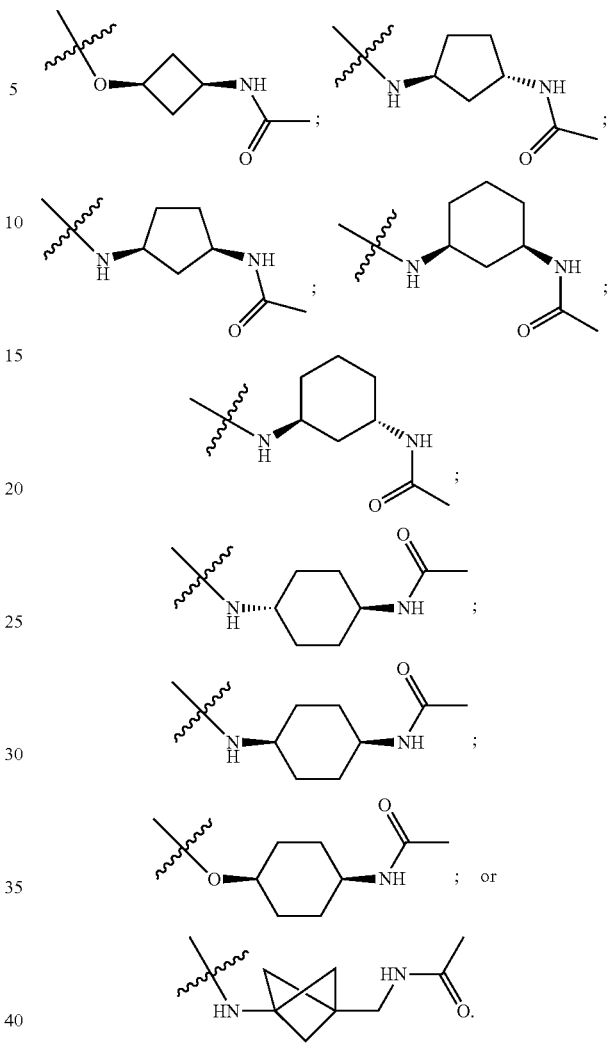

18. The compound of any one of embodiments 1 to 17, or a pharmaceutically acceptable salt, solvate, stereoisomer, isotopic variant, or N-oxide thereof, wherein $R^4$ is H.

19. The compound of any one of embodiments 1 to 18, or a pharmaceutically acceptable salt, solvate, stereoisomer, isotopic variant, or N-oxide thereof, wherein A is

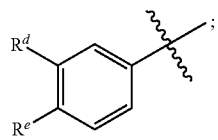

wherein $R^d$ is Cl, F, $C_{1-4}$alkyl, $CH_2OH$, $C_{1-4}$haloalkyl, $OC_{1-4}$alkyl, or $OC_{1-4}$haloalkyl; and $R^e$ is halo, $C_{1-4}$alkyl, $CH_2OH$, $OC_{1-4}$alkyl, $C_{1-4}$haloalkyl, $OC_{1-4}$haloalkyl, or $(C=O)CH_3$.

20. The compound of any one of embodiments 1 to 18, or a pharmaceutically acceptable salt, solvate, stereoisomer, isotopic variant, or N-oxide thereof, wherein A is

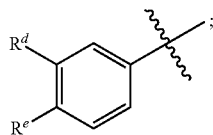

wherein $R^d$ is Cl, $CH_3$, or F; and $R^e$ is $C_{1-4}$haloalkyl or $OC_{1-4}$haloalkyl.

21. The compound of any one of embodiments 1 to 18, or a pharmaceutically acceptable salt, solvate, stereoisomer, isotopic variant, or N-oxide thereof, wherein A is 3-fluoro-4-(trifluoromethoxy)phenyl, 3-chloro-4-(trifluoromethoxy)phenyl, 3-methyl-4-(trifluoromethoxy)phenyl, 3-methoxy-4-(trifluoromethoxy)phenyl, 4-(trifluoromethoxy)-3-(trifluoromethyl)phenyl, 3-(hydroxymethyl)-4-(trifluoromethoxy)phenyl, 3-fluoro-4-(2,2,2-trifluoroethoxy)phenyl, 4-(difluoromethoxy)-3-fluoro-phenyl, 3-(difluoromethoxy)-4-fluoro-phenyl, 3-chloro-4-(trifluoromethyl)phenyl, 3-fluoro-4-(trifluoromethyl)phenyl, 3-methyl-4-(trifluoromethyl)phenyl, 4-chloro-3-fluoro-phenyl, 4-chloro-3-methyl-phenyl, 3,4-dichlorophenyl, 3-fluoro-4-methoxy-phenyl, 3-chloro-4-methoxy-phenyl, 3-chloro-4-(hydroxymethyl)phenyl, 3-chloro-4-methyl-phenyl, 3-fluoro-4-methyl-phenyl, 4-(difluoromethoxy)-3-methyl-phenyl, 3-(difluoromethyl)-4-fluoro-phenyl, 3-fluoro-4-(trifluoromethyl)phenyl, 4-acetyl-3-fluoro-phenyl, 3-fluoro-4-isopropoxy-phenyl, or 4-ethoxy-3-fluoro-phenyl.

22. The compound of any one of embodiments 1 to 18, or a pharmaceutically acceptable salt, solvate, stereoisomer, isotopic variant, or N-oxide thereof, wherein A is 3-fluoro-4-(trifluoromethoxy)phenyl.

23. The compound of any one of embodiments 1 to 18, or a pharmaceutically acceptable salt, solvate, stereoisomer, isotopic variant, or N-oxide thereof, wherein A is

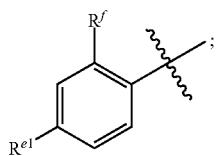

$R^f$ is H or F; and $R^{e1}$ is $CH_3$, $C_{1-4}$haloalkyl, or $OC_{1-4}$haloalkyl.

24. The compound of any one of embodiments 1 to 18, or a pharmaceutically acceptable salt, solvate, stereoisomer, isotopic variant, or N-oxide thereof, wherein A is 4-(trifluoromethoxy)phenyl.

25. The compound of any one of embodiments 1 to 18, or a pharmaceutically acceptable salt, solvate, stereoisomer, isotopic variant, or N-oxide thereof, wherein A is

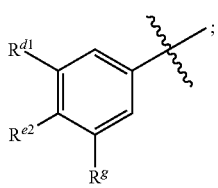

$R^{d1}$ and $R^{e2}$ are F; and $R^g$ is $OC_{1-4}$haloalkyl.

26. The compound of any one of embodiments 1 to 18, or a pharmaceutically acceptable salt, solvate, stereoisomer, isotopic variant, or N-oxide thereof, wherein A is 3,5-difluoro-4-(trifluoromethoxy)phenyl.

27. The compound of embodiment 1, or a pharmaceutically acceptable salt, solvate, stereoisomer, isotopic variant, or N-oxide thereof, having the structure of Formula (IA):

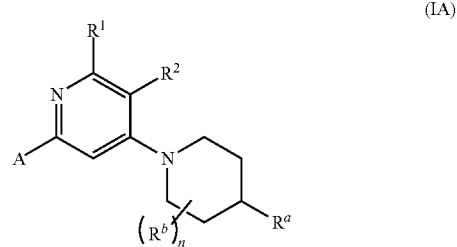

(IA)

wherein $R^1$ is selected from the group consisting of: H, $CH_3$, $CH_2OH$, $CH_2F$, $CHF_2$, $OCHF_2$, OH, $OCH_3$, and CN;

$R^2$ is selected from the group consisting of: H, F, $CH_3$, CN, and $OCH_3$;

$R^a$ is selected from the group consisting of: OH, (C=O)$NH_2$, $CH_2$(C=O)$NH_2$, $CH_2$C(=O)$CH_3$, NH(C=O)$C_{1-4}$alkyl, $NHSO_2CH_3$,

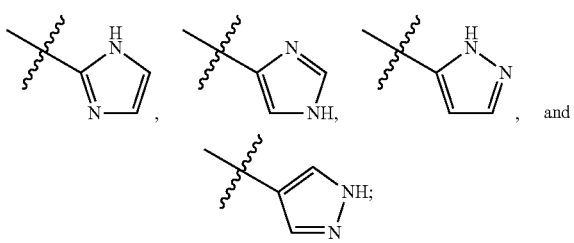

, and each $R^b$ is independently selected from the group consisting of: H, F, $CH_3$ and OH;

n is 0, 1 or 2; and

A is selected from the group consisting of: 4-(methyl)phenyl, 4-(1,1-difluoroethyl)phenyl, 4-(difluoromethyl)phenyl, 4-(trifluoromethyl)phenyl, 4-(difluoromethoxy)phenyl, 4-(trifluoromethoxy)phenyl, 3-fluoro-4-(trifluoromethoxy)phenyl, 4-chloro-3-fluoro-phenyl, 3-fluoro-4-(trifluoromethyl)phenyl, 3-(difluoromethyl)-4-fluoro-phenyl, 3-fluoro-4-methoxy-phenyl, 4-acetyl-3-fluoro-phenyl, 4-(difluoromethoxy)-3-methyl-phenyl, 4-(difluoromethoxy)-3-fluoro-phenyl, 3-(difluoromethoxy)-4-fluoro-phenyl, 4-(difluoromethoxy)-3-fluoro-phenyl, 4-ethoxy-3-fluoro-phenyl, 3-methyl-4-(trifluoromethoxy)phenyl, 3-fluoro-4-isopropoxy-phenyl, 3-fluoro-4-(2,2,2-trifluoroethoxy)phenyl, 3-chloro-4-(trifluoromethoxy)phenyl, and 3,5-difluoro-4-(trifluoromethoxy)phenyl.

28. The compound of embodiment 1, or a pharmaceutically acceptable salt, solvate, stereoisomer, isotopic variant, or N-oxide thereof, having the structure of Formula (IB):

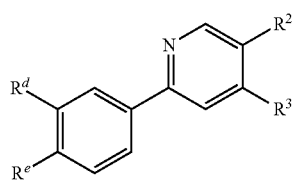
wherein
R² is H or F;
R³ is:
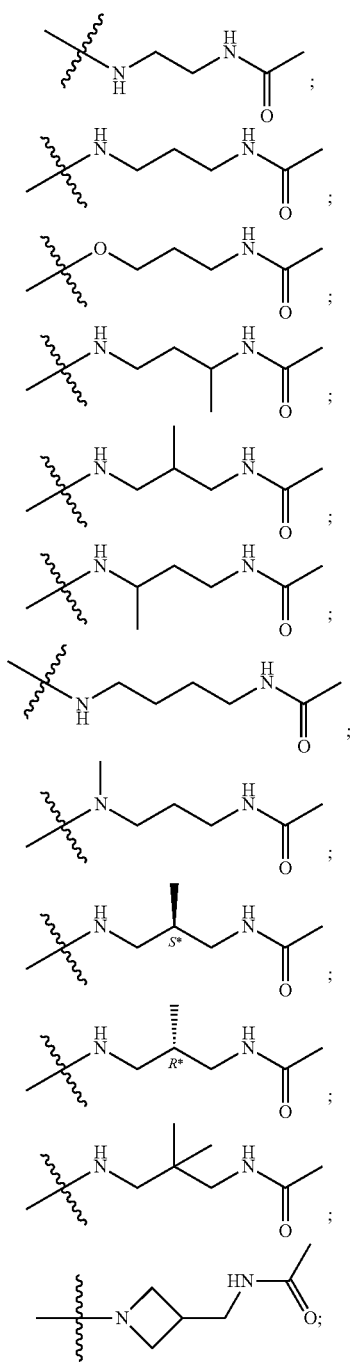
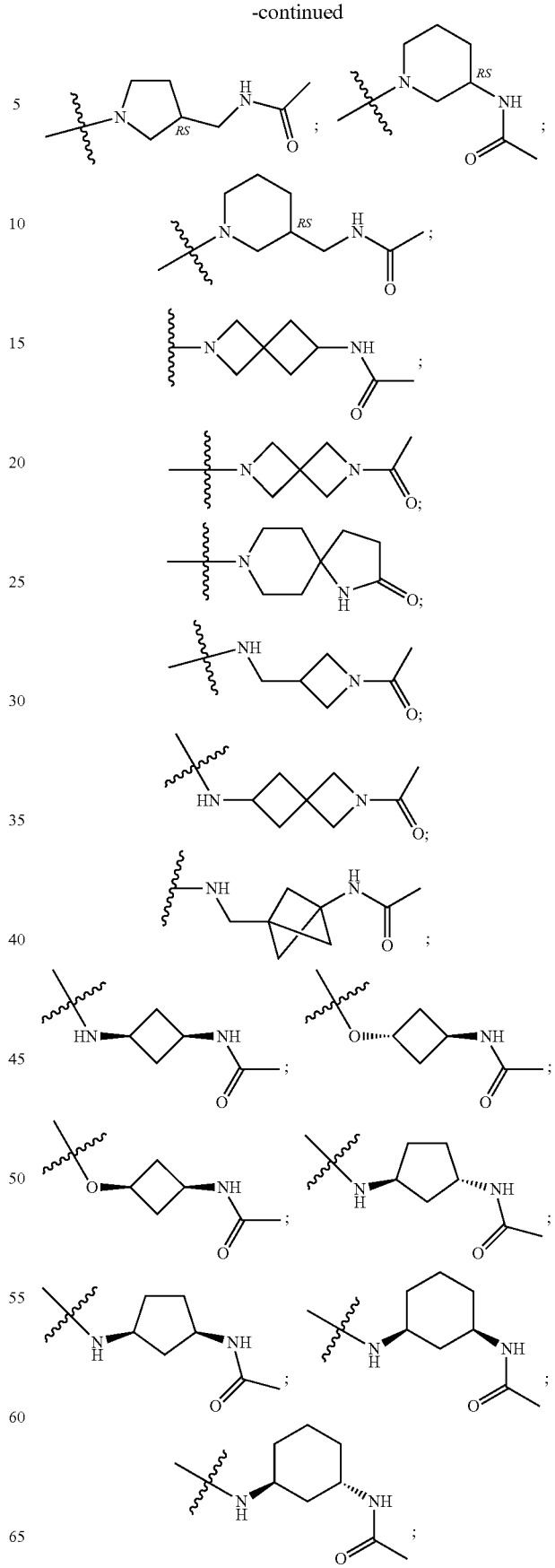

-continued

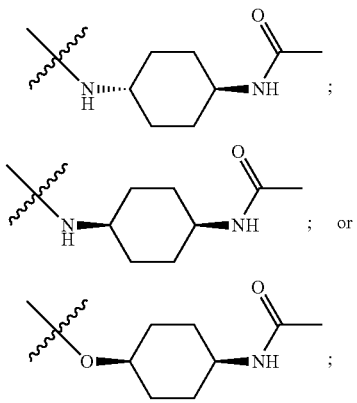

$R^d$ is halo or $C_{1-4}$haloalkyl; and
$R^e$ is halo or $OC_{1-4}$haloalkyl.

29. The compound of embodiment 28, or a pharmaceutically acceptable salt, solvate, stereoisomer, isotopic variant, or N-oxide thereof, wherein
R³ is

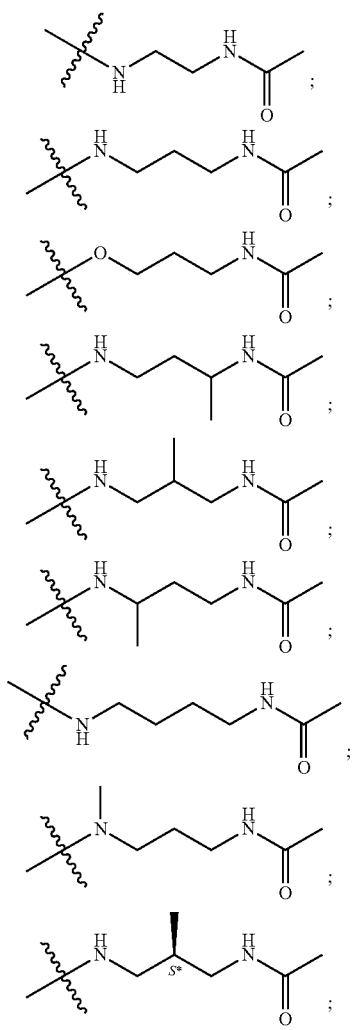

-continued

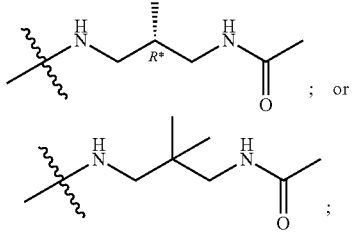

$R^d$ is F, or $C_{1-4}$haloalkyl; and
$R^e$ is F, or $OC_{1-4}$haloalkyl.

30. The compound of embodiment 28, or a pharmaceutically acceptable salt, solvate, stereoisomer, isotopic variant, or N-oxide thereof, wherein
R³ is

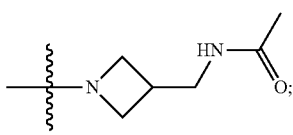

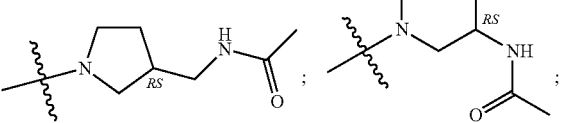

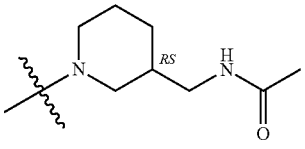

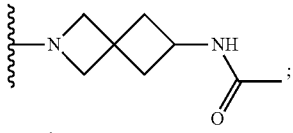

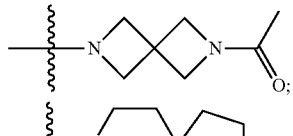

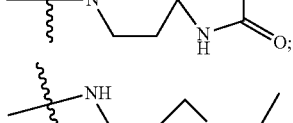

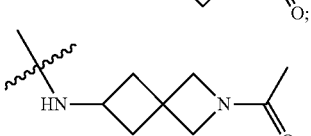

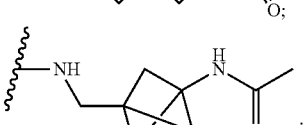

$R^d$ is F, or $C_{1-4}$haloalkyl; and
$R^e$ is F, or $OC_{1-4}$haloalkyl.

31. The compound of embodiment 28, or a pharmaceutically acceptable salt, solvate, stereoisomer, isotopic variant, or N-oxide thereof, wherein
$R^3$ is

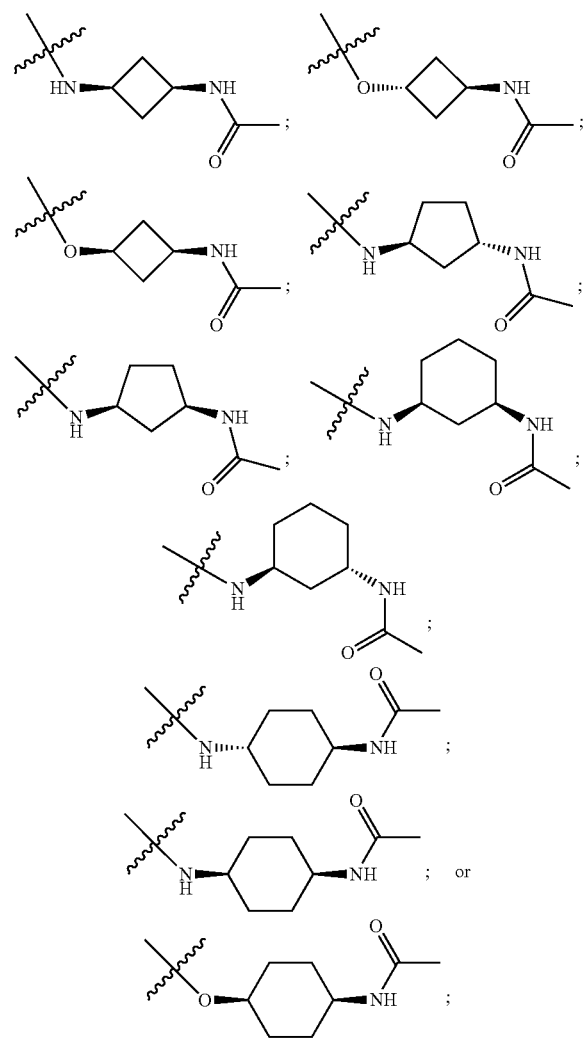

$R^d$ is F, or $C_{1-4}$haloalkyl; and
$R^e$ is F, or $OC_{1-4}$haloalkyl.

32. The compound of embodiment 1, or a pharmaceutically acceptable salt, solvate, stereoisomer, isotopic variant, or N-oxide thereof, having the structure of Formula (IC):

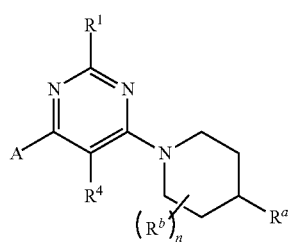

(IC)

wherein
$R^1$ is selected from the group consisting of: H, $CH_3$, $CH_2CH_3$, $CH_2OH$, $OCH_3$, and cyclopropyl;

$R^a$ is selected from the group consisting of: OH, (C=O)NH$_2$, (C=O)NHCH$_3$, (C=O)NHCH$_2$CH$_2$OH, CH$_2$(C=O)NH$_2$, CH$_2$C(=O)CH$_3$, (C=O)CH$_3$, CH$_2$NH(C=O)CH$_3$, NH(C=O)C$_{1-4}$alkyl, NCH$_3$(C=O)C$_{1-4}$alkyl, NH(C=O)CH$_2$CH$_2$NH$_2$, NH(C=O)CH$_2$CH$_2$OH, NH(C=O)CHF$_2$, NH(C=O)cyclopropyl, NHSO$_2$CH$_3$,

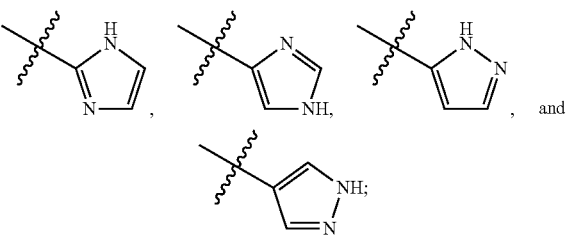

, and

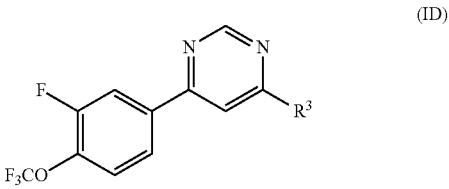

each $R^b$ is independently selected from the group consisting of: H, F, and CH$_3$;
n is 0, 1 or 2;
$R^4$ is H or CH$_3$; and
A is 4-(trifluoromethoxy)phenyl, 4-(trifluoromethyl)phenyl, 4-(1,1-difluoroethyl)phenyl, 4-(difluoromethoxy)phenyl, 4-(difluoromethyl)phenyl, 3-fluoro-4-(trifluoromethoxy)phenyl, 3-methyl-4-(trifluoromethoxy)phenyl, 3-methoxy-4-(trifluoromethoxy)phenyl, 3-chloro-4-(trifluoromethoxy)phenyl, 3-(hydroxymethyl)-4-(trifluoromethoxy)phenyl, 4-(trifluoromethoxy)-3-(trifluoromethyl)phenyl, 3-fluoro-4-(trifluoromethyl)phenyl, 3-fluoro-4-(2,2,2-trifluoroethoxy)phenyl, 3-chloro-4-(trifluoromethyl)phenyl, 3-fluoro-4-methyl-phenyl, 3-fluoro-4-methoxy-phenyl, 3-chloro-4-methyl-phenyl, 4-chloro-3-methyl-phenyl, 4-chloro-3-fluoro-phenyl, 3-chloro-4-(hydroxymethyl)phenyl, 3-chloro-4-methoxy-phenyl, 3,4-dichlorophenyl, 3-(difluoromethoxy)-4-fluoro-phenyl, 3-methyl-4-(trifluoromethyl)phenyl, 4-(difluoromethoxy)-3-fluoro-phenyl, or 3,5-difluoro-4-(trifluoromethoxy)phenyl.

33. The compound of embodiment 32, or a pharmaceutically acceptable salt, solvate, stereoisomer, isotopic variant, or N-oxide thereof, wherein
$R^1$ is H;
$R^a$ is (C=O)NH$_2$, (C=O)NHCH$_3$, or NH(C=O)C$_{1-4}$alkyl;
each $R^b$ is independently selected from the group consisting of: H, F, and CH$_3$;
n is 0 or 1;
$R^4$ is H; and
A is 3-fluoro-4-(trifluoromethoxy)phenyl, 3-methyl-4-(trifluoromethoxy)phenyl, 3-methoxy-4-(trifluoromethoxy)phenyl, or 3-chloro-4-(trifluoromethoxy)phenyl.

34. The compound of embodiment 1, or a pharmaceutically acceptable salt, solvate, stereoisomer, isotopic variant, or N-oxide thereof, having the structure of Formula (ID):

(ID)

wherein $R^3$ is

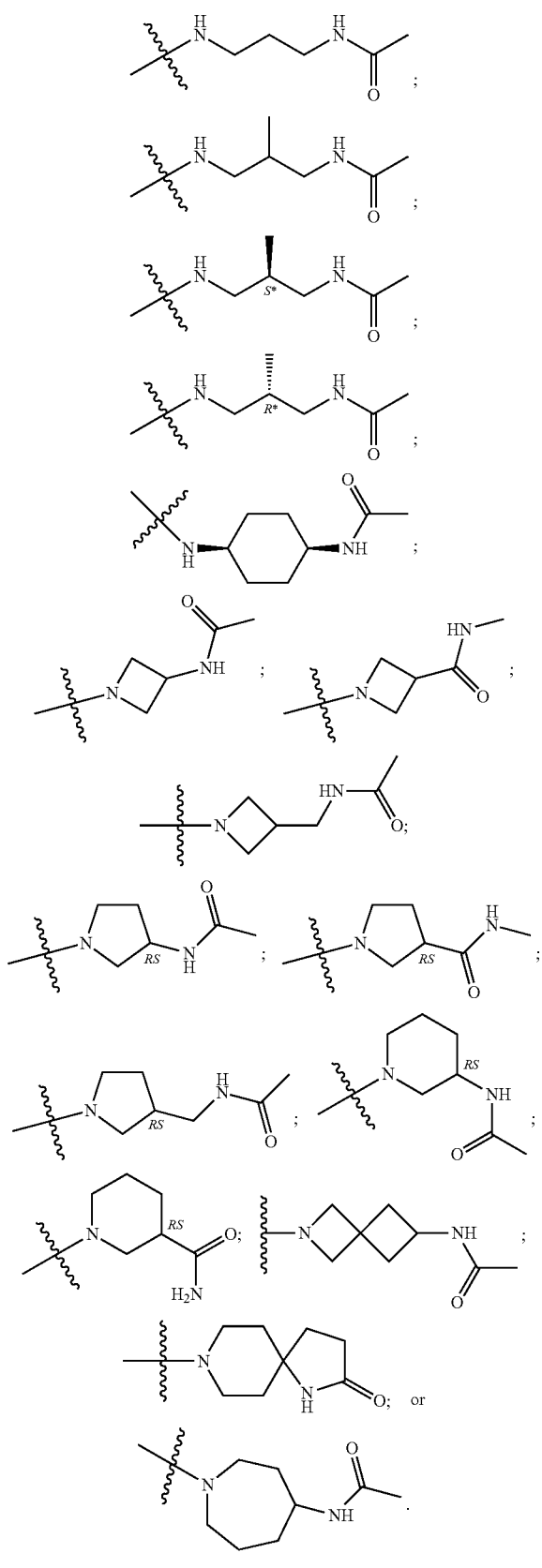

35. A compound, or a pharmaceutically acceptable salt, solvate, stereoisomer, isotopic variant, or N-oxide thereof, wherein the compound is selected from the group consisting of:

N-[1-[2-[3-Fluoro-4-(trifluoromethoxy)phenyl]-4-pyridyl]-4-piperidyl]acetamide;
N-[1-[2-[3-(Difluoromethoxy)-4-fluoro-phenyl]-4-pyridyl]-4-piperidyl]acetamide;
N-[1-[2-[4-(Difluoromethyl)phenyl]-4-pyridyl]-4-piperidyl]acetamide;
N-[1-[2-[3,5-Difluoro-4-(trifluoromethoxy)phenyl]-4-pyridyl]-4-piperidyl]acetamide;
N-[1-[5-Fluoro-2-[3-fluoro-4-(trifluoromethoxy)phenyl]-4-pyridyl]-4-piperidyl]acetamide;
(trans)-N-[3-Fluoro-1-[2-[3-fluoro-4-(trifluoromethoxy)phenyl]-4-pyridyl]-4-piperidyl]acetamide;
(*R/*R)—N-[3-Fluoro-1-[5-fluoro-2-[3-fluoro-4-(trifluoromethoxy)phenyl]-4-pyridyl]-4-piperidyl]acetamide;
(racemic)-N-[1-[2-[3-Fluoro-4-(trifluoromethoxy)phenyl]-4-pyridyl]-2-methyl-4-piperidyl]acetamide;
N-[1-[5-Cyano-2-[4-(trifluoromethoxy)phenyl]-4-pyridyl]-4-piperidyl]acetamide;
N-[1-[2-Cyano-6-[3-fluoro-4-(trifluoromethoxy)phenyl]-4-pyridyl]-4-piperidyl]acetamide;
N-[1-[2-[3-Fluoro-4-(trifluoromethoxy)phenyl]-6-methyl-4-pyridyl]-4-piperidyl]acetamide;
1-[2-[2-[3-Fluoro-4-(trifluoromethoxy)phenyl]-4-pyridyl]-2,6-diazaspiro[3;3]heptan-6-yl]ethanone;
1-[2-[2-[4-(Difluoromethoxy)-3-fluoro-phenyl]-4-pyridyl]-2,6-diazaspiro[3;3]heptan-6-yl]ethanone;
N-[4-[[2-[3-Fluoro-4-(trifluoromethoxy)phenyl]-4-pyridyl]oxy]cyclohexyl]acetamide;
(racemic)-N-[3-[[2-[3-Fluoro-4-(trifluoromethoxy)phenyl]-6-(hydroxymethyl)-4-pyridyl]amino]-2-methyl-propyl]acetamide;
1-[2-[3-Fluoro-4-(trifluoromethoxy)phenyl]-4-pyridyl]piperidin-4-ol;
N-[1-[2-[4-(Trifluoromethoxy)phenyl]-4-pyridyl]-4-piperidyl]acetamide;
N-[1-[2-[3-Methyl-4-(trifluoromethoxy)phenyl]-4-pyridyl]-4-piperidyl]acetamide;
N-[1-[2-[4-(Difluoromethoxy)-3-methyl-phenyl]-4-pyridyl]-4-piperidyl]acetamide;
1-[2-[3-Fluoro-4-(trifluoromethoxy)phenyl]-4-pyridyl]piperidine-4-carboxamide;
1-[1-[2-[3-Fluoro-4-(trifluoromethoxy)phenyl]-4-pyridyl]-4-piperidyl]propan-2-one;
2-[1-[2-[3-Fluoro-4-(trifluoromethoxy)phenyl]-4-pyridyl]-4-piperidyl]acetamide;
2-[3-Fluoro-4-(trifluoromethoxy)phenyl]-4-[4-(1H-pyrazol-5-yl)-1-piperidyl]pyridine;
2-[3-Fluoro-4-(trifluoromethoxy)phenyl]-4-[4-(1H-imidazol-4-yl)-1-piperidyl]pyridine;
2-[3-Fluoro-4-(trifluoromethoxy)phenyl]-4-[4-(1H-imidazol-2-yl)-1-piperidyl]pyridine;
2-[3-Fluoro-4-(trifluoromethoxy)phenyl]-4-[4-(1H-pyrazol-4-yl)-1-piperidyl]pyridine;
8-[2-[3-Fluoro-4-(trifluoromethoxy)phenyl]-4-pyridyl]-4,8-diazaspiro[4;5]decan-3-one;
N-[1-[2-[3-Fluoro-4-(trifluoromethoxy)phenyl]-4-pyridyl]-4-piperidyl]methanesulfonamide;
N-[1-[2-[4-(Difluoromethoxy)phenyl]-4-pyridyl]-4-piperidyl]acetamide;
N-[1-[2-[4-(Difluoromethoxy)-3-fluoro-phenyl]-4-pyridyl]-4-piperidyl]acetamide;
N-[1-[2-[3-(Difluoromethyl)-4-fluoro-phenyl]-4-pyridyl]-4-piperidyl]acetamide;

N-[1-[2-(p-Tolyl)-4-pyridyl]-4-piperidyl]acetamide;
N-[1-[2-[4-(1,1-Difluoroethyl)phenyl]-4-pyridyl]-4-piperidyl]acetamide;
N-[1-[2-[4-(Trifluoromethyl)phenyl]-4-pyridyl]-4-piperidyl]acetamide;
N-[1-[2-[3-Chloro-4-(trifluoromethoxy)phenyl]-4-pyridyl]-4-piperidyl]acetamide;
N-[1-[2-[2-Fluoro-4-(trifluoromethoxy)phenyl]-4-pyridyl]-4-piperidyl]acetamide;
N-[1-[2-[3-Fluoro-4-(2,2,2-trifluoroethoxy)phenyl]-4-pyridyl]-4-piperidyl]acetamide;
N-[1-[2-(4-Chloro-3-fluoro-phenyl)-4-pyridyl]-4-piperidyl]acetamide;
N-[1-[2-(3-Fluoro-4-methoxy-phenyl)-4-pyridyl]-4-piperidyl]acetamide;
N-[1-[2-[3-Fluoro-4-(trifluoromethyl)phenyl]-4-pyridyl]-4-piperidyl]acetamide;
N-[1-[2-(4-Acetyl-3-fluoro-phenyl)-4-pyridyl]-4-piperidyl]acetamide;
N-[1-[2-[3-Fluoro-4-(trifluoromethoxy)phenyl]-5-methyl-4-pyridyl]-4-piperidyl]acetamide;
N-[1-[2-[3-Fluoro-4-(trifluoromethoxy)phenyl]-5-methoxy-4-pyridyl]-4-piperidyl]acetamide;
N-[1-[2-[4-(Difluoromethoxy)phenyl]-6-methyl-4-pyridyl]-4-piperidyl]acetamide;
N-[1-[2-[4-(1,1-Difluoroethyl)phenyl]-6-methyl-4-pyridyl]-4-piperidyl]acetamide;
N-[1-[2-[4-(Difluoromethoxy)-3-fluoro-phenyl]-6-methyl-4-pyridyl]-4-piperidyl]acetamide;
N-[1-[2-(Fluoromethyl)-6-[3-fluoro-4-(trifluoromethoxy)phenyl]-4-pyridyl]-4-piperidyl]acetamide;
N-[1-[2-(Difluoromethyl)-6-[3-fluoro-4-(trifluoromethoxy)phenyl]-4-pyridyl]-4-piperidyl]acetamide;
N-[1-[2-[3-Fluoro-4-(trifluoromethoxy)phenyl]-6-(hydroxymethyl)-4-pyridyl]-4-piperidyl]acetamide;
N-[1-[2-(3-Fluoro-4-isopropoxy-phenyl)-6-(hydroxymethyl)-4-pyridyl]-4-piperidyl]acetamide;
N-[1-[2-(4-Ethoxy-3-fluoro-phenyl)-6-(hydroxymethyl)-4-pyridyl]-4-piperidyl]acetamide;
N-[1-[2-[3-Fluoro-4-(trifluoromethoxy)phenyl]-6-methoxy-4-pyridyl]-4-piperidyl]acetamide;
N-[1-[2-[3-Fluoro-4-(trifluoromethoxy)phenyl]-6-hydroxy-4-pyridyl]-4-piperidyl]acetamide;
N-[1-[2-(Difluoromethoxy)-6-[3-fluoro-4-(trifluoromethoxy)phenyl]-4-pyridyl]-4-piperidyl]acetamide;
(cis)-N-[3-Fluoro-1-[2-[3-fluoro-4-(trifluoromethoxy)phenyl]-4-pyridyl]-4-piperidyl]acetamide;
(*R/*R)—N-[3-Fluoro-1-[2-[3-fluoro-4-(trifluoromethoxy)phenyl]-4-pyridyl]-4-piperidyl]acetamide;
(*S/*S)—N-[3-Fluoro-1-[2-[3-fluoro-4-(trifluoromethoxy)phenyl]-4-pyridyl]-4-piperidyl]acetamide;
(*S/*S)—N-[3-Fluoro-1-[5-fluoro-2-[3-fluoro-4-(trifluoromethoxy)phenyl]-4-pyridyl]-4-piperidyl]acetamide;
(trans)-N-[1-[2-[3-Fluoro-4-(trifluoromethoxy)phenyl]-4-pyridyl]-3-hydroxy-4-piperidyl]acetamide;
(racemic)-N-[1-[2-[3-Fluoro-4-(trifluoromethoxy)phenyl]-4-pyridyl]-3-methyl-4-piperidyl]acetamide;
(trans)-N-[1-[2-[3-Fluoro-4-(trifluoromethoxy)phenyl]-4-pyridyl]-3-methyl-4-piperidyl]acetamide;
(cis)-N-[1-[2-[3-Fluoro-4-(trifluoromethoxy)phenyl]-4-pyridyl]-3-methyl-4-piperidyl]acetamide;
N-[[1-[2-[3-Fluoro-4-(trifluoromethoxy)phenyl]-4-pyridyl]azetidin-3-yl]methyl]acetamide;
(racemic)-N-[[1-[2-[3-Fluoro-4-(trifluoromethoxy)phenyl]-4-pyridyl]pyrrolidin-3-yl]methyl]acetamide;
(racemic)-N-[1-[2-[3-Fluoro-4-(trifluoromethoxy)phenyl]-4-pyridyl]-3-piperidyl]acetamide;
(racemic)-N-[1-[2-[3-Fluoro-4-(trifluoromethoxy)phenyl]-4-pyridyl]-3,3-dimethyl-4-piperidyl]acetamide;
N-[[1-[2-[3-Fluoro-4-(trifluoromethoxy)phenyl]-4-pyridyl]-4-piperidyl]methyl]acetamide;
(racemic)-N-[[1-[2-[3-Fluoro-4-(trifluoromethoxy)phenyl]-4-pyridyl]-3-piperidyl]methyl]acetamide;
1-[2-[2-[3-(Difluoromethyl)-4-fluoro-phenyl]-4-pyridyl]-2,6-diazaspiro[3;3]heptan-6-yl]ethanone;
1-[2-[2-[4-(Trifluoromethoxy)phenyl]-4-pyridyl]-2,6-diazaspiro[3;3]heptan-6-yl]ethanone;
1-[2-[[2-[3-Fluoro-4-(trifluoromethoxy)phenyl]-4-pyridyl]amino]-6-azaspiro[3;3]heptan-6-yl]ethanone;
N-[6-[2-[3-Fluoro-4-(trifluoromethoxy)phenyl]-4-pyridyl]-6-azaspiro[3;3]heptan-2-yl]acetamide;
N-[3-[[2-[3-Fluoro-4-(trifluoromethoxy)phenyl]-4-pyridyl]amino]cyclobutyl]acetamide;
(trans)-N-[3-[[2-[3-Fluoro-4-(trifluoromethoxy)phenyl]-4-pyridyl]amino]cyclopentyl]acetamide;
(cis)-N-[3-[[2-[3-Fluoro-4-(trifluoromethoxy)phenyl]-4-pyridyl]amino]cyclopentyl]acetamide;
(trans)-N-[3-[[2-[3-Fluoro-4-(trifluoromethoxy)phenyl]-4-pyridyl]amino]cyclohexyl]acetamide;
(cis)-N-[3-[[2-[3-Fluoro-4-(trifluoromethoxy)phenyl]-4-pyridyl]amino]cyclohexyl]acetamide;
N-[4-[[2-[3-Fluoro-4-(trifluoromethoxy)phenyl]-4-pyridyl]amino]cyclohexyl]acetamide;
N-[4-[[2-[3-Fluoro-4-(trifluoromethoxy)phenyl]-4-pyridyl]amino]cyclohexyl]acetamide;
1-[3-[[[2-[3-Fluoro-4-(trifluoromethoxy)phenyl]-4-pyridyl]amino]methyl]azetidin-1-yl]ethanone;
N-[1-[[[2-[3-Fluoro-4-(trifluoromethoxy)phenyl]-4-pyridyl]amino]methyl]-3-bicyclo[1;1;1]pentanyl]acetamide;
N-[2-[[2-[3-Fluoro-4-(trifluoromethoxy)phenyl]-4-pyridyl]amino]ethyl]acetamide;
N-[3-[[2-[3-Fluoro-4-(trifluoromethoxy)phenyl]-4-pyridyl]amino]propyl]acetamide;
N-[3-[[2-[3-Fluoro-4-(trifluoromethoxy)phenyl]-4-pyridyl]-methylamino]propyl]acetamide;
(racemic)-N-[3-[[2-[3-Fluoro-4-(trifluoromethoxy)phenyl]-4-pyridyl]amino]butyl]acetamide;
(racemic)-N-[3-[[2-[3-Fluoro-4-(trifluoromethoxy)phenyl]-4-pyridyl]amino]-2-methyl-propyl]acetamide;
(*R)—N-[3-[[2-[3-Fluoro-4-(trifluoromethoxy)phenyl]-4-pyridyl]amino]-2-methyl-propyl]acetamide;
(*S)—N-[3-[[2-[3-Fluoro-4-(trifluoromethoxy)phenyl]-4-pyridyl]amino]-2-methyl-propyl]acetamide;
(racemic)-N-[3-[[2-[3-Fluoro-4-(trifluoromethoxy)phenyl]-4-pyridyl]amino]-1-methyl-propyl]acetamide;
N-[3-[[2-[3-Fluoro-4-(trifluoromethoxy)phenyl]-4-pyridyl]amino]-2,2-dimethyl-propyl]acetamide;
N-[4-[[2-[3-Fluoro-4-(trifluoromethoxy)phenyl]-4-pyridyl]amino]butyl]acetamide;
N-[3-[[2-[3-Fluoro-4-(trifluoromethoxy)phenyl]-4-pyridyl]oxy]propyl]acetamide;
N-[3-[[2-[3-Fluoro-4-(trifluoromethoxy)phenyl]-4-pyridyl]oxy]cyclobutyl]acetamide;
N-[3-[[2-[3-Fluoro-4-(trifluoromethoxy)phenyl]-4-pyridyl]oxy]cyclobutyl]acetamide;
N-(4-(2-(3-Fluoro-4-(trifluoromethoxy)phenyl)pyridin-4-yl)cyclohexyl)acetamide;
(R/S)—N-(3-((5-Fluoro-2-(3-fluoro-4-(trifluoromethoxy)phenyl)pyridin-4-yl)amino)-2-methylpropyl)acetamide; and
N-(3-((5-Fluoro-2-(3-fluoro-4-(trifluoromethoxy)phenyl)pyridin-4-yl)amino)propyl)acetamide.

36. A compound or a pharmaceutically acceptable salt, solvate, stereoisomer, isotopic variant, or N-oxide thereof, wherein the is compound is selected from the group consisting of:

1-[6-[4-(Trifluoromethoxy)phenyl]pyrimidin-4-yl]piperidine-4-carboxamide;
N-[1-[6-[3-Fluoro-4-(trifluoromethoxy)phenyl]pyrimidin-4-yl]-4-piperidyl]acetamide;
N-[1-[6-[3-Chloro-4-(trifluoromethoxy)phenyl]-2-methyl-pyrimidin-4-yl]-4-piperidyl]acetamide;
(trans)-N-[3-Fluoro-1-[2-methyl-6-[4-(trifluoromethoxy)phenyl]pyrimidin-4-yl]-4-piperidyl]acetamide;
N-[1-[6-[3-Fluoro-4-(trifluoromethoxy)phenyl]-2-(hydroxymethyl)pyrimidin-4-yl]-4-piperidyl]acetamide;
(racemic)-N-Methyl-1-[6-[4-(trifluoromethoxy)phenyl]pyrimidin-4-yl]pyrrolidine-3-carboxamide;
(Trans)-N-[3-Fluoro-1-[6-[3-fluoro-4-(trifluoromethoxy)phenyl]-2-methyl-pyrimidin-4-yl]-4-piperidyl]acetamide;
N-[1-[6-[3-Fluoro-4-(trifluoromethoxy)phenyl]pyrimidin-4-yl]-4-piperidyl]cyclopropanecarboxamide;
3-Amino-N-[1-[6-[3-fluoro-4-(trifluoromethoxy)phenyl]pyrimidin-4-yl]-4-piperidyl]propanamide;
N-[1-[6-[3-Fluoro-4-(trifluoromethoxy)phenyl]pyrimidin-4-yl]azetidin-3-yl]acetamide;
1-[6-[4-(Trifluoromethoxy)phenyl]pyrimidin-4-yl]piperidine-3-carboxamide;
1-[6-[4-(Difluoromethoxy)phenyl]pyrimidin-4-yl]piperidine-4-carboxamide;
1-[2-Methyl-6-[4-(trifluoromethoxy)phenyl]pyrimidin-4-yl]piperidine-4-carboxamide;
1-[6-[3-(Difluoromethoxy)-4-fluoro-phenyl]pyrimidin-4-yl]piperidine-4-carboxamide;
1-[6-[4-(Trifluoromethyl)phenyl]pyrimidin-4-yl]piperidine-4-carboxamide;
1-[6-[3-Fluoro-4-(trifluoromethoxy)phenyl]pyrimidin-4-yl]piperidine-4-carboxamide;
1-[5-Methyl-6-[4-(trifluoromethoxy)phenyl]pyrimidin-4-yl]piperidine-4-carboxamide;
1-[6-[3-Fluoro-4-(trifluoromethoxy)phenyl]-2-methyl-pyrimidin-4-yl]piperidine-4-carboxamide;
1-[6-[3-Fluoro-4-(2,2,2-trifluoroethoxy)phenyl]pyrimidin-4-yl]piperidine-4-carboxamide;
1-[2-Cyclopropyl-6-[4-(trifluoromethoxy)phenyl]pyrimidin-4-yl]piperidine-4-carboxamide;
1-[2,5-Dimethyl-6-[4-(trifluoromethoxy)phenyl]pyrimidin-4-yl]piperidine-4-carboxamide;
1-[6-[3-Chloro-4-(trifluoromethoxy)phenyl]pyrimidin-4-yl]piperidine-4-carboxamide;
1-[6-[3-Methyl-4-(trifluoromethoxy)phenyl]pyrimidin-4-yl]piperidine-4-carboxamide;
1-[6-[3-Methoxy-4-(trifluoromethoxy)phenyl]pyrimidin-4-yl]piperidine-4-carboxamide;
1-[2-Ethyl-6-[4-(trifluoromethoxy)phenyl]pyrimidin-4-yl]piperidine-4-carboxamide;
1-[2-Methoxy-6-[4-(trifluoromethoxy)phenyl]pyrimidin-4-yl]piperidine-4-carboxamide;
N-[1-[6-[4-(Difluoromethyl)phenyl]pyrimidin-4-yl]-4-piperidyl]acetamide;
N-[1-[6-[3-Methyl-4-(trifluoromethyl)phenyl]pyrimidin-4-yl]-4-piperidyl]acetamide;
N-[1-[6-[3-Fluoro-4-(trifluoromethoxy)phenyl]-2-methyl-pyrimidin-4-yl]-4-piperidyl]acetamide;
N-[1-[6-[3-Chloro-4-(trifluoromethoxy)phenyl]pyrimidin-4-yl]-4-piperidyl]acetamide;
1-[6-[3-Fluoro-4-(trifluoromethoxy)phenyl]-2-methyl-pyrimidin-4-yl]-N-(2-hydroxyethyl)piperidine-4-carboxamide;
1-[6-[3-Chloro-4-(trifluoromethoxy)phenyl]pyrimidin-4-yl]-N-(2-hydroxyethyl)piperidine-4-carboxamide;
1-[6-[3-Chloro-4-(trifluoromethoxy)phenyl]-2-methyl-pyrimidin-4-yl]-N-(2-hydroxyethyl)piperidine-4-carboxamide;
N-[1-[2-Methyl-6-[3-methyl-4-(trifluoromethoxy)phenyl]pyrimidin-4-yl]-4-piperidyl]acetamide;
N-[1-[6-[3-Methyl-4-(trifluoromethoxy)phenyl]pyrimidin-4-yl]-4-piperidyl]acetamide;
N-methyl-N-[1-[6-[3-methyl-4-(trifluoromethoxy)phenyl]pyrimidin-4-yl]-4-piperidyl]acetamide;
N-(2-Hydroxyethyl)-1-[2-methyl-6-[3-methyl-4-(trifluoromethoxy)phenyl]pyrimidin-4-yl]piperidine-4-carboxamide;
N-(2-Hydroxyethyl)-1-[6-[3-methyl-4-(trifluoromethoxy)phenyl]pyrimidin-4-yl]piperidine-4-carboxamide;
N-[1-[6-[4-(1,1-Difluoroethyl)phenyl]pyrimidin-4-yl]-4-piperidyl]acetamide;
N-[1-[6-[3-Fluoro-4-(trifluoromethyl)phenyl]pyrimidin-4-yl]-4-piperidyl]acetamide;
N-[1-[6-(3-Fluoro-4-methoxy-phenyl)pyrimidin-4-yl]-4-piperidyl]acetamide;
N-[1-[6-(3-Chloro-4-methoxy-phenyl)pyrimidin-4-yl]-4-piperidyl]acetamide;
N-[1-[6-[3-Chloro-4-(trifluoromethyl)phenyl]pyrimidin-4-yl]-4-piperidyl]acetamide;
N-[1-[6-(4-Chloro-3-fluoro-phenyl)pyrimidin-4-yl]-4-piperidyl]acetamide;
N-[1-[6-(3-Chloro-4-methyl-phenyl)pyrimidin-4-yl]-4-piperidyl]acetamide;
N-[1-[6-(4-Chloro-3-methyl-phenyl)pyrimidin-4-yl]-4-piperidyl]acetamide;
N-[1-[6-[3-Chloro-4-(hydroxymethyl)phenyl]pyrimidin-4-yl]-4-piperidyl]acetamide;
N-[1-[6-(3,4-Dichlorophenyl)pyrimidin-4-yl]-4-piperidyl]acetamide;
N-[1-[6-(3-Fluoro-4-methyl-phenyl)pyrimidin-4-yl]-4-piperidyl]acetamide;
N-[1-[6-[4-(Difluoromethoxy)-3-fluoro-phenyl]pyrimidin-4-yl]-4-piperidyl]acetamide;
N-[1-[6-[3-(Hydroxymethyl)-4-(trifluoromethoxy)phenyl]pyrimidin-4-yl]-4-piperidyl]acetamide;
N-[1-[6-[3,5-Difluoro-4-(trifluoromethoxy)phenyl]pyrimidin-4-yl]-4-piperidyl]acetamide;
N-[1-[2-Methyl-6-[4-(trifluoromethoxy)phenyl]pyrimidin-4-yl]-4-piperidyl]acetamide;
(trans)-N-[3-Fluoro-1-[2-methyl-6-[3-methyl-4-(trifluoromethoxy)phenyl]pyrimidin-4-yl]-4-piperidyl]acetamide;
N-[1-[6-[4-(Trifluoromethoxy)-3-(trifluoromethyl)phenyl]pyrimidin-4-yl]-4-piperidyl]acetamide;
N-Methyl-1-[6-[4-(trifluoromethoxy)phenyl]pyrimidin-4-yl]piperidine-4-carboxamide;
N-(2-Hydroxyethyl)-1-[6-[4-(trifluoromethoxy)phenyl]pyrimidin-4-yl]piperidine-4-carboxamide;
4-[4-(1H-Imidazol-4-yl)-1-piperidyl]-6-[4-(trifluoromethoxy)phenyl]pyrimidine;
N-(2-Hydroxyethyl)-1-[2-methyl-6-[4-(trifluoromethoxy)phenyl]pyrimidin-4-yl]piperidine-4-carboxamide;
4-[4-(1H-Imidazol-4-yl)-1-piperidyl]-2-methyl-6-[4-(trifluoromethoxy)phenyl]pyrimidine;
1-[6-[3-Fluoro-4-(trifluoromethoxy)phenyl]pyrimidin-4-yl]-N-(2-hydroxyethyl)piperidine-4-carboxamide;
4-[3-Fluoro-4-(trifluoromethoxy)phenyl]-6-[4-(1H-imidazol-4-yl)-1-piperidyl]pyrimidine;
2-[1-[6-[4-(Trifluoromethoxy)phenyl]pyrimidin-4-yl]-4-piperidyl]acetamide;

N-[1-[6-[4-(Trifluoromethoxy)phenyl]pyrimidin-4-yl]-4-piperidyl]acetamide;
4-[4-(1H-Imidazol-2-yl)-1-piperidyl]-6-[4-(trifluoromethoxy)phenyl]pyrimidine;
N-[[1-[6-[4-(Trifluoromethoxy)phenyl]pyrimidin-4-yl]-4-piperidyl]methyl]acetamide;
8-[6-[3-Fluoro-4-(trifluoromethoxy)phenyl]pyrimidin-4-yl]-4,8-diazaspiro[4;5]decan-3-one;
1-[6-[3-Fluoro-4-(trifluoromethoxy)phenyl]-2-methyl-pyrimidin-4-yl]piperidin-4-ol;
N-Methyl-1-[6-[4-(trifluoromethoxy)phenyl]pyrimidin-4-yl]azetidine-3-carboxamide;
(*R/*R)—N-[3-Fluoro-1-[6-[3-fluoro-4-(trifluoromethoxy)phenyl]-2-methyl-pyrimidin-4-yl]-4-piperidyl]acetamide;
(*S/*S)—N-[3-Fluoro-1-[6-[3-fluoro-4-(trifluoromethoxy)phenyl]-2-methyl-pyrimidin-4-yl]-4-piperidyl]acetamide;
(trans)-N-[3-Fluoro-1-[6-[3-fluoro-4-(trifluoromethoxy)phenyl]pyrimidin-4-yl]-4-piperidyl]acetamide;
(*S/*S)—N-[3-Fluoro-1-[6-[3-fluoro-4-(trifluoromethoxy)phenyl]pyrimidin-4-yl]-4-piperidyl]acetamide;
(*R/*R)—N-[3-Fluoro-1-[6-[3-fluoro-4-(trifluoromethoxy)phenyl]pyrimidin-4-yl]-4-piperidyl]acetamide;
(trans)-N-[3-Fluoro-1-[6-[3-methyl-4-(trifluoromethoxy)phenyl]pyrimidin-4-yl]-4-piperidyl]acetamide;
(*S/*S)—N-[3-Fluoro-1-[6-[3-methyl-4-(trifluoromethoxy)phenyl]pyrimidin-4-yl]-4-piperidyl]acetamide;
(*R/*R)—N-[3-Fluoro-1-[6-[3-methyl-4-(trifluoromethoxy)phenyl]pyrimidin-4-yl]-4-piperidyl]acetamide;
(trans)-N-[1-[6-[3-Chloro-4-(trifluoromethoxy)phenyl]pyrimidin-4-yl]-3-fluoro-4-piperidyl]acetamide;
(*S/*S)—N-[1-[6-[3-Chloro-4-(trifluoromethoxy)phenyl]pyrimidin-4-yl]-3-fluoro-4-piperidyl]acetamide;
(*R/*R)—N-[1-[6-[3-Chloro-4-(trifluoromethoxy)phenyl]pyrimidin-4-yl]-3-fluoro-4-piperidyl]acetamide;
(cis)-N-[3-Fluoro-1-[6-[3-fluoro-4-(trifluoromethoxy)phenyl]pyrimidin-4-yl]-4-piperidyl]acetamide;
(*R/*S)—N-[3-Fluoro-1-[6-[3-fluoro-4-(trifluoromethoxy)phenyl]pyrimidin-4-yl]-4-piperidyl]acetamide;
(*S/*R)—N-[3-Fluoro-1-[6-[3-fluoro-4-(trifluoromethoxy)phenyl]pyrimidin-4-yl]-4-piperidyl]acetamide;
N-[1-[6-[3-fluoro-4-(trifluoromethoxy)phenyl]-2-methyl-pyrimidin-4-yl]-4-methyl-4-piperidyl]acetamide;
N-[1-[6-[3-Fluoro-4-(trifluoromethoxy)phenyl]-2-methyl-pyrimidin-4-yl]-4-piperidyl]methanesulfonamide;
4-[3-Fluoro-4-(trifluoromethoxy)phenyl]-2-methyl-6-[4-(1H-pyrazol-5-yl)-1-piperidyl]pyrimidine;
1-[1-[6-[3-Fluoro-4-(trifluoromethoxy)phenyl]pyrimidin-4-yl]-4-piperidyl]ethanone;
1-[1-[6-[3-Fluoro-4-(trifluoromethoxy)phenyl]pyrimidin-4-yl]-4-piperidyl]propan-2-one;
N-[[1-[6-[3-Fluoro-4-(trifluoromethoxy)phenyl]pyrimidin-4-yl]azetidin-3-yl]methyl]acetamide;
(racemic)-N-[[1-[6-[3-Fluoro-4-(trifluoromethoxy)phenyl]pyrimidin-4-yl]pyrrolidin-3-yl]methyl]acetamide;
(racemic)-N-[1-[6-[3-Fluoro-4-(trifluoromethoxy)phenyl]pyrimidin-4-yl]pyrrolidin-3-yl]acetamide;
(racemic)-N-[1-[6-[3-Fluoro-4-(trifluoromethoxy)phenyl]pyrimidin-4-yl]-3-piperidyl]acetamide;
(racemic)-N-[1-[6-[3-Fluoro-4-(trifluoromethoxy)phenyl]pyrimidin-4-yl]azepan-4-yl]acetamide;
(trans)-N-[3-Fluoro-1-[6-[4-(trifluoromethoxy)phenyl]pyrimidin-4-yl]-4-piperidyl]acetamide;
(racemic)-N-[1-[6-[3-Fluoro-4-(trifluoromethoxy)phenyl]pyrimidin-4-yl]-3-methyl-4-piperidyl]acetamide;
(racemic)-N-[1-[6-[3-Fluoro-4-(trifluoromethoxy)phenyl]pyrimidin-4-yl]-2-methyl-4-piperidyl]acetamide;
2,2-Difluoro-N-[1-[6-[3-fluoro-4-(trifluoromethoxy)phenyl]pyrimidin-4-yl]-4-piperidyl]acetamide;
1-[2-[6-[3-Fluoro-4-(trifluoromethoxy)phenyl]pyrimidin-4-yl]-2,6-diazaspiro[3;3]heptan-6-yl]ethanone;
N-[4-[[6-[3-Fluoro-4-(trifluoromethoxy)phenyl]pyrimidin-4-yl]amino]cyclohexyl]acetamide;
N-[1-[6-[3-Fluoro-4-(trifluoromethoxy)phenyl]pyrimidin-4-yl]-4-piperidyl]propanamide;
N-[1-[6-[3-Fluoro-4-(trifluoromethoxy)phenyl]pyrimidin-4-yl]-4-piperidyl]-3-hydroxy-propanamide;
(trans)-3-Amino-N-[3-fluoro-1-[6-[3-fluoro-4-(trifluoromethoxy)phenyl]pyrimidin-4-yl]-4-piperidyl]propanamide;
N-[3-[[6-[3-Fluoro-4-(trifluoromethoxy)phenyl]pyrimidin-4-yl]amino]propyl]acetamide;
(racemic)-N-[3-[[6-[3-Fluoro-4-(trifluoromethoxy)phenyl]pyrimidin-4-yl]amino]-2-methyl-propyl]acetamide;
(*R)—N-[3-[[6-[3-Fluoro-4-(trifluoromethoxy)phenyl]pyrimidin-4-yl]amino]-2-methyl-propyl]acetamide; and
(*S)—N-[3-[[6-[3-Fluoro-4-(trifluoromethoxy)phenyl]pyrimidin-4-yl]amino]-2-methyl-propyl]acetamide.

37. A compound or a pharmaceutically acceptable salt, solvate, stereoisomer, isotopic variant, or N-oxide thereof, wherein the compound is selected from the group consisting of:
N-[1-[6-[3-Fluoro-4-(trifluoromethoxy)phenyl]pyrimidin-4-yl]-4-piperidyl]acetamide;
N-[1-[2-[3-Fluoro-4-(trifluoromethoxy)phenyl]-4-pyridyl]-4-piperidyl]acetamide;
N-[1-[6-[3-Methyl-4-(trifluoromethoxy)phenyl]pyrimidin-4-yl]-4-piperidyl]acetamide;
N-[1-[2-[4-(Trifluoromethoxy)phenyl]-4-pyridyl]-4-piperidyl]acetamide;
N-[1-[2-[3-Methyl-4-(trifluoromethoxy)phenyl]-4-pyridyl]-4-piperidyl]acetamide;
N-[1-[2-[4-(Difluoromethoxy)-3-methyl-phenyl]-4-pyridyl]-4-piperidyl]acetamide;
2-[1-[2-[3-Fluoro-4-(trifluoromethoxy)phenyl]-4-pyridyl]-4-piperidyl]acetamide;
N-[1-[2-[3-Chloro-4-(trifluoromethoxy)phenyl]-4-pyridyl]-4-piperidyl]acetamide;
N-[1-[2-(Fluoromethyl)-6-[3-fluoro-4-(trifluoromethoxy)phenyl]-4-pyridyl]-4-piperidyl]acetamide;
N-[1-[2-[3-Fluoro-4-(trifluoromethoxy)phenyl]-6-(hydroxymethyl)-4-pyridyl]-4-piperidyl]acetamide;
(*R/*R)—N-[3-Fluoro-1-[2-[3-fluoro-4-(trifluoromethoxy)phenyl]-4-pyridyl]-4-piperidyl]acetamide; and
(*S)—N-[3-[[2-[3-Fluoro-4-(trifluoromethoxy)phenyl]-4-pyridyl]amino]-2-methyl-propyl]acetamide.

38. The compound of any one of embodiments 1 to 37 or a pharmaceutically acceptable salt thereof.

39. A pharmaceutical composition comprising a compound of any one of embodiments 1 to 37, or a pharmaceutically acceptable salt, solvate, stereoisomer, isotopic variant, or N-oxide thereof, and a pharmaceutically acceptable excipient.

40. A pharmaceutical composition comprising a compound of any one of embodiments 1 to 37, or a pharmaceutically acceptable salt thereof, and a pharmaceutically acceptable excipient.

41. A method of treating a subject suffering from or diagnosed with a disease, disorder, or medical condition mediated by NR2B receptor activity, comprising administering to the subject an effective amount of a compound of any one of embodiments 1 to 37 or a pharmaceutically acceptable salt, solvate, stereoisomer, isotopic variant, or N-oxide thereof, or the pharmaceutical composition of embodiment 39 or embodiment 40.

42. The method of embodiment 41, wherein the disease, disorder, or medical condition mediated by the NR2B receptor is selected from the group consisting of: bipolar disorder, major depressive disorder, treatment-resistant depression, post-partum depression, seasonal affective disorder, Alzheimer's disease, Parkinson's disease, Huntington's chorea, multiple sclerosis, cognitive impairment, head injury, spinal cord injury, stroke, epilepsy, dyskinesias, amyotrophic lateral sclerosis, neurodegeneration associated with bacterial or chronic infections, pain, diabetic neuropathy, migraine, cerebral ischemia, schizophrenia, encephalitis, autism and autism spectrum disorders, memory and learning disorders, obsessive compulsive disorder, attention deficit hyperactivity disorder (ADHD), and addictive illnesses.

43. The method of embodiment 42, wherein the disease, disorder, or medical condition is selected from the group consisting of treatment-resistant depression, major depressive disorder and bipolar disorder.

What is claimed:

1. A compound having the structure of Formula (I):

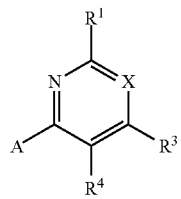

(I)

or a pharmaceutically acceptable salt, solvate, stereoisomer, isotopic variant, or N-oxide thereof, wherein $R^1$ is selected from the group consisting of: H, OH, $C_{1-4}$alkyl, $CH_2OH$, $CH_2F$, $CHF_2$, $OC_{1-4}$alkyl, $OCHF_2$, CN, and cyclopropyl;

X is C—$R^2$; wherein $R^2$ is selected from the group consisting of: H, halo, $C_{1-4}$alkyl, $OC_{1-4}$alkyl, and CN;

$R^3$ is:

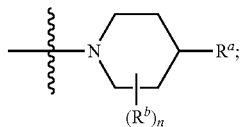

(a)

wherein $R^a$ is selected from the group consisting of OH, (C=O)NH_2, (C=O)NHCH_3, (C=O)NHCH_2CH_2OH, $CH_2$(C=O)NH_2, $CH_2C$(=O)CH_3, (C=O)CH_3, $CH_2NH$(C=O)CH_3, NH(C=O)$C_{1-4}$alkyl, NCH_3(C=O)$C_{1-4}$alkyl, NH(C=O)$CH_2CH_2NH_2$, NH(C=O)$CH_2CH_2OH$, NH(C=O)halo$C_{1-4}$alkyl, NH(C=O)cycopropyl, $NHSO_2CH_3$,

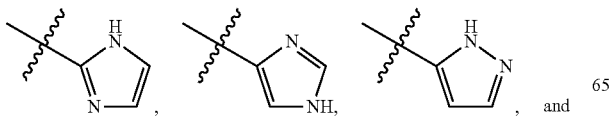, and

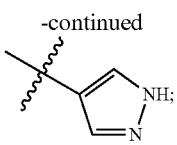

each $R^b$ is independently selected from the group consisting of: H, F, $CH_3$, and OH; and n is 0, 1, or 2; or

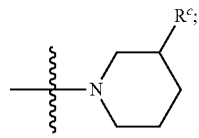

(b)

wherein $R^c$ is selected from the group consisting of: NH(C=O)$CH_3$, $CH_2NH$(C=O)$CH_3$, (C=O)$CH_3$, and (C=O)$NHCH_3$;

$R^4$ is H or $CH_3$; and

A is selected from the group consisting of:

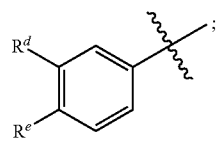

(a)

wherein $R^d$ is selected from the group consisting of: halo, $C_{1-4}$alkyl, $CH_2H$, $C_{1-4}$haloalkyl, $OC_{1-4}$alkyl, and $OC_{1-4}$haloalkyl; and $R^e$ is selected from the group consisting of: halo, $C_{1-4}$alkyl, $CH_2H$, $OC_{1-4}$alkyl, $C_{1-4}$haloalkyl, $OC_{1-4}$haloalkyl, and (C=O)$CH_3$;

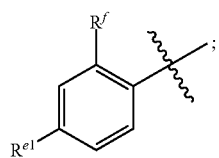

(b)

wherein $R^f$ is H or F; and $R^{ei}$ is selected from the group consisting of: $C_{1-4}$alkyl, $C_{1-4}$haloalkyl, and $OC_{1-4}$haloalkyl;

and

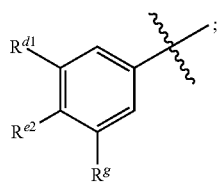

(c)

wherein $R^{d1}$ and $R^{e2}$ are halo; and $R^g$ is $OC_{1-4}$haloalkyl.

2. The compound of claim 1, or a pharmaceutically acceptable salt, solvate, stereoisomer, isotopic variant, or N-oxide thereof, wherein $R^1$ is H, OH, $CH_3$, $CH_2CH_3$, $CH_2OH$, $OCH_3$, $CH_2F$, $CHF_2$, $OCHF_2$, CN, or cyclopropyl.

3. The compound of claim 1, or a pharmaceutically acceptable salt, solvate, stereoisomer, isotopic variant, or N-oxide thereof, wherein $R^2$ is H, F, $CH_3$, $OCH_3$, or CN.

4. The compound of claim 1, or a pharmaceutically acceptable salt, solvate, stereoisomer, isotopic variant, or N-oxide thereof, wherein $R^3$ is

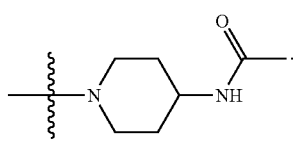

5. The compound of claim 1, or a pharmaceutically acceptable salt, solvate, steroisomer, isotopic variant, or N-oxide thereof, wherein $R^3$ is

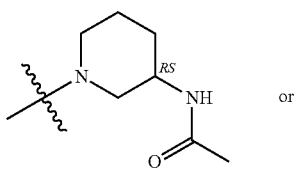

or

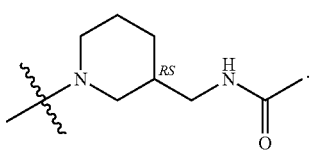

6. The compound of claim 1, or a pharmaceutically acceptable salt, solvate, stereoisomer, isotopic variant, or N-oxide thereof, wherein $R^4$ is H.

7. The compound of claim 1, or a pharmaceutically acceptable salt, solvate, stereoisomer, isotopic variant, or N-oxide thereof, wherein A is

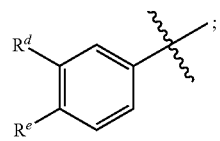

wherein $R^d$ is Cl, F, $C_{1-4}$alkyl, $CH_2OH$, $C_{1-4}$haloalkyl, $OC_{1-4}$alkyl, or $OC_{1-4}$haloalkyl; and $R^e$ is halo, $C_{1-4}$alkyl, $CH_2OH$, $OC_{1-4}$alkyl, $C_{1-4}$haloalkyl, $OC_{1-4}$haloalkyl, or $(C=O)CH_3$.

8. A compound having the structure of Formula (IA):

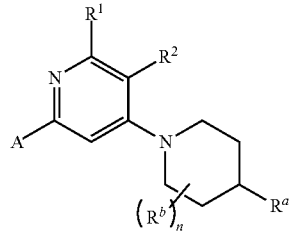

(IA)

or a pharmaceutically acceptable salt, solvate, stereoisomer, isotopic variant, or N-oxide thereof, wherein $R^1$ is selected from the group consisting of H, $CH_3$, $CH_2OH$, $CH_2F$, $CHF_2$, $OCHF_2$, OH, $OCH_3$, and CN;

$R^2$ is selected from the group consisting of: H, F, $CH_3$, CN, and $OCH_3$;

$R^a$ is selected from the group consisting of OH, (C=O)$NH_2$, $CH_2(C=O)NH_2$, $CH_2C(=O)CH_3$, NH(C=O)$C_{1-4}$alkyl, $NHSO_2CH_3$,

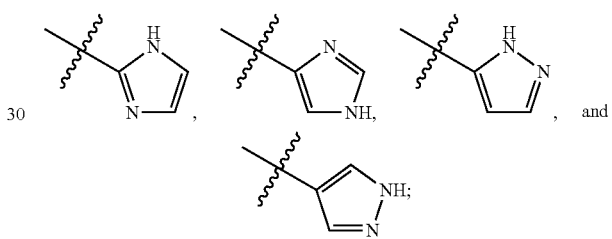

, and each $R^b$ is independently selected from the group consisting of: H, F, $CH_3$, and OH;

n is 0, 1, or 2; and

A is selected from the group consisting of: 4-(methyl)phenyl, 4-(1,1-difluoroethyl)phenyl, 4-(difluoromethyl)phenyl, 4-(trifluoromethyl)phenyl, 4-(difluoromethoxy)phenyl, 4-(tifluoromethoxy)phenyl, 3-fluoro-4-(tifluoromethoxy)phenyl, 4-chloro-3-fluorophenyl, 3-fluoro-4-(trifluoromethyl)phenyl, 3-(difluoromethyl)-4-fluoro-phenyl, 3-fluoro-4-methoxy-phenyl, 4-acetyl-3-fluoro-phenyl, 4-(difluoromethoxy)-3-methyl-phenyl, 4-(difluoromethoxy)-3-fluoro-phenyl, 3-(difluoromethoxy)-4-fluoro-phenyl, 4-(difluoromethoxy)-3-fluoro-phenyl, 4-ethoxy-3-fluoro-phenyl, 3-methyl-4-(trifluoromethoxy)phenyl, 3-fluoro-4-isopropoxy-phenyl, 3-fluoro-4-(2,2,2-trifluoroethoxy)phenyl, 3-chloro-4-(trifluoromethoxy)phenyl, and 3,5-difluoro-4-(tifluoromethoxy)phenyl.

9. The compound of claim 1 having the structure of Formula (IB):

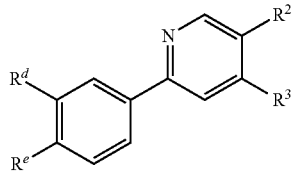

(IB)

or a pharmaceutically acceptable salt, solvate, stereoisomer, isotopic variant, or N-oxide thereof,
wherein
R² is H or F;
R³ is:

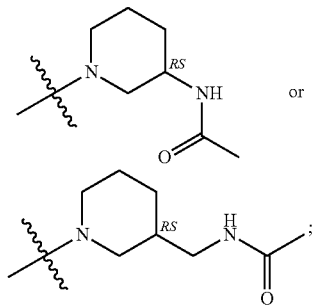

R^d is halo or C₁₋₄haloalkyl; and
R^e is halo or OC₁₋₄haloalkyl.

10. A compound selected from the group consisting of:
N-[1-[2-[3-Fluoro-4-(trifluoromethoxy)phenyl]-4-pyridyl]-4-piperidyl]acetamide;
N-[1-[2-[3-(Difluoromethoxy)-4-fluoro-phenyl]-4-pyridyl]-4-piperidyl]acetamide;
N-[1-[2-[4-(Difluoromethyl)phenyl]-4-pyridyl]-4-piperidyl]acetamide;
N-[1-[2-[3,5-Difluoro-4-(trifluoromethoxy)phenyl]-4-pyridyl]-4-piperidyl]acetamide;
N-[1-[5-Fluoro-2-[3-fluoro-4-(trifluoromethoxy)phenyl]-4-pyridyl]-4-piperidyl]acetamide;
(trans)-N-[3-Fluoro-1-[2-[3-fluoro-4-(trifluoromethoxy)phenyl]-4-pyridyl]-4-piperidyl]acetamide;
(*R/*R)—N-[3-Fluoro-1-[5-fluoro-2-[3-fluoro-4-(trifluoromethoxy)phenyl]-4-pyridyl]-4-piperidyl]acetamide;
(racemic)-N-[1-[2-[3-Fluoro-4-(trifluoromethoxy)phenyl]-4-pyridyl]-2-methyl-4-piperidyl]acetamide;
N-[1-[5-Cyano-2-[4-(trifluoromethoxy)phenyl]-4-pyridyl]-4-piperidyl]acetamide;
N-[1-[2-Cyano-6-[3-fluoro-4-(trifluoromethoxy)phenyl]-4-pyridyl]-4-piperidyl]acetamide;
N-[1-[2-[3-Fluoro-4-(trifluoromethoxy)phenyl]-6-methyl-4-pyridyl]-4-piperidyl]acetamide;
1-[2-[3-Fluoro-4-(trifluoromethoxy)phenyl]-4-pyridyl]piperidin-4-ol;
N-[1-[2-[4-(Trifluoromethoxy)phenyl]-4-pyridyl]-4-piperidyl]acetamide;
N-[1-[2-[3-Methyl-4-(trifluoromethoxy)phenyl]-4-pyridyl]-4-piperidyl]acetamide;
N-[1-[2-[4-(Difluoromethoxy)-3-methyl-phenyl]-4-pyridyl]-4-piperidyl]acetamide;
1-[2-[3-Fluoro-4-(trifluoromethoxy)phenyl]-4-pyridyl]piperidine-4-carboxamide;
1-[1-[2-[3-Fluoro-4-(trifluoromethoxy)phenyl]-4-pyridyl]-4-piperidyl]propan-2-one;
2-[1-[2-[3-Fluoro-4-(trifluoromethoxy)phenyl]-4-pyridyl]-4-piperidyl]acetamide;
2-[3-Fluoro-4-(trifluoromethoxy)phenyl]-4-[4-(1H-pyrazol-5-yl)-1-piperidyl]pyridine;
2-[3-Fluoro-4-(trifluoromethoxy)phenyl]-4-[4-(1H-imidazol-4-yl)-1-piperidyl]pyridine;
2-[3-Fluoro-4-(trifluoromethoxy)phenyl]-4-[4-(1H-imidazol-2-yl)-1-piperidyl]pyridine;
2-[3-Fluoro-4-(trifluoromethoxy)phenyl]-4-[4-(1H-pyrazol-4-yl)-1-piperidyl]pyridine;
N-[1-[2-[3-Fluoro-4-(trifluoromethoxy)phenyl]-4-pyridyl]-4-piperidyl]methanesulfonamide;
N-[1-[2-[4-(Difluoromethoxy)phenyl]-4-pyridyl]-4-piperidyl]acetamide;
N-[1-[2-[4-(Difluoromethoxy)-3-fluoro-phenyl]-4-pyridyl]-4-piperidyl]acetamide;
N-[1-[2-[3-(Difluoromethyl)-4-fluoro-phenyl]-4-pyridyl]-4-piperidyl]acetamide;
N-[1-[2-(p-Tolyl)-4-pyridyl]-4-piperidyl]acetamide;
N-[1-[2-[4-(1,1-Difluoroethyl)phenyl]-4-pyridyl]-4-piperidyl]acetamide;
N-[1-[2-[4-(Trifluoromethyl)phenyl]-4-pyridyl]-4-piperidyl]acetamide;
N-[1-[2-[3-Chloro-4-(trifluoromethoxy)phenyl]-4-pyridyl]-4-piperidyl]acetamide;
N-[1-[2-[2-Fluoro-4-(trifluoromethoxy)phenyl]-4-pyridyl]-4-piperidyl]acetamide;
N-[1-[2-[3-Fluoro-4-(2,2,2-trifluoroethoxy)phenyl]-4-pyridyl]-4-piperidyl]acetamide;
N-[1-[2-(4-Chloro-3-fluoro-phenyl)-4-pyridyl]-4-piperidyl]acetamide;
N-[1-[2-[3-Fluoro-4-methoxy-phenyl]-4-pyridyl]-4-piperidyl]acetamide;
N-[1-[2-[3-Fluoro-4-(trifluoromethyl)phenyl]-4-pyridyl]-4-piperidyl]acetamide;
N-[1-[2-(4-Acetyl-3-fluoro-phenyl)-4-pyridyl]-4-piperidyl]acetamide;
N-[1-[2-[3-Fluoro-4-(trifluoromethoxy)phenyl]-5-methyl-4-pyridyl]-4-piperidyl]acetamide;
N-[1-[2-[3-Fluoro-4-(trifluoromethoxy)phenyl]-5-methoxy-4-pyridyl]-4-piperidyl]acetamide;
N-[1-[2-[4-(Difluoromethoxy)phenyl]-6-methyl-4-pyridyl]-4-piperidyl]acetamide;
N-[1-[2-[4-(1,1-Difluoroethyl)phenyl]-6-methyl-4-pyridyl]-4-piperidyl]acetamide;
N-[1-[2-[4-(Difluoromethoxy)-3-fluoro-phenyl]-6-methyl-4-pyridyl]-4-piperidyl]acetamide;
N-[1-[2-(Fluoromethyl)-6-[3-fluoro-4-(trifluoromethoxy)phenyl]-4-pyridyl]-4-piperidyl]acetamide;
N-[1-[2-(Difluoromethyl)-6-[3-fluoro-4-(trifluoromethoxy)phenyl]-4-pyridyl]-4-piperidyl]acetamide;
N-[1-[2-[3-Fluoro-4-(trifluoromethoxy)phenyl]-6-(hydroxymethyl)-4-pyridyl]-4-piperidyl]acetamide;
N-[1-[2-(3-Fluoro-4-isopropoxy-phenyl)-6-(hydroxymethyl)-4-pyridyl]-4-piperidyl]acetamide;
N-[1-[2-(4-Ethoxy-3-fluoro-phenyl)-6-(hydroxymethyl)-4-pyridyl]-4-piperidyl]acetamide;
N-[1-[2-[3-Fluoro-4-(trifluoromethoxy)phenyl]-6-methoxy-4-pyridyl]-4-piperidyl]acetamide;
N-[1-[2-[3-Fluoro-4-(trifluoromethoxy)phenyl]-6-hydroxy-4-pyridyl]-4-piperidyl]acetamide;
N-[1-[2-(Difluoromethoxy)-6-[3-fluoro-4-(trifluoromethoxy)phenyl]-4-pyridyl]-4-piperidyl]acetamide;
(cis)-N-[3-Fluoro-1-[2-[3-fluoro-4-(trifluoromethoxy)phenyl]-4-pyridyl]-4-piperidyl]acetamide;
(*R/*R)—N-[3-Fluoro-1-[2-[3-fluoro-4-(trifluoromethoxy)phenyl]-4-pyridyl]-4-piperidyl]acetamide;
(*S/*S)—N-[3-Fluoro-1-[2-[3-fluoro-4-(trifluoromethoxy)phenyl]-4-pyridyl]-4-piperidyl]acetamide;
(*S/*S)—N-[3-Fluoro-1-[5-fluoro-2-[3-fluoro-4-(trifluoromethoxy)phenyl]-4-pyridyl]-4-piperidyl]acetamide;
(trans)-N-[1-[2-[3-Fluoro-4-(trifluoromethoxy)phenyl]-4-pyridyl]-3-hydroxy-4-piperidyl]acetamide;
(racemic)-N-[1-[2-[3-Fluoro-4-(trifluoromethoxy)phenyl]-4-pyridyl]-3-methyl-4-piperidyl]acetamide;

(trans)-N-[1-[2-[3-Fluoro-4-(trifluoromethoxy)phenyl]-4-pyridyl]-3-methyl-4-piperidyl]acetamide;
(cis)-N-[1-[2-[3-Fluoro-4-(trifluoromethoxy)phenyl]-4-pyridyl]-3-methyl-4-piperidyl]acetamide;
(racemic)-N-[1-[2-[3-Fluoro-4-(trifluoromethoxy)phenyl]-4-pyridyl]-3-piperidyl]acetamide;
(racemic)-N-[1-[2-[3-Fluoro-4-(trifluoromethoxy)phenyl]-4-pyridyl]-3,3-dimethyl-4-piperidyl]acetamide;
N-[[1-[2-[3-Fluoro-4-(trifluoromethoxy)phenyl]-4-pyridyl]-4-piperidyl]methyl]acetamide; and
(racemic)-N-[[1-[2-[3-Fluoro-4-(trifluoromethoxy)phenyl]-4-pyridyl]-3-piperidyl]methyl]acetamide;
and pharmaceutically acceptable salts, solvates, stereoisomers, isotopic variants, and N-oxides thereof.

11. A compound selected from the group consisting of:
N-[1-[2-[3-Fluoro-4-(trifluoromethoxy)phenyl]-4-pyridyl]-4-piperidyl]acetamide;
N-[1-[2-[4-(Trifluoromethoxy)phenyl]-4-pyridyl]-4-piperidyl]acetamide;
N-[1-[2-[3-Methyl-4-(trifluoromethoxy)phenyl]-4-pyridyl]-4-piperidyl]acetamide;
N-[1-[2-[4-(Difluoromethoxy)-3-methyl-phenyl]-4-pyridyl]-4-piperidyl]acetamide;
2-[1-[2-[3-Fluoro-4-(trifluoromethoxy)phenyl]-4-pyridyl]-4-piperidyl]acetamide;
N-[1-[2-[3-Chloro-4-(trifluoromethoxy)phenyl]-4-pyridyl]-4-piperidyl]acetamide;
N-[1-[2-(Fluoromethyl)-6-[3-fluoro-4-(trifluoromethoxy)phenyl]-4-pyridyl]-4-piperidyl]acetamide;
N-[1-[2-[3-Fluoro-4-(trifluoromethoxy)phenyl]-6-(hydroxymethyl)-4-pyridyl]-4-piperidyl]acetamide; and
(*R/*R)—N-[3-Fluoro-1-[2-[3-fluoro-4-(trifluoromethoxy)phenyl]-4-pyridyl]-4-piperidyl]acetamide;
and pharmaceutically acceptable salts, solvates, stereoisomers, isotopic variants, and N-oxides thereof.

12. The compound of claim 1 or a pharmaceutically acceptable salt thereof.

13. A pharmaceutical composition comprising a compound of claim 1, or a pharmaceutically acceptable salt, solvate, stereoisomer, isotopic variant, or N-oxide thereof, and a pharmaceutically acceptable excipient.

14. A method of treating a subject suffering from or diagnosed with treatment-resistant depression, comprising administering to the subject an effective amount of a compound of claim 1 or a pharmaceutically acceptable salt, solvate, stereoisomer, isotopic variant, or N-oxide thereof.

15. A method of treating a subject suffering from or diagnosed with major depressive disorder, comprising administering to the subject an effective amount of a compound of claim 1 or a pharmaceutically acceptable salt, solvate, stereoisomer, isotopic variant, or N-oxide thereof.

* * * * *